US012394502B2

(12) United States Patent
Hacohen et al.

(10) Patent No.: US 12,394,502 B2
(45) Date of Patent: Aug. 19, 2025

(54) METHOD FOR PREDICTING HLA-BINDING PEPTIDES USING PROTEIN STRUCTURAL FEATURES

(71) Applicants: The General Hospital Corporation, Boston, MA (US); Dana-Farber Cancer Institute, Inc., Boston, MA (US); The Broad Institute, Inc., Cambridge, MA (US)

(72) Inventors: Nir Hacohen, Boston, MA (US); Catherine J. Wu, Boston, MA (US); Siranush Sarkizova, Boston, MA (US); Matthew Bakalar, Cambridge, MA (US)

(73) Assignees: The General Hospital Corporation, Boston, MA (US); Dana-Farber Cancer Institute, Inc., Boston, MA (US); The Broad Institute, Inc., Cambridge, MA (US)

( * ) Notice: Subject to any disclaimer, the term of this patent is extended or adjusted under 35 U.S.C. 154(b) by 868 days.

(21) Appl. No.: 17/062,335

(22) Filed: Oct. 2, 2020

(65) Prior Publication Data

US 2021/0104294 A1    Apr. 8, 2021

Related U.S. Application Data

(60) Provisional application No. 62/909,752, filed on Oct. 2, 2019.

(51) Int. Cl.
*G16B 15/30* (2019.01)
*G16B 40/20* (2019.01)
*G16B 40/30* (2019.01)

(52) U.S. Cl.
CPC .............. *G16B 15/30* (2019.02); *G16B 40/20* (2019.02); *G16B 40/30* (2019.02)

(58) Field of Classification Search
USPC .......................................................... 703/11
See application file for complete search history.

(56) References Cited

U.S. PATENT DOCUMENTS

| | | |
|---|---|---|
| 3,870,790 A | 3/1975 | Lowey et al. |
| 4,210,644 A | 7/1980 | Desjardins et al. |
| 4,226,859 A | 10/1980 | Stach |
| 4,369,172 A | 1/1983 | Schor et al. |
| 4,379,454 A | 4/1983 | Campbell et al. |
| 4,588,585 A | 5/1986 | Mark et al. |
| 4,603,112 A | 7/1986 | Paoletti et al. |
| 4,690,915 A | 9/1987 | Rosenberg |
| 4,743,249 A | 5/1988 | Loveland |
| 4,751,180 A | 6/1988 | Cousens et al. |
| 4,769,330 A | 9/1988 | Paoletti et al. |
| 4,816,540 A | 3/1989 | Onishi |
| 4,842,866 A | 6/1989 | Horder et al. |
| 4,844,893 A | 7/1989 | Honsik et al. |
| 4,906,169 A | 3/1990 | Chien et al. |
| 4,935,233 A | 6/1990 | Bell et al. |
| 4,973,468 A | 11/1990 | Chiang et al. |
| 5,023,084 A | 6/1991 | Chien et al. |
| 5,035,891 A | 7/1991 | Runkel et al. |
| 5,110,587 A | 5/1992 | Paoletti et al. |
| 5,174,993 A | 12/1992 | Paoletti |
| 5,185,146 A | 2/1993 | Altenburger |
| 5,198,223 A | 3/1993 | Gale et al. |
| 5,204,253 A | 4/1993 | Sanford et al. |
| 5,217,720 A | 6/1993 | Sekigawa et al. |
| 5,279,833 A | 1/1994 | Rose |
| 5,364,773 A | 11/1994 | Paoletti et al. |
| 5,422,119 A | 6/1995 | Casper |
| 5,494,807 A | 2/1996 | Paoletti et al. |
| 5,541,171 A | 7/1996 | Rhodes et al. |
| 5,580,859 A | 12/1996 | Felgner et al. |
| 5,589,466 A | 12/1996 | Felgner et al. |
| 5,658,785 A | 8/1997 | Johnson |
| 5,686,281 A | 11/1997 | Roberts |
| 5,705,190 A | 1/1998 | Broad et al. |
| 5,756,101 A | 5/1998 | Paoletti et al. |
| 5,762,938 A | 6/1998 | Paoletti et al. |
| 5,766,597 A | 6/1998 | Paoletti et al. |
| 5,766,882 A | 6/1998 | Falkner et al. |

(Continued)

FOREIGN PATENT DOCUMENTS

| | | |
|---|---|---|
| WO | 91/06309 A1 | 5/1991 |
| WO | 92/15322 A1 | 9/1992 |

(Continued)

OTHER PUBLICATIONS

Guo, Yugang, Kewen Lei, and Li Tang. "Neoantigen vaccine delivery for personalized anticancer immunotherapy." Frontiers in immunology 9 (2018): 1499. (Year: 2018).*
London, Nir, et al. "Rosetta FlexPepDock web server-high resolution modeling of peptide-protein interactions." Nucleic acids research 39.suppl_2 (2011): W249-W253.*
Abelin, et al., "Mass Spectrometry Profiling of HLA-Associated Peptidomes in Mono-allelic Cells Enables More Accurate Epitope Prediction", Immunity, vol. 46, Issue 2, Feb. 21, 2017, 315-326.
Bassani-Sternberg, et al., "Direct Identification of Clinically Relevant Neoepitopes Presented on Native Human Melanoma Tissue by Mass Spectrometry", Nature Communications, vol. 7, No. 13404, Nov. 21, 2016, 16 pages.

(Continued)

*Primary Examiner* — G. Steven Vanni
(74) *Attorney, Agent, or Firm* — Day Pitney LLP; Christopher R. Cowles; Richard B. Emmons

(57) ABSTRACT

The present invention discloses a method for predicting peptides that are capable of binding to HLA molecules that incorporate the crystal structure of HLA molecules. An improved HLA-specific peptide docking workflow is used to simulate the occupancy of a peptide on the binding pocket of an HLA molecule, and three models are trained to predict the binding of the peptide to HLA molecules. The results show that these models predict HLA-allele specific binding peptides with extremely high accuracy.

19 Claims, 70 Drawing Sheets

Specification includes a Sequence Listing.

(56) References Cited

U.S. PATENT DOCUMENTS

| | | |
|---|---|---|
| 5,770,212 A | 6/1998 | Falkner et al. |
| 5,811,104 A | 9/1998 | Dale et al. |
| 5,833,975 A | 11/1998 | Paoletti et al. |
| 5,843,728 A | 12/1998 | Seed et al. |
| 5,849,303 A | 12/1998 | Wasmoen et al. |
| 5,851,828 A | 12/1998 | Seed et al. |
| 5,858,358 A | 1/1999 | June et al. |
| 5,883,223 A | 3/1999 | Gray |
| 5,906,936 A | 5/1999 | Eshhar et al. |
| 5,912,170 A | 6/1999 | Seed et al. |
| 5,912,172 A | 6/1999 | Eshhar et al. |
| 5,942,235 A | 8/1999 | Paoletti |
| 5,989,562 A | 11/1999 | Wasmoen et al. |
| 5,990,091 A | 11/1999 | Tartaglia et al. |
| 5,994,136 A | 11/1999 | Naldini et al. |
| 6,004,777 A | 12/1999 | Tartaglia et al. |
| 6,004,811 A | 12/1999 | Seed et al. |
| 6,013,516 A | 1/2000 | Verma et al. |
| 6,040,177 A | 3/2000 | Riddell et al. |
| 6,090,393 A | 7/2000 | Fischer |
| 6,130,066 A | 10/2000 | Tartaglia et al. |
| 6,156,567 A | 12/2000 | Fischer |
| 6,159,477 A | 12/2000 | Audonnet et al. |
| 6,165,782 A | 12/2000 | Naldini et al. |
| 6,214,353 B1 | 4/2001 | Paoletti et al. |
| 6,228,846 B1 | 5/2001 | Audonnet et al. |
| 6,258,595 B1 | 7/2001 | Gao et al. |
| 6,265,189 B1 | 7/2001 | Paoletti et al. |
| 6,277,558 B1 | 8/2001 | Hudson |
| 6,284,240 B1 | 9/2001 | Seed et al. |
| 6,309,647 B1 | 10/2001 | Paoletti et al. |
| 6,312,682 B1 | 11/2001 | Kingsman et al. |
| 6,352,694 B1 | 3/2002 | June et al. |
| 6,392,013 B1 | 5/2002 | Seed et al. |
| 6,406,705 B1 | 6/2002 | Davis et al. |
| 6,410,014 B1 | 6/2002 | Seed et al. |
| 6,428,953 B1 | 8/2002 | Naldini et al. |
| 6,475,769 B1 | 11/2002 | Wilson et al. |
| 6,489,458 B2 | 12/2002 | Hackett et al. |
| 6,534,055 B1 | 3/2003 | June et al. |
| 6,537,540 B1 | 3/2003 | Burstein et al. |
| 6,537,594 B1 | 3/2003 | Paoletti et al. |
| 6,569,457 B2 | 5/2003 | Ullah et al. |
| 6,638,534 B1 | 10/2003 | Ishibashi et al. |
| 6,682,743 B2 | 1/2004 | Mayr |
| 6,713,068 B1 | 3/2004 | Audonnet et al. |
| 6,753,162 B1 | 6/2004 | Seed et al. |
| 6,761,893 B2 | 7/2004 | Chaplin et al. |
| 6,780,407 B1 | 8/2004 | Paoletti et al. |
| 6,780,417 B2 | 8/2004 | Kaslow et al. |
| 6,793,926 B1 | 9/2004 | Rasty et al. |
| 6,797,514 B2 | 9/2004 | Berenson et al. |
| 6,867,041 B2 | 3/2005 | Berenson et al. |
| 6,869,794 B2 | 3/2005 | Vogels et al. |
| 6,887,466 B2 | 5/2005 | June et al. |
| 6,893,865 B1 | 5/2005 | Lockert et al. |
| 6,905,680 B2 | 6/2005 | June et al. |
| 6,905,681 B1 | 6/2005 | June et al. |
| 6,905,874 B2 | 6/2005 | Berenson et al. |
| 6,913,752 B2 | 7/2005 | Chaplin et al. |
| 6,913,922 B1 | 7/2005 | Bout et al. |
| 6,924,128 B2 | 8/2005 | Allen |
| 6,936,466 B2 | 8/2005 | Feldhaus |
| 6,943,019 B2 | 9/2005 | Wilson et al. |
| 6,953,690 B1 | 10/2005 | Gao et al. |
| 6,955,808 B2 | 10/2005 | Curiel |
| 6,974,695 B2 | 12/2005 | Vogels et al. |
| 6,991,797 B2 | 1/2006 | Andersen et al. |
| 7,029,848 B2 | 4/2006 | Vogels et al. |
| 7,045,313 B1 | 5/2006 | Moss et al. |
| 7,097,842 B2 | 8/2006 | Suter et al. |
| 7,115,391 B1 | 10/2006 | Chen et al. |
| 7,144,575 B2 | 12/2006 | June et al. |
| 7,148,203 B2 | 12/2006 | Hackett et al. |
| 7,160,682 B2 | 1/2007 | Jackett et al. |
| 7,172,893 B2 | 2/2007 | Rabinowitz et al. |
| 7,175,843 B2 | 2/2007 | June et al. |
| 7,189,536 B2 | 3/2007 | Chaplin et al. |
| 7,198,784 B2 | 4/2007 | Kingsman et al. |
| 7,232,566 B2 | 6/2007 | June et al. |
| 7,255,862 B1 | 8/2007 | Tartaglia et al. |
| 7,259,015 B2 | 8/2007 | Kingsman et al. |
| 7,303,910 B2 | 12/2007 | Bebbington et al. |
| 7,335,364 B2 | 2/2008 | Chaplin et al. |
| 7,351,585 B2 | 4/2008 | Mitrophanous et al. |
| 7,384,644 B2 | 6/2008 | Chaplin et al. |
| 7,445,924 B2 | 11/2008 | Chaplin et al. |
| 7,446,190 B2 | 11/2008 | Sadelain et al. |
| 7,459,270 B2 | 12/2008 | Chaplin et al. |
| 7,572,631 B2 | 8/2009 | Berenson et al. |
| 7,608,279 B2 | 10/2009 | Parisot et al. |
| 7,628,980 B2 | 12/2009 | Suter et al. |
| 7,741,465 B1 | 6/2010 | Eshhar et al. |
| 7,767,449 B1 | 8/2010 | Paoletti |
| 7,892,533 B2 | 2/2011 | Suter et al. |
| 7,897,156 B2 | 3/2011 | Ackermann et al. |
| 7,923,017 B2 | 4/2011 | Chaplin et al. |
| 7,939,086 B2 | 5/2011 | Chaplin et al. |
| 7,964,395 B2 | 6/2011 | Chaplin et al. |
| 7,964,396 B2 | 6/2011 | Chaplin et al. |
| 7,964,398 B2 | 6/2011 | Chaplin et al. |
| 7,985,739 B2 | 7/2011 | Kay et al. |
| 8,034,334 B2 | 10/2011 | Dudley et al. |
| 8,088,379 B2 | 1/2012 | Robbins et al. |
| 8,163,293 B2 | 4/2012 | Chaplin |
| 8,211,422 B2 | 7/2012 | Eshhar et al. |
| 8,227,432 B2 | 7/2012 | Hackett et al. |
| 8,236,560 B2 | 8/2012 | Chaplin et al. |
| 8,268,325 B2 | 9/2012 | Chaplin et al. |
| 8,268,329 B2 | 9/2012 | Chaplin et al. |
| 8,278,036 B2 | 10/2012 | Kariko et al. |
| 8,309,098 B2 | 11/2012 | Howley et al. |
| 8,372,622 B2 | 2/2013 | Suter et al. |
| 8,399,645 B2 | 3/2013 | Campana et al. |
| 8,404,658 B2 | 3/2013 | Hajjar et al. |
| 8,454,972 B2 | 6/2013 | Nabel et al. |
| 8,470,598 B2 | 6/2013 | Chaplin et al. |
| 8,637,307 B2 | 1/2014 | June et al. |
| 8,697,854 B2 | 4/2014 | Schendel et al. |
| 8,906,682 B2 | 12/2014 | June et al. |
| 8,911,993 B2 | 12/2014 | June et al. |
| 8,916,381 B1 | 12/2014 | June et al. |
| 8,975,071 B1 | 3/2015 | June et al. |
| 9,101,584 B2 | 8/2015 | June et al. |
| 9,102,760 B2 | 8/2015 | June et al. |
| 9,102,761 B2 | 8/2015 | June et al. |
| 9,233,125 B2 | 1/2016 | Davila et al. |
| 2003/0104008 A1 | 6/2003 | Loosmore et al. |
| 2004/0013648 A1 | 1/2004 | Kingsman et al. |
| 2004/0224402 A1 | 11/2004 | Bonyhadi et al. |
| 2006/0258607 A1 | 11/2006 | Jarosch et al. |
| 2007/0025970 A1 | 2/2007 | Kingsman et al. |
| 2007/0134197 A1 | 6/2007 | Eichner et al. |
| 2008/0254008 A1 | 10/2008 | Dropulic et al. |
| 2009/0111106 A1 | 4/2009 | Mitrophanous et al. |
| 2010/0104509 A1 | 4/2010 | King et al. |
| 2011/0293571 A1 | 12/2011 | Widdowson et al. |
| 2012/0244133 A1 | 9/2012 | Rosenberg et al. |
| 2012/0295960 A1 | 11/2012 | Palfi et al. |
| 2013/0071414 A1 | 3/2013 | Dotti et al. |
| 2015/0368342 A1 | 12/2015 | Wu et al. |
| 2015/0368360 A1 | 12/2015 | Liang et al. |
| 2016/0046724 A1 | 2/2016 | Brogdon et al. |
| 2016/0129109 A1 | 5/2016 | Davila et al. |
| 2016/0175359 A1 | 6/2016 | Spencer et al. |
| 2017/0283504 A1 | 10/2017 | Wiltzius et al. |
| 2018/0085444 A1 | 3/2018 | Morgan et al. |
| 2019/0065675 A1* | 2/2019 | Yelensky ............... G16B 40/10 |
| 2022/0130489 A1* | 4/2022 | Jung ...................... G16B 20/20 |

FOREIGN PATENT DOCUMENTS

| | | |
|---|---|---|
| WO | 93/24640 A2 | 12/1993 |
| WO | 94/26877 A1 | 11/1994 |

(56) References Cited

FOREIGN PATENT DOCUMENTS

| | | |
|---|---|---|
| WO | 95/30018 A2 | 11/1995 |
| WO | 96/18372 A2 | 6/1996 |
| WO | 03/020763 A2 | 3/2003 |
| WO | 03/057171 A2 | 7/2003 |
| WO | 2004/033685 A1 | 4/2004 |
| WO | 2004/044004 A2 | 5/2004 |
| WO | 2004/074322 A1 | 9/2004 |
| WO | 2005/113595 A2 | 12/2005 |
| WO | 2005/114215 A2 | 12/2005 |
| WO | 2006/000830 A2 | 1/2006 |
| WO | 2006/125962 A2 | 11/2006 |
| WO | 2008/038002 A2 | 4/2008 |
| WO | 2008/039818 A2 | 4/2008 |
| WO | 2011/051489 A2 | 5/2011 |
| WO | 2011/146862 A1 | 11/2011 |
| WO | 2012/058460 A2 | 5/2012 |
| WO | 2012/079000 A1 | 6/2012 |
| WO | 2012/159643 A1 | 11/2012 |
| WO | 2012/159754 A2 | 11/2012 |
| WO | 2013/039889 A1 | 3/2013 |
| WO | 2013/040371 A2 | 3/2013 |
| WO | 2013/044225 A1 | 3/2013 |
| WO | 2013/154760 A1 | 10/2013 |
| WO | 2013/166321 A1 | 11/2013 |
| WO | 2013/176915 A1 | 11/2013 |
| WO | 2014/011987 A1 | 1/2014 |
| WO | 2014/018863 A1 | 1/2014 |
| WO | 2014/059173 A2 | 4/2014 |
| WO | 2014/083173 A1 | 6/2014 |
| WO | 2014/133567 A1 | 9/2014 |
| WO | 2014/133568 A1 | 9/2014 |
| WO | 2014/134165 A1 | 9/2014 |
| WO | 2014/172606 A1 | 10/2014 |
| WO | 2014/184744 A1 | 11/2014 |
| WO | 2014/191128 A1 | 12/2014 |
| WO | 2015/057834 A1 | 4/2015 |
| WO | 2015/057852 A1 | 4/2015 |
| WO | 2015/085147 A1 | 6/2015 |
| WO | 2015/120096 A2 | 8/2015 |
| WO | 2015/142675 A2 | 9/2015 |
| WO | 2015/158671 A1 | 10/2015 |
| WO | 2015/187528 A1 | 12/2015 |
| WO | 2016/000304 A1 | 1/2016 |
| WO | 2016/011210 A2 | 1/2016 |
| WO | 2016/014789 A2 | 1/2016 |
| WO | 2016/070061 A1 | 5/2016 |
| WO | 2016/191756 A1 | 12/2016 |
| WO | 2016/196388 A1 | 12/2016 |
| WO | 2017/011804 A1 | 1/2017 |
| WO | 2017/070395 A1 | 4/2017 |
| WO | 2017/184590 A1 | 10/2017 |
| WO | 2017/211900 A1 | 12/2017 |
| WO | 2018/028647 A1 | 2/2018 |
| WO | 2020/072700 A1 | 4/2020 |
| WO | 2020/131586 A1 | 6/2020 |

OTHER PUBLICATIONS

Bordner, et al., "Ab Initio Prediction of Peptide-MHC Binding Geometry for Diverse Class I MHC Allotypes", Proteins, vol. 63, No. 3, 2006, 512-526.
Bulik-Sullivan, et al., "Deep Learning Using Tumor HLA Peptide Mass Spectrometry Datasets Improves Neoantigen Identification", Nature Biotechnology, vol. 37, No. 1, Jan. 2019, 17 pages.
Chaudhury, et al., "Pyrosetta: A Script-based Interface for Implementing Molecular Modeling Algorithms using Rosetta", Bioinformatics, vol. 26, No. 5, 2010, 689-691.
Gfeller, et al., "The Length Distribution and Multiple Specificity of Naturally Presented HLA-I Ligands", Journal of Immunology, vol. 201, Nov. 2018, 13 pages.
Jurtz, et al., "NetMHCpan-4.0: Improved Peptide-MHC Class I Interaction Predictions Integrating Eluted Ligand and Peptide Binding Affinity Data", Journal of Immunology, vol. 199, No. 9, Oct. 2017, 3360-3368.
Khan, et al., "pDOCK: A New Technique for Rapid and Accurate Docking of Peptide Ligands to Major Histocompatibility Complexes", Immunome Research, vol. 6, Sep. 26-28, 2010, 16 pages.
Liu, et al., "Subangstrom Accuracy in pHLA-I Modeling by Rosetta FlexPepDock Refinement Protocol", Journal of Chemical Information and Modeling, vol. 54, No. 8, Jul. 22, 2014, 2233-2242.
Di Marco, et al., "Unveiling the Peptide Motifs of HLA-C and HLA-G from Naturally Presented Peptides and Generation of Binding Prediction Matrices", Journal of Immunology, vol. 199, Sep. 13, 2017, 14 pages.
Nielsen, et al., "NetMHCpan-3.0; Improved Prediction of Binding to MHC Class I Molecules Integrating Information from Multiple Receptor and Peptide Length Datasets", Genome Medicine, vol. 8, No. 33, 2016, 9 pages.
O'Donnell, "MHCflurry: Open-Source Class I MHC Binding Affinity Prediction", Cell Systems, vol. 7, No. 1, Jul. 25, 2018, 8 pages.
O'Meara, et al., "A Combined Covalent-electrostatic Model of Hydrogen Bonding Improves Structure Prediction with Rosetta", Journal of Chemical Theory and Computation, vol. 11, No. 2, 2015, 29 pages.
Ott, et al., "An Immunogenic Personal Neoantigen Vaccine for Patients with Melanoma", Nature, vol. 547, No. 7662, Jul. 13, 2017, 22 pages.
Raveh, et al., "Rosetta FlexPepDock ab-initio: Simultaneous Folding, Docking and Refinement of Peptides onto Their Receptors", PLoS One, vol. 6, Issue 4, Apr. 2011, 10 pages.
Rigo, et al., "Docktope: A Web-based Tool for Automated pMHC-i Modelling", Scientific Reports, vol. 5, No. 18413, Dec. 17, 2015, 13 pages.
Riley, et al., "Structure Based Prediction of Neoantigen Immunogenicity", Frontiers in Immunology, vol. 10, Article 2047, Aug. 2019, 14 pages.
Sarkizova, et al., "A Large Peptidome Dataset Improves HLA Class I Epitope Prediction Across Most of The Human Population", Nature Biotechnology, vol. 38, No. 2, Feb. 2020, 34 pages.
Schuster, et al., "The Immunopeptidomic Landscape of Ovarian Carcinomas", Proceedings of the National Academy of Sciences of the United States of America, vol. 114, No. 46, Nov. 1, 2017, 10 pages.
Trellet, et al., "A Unified Conformational Selection and Induced Fit Approach to Protein-Peptide Docking", Plos One, vol. 8, Issue 3, Mar. 2013, 13 pages.

* cited by examiner

SEQ ID NOS: 1-29

| | | Peptide | MS (score) | netMHCPan 2.8 (nM) | netMHC 4.0 (nM) | nM (measured) |
|---|---|---|---|---|---|---|
| A*01:01 | 1 | FLWPEAFLY | 0.98 | 409.9 | 1235.4 | 1.3 |
| | 2 | YVPEHWEYY | 0.96 | 551.9 | 235.3 | 11.1 |
| | 3 | KLDLLEQEY | 0.91 | 466.7 | 105.6 | 70.6 |
| | 4 | TTDGYLLRL | 0.80 | 792.1 | 283.0 | 78.9 |
| | 5 | DTEFPNFKY | 0.66 | 344.0 | 123.8 | 80.8 |
| | 6 | AHDGKVLLW | 0.97 | 532.5 | 945.4 | 191.4 |
| B*51:01 | 1 | DGLLRVLTV | 0.87 | 11221.3 | 15547.6 | 0.2 |
| | 2 | DAPLNIRSI | 0.56 | 17149.1 | 13149.4 | 6.5 |
| | 3 | DGLRDLPSI | 0.96 | 12708.1 | 18806.8 | 12.6 |
| | 4 | DGYVKETI | 0.98 | 13414.5 | 13070.7 | 13.4 |
| | 5 | DGRLVINRV | 0.60 | 18358.8 | 26689.8 | 13.5 |
| | 6 | DAYPQRIKF | 0.63 | 12680.6 | 9538.1 | 31.0 |
| | 7 | IIYPTPKVV | 0.92 | 11654.4 | 4611.5 | 38.0 |
| | 8 | VPPLVPKVL | 0.79 | 11306.6 | 3799.2 | 56.3 |
| | 9 | TPESKIRFV | 0.86 | 9336.0 | 10184.8 | 84.8 |
| | 10 | VALLVGEKV | 0.93 | 9509.3 | 3785.9 | 143.6 |
| | 11 | YIIEREPLI | 0.84 | 16193.4 | 10011.8 | 1791.8 |
| A*29:02 | 1 | FYPELKLAY | 0.89 | 396.3 | 66.1 | 0.2 |
| | 2 | HFLDRHLVF | 0.89 | 825.4 | 235.6 | 1.6 |
| | 3 | YLPALKVEY | 0.82 | 113.3 | 80.9 | 2.6 |
| | 4 | LPLDIQIFY | 0.96 | 359.2 | 116.7 | 4.6 |
| | 5 | ALSDLALHF | 0.97 | 217.6 | 418.3 | 6.0 |
| | 6 | GLDDKLLHY | 0.90 | 157.5 | 211.0 | 21.3 |
| | 7 | GLPDLVAKY | 0.98 | 123.9 | 668.7 | 29.7 |
| B*54:01 | 1 | YPVYQPVGP | 0.67 | 8015.0 | 1237.9 | 1.7 |
| | 2 | YGFVNYVTA | 0.60 | 5011.5 | 391.5 | 6.0 |
| | 3 | FVEILIPVA | 0.80 | 6043.1 | 812.6 | 12.2 |
| | 4 | FPKETFEGP | 0.82 | 8478.9 | 882.8 | 16.4 |
| | 5 | SAPVNFISA | 0.83 | 5762.2 | 7614.0 | 16.6 |

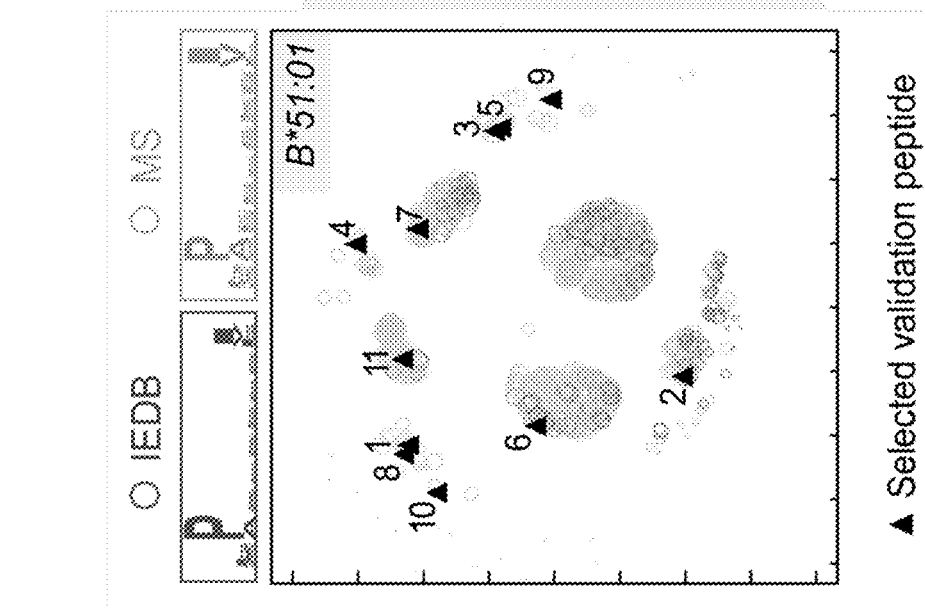

FIG. 8

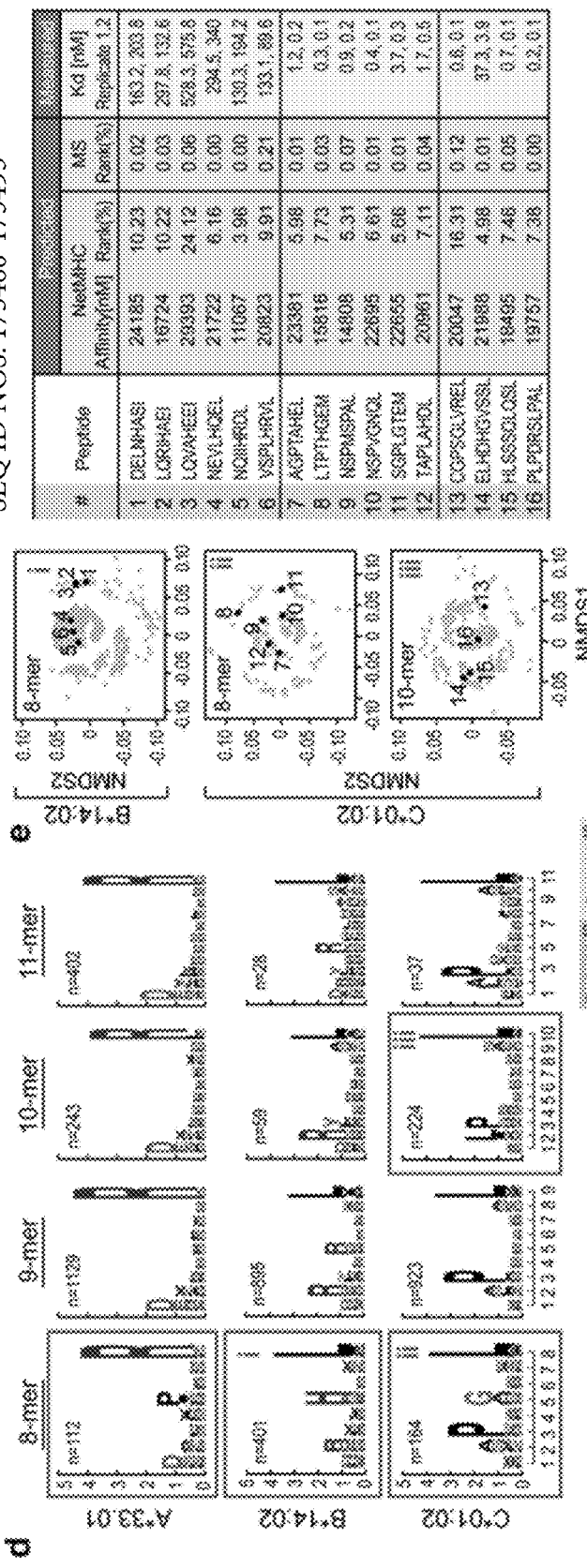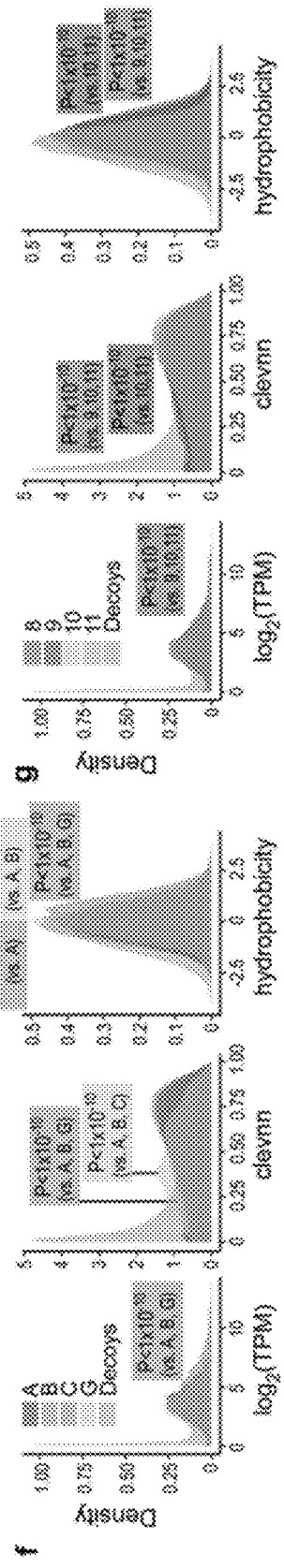
FIG. 28D-28G

METHOD FOR PREDICTING HLA-BINDING PEPTIDES USING PROTEIN STRUCTURAL FEATURES

CROSS-REFERENCE TO RELATED APPLICATIONS

This application claims the benefit of U.S. Provisional Application No. 62/909,752, filed Oct. 2, 2019. The entire contents of the above-identified application are hereby fully incorporated herein by reference.

STATEMENT REGARDING FEDERALLY SPONSORED RESEARCH

This invention was made with government support under Grant No.(s) CA155010, HL103532, CA216772, CA101942, CA210986, CA214125 and CA160034 awarded by the National Institutes of Health. The government has certain rights in the invention.

REFERENCE TO AN ELECTRONIC SEQUENCE LISTING

The contents of the electronic sequence listing (BROD_4940US_ST25.txt"; Size is 27.5 megabytes and it was created on Sep. 30, 2020) is herein incorporated by reference in its entirety.

TECHNICAL FIELD

The subject matter disclosed herein is generally directed to a method that predicts presentation of peptides on human leukocyte antigen (HLA) alleles using structural features.

BACKGROUND

Human leukocyte antigen (HLA) class I glycoproteins (HLA-A, -B, and -C) are expressed on the surface of almost all nucleated cells in the human body and are required for presentation of short peptides for detection by T cell receptors. The HLA genes are the most polymorphic genes across the human population; with more than 16,200 distinct HLA class I allele variants identified as of May 2019 (Lefranc, M.-P. et al. IMGT®, the international ImMunoGeneTics information System® 25 years on. Nucleic Acids Res. 43, D413-22 (2015); and Robinson, J. et al. The IPD and IMGT/HLA database: allele variant databases. Nucleic Acids Res. 43, D423-31 (2015)). Each HLA allele is estimated to bind and present ~1,000-10,000 unique peptides to T cells (Hunt D F, Henderson R A, Shabanowitz J, Sakaguchi K, Michel H, Sevilir N, Cox A L, Appella E, Engelhard V H. Characterization of peptides bound to the class I MHC molecule HLA-A2.1 by mass spectrometry. Science. 1992; 255:1261-1263; Rammensee H G, Friede T, Stevanoviic S. MHC ligands and peptide motifs: first listing. Immunogenetics. 1995; 41:178-228; Vita R, Overton J A, Greenbaum J A, Ponomarenko J, Clark J D, Cantrell J R, Wheeler D K, Gabbard J L, Hix D, Sette A, Peters B. The immune epitope database (IEDB) 3.0. Nucleic Acids Res. 2015; 43:D405-D412), less than 0.1% of the estimated 10 million potential 9-mer peptides from human protein-coding genes. Given such diversity in HLA binding, accurate prediction of whether a peptide is likely to bind to a specific HLA allele is highly challenging.

Rules for peptide binding to HLA molecules have been studied extensively for a subset of HLA alleles (Vita R, Overton J A, Greenbaum J A, Ponomarenko J, Clark J D, Cantrell J R, Wheeler D K, Gabbard J L, Hix D, Sette A, Peters B. The immune epitope database (IEDB) 3.0. Nucleic Acids Res. 2015; 43:D405-D412) and have been encoded in modern advanced neural-network-based algorithms (Hoof I, Peters B, Sidney J, Pedersen L E, Sette A, Lund O, Buus S, Nielsen M. NetMHCpan, a method for MHC class I binding prediction beyond humans. Immunogenetics. 2009; 61:1-13; Lundegaard C, Lamberth K, Harndahl M, Buus S, Lund O, Nielsen M. NetMHC-3.0: accurate web accessible predictions of human, mouse and monkey MHC class I affinities for peptides of length 8-11. Nucleic Acids Res. 2008; 36:W509-12). However, the algorithms in common use today (Trolle T, Metushi I G, Greenbaum J A, Kim Y, Sidney J, Lund O, Sette A, Peters B, Nielsen M. Automated benchmarking of peptide-MHC class I binding predictions. Bioinformatics. 2015; 31:2174-2181) are trained almost exclusively on measurements of biochemical affinity of synthetic peptides. This imparts several disadvantages. First, the throughput of these methods is limited because only a very small percentage of peptides are expected to bind, and therefore researchers must synthesize and experimentally assess potentially 1,000s of negative examples to identify 10s of strong-binding positive examples. Biased sampling can improve these odds but carries the risk of skewing the results or missing subdominant motifs. Meanwhile, other unintentional forms of bias, such as pre-existing notions of the length distribution or limitations on peptide synthesis and solubility, are difficult to avoid. Most importantly, these approaches do not necessarily consider the endogenous processing and transport of peptides prior to HLA binding. Mass spectrometry (MS)-based approaches yield a large and relatively unbiased portrait of the population of processed and presented peptides and should theoretically address most of these problems. However, historically liquid chromatography-tandem mass spectrometry (LC-MS/MS) methods have required large cellular input, which limits throughput, and the multi-allelic nature of the data complicates productive motif learning.

Citation or identification of any document in this application is not an admission that such a document is available as prior art to the present invention.

SUMMARY

In one aspect, the present invention provides for a method of predicting peptides capable of binding to an HLA allele comprising: identifying structural features indicative of occupancy of one or more candidate peptides on the binding pocket of the HLA allele; and predicting the candidate peptides that bind to the HLA molecule using a machine learning algorithm model trained using structural features extracted from one or more output models simulating occupancy of one or more binding peptides and one or more non-binding peptides on the HLA binding pocket in a crystal structure of the HLA allele or the crystal structure of a similar HLA allele. In certain embodiments, the structural features are identified by: providing a crystal structure of the HLA allele or the crystal structure of a similar HLA allele; generating one or more output models simulating occupancy of the one or more candidate peptides on the HLA binding pocket in the crystal structure; and extracting structural features from the output models. In certain embodiments, the structural features are identified by a second machine learning algorithm model that infers occupancy of the one or more candidate peptides on the HLA binding pocket, and wherein the second machine learning algorithm model is trained using one or more output models simulating occupancy of one or more binding peptides and one or more non-binding peptides on the HLA binding pocket in a crystal structure of the HLA allele or the crystal structure of a similar HLA allele. In certain embodiments, the method further comprises: providing a crystal structure of the HLA allele or the crystal structure of a similar HLA allele; simulating occupancy of one or more binding peptides and one or more non-binding peptides on the HLA binding pocket in the crystal structure to generate one or more output models; extracting structural features from the output models; and training the machine learning algorithm model using the extracted features. In certain embodiments, at least 100 to 300 output models are generated for each peptide.

In certain embodiments, the machine learning algorithm model is trained with one or more peptides bound to HLA molecules in cell lines monoallelic for the HLA allele. In certain embodiments, the one or more binding peptides are selected from the group consisting of: A*01:01 (SEQ ID Nos: 44-1120); A*02:01 (SEQ ID Nos: 1121-4202); A*02:02 (SEQ ID Nos: 4203-7373); A*02:03 (SEQ ID Nos: 7374-9953); A*02:04 (SEQ ID Nos: 9954-11940); A*02:05 (SEQ ID Nos: 11941-14981); A*02:06 (SEQ ID Nos: 14982-17191); A*02:07 (SEQ ID Nos: 17192-20710); A*02:11 (SEQ ID Nos: 20711-22696); A*03:01 (SEQ ID Nos: 22697-24233); A*11:01 (SEQ ID Nos: 24234-27505); A*11:02 (SEQ ID Nos: 27506-29812); A*23:01 (SEQ ID Nos: 29813-32133); A*24:02 (SEQ ID Nos: 32134-34347); A*24:07 (SEQ ID Nos: 34348-35681); A*25:01 (SEQ ID Nos: 35682-36682); A*26:01 (SEQ ID Nos: 36683-37957); A*29:02 (SEQ ID Nos: 37958-38921); A*30:01 (SEQ ID Nos: 38922-40029); A*30:02 (SEQ ID Nos: 40030-42114); A*31:01 (SEQ ID Nos: 42115-42919); A*32:01 (SEQ ID Nos: 42920-44874); A*33:01 (SEQ ID Nos: 44875-46761); A*33:03 (SEQ ID Nos: 46762-49053); A*34:01 (SEQ ID Nos: 49054-50948); A*34:02 (SEQ ID Nos: 50949-53677); A*36:01 (SEQ ID Nos: 53678-55165); A*66:01 (SEQ ID Nos: 55166-56901); A*68:01 (SEQ ID Nos: 56902-58374); A*68:02 (SEQ ID Nos: 58375-59804); A*74:01 (SEQ ID Nos: 59805-61821); B*07:02 (SEQ ID Nos: 61822-63473); B*07:04 (SEQ ID Nos: 63474-64885); B*08:01 (SEQ ID Nos: 64886-65609); B*13:01 (SEQ ID Nos: 65610-69419); B*13:02 (SEQ ID Nos: 69420-71587); B*14:02 (SEQ ID Nos: 71588-72970); B*15:01 (SEQ ID Nos: 72971-76378); B*15:02 (SEQ ID Nos: 76379-77762); B*15:03 (SEQ ID Nos: 77763-80458); B*15:10 (SEQ ID Nos: 80459-81940); B*15:17 (SEQ ID Nos: 81941-83632); B*18:01 (SEQ ID Nos: 83633-85593); B*27:05 (SEQ ID Nos: 85594-87076); B*35:01 (SEQ ID Nos: 87077-87772); B*35:03 (SEQ ID Nos: 87773-89157); B*35:07 (SEQ ID Nos: 89158-90977); B*37:01 (SEQ ID Nos: 90978-92452); B*38:01 (SEQ ID Nos: 92453-94858); B*38:02 (SEQ ID Nos: 94859-97742); B*40:01 (SEQ ID Nos: 97743-100731); B*40:02 (SEQ ID Nos: 100732-104409); B*40:06 (SEQ ID Nos: 104410-106653); B*42:01 (SEQ ID Nos: 106612-019885); B*44:02 (SEQ ID Nos: 109886-110903); B*44:03 (SEQ ID Nos: 110904-111749); B*45:01 (SEQ ID Nos: 111750-113153); B*46:01 (SEQ ID Nos: 113154-114113); B*49:01 (SEQ ID Nos: 114114-117833); B*50:01 (SEQ ID Nos: 117834-118468); B*51:01 (SEQ ID Nos: 118469-119991); B*52:01 (SEQ ID Nos: 119992-121525); B*53:01 (SEQ ID Nos: 121526-123560); 54:01 (SEQ ID Nos: 123561-124684); B*55:01 (SEQ ID Nos: 124685-126136); B*55:02 (SEQ ID Nos: 126137-127557); B*56:01 (SEQ ID Nos: 127558-129239); B*57:01 (SEQ ID Nos: 129240-130274); B*57:03 (SEQ ID Nos: 130275-132636); B*58:01 (SEQ ID Nos: 132637-134577); B*58:02 (SEQ ID Nos: 134578-135530); C*01:02 (SEQ ID Nos: 135531-136878); C*02:02 (SEQ ID Nos: 136879-137802); C*03:02 (SEQ ID Nos: 137803-138984); C*03:03 (SEQ ID Nos: 138985-141074); C*03:04 (SEQ ID Nos: 141075-143394); C*04:01 (SEQ ID Nos: 143395-145236); C*04:03 (SEQ ID Nos: 145237-146269); C*05:01 (SEQ ID Nos: 146270-147708); C*06:02 (SEQ ID Nos: 147709-149028); C*07:01 (SEQ ID Nos: 149029-149822); C*07:02 (SEQ ID Nos: 149823-150900); C*07:04 (SEQ ID Nos: 150901-151615); C*08:01 (SEQ ID Nos: 151616-153388); C*08:02 (SEQ ID Nos: 153389-156499); C*12:02 (SEQ ID Nos: 156500-157889); C*12:03 (SEQ ID Nos: 157890-160043); C*14:02 (SEQ ID Nos: 160044-161408); C*14:03 (SEQ ID Nos: 161409-164186); C*15:02 (SEQ ID Nos: 164187-167475); C*16:01 (SEQ ID Nos: 167476-170317); C*17:01 (SEQ ID Nos: 170318-171281); G*01:01 (SEQ ID Nos: 171282-172073); G*01:03 (SEQ ID Nos: 172074-172742) and G*01:04 (SEQ ID Nos: 172743-173477).

In certain embodiments, simulating occupancy is performed using one or more protein-peptide docking models and/or molecular dynamics simulation. In certain embodiments, the structural features are selected from the group consisting of amino acid residues capable of fitting a model of peptide occupancy on the binding pocket of HLA alleles, hydrophobicity, exposed hydrophobic surface, the size and position of the amino acid side chains, energies of attraction, energies of repulsion, energies of solvation, energies of side chain and backbone hydrogen bonds, energies of side chain and backbone conformations, and any energy terms listed in table 1. In certain embodiments, the machine learning algorithm model further comprises training with non-structural features of the one or more binding peptides and one or more non-binding peptides, whereby the model combines structural and non-structural features. In certain embodiments, the non-structural features comprise peptide sequence, amino acid physical properties, peptide physical properties, expression level of the source protein of a peptide, protein stability, protein translation rate, protein degradation rate, translational efficiencies from ribosomal profiling, protein cleavability, protein localization, motifs of host proteins that facilitate TAP transport, whether host protein is subject to autophagy, motifs that favor ribosomal stalling, protein features that favor nonsense-mediated mRNA decay (NMD), peptide cleavability, dummy peptide encoding, PCA peptide encoding, and/or Kidera peptide-level features. In certain embodiments, the expression level of the source protein of a peptide comprises the protein levels and/or transcripts of the source protein. In certain embodiments, protein features that favor nonsense-mediated mRNA decay (NMD) comprise a long 3' UTR and stop codon >50 nt upstream of last exon-exon junction. In certain embodiments, motifs that favor ribosomal stalling comprise polyproline stretches. In certain embodiments, the machine learning algorithm model comprises a neural network model. In certain embodiments, the neural network model comprises a single hidden layer neural network model and/or convolutional neural network model. In certain embodiments, the machine learning algorithm model comprises one or more peptide encoding schemes. In certain embodiments, the one or more peptide encoding schemes comprise one-hot/dummy encoding, blosum62 encoding, or peptide: MHC binding energy covariance (PMBEC) encoding.

In certain embodiments, the candidate peptide is predicted to bind to one or more HLA alleles. In certain embodiments, the HLA binding peptides are 8, 9, 10, or 11 amino acids in length. In certain embodiments, the HLA binding peptides are any combination of peptides selected from the group consisting of 8, 9, 10, and 11 amino acids in length. In certain embodiments, the accuracy of prediction is evaluated using metrics comprising area under the curve for the receiver operating characteristic curve and positive predictive value. In certain embodiments, the HLA-allele is an HLA-A allele, HLA-B allele, HLA-C allele, or HLA-G allele.

In certain embodiments, the candidate peptides are selected from a subject and the HLA allele is expressed in the subject. In certain embodiments, the subject is suffering from a disease or condition. In certain embodiments, the disease or condition is selected from the group consisting of cancer, an infection, an autoimmune disease, and a transplant. In certain embodiments, the peptides are identified by nucleic acid sequencing of a sample obtained from the subject, wherein the sample comprises tumor cells, infected cells, cells targeted by the autoimmune response, or cells to be transplanted. In certain embodiments, the disease is cancer and the peptides are neoantigens and/or novel unannotated open reading frames (nuORFs).

In another aspect, the present invention provides for an immunogenic composition for use in a method of inducing a tumor specific or infection specific immune response or inducing immune tolerance, said immunogenic composition comprising one or more peptides identified with the method of any embodiment herein. In certain embodiments, the immunogenic composition comprises autologous dendritic cells or antigen presenting cells that have been pulsed with the one or more peptides. In certain embodiments, the immunogenic composition comprises at least one vector capable of expressing the one or more peptides. In certain embodiments, the immunogenic composition comprises at least one mRNA capable of expressing the one or more peptides.

In another aspect, the present invention provides for an immunogenic composition for use in a method of inducing a tumor specific or infection specific immune response or inducing immune tolerance, said immunogenic composition comprising two or more peptides identified with the method of any embodiment herein and a pharmaceutically acceptable carrier.

In another aspect, the present invention provides for an immunogenic composition for use in a method of inducing a tumor specific or infection specific immune response or inducing immune tolerance, comprising autologous dendritic cells or antigen presenting cells that have been pulsed with the two or more peptides identified with the method of any embodiment herein.

The immunogenic composition according to any embodiment herein may be for use in a method of inducing a tumor or infection specific immune response or inducing immune tolerance, comprising at least one vector capable of expressing two or more peptides identified with the method of any embodiment herein. In certain embodiments, the vector is a viral vector.

In another aspect, the present invention provides for an immune cell specific for a peptide identified with the method of any embodiment herein. In certain embodiments, the immune cell is a CD8+ T cell. In certain embodiments, the immune cell expresses a chimeric antigen receptor (CAR) or exogenous T cell receptor (TCR) specific to the peptide. In certain embodiments, the immune cell is a dendritic cell loaded with the peptide.

These and other aspects, objects, features, and advantages of the example embodiments will become apparent to those having ordinary skill in the art upon consideration of the following detailed description of example embodiments.

BRIEF DESCRIPTION OF THE DRAWINGS

An understanding of the features and advantages of the present invention will be obtained by reference to the following detailed description that sets forth illustrative embodiments, in which the principles of the invention may be utilized, and the accompanying drawings of which:

FIG. 6A) Single HLA Class I allele expression on B721.221 cells. No inference of peptide binding to allele based on preexisting predictors. Unambiguous peptide-to-allele assignment. Enables creation of new predictors and comprehensive allele-specific and pan-allele analyses of binding preferences. FIG. 6B) Allele expression is confirmed by FACS. Sample preparation for HLA-peptides includes sample preparation (50 Mio cells per IP, 3 IPs pooled for 2 injections, acid elution and desalt), LC-MS/MS (QE+, QE-HF or Lumos, Lumos: include 1+ precursor fragmentation, 2 injections/replicate) and data analysis: spectrum mill (No enzyme specificity search, Improved scoring for HLA-derived peptides, FDR filtering to 1%).

FIG. 8—Applicants systematically selected MS-enriched binding motifs (left) and validated their binding strength in vitro (right) (SEQ ID NO:1-29). Of 33 peptides selected for validation across 5 alleles, 32 were confirmed as strong binders showing the feasibility and benefit of an endogenous unbiased profiling approach. Peptides that represent novel binding motifs were validated as strong binders with tradition affinity measurement assays.

FIG. 26A) Schematic of the experimental design: HLA-null B721.221 cells transfected to express a single HLA allele (31 HLA-A, 40 HLA-B, 21 HLA-C and 3 HLA-G) were subjected to HLA class I-immunoprecipitation with W6/32 antibody from 50-300 million cells per allele followed by identification of eluted peptides by LC-MS/MS, in order to generate endogenous peptide binding data used to characterize allele-specific or pan-allele binding preferences and train neural network predictors of antigen processing and presentation. FIG. 26B) Surface expression of each transfected HLA-alleles was confirmed by flow cytometric detection against parental cells transfected with an empty vector (MFI: Mean fluorescence intensity; profiles of all lines in FIG. 32A). FIG. 26C) Overlap of human genes represented by at least two HLA-associated peptides (pink), detected in RNA sequencing (TPM>2, light grey) or identified in deep proteome analysis (>2 unique peptides, dark grey) of the B721.221 mono-allelic cells lines. FIG. 26D) Top: Numbers of HLA-bound peptides identified per allele by MS-based profiling (circles; filled: newly generated data; open: previously reported (Abelin et al. 2017); or recorded in IEDB (diamonds). Bottom: Heatmaps of relative median population frequencies per allele across racial groups (AFA: African American, API: Asian or Pacific Islander, HIS: Hispanic, CAU: Caucasian) in the US population (Gragert et al. 2013) and worldwide.

FIG. 27A) Pair-wise correlations between the 95 HLA-A, -B, —C, and -G binding motifs, each represented as a vector of amino acid frequencies (left), and pair-wise distances between the 95 HLA binding pockets, each represented by the properties of amino acids that are in contact with the peptide (right). Examples of groups of alleles with high similarity (middle) and the corresponding binding motif of each group (bottom). FIG. 27B) Average correlations of A to A (i.e. each dot represents an HLA-A allele and the y-axis is the mean of the correlations between that allele and all other HLA-A alleles), B to B, C to C and G to G alleles show that C and G alleles are more similar to each other than A and B alleles in both peptide motif (left) and protein (right) space. FIG. 27C) Number of alleles sharing a submotif colored according to HLA locus (A: purple, B: blue, C: orange, G: yellow). FIG. 27D) 2D-visualization of submotifs identified across the 95 alleles (middle), colored according to HLA locus (A:purple; B:blue; C:orange; G:yellow) and scaled in size according to the number of underlying peptides making up the sub-cluster. The collection of all allele-specific submotifs was clustered to identify groups of alleles that share a submotif (shown in FIG. 34B). Four examples of clusters of submotifs are highlighted with dashed circles, along with the respective motifs they represent and the allele-specific clusters that contribute to each shared motif.

FIGS. 28A-28G—Mono-allelic data uncovers lengths-specific HLA-binding preferences. FIG. 28A) Frequencies of peptide lengths observed across alleles (8: pink, 9: violet, 10: green, 11: cyan). All but two HLA-B alleles preferentially present 9-mers. HLA-A alleles bind longer peptides more frequently than B and C alleles, while B and C alleles have a higher propensity for short peptides. FIG. 28B) 8-, 10-, and 11-mer binding motifs were transformed to pseudo 9-mer motifs by adding (8-mers: positions 4 or 5) or removing (10-mers: positions 5 or 6; 11-mers positions 5, 6, or 7) middle residues and selecting the pseudo-9-mer motif which was most similar to the corresponding 9-mer motifs. The maximum difference amongst peptide positions between the 8-, 10-, and 11-mer pseudo 9-mer motifs and the corresponding 9-mer motif in amino acid frequency (x-axis) and entropy (y-axis) are shown. Circle size reflects number of peptides, dotted lines indicate cutoff values. Circles in color and label denote alleles with >100 peptides with change in amino acid frequency or entropy greater than the selected cutoffs. FIG. 28C) Percent motif changes within each HLA type colored by length. FIG. 28D) Length dependent logo plots for A*33:01, B*14:02 and C*01:02; red boxes outline the changing motifs. FIG. 28E) Experimental validation of selected peptides (indicated with black dots on the NMDS plots) by in vitro binding assays compared to their predicted scores by NetMHC and MS models (SEQ ID NO: 173480-173495). FIG. 28F)-FIG. 28G) Expression, predicted cleavability and hydrophobicity stratified by HLA loci and peptide length.

FIG. 29A) Three types of primary tumor cell lines (melanoma [MEL], glioblastoma [GBM] and clear cell renal cell carcinoma [ccRCC]) used to identify HLA-associated peptidomes. FIG. 29B) Changes in relative protein abundance of proteasomal subunits and IFNγ inducible genes in patient-derived GBM cells with or without IFNγ-treatment based on MS proteome analysis. FIG. 29C) Schematic of proteasomal cleavage signature analysis. FIG. 29D) Peptide processing signatures of HLA ligands presented by primary tumor and cancer cell lines at baseline (top) and following IFN7 treatment (bottom), showing overrepresented (red) or underrepresented (blue) amino acid residues upstream and downstream of the HLA peptide. The number in each cell denotes percent change over a background decoy set; color intensity indicates significance (see key). FIG. 29E) Peptide processing signatures of HLA peptides in normal tissue (primary skin and fibroblast cells). FIG. 29F) Heatmap of Spearman correlations between the processing preferences in untreated and IFNγ-treated samples at upstream and downstream positions. Signatures for peptides from the IFNγ treated cells correlate well with peptides eluted from untreated cells suggesting minimal to no difference between the two patterns.

FIG. 30A) Contribution of predictor variables (peptide binding, transcript expression, cleavability, and gene presentation bias) to positive predictive value (PPV) as the most informative variable is added on at a time. FIG. 30B) Schematic of the neural networks used to generate allele-length-specific and pan predictive models. FIG. 30C) Comparison of PPVs across each of the 95 HLA alleles (grey lines) by testing novel length-specific and pan-allele MS based-models on internal data against NetMHC and MHCflurry. FIG. 30D) Summary of PPVs for state-of-the-art and MS-based models resulting in a 2-fold improvement for PPV at top 0.1% of observed peptides, or 7-fold for PPV at 40% recall of positives. FIG. 30E) Prediction of peptides presented by C-alleles (Di Marco et al. 2017) using NetMHC, MHCflurry and MS-based models. FIG. 30F) Correlation of actual PPV vs predicted PPV using a linear model, with variables in the linear model and their respective significance tabulated. FIG. 30G) pie chart.

FIG. 31A) schematic of evaluation: generation of the dataset of observed peptides displayed on primary tumor specimens, prediction of epitopes based on unique HLA identities of each set of cells, and comparison of predicted to observed peptides across 7 prediction models in order to determine performance and accuracy. FIG. 31B) MS-based predictor ranks MS detected peptides better than NetMHCpan and MHCflurry. Internal data on 12 patients (5 Mel, 3 GBM, 3 CLL, 1 OV), and external data(Bassani-Sternberg et al. 2016; Schuster et al. 2017). FIG. 31C) Using the best scoring peptide-allele combination, peptides can be reassigned to the respective allele. Allele contribution to peptide presentation is tumor and individual dependent and includes A, -B, and -C alleles in endogenous datasets. FIG. 31D) Fraction of peptides contributing per allele type+/− IFNγ. Peptides presentation on HLA-B increased with IFNγ stimulation.

FIG. 32N) Correlation analysis of mean aliphatic index of peptides per allele and number of identified peptides does not indicate a bias during ionization towards peptides with charged residues and less aliphatic residues.

FIG. 33B) 2D visualization of all submotifs as in FIG. 27D but colored by identified cluster. FIG. 33C)

Clustering of submotifs colored by HLA-type (middle). For circled clusters, the respective motif and the allele-specific clusters contributing to the shared motif are highlighted.

Figure 34A:
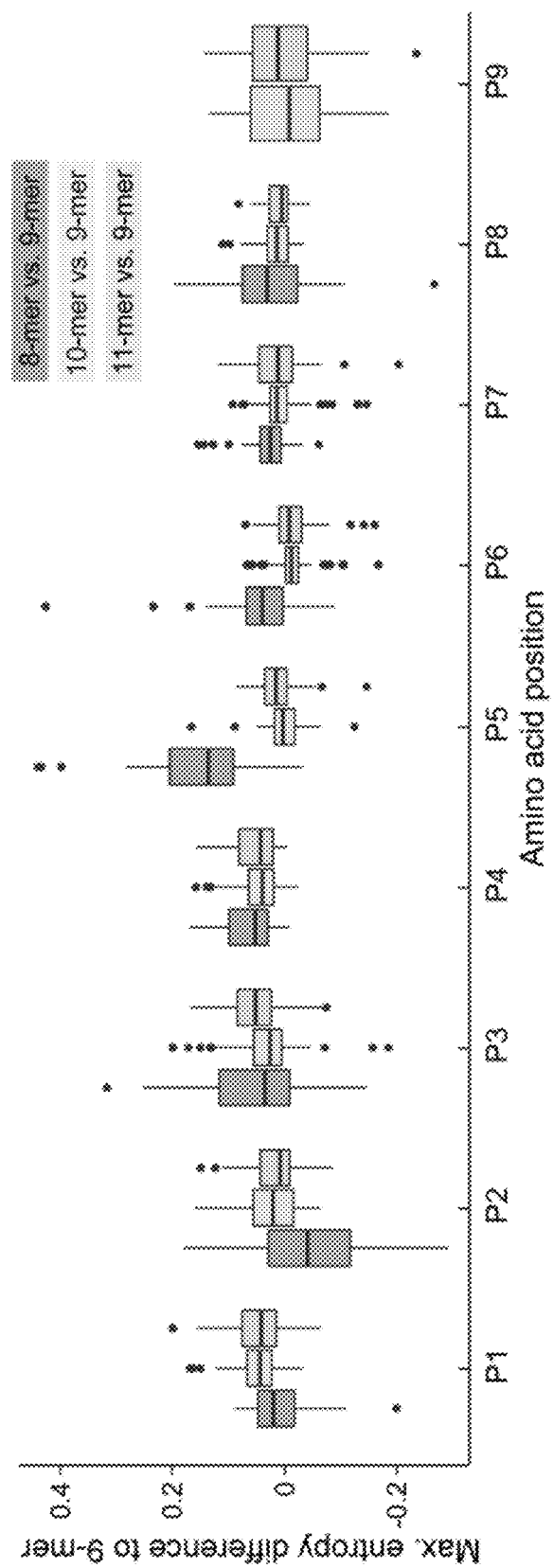
Figure 34B:
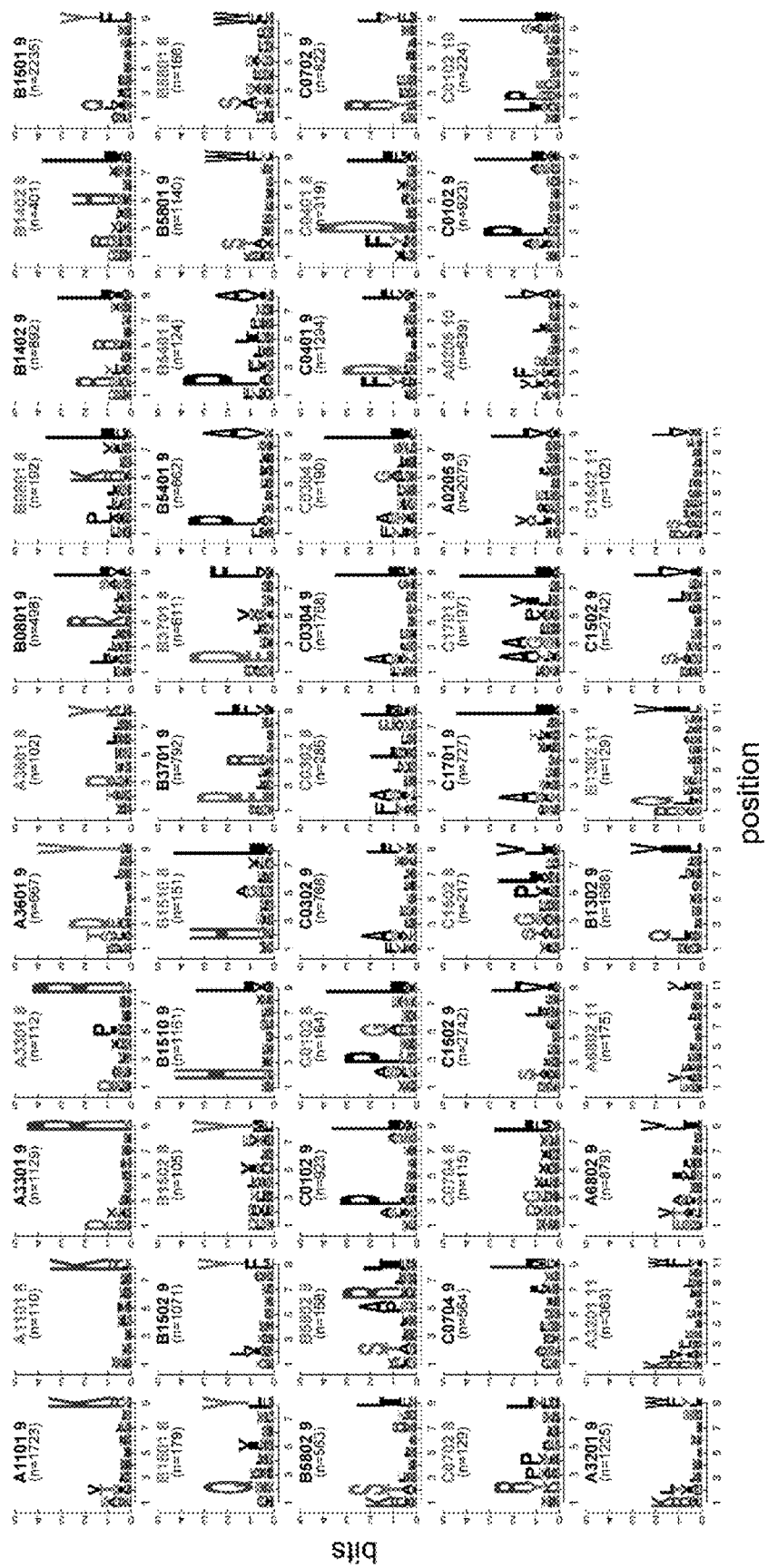
Figure 34C:
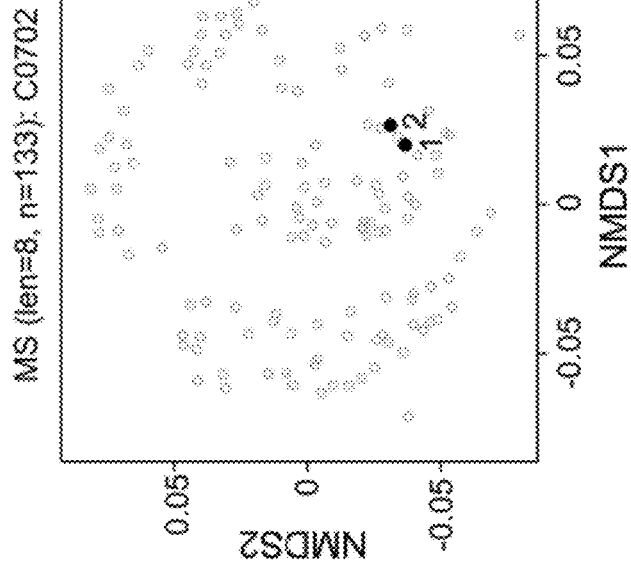

FIGS. 34A-34C—FIG. 34A) Amino acid entropy difference for each peptide position in 8-, 10-, 11-mers compared to 9-mers. 8-mers show significantly higher entropy at P5 indicating that this position is part of an 8-mer specific motif. FIG. 34B) Motif logo plots of alleles that differ from their corresponding 9-mer. FIG. 34C) Experimental validation of selected 8-mer peptides for C*07:02 (indicated with black dots on the NMDS plots) by in vitro binding assays compared to their predicted scores by NetMHC and MS models (SEQ ID NOS: 173496-173497).

Figure 35A:
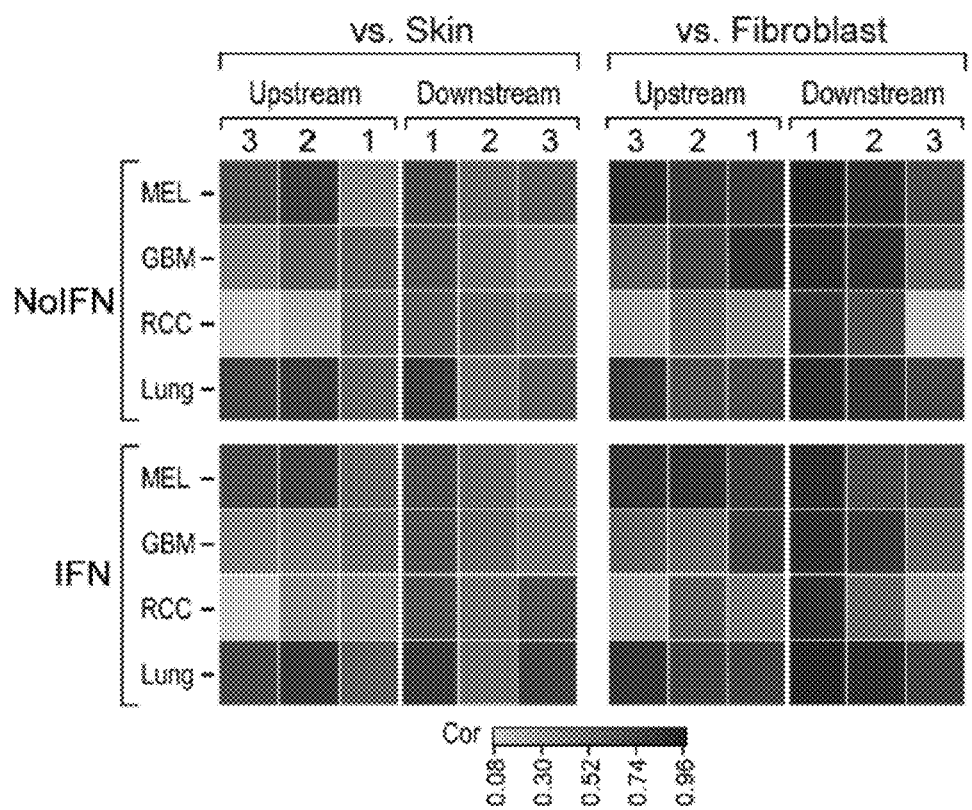
Figure 35B:
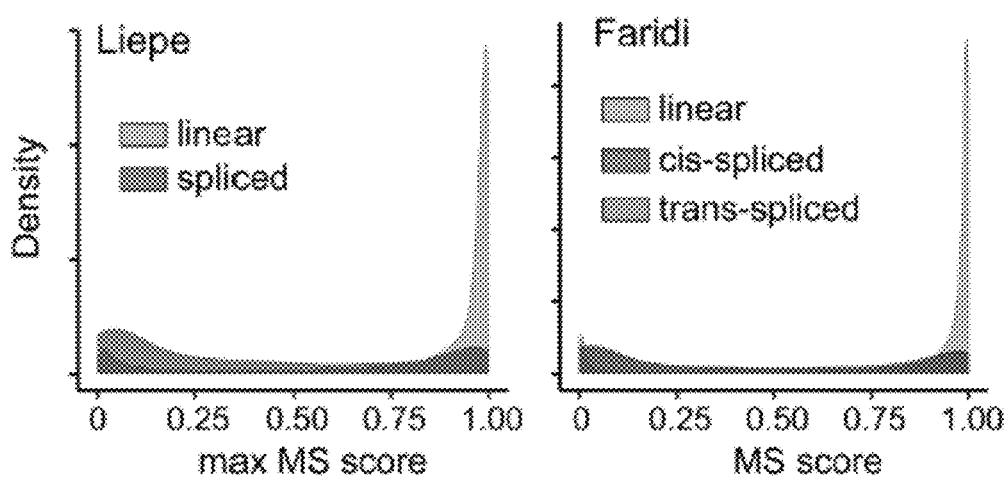

FIGS. 35A-35B—FIG. 35A) Heatmap of correlations between processing differences in evaluated tumor lineages (MEL, GBM, ccRCC, lung) compared to healthy tissues (skin, fibroblast) at upstream and downstream positions for untreated and IFNγ stimulated tumor samples. FIG. 35B) Potential proteasomal spliced peptides (data from Liepe et al. and Faridi et al. (Liepe et al. 2016; Faridi et al. 2018)) are distributed over a wide range of predicted binding score whereas linear peptides are predicted with very high affinity.

Figures 36A, 36B:
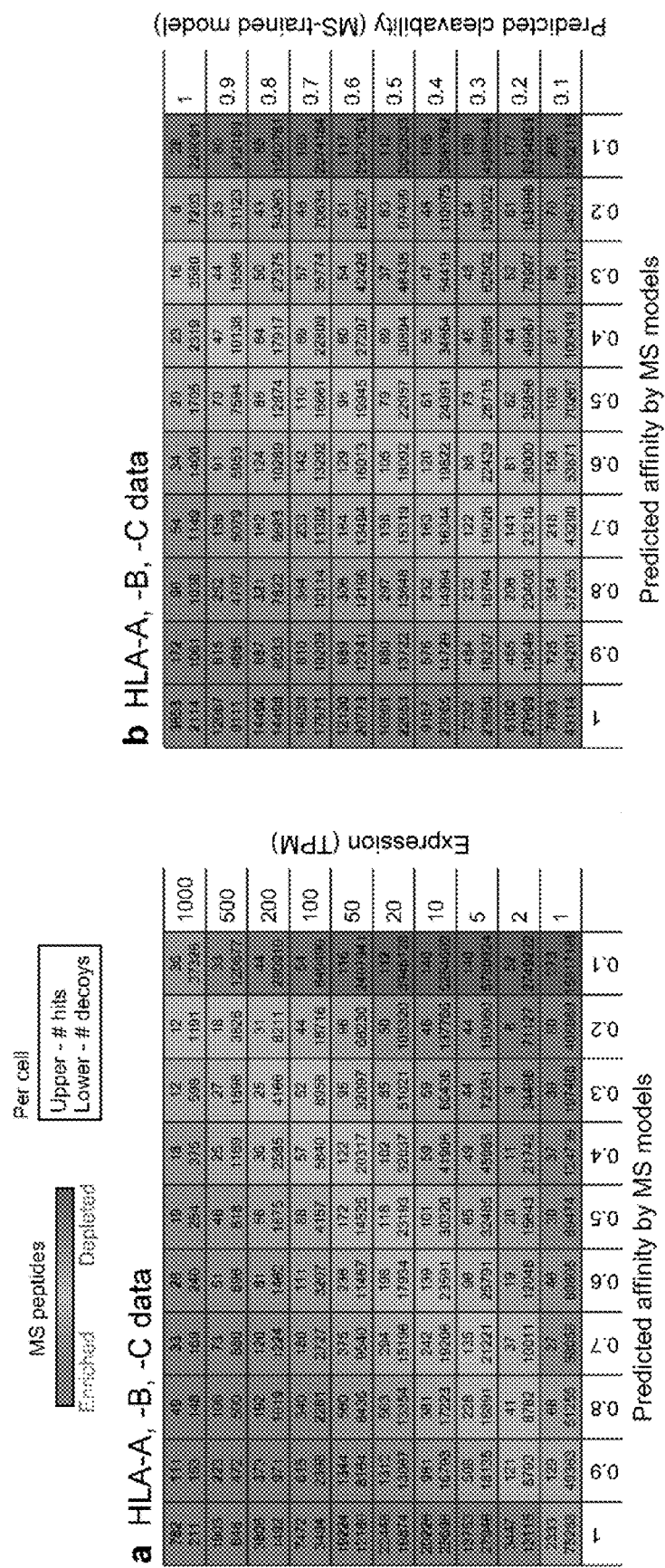

FIGS. 36A-36B—Gene expression and cleavability influence HLA presentation. Hits and decoys are binned according to (FIG. 36A) source transcript expression (per RNA-seq; y axis) or (FIG. 36B) predicted cleavability and predicted affinity (x-axis) for each allele. Per bin, hits (top) and decoys (bottom) counts are reported. Each cell is colored according to the hit:decoy ratio (red=enriched for hits; blue=depleted of hits).

Figures 37A, 37B:
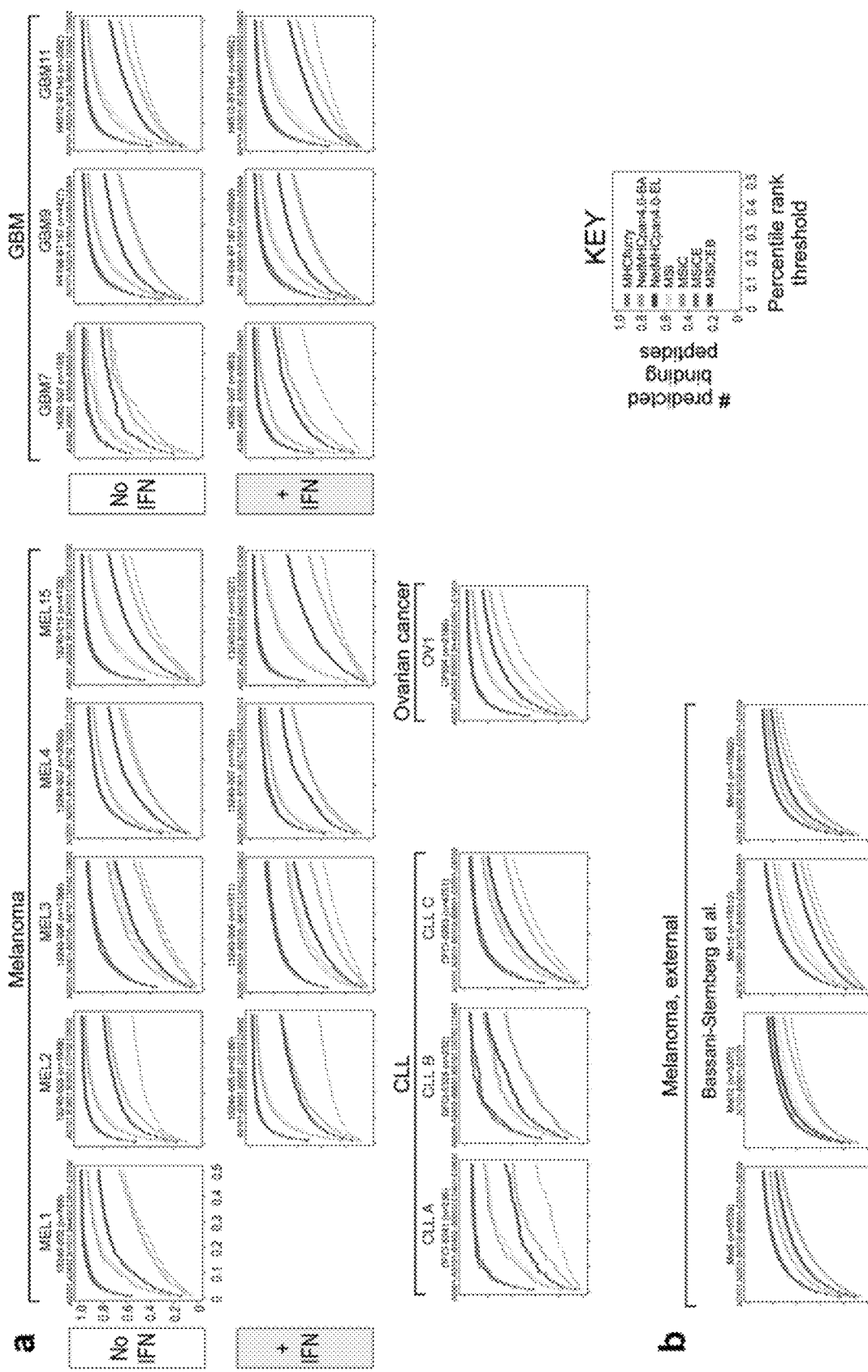
Figure 37C:
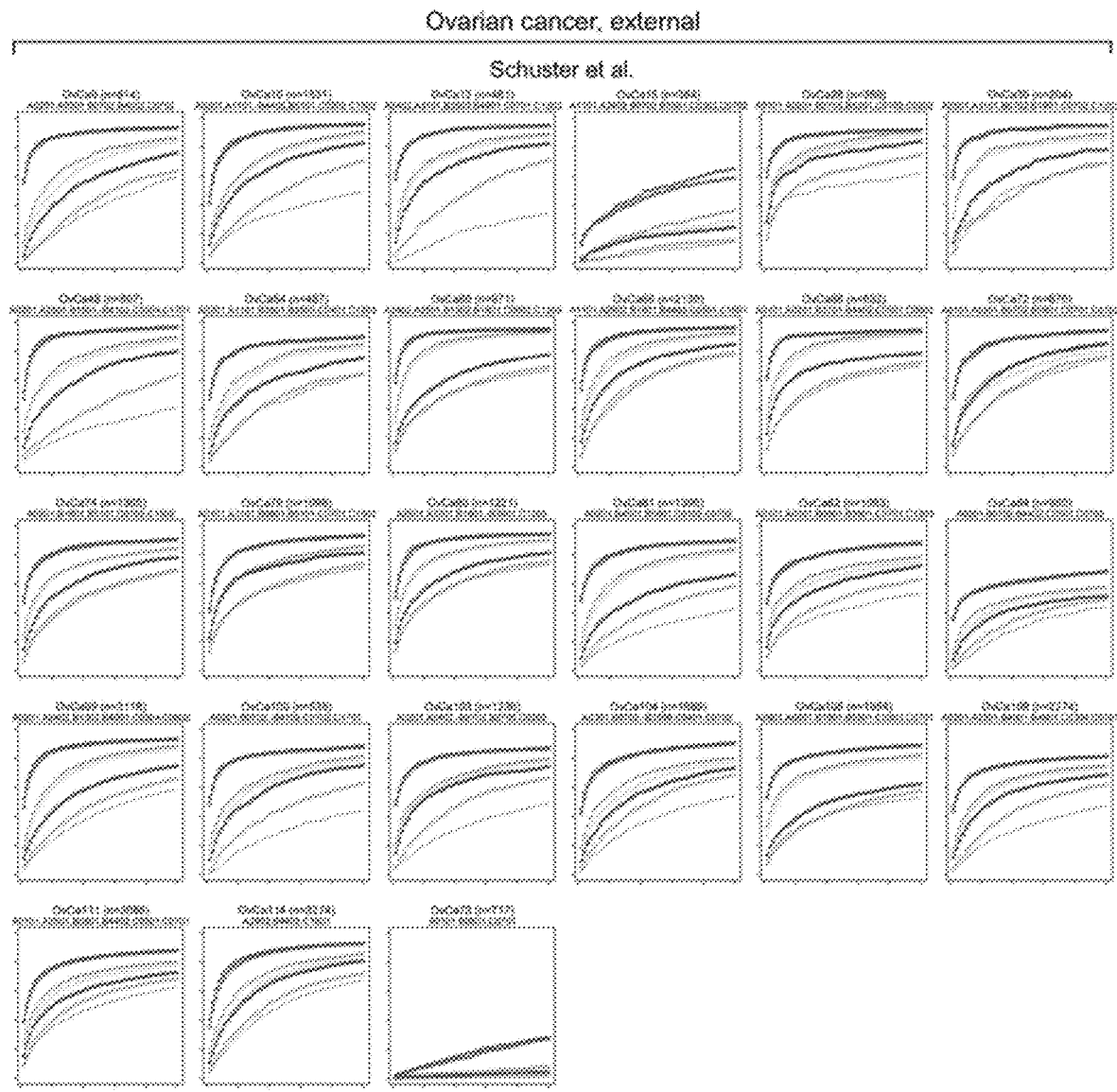

FIGS. 37A-37C—Evaluation of MS informed models compared to other prediction tools MHCflurry, NetMHCpan4.0-BA, NetMHCpan4.0-EL for patient derived tumor samples FIG. 37A) on internally generated data, FIG. 37B) and FIG. 37C) on external datasets (Bassani-Sternberg et al. 2016; Schuster et al. 2017). Predictions were made with the allele-and-length-specific models for covered alleles (n=50), while missing alleles (n=7; indicated by '-' in front of the allele name, e.g. -B4701) were scored by the pan-allele-pan-length predictors. Performance was evaluated by number of predicted binding peptides at percentile rank thresholds.

Figure 38:
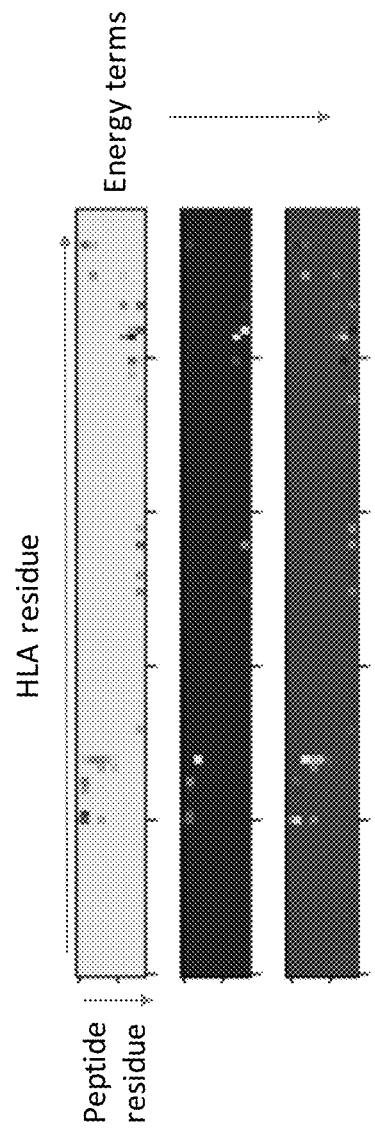

FIG. 38.—A schematic to depict the protein-peptide docking working flow. The input structure is prepacked to avoid the interference of side chains to the interaction between the peptide and the HLA molecule.

Figure 39:
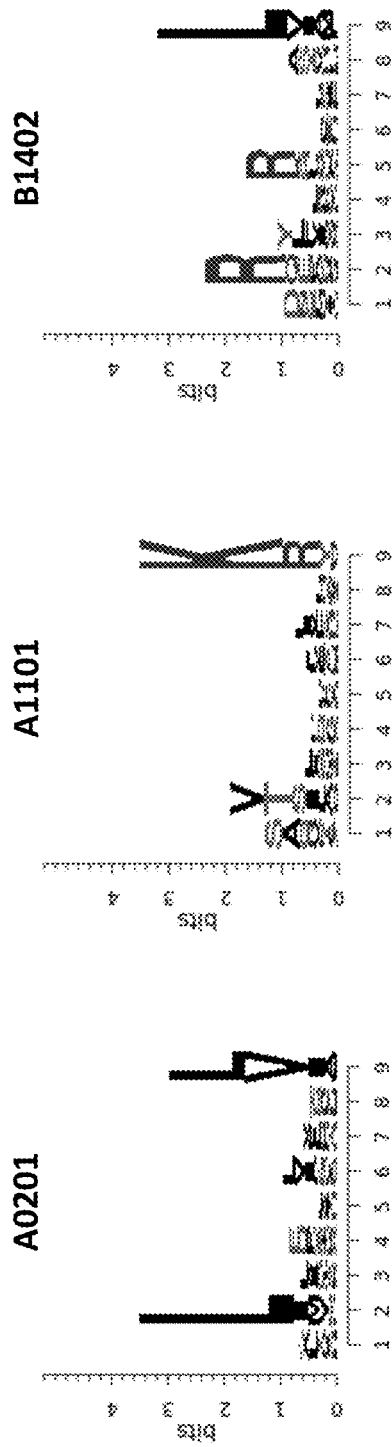

FIG. 39.—As a proof a concept, training dataset and test datasets are used for evaluating the candidate peptides capable of binding to HLA allele A02:01, A11:01, and B14:02.

Figure 40A:
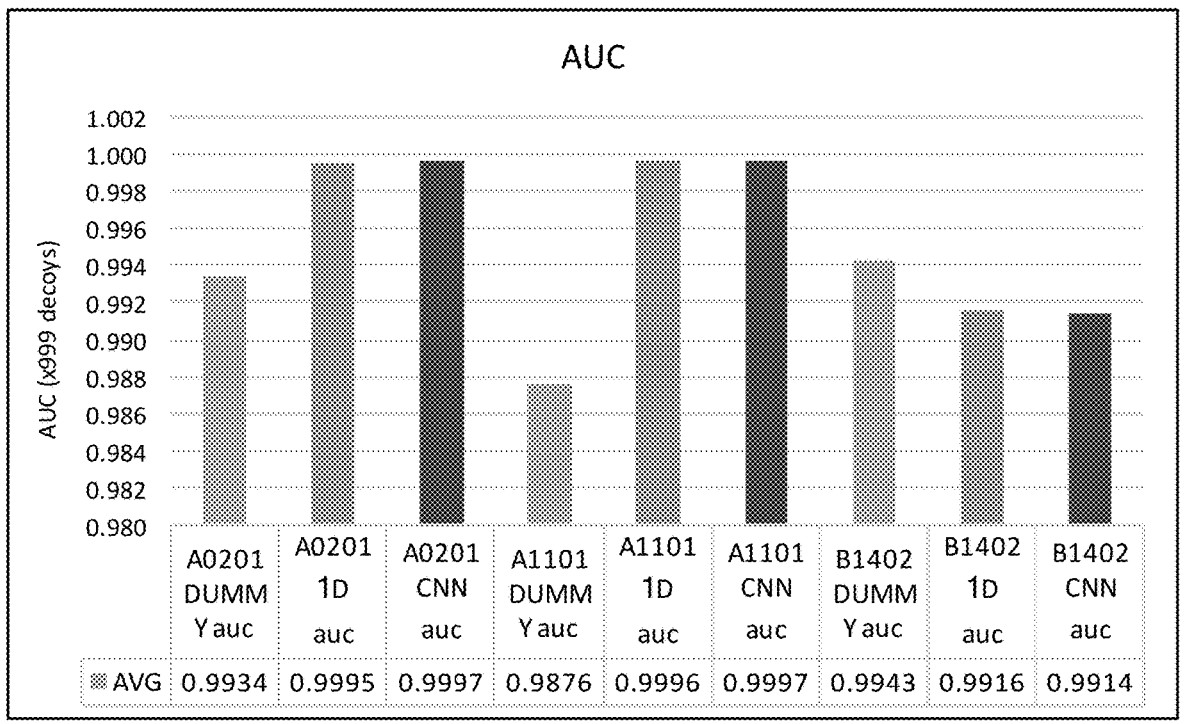
Figure 40B:
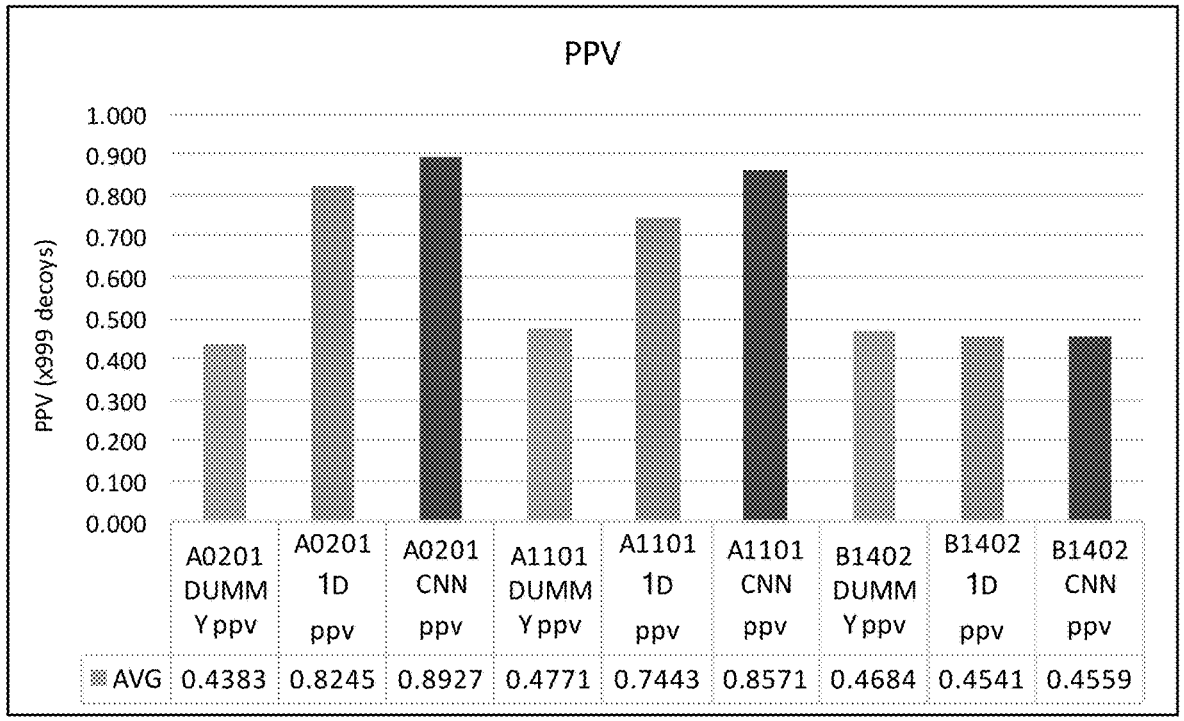

FIGS. 40A-40B.—Three models (DUMMY, 1D, CNN) are used for predicting the binding of peptides to HLA molecules. The AUC (FIG. 40A) and PPV (FIG. 40B) values are shown for each method on each HLA allele.

The figures herein are for illustrative purposes only and are not necessarily drawn to scale.

DETAILED DESCRIPTION OF THE EXAMPLE EMBODIMENTS

General Definitions

Unless defined otherwise, technical and scientific terms used herein have the same meaning as commonly understood by one of ordinary skill in the art to which this disclosure pertains. Definitions of common terms and techniques in molecular biology may be found in Molecular Cloning: A Laboratory Manual, 2$^{nd}$ edition (1989) (Sambrook, Fritsch, and Maniatis); Molecular Cloning: A Laboratory Manual, 4$^{th}$ edition (2012) (Green and Sambrook); Current Protocols in Molecular Biology (1987) (F. M. Ausubel et al. eds.); the series Methods in Enzymology (Academic Press, Inc.): PCR 2: A Practical Approach (1995) (M. J. MacPherson, B. D. Hames, and G. R. Taylor eds.): Antibodies, A Laboratory Manual (1988) (Harlow and Lane, eds.): Antibodies A Laboratory Manual, 2$^{nd}$ edition 2013 (E. A. Greenfield ed.); Animal Cell Culture (1987) (R. I. Freshney, ed.); Benjamin Lewin, Genes IX, published by Jones and Bartlet, 2008 (ISBN 0763752223); Kendrew et al. (eds.), The Encyclopedia of Molecular Biology, published by Blackwell Science Ltd., 1994 (ISBN 0632021829); Robert A. Meyers (ed.), Molecular Biology and Biotechnology: a Comprehensive Desk Reference, published by VCH Publishers, Inc., 1995 (ISBN 9780471185710); Singleton et al., Dictionary of Microbiology and Molecular Biology 2$^{nd}$ ed., J. Wiley & Sons (New York, N.Y. 1994), March, Advanced Organic Chemistry Reactions, Mechanisms and Structure 4$^{th}$ ed., John Wiley & Sons (New York, N.Y. 1992); and Marten H. Hofker and Jan van Deursen, Transgenic Mouse Methods and Protocols, 2$^{nd}$ edition (2011).

As used herein, the singular forms "a" "an", and "the" include both singular and plural referents unless the context clearly dictates otherwise.

The term "optional" or "optionally" means that the subsequent described event, circumstance or substituent may or may not occur, and that the description includes instances where the event or circumstance occurs and instances where it does not.

The recitation of numerical ranges by endpoints includes all numbers and fractions subsumed within the respective ranges, as well as the recited endpoints.

The terms "about" or "approximately" as used herein when referring to a measurable value such as a parameter, an amount, a temporal duration, and the like, are meant to encompass variations of and from the specified value, such as variations of +/−10% or less, +/−5% or less, +/−1% or less, and +/−0.1% or less of and from the specified value, insofar such variations are appropriate to perform in the disclosed invention. It is to be understood that the value to which the modifier "about" or "approximately" refers is itself also specifically, and preferably, disclosed.

As used herein, a "biological sample" may contain whole cells and/or live cells and/or cell debris. The biological sample may contain (or be derived from) a "bodily fluid". The present invention encompasses embodiments wherein the bodily fluid is selected from amniotic fluid, aqueous humour, vitreous humour, bile, blood serum, breast milk, cerebrospinal fluid, cerumen (earwax), chyle, chyme, endolymph, perilymph, exudates, feces, female ejaculate, gastric acid, gastric juice, lymph, mucus (including nasal drainage and phlegm), pericardial fluid, peritoneal fluid, pleural fluid, pus, rheum, saliva, sebum (skin oil), semen, sputum, synovial fluid, sweat, tears, urine, vaginal secretion, vomit and mixtures of one or more thereof. Biological samples include cell cultures, bodily fluids, cell cultures from bodily fluids. Bodily fluids may be obtained from a mammal organism, for example by puncture, or other collecting or sampling procedures.

The terms "subject," "individual," and "patient" are used interchangeably herein to refer to a vertebrate, preferably a mammal, more preferably a human. Mammals include, but are not limited to, murines, simians, humans, farm animals, sport animals, and pets. Tissues, cells and their progeny of a biological entity obtained in vivo or cultured in vitro are also encompassed.

Various embodiments are described hereinafter. It should be noted that the specific embodiments are not intended as an exhaustive description or as a limitation to the broader aspects discussed herein. One aspect described in conjunction with a particular embodiment is not necessarily limited to that embodiment and can be practiced with any other embodiment(s). Reference throughout this specification to "one embodiment", "an embodiment," "an example embodiment," means that a particular feature, structure or characteristic described in connection with the embodiment is included in at least one embodiment of the present invention. Thus, appearances of the phrases "in one embodiment," "in an embodiment," or "an example embodiment" in various places throughout this specification are not necessarily all referring to the same embodiment, but may. Furthermore, the particular features, structures or characteristics may be combined in any suitable manner, as would be apparent to a person skilled in the art from this disclosure, in one or more embodiments. Furthermore, while some embodiments described herein include some but not other features included in other embodiments, combinations of features of different embodiments are meant to be within the scope of the invention. For example, in the appended claims, any of the claimed embodiments can be used in any combination.

Reference is made to international patent application Serial No. PCT/US2017/028122 filed 18 Apr. 2017, which published as PCT Publication No. WO 2017/184590 on 26 Oct. 2017, which claims priority to U.S. provisional patent application Ser. Nos. 62/324,228 18 filed April 2016, 62/345,556 03 filed June 2016 and 62/458,954 filed 14 Feb. 2017. Reference is also made to international patent application Serial No. PCT/US2019/054365 filed Oct. 2, 2019, which published as PCT Publication No. WO 2020/072700 on Apr. 9, 2020, which claims priority to U.S. provisional patent application Ser. Nos. 62/740,324, filed Oct. 2, 2018, and 62/852,924, filed May 24, 2019. Reference is also made to Sarkizova S, Klaeger S, Le P M, et al. A large peptidome dataset improves HLA class I epitope prediction across most of the human population. Nat Biotechnol. 2020; 38(2):199-209. doi:10.1038/s41587-019-0322-9.

All publications, published patent documents, and patent applications cited herein are hereby incorporated by reference to the same extent as though each individual publication, published patent document, or patent application was specifically and individually indicated as being incorporated by reference.

Overview

Immune System and Antigen Presentation

The immune system can be classified into two functional subsystems: the innate and the acquired immune system. The innate immune system is the first line of defense against infections, and most potential pathogens are rapidly neutralized by this system before they can cause, for example, a noticeable infection. The acquired immune system reacts to molecular structures, referred to as antigens, of the intruding organism. There are two types of acquired immune reactions, which include the humoral immune reaction and the cell-mediated immune reaction. In the humoral immune reaction, antibodies secreted by B cells into bodily fluids bind to pathogen-derived antigens, leading to the elimination of the pathogen through a variety of mechanisms, e.g. complement-mediated lysis. In the cell-mediated immune reaction, T cells capable of destroying other cells are activated. For example, if proteins associated with a disease are present in a cell, they are fragmented proteolytically to peptides within the cell. Specific cell proteins then attach themselves to the antigen or peptide formed in this manner and transport them to the surface of the cell, where they are presented to the molecular defense mechanisms, in particular T cells, of the body. Cytotoxic T cells recognize these antigens and kill the cells that harbor the antigens.

The molecules that transport and present peptides on the cell surface are referred to as proteins of the major histocompatibility complex (MHC). MHC proteins are classified into two types, referred to as MHC class I and MHC class II. The structures of the proteins of the two MHC classes are very similar; however, they have very different functions. Proteins of MHC class I are present on the surface of almost all cells of the body, including most tumor cells. MHC class I proteins are loaded with antigens that usually originate from endogenous proteins or from pathogens present inside cells, and are then presented to naïve or cytotoxic T-lymphocytes (CTLs). MHC class II proteins are present on dendritic cells, B-lymphocytes, macrophages and other antigen-presenting cells. They mainly present peptides, which are processed from external antigen sources, i.e. outside of the cells, to T-helper (Th) cells. Most of the peptides bound by the MHC class I proteins originate from cytoplasmic proteins produced in the healthy host cells of an organism itself, and do not normally stimulate an immune reaction. Accordingly, cytotoxic T-lymphocytes that recognize such self-peptide-presenting MHC molecules of class I are deleted in the thymus (central tolerance) or, after their release from the thymus, are deleted or inactivated, i.e. tolerized (peripheral tolerance). MHC molecules are capable of stimulating an immune reaction when they present peptides to non-tolerized T-lymphocytes. Cytotoxic T-lymphocytes have both T cell receptors (TCR) and CD8 molecules on their surface. T cell receptors are capable of recognizing and binding peptides complexed with the molecules of MHC class I. Each cytotoxic T-lymphocyte expresses a unique T cell receptor which is capable of binding specific MHC/peptide complexes.

The peptide antigens attach themselves to the molecules of MHC class I by competitive affinity binding within the endoplasmic reticulum, before they are presented on the cell surface. Here, the affinity of an individual peptide antigen is directly linked to its amino acid sequence and the presence of specific binding motifs in defined positions within the amino acid sequence. If the sequence of such a peptide is known, it is possible to manipulate the immune system against diseased cells using, for example, peptide vaccines. The human leukocyte antigen (HLA) system is a gene complex encoding the major histocompatibility complex (MHC) proteins in humans.

By "proteins or molecules of the major histocompatibility complex (MHC)", "MHC molecules", "MHC proteins" or "HLA proteins" is thus meant proteins capable of binding peptides resulting from the proteolytic cleavage of protein antigens and representing potential T-cell epitopes, transporting them to the cell surface and presenting them there to specific cells, in particular cytotoxic T-lymphocytes or T-helper cells. MHC molecules of class I consist of a heavy chain and a light chain and are capable of binding a peptide of about 8 to 11 amino acids, but usually 9 or 10 amino acids, if this peptide has suitable binding motifs, and presenting it to cytotoxic T-lymphocytes. The peptide bound by the MHC molecules of class I originates from an endogenous protein antigen. The heavy chain of the MHC molecules of class I is preferably an HLA-A, HLA-B or HLA-C monomer, and the light chain is β-2-microglobulin (B2M).

The present invention provides methods for predicting peptides capable of binding to HLA alleles. The embodiments take a set of candidate peptide sequences and identify one or more structural features indicative of occupancy of the candidate peptides on the binding pocket of HLA alleles. These structural features are input into a machine learning algorithm model that was trained using structural features extracted from one or more output models simulating occupancy of one or more binding peptides and one or more non-binding peptides on the HLA binding pocket in a crystal structure of the HLA allele or the crystal structure of a similar HLA allele. The structural features can be identified by simulating occupancy of the one or more candidate peptides on the HLA binding pocket in a crystal structure of the HLA allele or the crystal structure of a similar HLA allele. The structural features can be extracted from the output models generated during the simulations. The structural features can also be identified using a machine learning algorithm model that infers occupancy of the one or more candidate peptides on the HLA binding pocket. The inference can be based on the model being trained with simulated models of peptides verified to bind to the HLA allele and verified peptides that do not bind to the HLA allele.

Applicants can train the algorithms with binding peptides previously identified. Applicants utilized a single-allele method to profile naturally presented peptides on HLA molecules via mass spectrometry to collect endogenous ligandome data for 95 HLA-A, B, C and G alleles, identifying >185,000 peptides. In addition, endogenously presented antigens on primary tumor-derived cell lines from 11 patients (3 chronic lymphocytic leukemia, 1 ovarian, 3 glioblastoma, 4 melanoma) were also identified by MS.

Vaccine therapies (e.g., cancer and infections) rely on accurate selection of immunizing peptides to potentiate immune responses (e.g., against tumor-specific neoepitopes or viral epitopes). Given the patient's particular complement of HLA alleles, the ability to predict which epitopes will be presented is a fundamental prerequisite for successful vaccine design. Additionally, given the unique accumulation of mutations in different tumors as well as the patient's particular complement of HLA alleles, the ability to predict which epitopes will be presented is a fundamental prerequisite for successful cancer vaccine design. Additionally, epitopes recognized in autoimmune diseases for patients having specific HLA alleles is a prerequisite for designing treatments aimed at blocking an immune response against the target proteins. Applicants recently showed that prediction of endogenous antigen presentation is greatly improved when models utilize single HLA allele ligandome datasets and integrate intracellular processes such as proteasomal processing and gene expression. Applicants now extend the approach to include structural features.

In some embodiments, an improved prediction method is provided herein for predicting peptides capable of binding to a given HLA molecule based on the crystal structure of the HLA molecule. Models are provided for the prediction of binding peptides, and the models with best performance (highest AUC and PPV values) are disclosed.

Providing One or More Candidate Peptide Sequences

In certain example embodiments, the invention takes as an initial input a candidate peptide or a set of candidate peptides. In certain embodiments, the candidate peptide or set of candidate peptides may be obtained from a subject or group of subjects in need of an immune response or modified immune response. In certain embodiments, candidate peptides can be identified in a peptide sequence database (e.g., derived from sequencing of subjects having a specific condition where an immunogenic composition would be useful).

In certain embodiments, a peptide sequence database includes HLA allele binding and non-binding peptides. Such a database is very useful for predicting suitable HLA-binding peptides, identifying factors which play a role in HLA-peptide presentation and generating a more accurate prediction algorithm for identifying HLA-allele specific binding peptides. Candidate peptides can be isolated and sequenced for each HLA-allele to identify HLA-binding peptides. In particular embodiments, candidate peptides can be obtained by providing a) a population of cells which expresses a single class I HLA allele or a single pair of class II HLA alleles (one a-chain and one β-chain); b) isolating the respective HLA-peptide complexes from said cells; c) isolating peptides from said HLA-peptide complexes; and d) sequencing said peptides. One of the advantages of the present method is the ability to identify a large number of HLA binding peptides which are specific for a particular HLA allele.

The population of cells may express either a single class I HLA allele, a single pair of class II HLA alleles, or a single class I HLA allele and a single pair of class II HLA alleles. Suitable cell populations include, e.g., class I deficient cells lines in which a single HLA class I allele is expressed, class II deficient cell lines in which a single pair of HLA class II alleles are expressed, or class I and class II deficient cell lines in which a single HLA class I and/or single pair of class II alleles are expressed. As an exemplary embodiment, the class I deficient B cell line is B721.221. However, it is clear to a skilled person that other cell populations can be generated which are class I and/or class II deficient. An exemplary method for deleting/inactivating endogenous class I or class II genes includes, CRISPR-Cas9 mediated genome editing.

The population of cells may be professional antigen presenting cells such as macrophages, B cells and dendritic cells. Preferably, the cells are B cells or dendritic cells. In preferred embodiments, the cells are tumor cells or cells from a tumor cell line. In particular embodiments, the cells are cells isolated from a patient. In preferred embodiments, the population of cells comprises at least $10^6$ cells.

In some embodiments, the population of cells are further modified, such as by increasing or decreasing the expression and/or activity of at least one gene. In preferred embodiments, the gene encodes a member of the immunoproteasome. The immunoproteasome is known to be involved in the processing of HLA class I binding peptides and includes the LMP2 (β1i), MECL-1 (β2i), and LMP7 (β5i) subunits. The immunoproteasome can also be induced by interferon-gamma. Accordingly, in some embodiments, the population of cells may be contacted with one or more cytokines, growth factors, or other proteins. Preferably, the cells are stimulated with inflammatory cytokines such as interferon-gamma, IL-Iβ, IL-6, and/or T F-α. The population of cells may also be subjected to various environmental conditions, such as stress (heat stress, oxygen deprivation, glucose starvation, DNA damaging agents, etc.). In some embodiments the cells are contacted with one or more of a chemotherapy drug, radiation, targeted therapies, immunotherapy. The methods disclosed herein can therefore be used to study the effect of various genes or conditions on HLA peptide processing and presentation. In particular embodiments, the conditions used are selected so as to match the condition of the patient for which the population of HLA-peptides is to be identified.

Any HLA allele may be expressed in the cell population. Typically, it will be of interest to sequentially perform the methods provided herein for different HLA alleles, such that resulting datasets can be used in combination. In particular embodiments, the HLA allele is selected so as to correspond to a genotype of interest. In a preferred embodiment, the HLA allele is a mutated HLA allele, which may be non-naturally occurring allele or a naturally occurring allele in an afflicted patient. The methods disclosed herein have the further advantage of identifying HLA binding peptides for HLA alleles associated with various disorders as well as alleles which are present at low frequency. Accordingly, in a preferred method the HLA allele is present at a frequency of less than 1% within a population, such as within the Caucasian population.

Vectors, promoters, etc. for expression. In some embodiments, the nucleic acid sequence encoding the HLA allele further comprises a peptide tag which can be used to immunopurify the HLA-protein. Suitable tags are well-known in the art and include Myc, VSV, V5, His, HA, and FLAG tags.

The methods further comprise isolating HLA-peptide complexes from said cells. In preferred embodiments, the complexes can be isolated using standard immunoprecipitation techniques known in the art with commercially available antibodies. Preferably, the cells are first lysed. HLA class I-peptide complexes can be isolated using HLA class I specific antibodies such as the W6/32 antibody, while HLA class II-peptide complexes can be isolated using HLA class II specific antibodies such as the M5/114.15.2 monoclonal antibody. In some embodiments, the single (or pair of) HLA alleles are expressed as a fusion protein with a peptide tag and the HLA-peptide complexes are isolated using binding molecules that recognize the peptide tags.

The methods further comprise isolating peptides from said HLA-peptide complexes and sequencing the peptides. The peptides are isolated from the complex by any method known to one of skill in the art, such as acid elution. While any sequencing method may be used, methods employing mass spectrometry, such as liquid chromatography-mass spectrometry (LC-MS or LC-MS/MS, or alternatively HPLC-MS or HPLC-MS/MS) are preferred. These sequencing methods are well-known to a skilled person and are reviewed in Medzihradszky K F and Chalkley R J. Mass Spectrom Rev. 2015 January-February; 34(1):43-63.

Typically, an HLA-allele specific binding peptide sequence database comprises at least 1000 different binding peptide sequences.

The methods disclosed herein may also be used to generate a database comprising the HLA-allele specific binding peptide sequences for more than one HLA-allele. In preferred embodiments, the methods comprise performing the step—a)-d) for at least two different HLA-alleles, preferably at least five, more preferably at least 10 different alleles.

In one aspect, the present disclosure provides a plurality of HLA-allele specific binding peptides, or the sequences thereof, which peptides correspond to the peptides which are presented by one specific HLA allele. More particularly, an HLA-allele specific binding peptide sequence database is provided obtained by carrying out the method according to the invention. In particular embodiments, combinations of pluralities of peptides, sets of sequences or databases is provided, represent HLA-allele specific peptides, sets of sequences or databases for different HLA alleles. The combination of databases is also referred to herein as a dataset. These combinations differentiate themselves over prior art datasets in that they represent HLA-specific peptides for each HLA-allele individually rather than combining HLA peptides obtained from a combination of HLA-alleles.

Predicting Peptide Binding to HLA Alleles

In one aspect, the present disclosure provides methods for generating a prediction algorithm for identifying HLA-allele specific binding peptides, which methods comprise training a neural network with one or more peptide sequence databases (i.e.; combinations of databases). In particular embodiments, the methods involve training a machine with one or more peptide sequence databases generated with a method according to the invention. More particularly, the methods comprise training a neural network running on a machine with several peptide sequence databases. In the methods provided herein, the sequences are compared so as to identify prediction algorithms for a peptide to be presented by said HLA-allele. In a preferred embodiment, the methods involve generating models based on predictive variables or features. As used herein, the terms variables and features are used interchangeably.

Generating a prediction algorithm by training a machine is a well-known technique. The most important in the training of the machine is the quality of the database used for the training. Typically, the machine combines one or more linear models, support vector machines, decision trees and/or a neural network.

Machine learning can be generalized as the ability of a learning machine to perform accurately on new, unseen examples/tasks after having experienced a learning data set. Machine learning may include the following concepts and methods. Supervised learning concepts may include AODE; Artificial neural network, such as Backpropagation, Autoencoders, Hopfield networks, Boltzmann machines, Restricted Boltzmann Machines, and Spiking neural networks; Bayesian statistics, such as Bayesian network and Bayesian knowledge base; Case-based reasoning; Gaussian process regression; Gene expression programming; Group method of data handling (GMDH); Inductive logic programming; Instance-based learning; Lazy learning; Learning Automata; Learning Vector Quantization; Logistic Model Tree; Minimum message length (decision trees, decision graphs, etc.), such as Nearest Neighbor Algorithm and Analogical modeling; Probably approximately correct learning (PAC) learning; Ripple down rules, a knowledge acquisition methodology; Symbolic machine learning algorithms; Support vector machines; Random Forests; Ensembles of classifiers, such as Bootstrap aggregating (bagging) and Boosting (meta-algorithm); Ordinal classification; Information fuzzy networks (IFN); Conditional Random Field; ANOVA; Linear classifiers, such as F'sher's linear discriminant, Linear regression, Logistic regression, Multinomial logistic regressnaïveNaive Bayes classifier, Perceptron, Support vector machines; Quadratic classifiers; k-nearest neighbor; Boosting; Decision trees, such as C4.5, Random forests, ID3, CART, SLIQ, SPRINT; Bayesian networksnaïveh as Naive Bayes; and Hidden Markov models. Unsupervised learning concepts may include; Expectation-maximization algorithm; Vector Quantization; Generative topographic map; Information bottleneck method; Artificial neural network, such as Self-organizing map; Association rule learning, such as, Apriori algorithm, Eclat algorithm, and FP-growth algorithm; Hierarchical clustering, such as Single-linkage clustering and Conceptual clustering; Cluster analysis, such as, K-means algorithm, Fuzzy clustering, DBSCAN, and OPTICS algorithm; and Outlier Detection, such as Local Outlier Factor. Semi-supervised learning concepts may include; Generative models; Low-density separation; Graph-based methods; and Co-training. Reinforcement learning concepts may include; Temporal difference learning; Q-learning; Learning Automata; and SARSA. Deep learning concepts may include; Deep belief networks;

Deep Boltzmann machines; Deep Convolutional neural networks; Deep Recurrent neural networks; and Hierarchical temporal memory.

Structural Features of Peptides

In one aspect, the present disclosure provides methods for identifying HLA-allele specific binding peptides, which method comprises analyzing structural features indicative of occupancy of a peptides on the binding pocket of HLA alleles. In certain embodiments, the structural features are amino acid residues capable of fitting a model of peptide occupancy on the binding pocket of HLA alleles (e.g., enrichment in hydrophobicity, exposed hydrophobic surface and charges determined' by the peptide's conformation within the binding pocket, as well as the size and position of the various amino acid side chains). In certain embodiments, the structural features are energetic features that are encoded not by peptide sequence, but by modeled three-dimensional structures of peptide occupancy on the binding pocket of an HLA allele (e.g., energies of attraction, repulsion, and solvation; energies of side chain and backbone hydrogen bonds; and energies and probabilities of side chain and backbone conformations) (see, e.g., Alford R F, Leaver-Fay A, Jeliazkov J R, O'Meara M J, DiMaio F P, Park H, et al. The rosetta all-atom energy function for macromolecular modeling and design. J Chem Theory Comput. (2017) 13:3031-48; and Riley et al., Structure Based Prediction of Neoantigen Immunogenicity. Front Immunol. 2019 Aug. 28; 10:2047). In certain embodiments, the structural features that are extracted are the standard rosetta energy terms (see, e.g., www.rosettacommons.org/docs/latest/rosetta_basics/scoring/score-types) (see, Table 1).

TABLE 1

| | Nonlimiting Energy Terms |
|---|---|
| fa_atr | Lennard-Jones attractive between atoms in different residues. Supports canonical and noncanonical residue types. |
| fa_rep | Lennard-Jones repulsive between atoms in different residues. Supports canonical and noncanonical residue types. |
| fa_sol | Lazaridis-Karplus solvation energy. Supports canonical and noncanonical residue types. |
| fa_intra_rep | Lennard-Jones repulsive between atoms in the same residue. Supports canonical and noncanonical residue types. |
| fa_elec | Coulombic electrostatic potential with a distance-dependent dielectric. Supports canonical and noncanonical residue types. |
| pro_close | Proline ring closure energy and energy of psi angle of preceding residue. Supports D- or L-proline, plus D- or L-oligourea-proline. |
| hbond_sr_bb | Backbone-backbone hbonds close in primary sequence. All hydrogen bonding terms support canonical and noncanonical types. |
| hbond_lr_bb | Backbone-backbone hbonds distant in primary sequence. |
| hbond_bb_sc | Sidechain-backbone hydrogen bond energy. |
| hbond_sc | Sidechain-sidechain hydrogen bond energy. |
| dslf_fa13 | Disulfide geometry potential. Supports D- and L-cysteine disulfides, plus homocysteine disulfides or disulfides involving beta-3-cysteine. |
| rama | Ramachandran preferences. Supports only the 20 canonical alpha-amino acids and their mirror images. |
| omega | Omega dihedral in the backbone. A Harmonic constraint on planarity with standard deviation of ~6 deg. Supports alpha-amino acids, beta-amino acids, and oligoureas. In the case of oligoureas, both amide bonds (called "mu" and "omega" in Rosetta) are constrained to planarity. |
| fa_dun | Internal energy of sidechain rotamers as derived from Dunbrack's statistics (2010 Rotamer Library used in Talaris2013). Supports any residue type for which a rotamer library is avalable. |
| p_aa_pp | Probability of amino acid at $\Phi/\Psi$. Supports only the 20 canonical alpha-amino acids and their mirror images. |
| ref | Reference energy for each amino acid. Balances internal energy of amino acid terms. Plays role in design. Supports only the 20 canonical alpha-amino acids and their mirror images. |

In certain embodiments, the binding pocket is determined by a structural analysis. Non-limiting structural analysis methods include X-ray crystallography and nuclear magnetic resonance (NMR) spectroscopy (see, e.g., Alberts B, Johnson A, Lewis J, et al. Molecular Biology ° f the Cell. 4th edition. New York: Garland Science; 2002. Analyzing Protein Structure and Function). In preferred embodiments, a crystal structure is used to determine the binding pocket. Any HLA-allele crystal structure may be used to simulate occupancy of peptides in the binding pocket. In certain embodiments, a structure is obtained by generating a crystal structure of an HLA-allele. In certain embodiments, the crystal structures for HLA molecules are obtained from a database (e.g., the Protein Data Bank (PDB, www.rcsb.org)). In certain embodiments, structures of similar HLA alleles are used if a structure for the HLA-allele of interest is unavailable or cannot be generated. In certain embodiments, similar HLA-alleles include HLA alleles having the highest similarity between the amino acid sequences of the binding pocket. The similarity of the binding pocket can be computed as the sum of pair-wise residue similarities according to a 20×20 amino acid similarity matrix. In certain embodiments, similar HLA-alleles include HLA alleles having similarity between the binding motifs (i.e. two alleles are considered similar if they bind similar peptides). In certain embodiments, the HLA alleles bind to two or more of the same peptides and do not bind to 2 or more of the same peptides. In certain embodiments, the HLA alleles bind to 10 or more of the same peptides and do not bind to 10 or more of the same peptides. In certain embodiments, similar HLA-alleles include HLA alleles from the same class (e.g., HLA-A, HLA-B, HLA-C, HLA-E, HLA-F, HLA-G, HLA-K and HLA-L). In certain embodiments, similar HLA-alleles include HLA alleles having the highest amino acid sequence identity to the HLA-allele of interest.

In certain embodiments, structural features are identified by simulating models of how the candidate peptides occupy the HLA binding pocket. In certain embodiments, the method comprises analyzing simulations of the occupancy of a peptides on the binding pocket of HLA alleles. In certain embodiments, one or more peptide docking tools are used to generate output models of peptide occupancy on the binding pocket of HLA alleles. In certain embodiments, molecular dynamics simulation is used to generate output models of peptide occupancy on the binding pocket of HLA alleles (see, e.g., Kmiecik et al., Coarse-Grained Protein Models and Their Applications. Chem Rev. 2016 Jul. 27; 116(14): 7898-936). In certain embodiments, output models of peptide occupancy on the binding pocket of HLA alleles is generated by docking, molecular dynamics simulations, protein threading, or combinations of these methods. In certain embodiments, more than one output model is generated by altering the position of the peptide and altering the position of the HLA allele. In certain embodiments, millions of docking models are tested (e.g., approximately 30 million) to generate hundreds of output models (e.g., approximately 200). In certain embodiments, the number of simulations is important for identifying the features of binding and non-binding peptides and not whether an output model or simulation is correct in how the peptide actually binds. Thus, having a large number of simulated output models is required to extract structural features. Non-limiting examples of peptide docking tools include, FlexPepDock, DockTope, pDOCK and HADDOCK (see, e.g., Chaudhury S, Lyskov S, Gray J J. PyRosetta: a script-based interface for implementing molecular modeling algorithms using Rosetta. Bioinformatics. (2010) 26:689-91; O'Meara M J, Leaver-Fay A, Tyka M D, Stein A, Houlihan K, DiMaio F, et al. Combined covalent-electrostatic model of hydrogen bonding improves structure prediction with rosetta. J Chem Theory Comput. (2015) 11:609-22); Rigo, et al., DockTope: a Web-based tool for automated pMHC-I modelling. Sci Rep. 2015 Dec. 17; 5:18413; Khan and Ranganathan, pDOCK: a new technique for rapid and accurate docking of peptide ligands to Major Histocompatibility Complexes. Immunome Res. 2010 Sep. 27; 6 Suppl 1(Suppl 1):52; Liu et al., Subangstrom accuracy in pHLA-I modeling by Rosetta FlexPepDock refinement protocol. J Chem Inf Model. 2014 Aug. 25; 54(8):2233-42; Raveh et al., Rosetta FlexPepDock ab-initio: simultaneous folding, docking and refinement of peptides onto their receptors. PLoS One. 2011 Apr. 29; 6(4):e18934; and Trellet, et al., A unified conformational selection and induced fit approach to protein-peptide docking, PLoS One. 2013; 8(3):e58769). Molecular dynamics simulation includes, but is not limited to coarse-grained Monte Carlo protein-peptide docking (~30 million per peptide)(see, e.g., Bordner A J, Abagyan R. Ab initio prediction of peptide-MHC binding geometry for diverse class I MHC allotypes. Proteins. 2006 May 15; 63(3):512-26).

In certain embodiments, the output models are used to generate structural feature maps. The structural feature maps can then be input into a prediction model that was trained by machine learning. In certain embodiments, a machine learning algorithm (i.e., the prediction model) is trained using feature maps generated from the structural simulations of peptides confirmed to bind to the HLA allele and non-binding peptides. In certain embodiments, a neural network is trained on energetic features that are encoded by the modeled three-dimensional structures of the peptide/HLA-A2 complexes. In certain embodiments, the model is trained using simulations of the peptides identified herein using mono-allelic cell lines. In certain embodiments, a machine is trained with a peptide sequence database obtained by carrying out the method according to the invention for said HLA-allele. In a preferred embodiment, the method comprises using information on the simulated binding outputs as a variable. Thus, in certain embodiments, simulated models generated for binding peptides or non-binding peptides to an HLA allele can be compared to simulated models generated for candidate peptides by a neural network or machine learning algorithm. Based on the simulations obtained the prediction model can determine if the candidate peptide has a certain probability of binding. Peptide binding can be validated by detecting binding of a peptide to the HLA allele using any known in vitro assay or cellular reporter assay.

In one aspect, the present disclosure provides methods for generating a prediction algorithm for identifying HLA-allele specific binding peptides, which methods comprise training a neural network with one or more structural features obtained by modeling occupancy of peptide sequence databases comprising peptides that have been experimentally determined to bind to an HLA allele and to not bind to an HLA allele (i.e., combinations of databases). In particular embodiments, the methods involve training a machine with one or more peptide sequence databases generated with a method according to the invention (i.e., peptides bound to HLA alleles expressed in monoallelic cell lines). More particularly, the methods comprise training a neural network running on a machine with several peptide sequence databases.

In one embodiment, how peptides occupy the HLA binding pocket is computationally simulated. Existing peptide docking protocols can be used with modifications to suit identifying structural features. This can be performed for a number of diverse HLA alleles and peptides and simulate both known binders as well as known non-binders, obtaining multiple high-scoring conformations for each peptide. One drawback of peptide docking techniques is that they are computationally intensive. Therefore, using a large dataset of confidently docked HLA-peptide pairs, machine learning can be used (input peptide sequence, output structure/structural features) to infer how peptides dock and thus be able to very quickly produce the structural features needed for presentation prediction. Machine learning can also be used to quickly produce computational simulations of the docked peptide-MHC structures. Thus, 'the m'del can 'learn' how to produce structural features directly from the peptide and HLA allele sequences.

In another embodiment, a large dataset of structures with both binding and non-binding peptides can be built. Those structures can be used to train a machine learning prediction algorithm that learns what the differentiating features between binders and non-binders are (incorporating signals from the structures as well as signals from the amino acid sequence and properties). With this model trained, it can then be applied to a new candidate peptide to obtain a numerical score that captures how likely the candidate peptide is to be presented by a given HLA allele.

Sequence Specific Features of Peptides

In certain embodiments, the prediction algorithm comprises structural features and non-structural features described herein. In certain embodiments, the structural features are used in combination with sequence only models described herein. In certain embodiments, models incorporating structural and sequence features predict HLA-allele specific binding peptides with higher accuracy than any previously described method.

In certain embodiments, non-structural features are also used as variables (such as sequence, amino acid properties, peptide characteristics). In alternative embodiments, the models also incorporate extrinsic features such as expression and cleavage information. In particular embodiments, the variables used to train the machine comprise one or more predictive variables selected from the group consisting of peptide sequence (e.g., dummy peptide encoding, PCA peptide encoding, Kidera peptide-level features), amino acid physical properties, peptide physical properties, protein stability, protein translation rate, protein degradation rate, translational efficiencies from ribosomal profiling, protein cleavability, protein localization, motifs of host protein that facilitate TAP transport, whether host protein is subject to autophagy, motifs that favor ribosomal stalling (polyproline stretches) and protein features that fa'or NMD (long 3' UTR, stop codon >50 nt upstream of last exon junction) (see, e.g., Kidera, et al., (1985). Statistical analysis of the physical properties of the 20 naturally occurring amino acids. Journal of Protein Chemistry, 4(1), 23-55; and Wang B, Kennedy M A. Principal components analysis of protein sequence clusters. J Struct Funct Genomics. 2014; 15(1):1-11. doi: 10.1007/s10969-014-9173-2). In particular embodiments, at least two of these features are used. In further embodiments, at least 3, 4, 5, 6, 7, 8, 9 or all ten of these features are used. In a preferred embodiment, the variables used to train the machine comprise the expression level of the source protein of a peptide within a cell. In a preferred embodiment, the variables used to train the machine comprise expression level of the source protein of a peptide within a cell, peptide sequence, amino acid physical properties, peptide physical properties, expression level of the source protein of a peptide within a cell, Protein stability, protein translation rate, protein degradation rate, translational efficiencies from ribosomal profiling, protein cleavability, protein localization, motifs of host protein that facilitate TAP transport, host protein is subject to autophagy, motifs that favor ribosomal stalling (polyproline stretches), protein features that favor NMD (long 3' UTR, stop codon >50 nt upstream of last exon junction and peptide cleavability).

In one aspect, the present disclosure provides methods for identifying HLA-allele specific binding peptides, which method comprises analyzing the sequence of a peptide with a machine which has been trained with a peptide sequence database obtained by carrying out the method according to the invention for said HLA-allele. In a preferred embodiment, the method comprises using information on the expression level of the source protein of the peptide within the cell as a variable. In further embodiments, the method comprises determining the expression level of the source protein of the peptide within a cell and using the source protein expression as one of the predictive variables used by the machine. Typically, the expression level is determined by measuring the amount of source protein or the amount of RNA encoding said source protein.

Applicants previously identified that expression and cleavability contribute to the likelihood of presentation independent of the peptide identity (amino acid sequence) or HLA allele. Therefore, a combination of structural and residue properties together with cleavage and expression will improve the overall performance of a model that predicts endogenous antigen presentation. To evaluate the improvements achieved by structural signals amino acid sequence-only models are compared to sequence+structure models. Orthogonal features can then be added to build the final models.

Therapeutic Peptides

It is demonstrated herein that the methods provided herein allow a more effective prediction of HLA-binding peptides than methods of the prior art, with fewer false positives. This is important as the number of immunogenic peptides that can practically be generated in the context of an immune therapy is limited. In particular embodiments, the methods are used to determine an effective neoantigen vaccine. In particular embodiments, the methods are used to determine an effective vaccine against a pathogen. In particular embodiments, the methods are used to determine an effective tolerizing vaccine. In these contexts, it is of interest to determine which peptides forming neoantigens, pathogen antigens, or self-antigens are likely to bind to a subject's HLA so as to effectively function as immunogenic peptides.

Subject specific HLA alleles or HLA genotype of a subject may be determined by any method known in the art. In preferred embodiments, HLA genotypes are determined by any method described in International Patent Application number PCT/US2014/068746, published Jun. 11, 2015 as WO2015085147. Briefly, the methods include determining polymorphic gene types that may comprise generating an alignment of reads extracted from a sequencing data set to a gene reference set comprising allele variants of the polymorphic gene, determining a first posterior probability or a posterior probability derived score for each allele variant in the alignment, identifying the allele variant with a maximum first posterior probability or posterior probability derived score as a first allele variant, identifying one or more overlapping reads that aligned with the first allele variant and one or more other allele variants, determining a second posterior probability or posterior probability derived score for the one or more other allele variants using a weighting factor, identifying a second allele variant by selecting the allele variant with a maximum second posterior probability or posterior probability derived score, the first and second allele variant defining the gene type for the polymorphic gene, and providing an output of the first and second allele variant.

One of the critical barriers to developing curative and tumor-specific immunotherapy is the identification and selection of highly specific and restricted tumor antigens to avoid autoimmunity. Tumor neoantigens, which arise as a result of genetic change (e.g., inversions, translocations, deletions, missense mutations, splice site mutations, etc.) within malignant cells, represent the most tumor-specific class of antigens. Neoantigens have rarely been used in cancer vaccine or immunogenic compositions due to technical difficulties in identifying them, selecting optimized neoantigens, and producing neoantigens for use in a vaccine or immunogenic composition. These problems may be addressed by: identifying mutations in neoplasias/tumors which are present at the DNA level in tumor but not in matched germline samples from a high proportion of subjects having cancer; analyzing the identified mutations with one or more peptide-MHC binding prediction algorithms to generate a plurality of neoantigen T cell epitopes that are expressed within the neoplasia/tumor and that bind to a high proportion of patient HLA alleles; and synthesizing the plurality of neoantigenic peptides selected from the sets of all neoantigen peptides and predicted binding peptides for use in a cancer vaccine or immunogenic composition suitable for treating a high proportion of subjects having cancer.

For example, translating sequencing information into a therapeutic vaccine may include: (1) Prediction of mutated peptides that can bind to HLA molecules of a high proportion of individuals. Efficiently choosing which particular mutations to utilize as immunogen requires the ability to predict which mutated peptides would efficiently bind to a high proportion of patient's HLA alleles. Recently, neural network based learning approaches with validated binding and non-binding peptides have advanced the accuracy of prediction algorithms for the major HLA-A and -B alleles; (2) Formulating the drug as a multi-epitope vaccine of long peptides. Targeting as many mutated epitopes as practically possible takes advantage of the enormous capacity of the immune system, prevents the opportunity for immunological escape by down-modulation of a particular immune targeted gene product, and compensates for the known inaccuracy of epitope prediction approaches. Synthetic peptides provide a particularly useful means to prepare multiple immunogens efficiently and to rapidly translate identification of mutant epitopes to an effective vaccine. Peptides can be readily synthesized chemically and easily purified utilizing reagents free of contaminating bacteria or animal substances. The small size allows a clear focus on the mutated region of the protein and also reduces irrelevant antigenic competition from other components (unmutated protein or viral vector antigens); (3) Combination with a strong vaccine adjuvant. Effective vaccines require a strong adjuvant to initiate an immune response. As described below, poly-ICLC, an agonist of TLR3 and the RNA helicase-domains of MDA5 and RIG3, has shown several desirable properties for a vaccine adjuvant. These properties include the induction of local and systemic activation of immune cells in vivo, production of stimulatory chemokines and cytokines, and stimulation of antigen-presentation by DCs. Furthermore, poly-ICLC can induce durable CD4+ and CD8+ responses in humans. Importantly, striking similarities in the upregulation of transcriptional and signal transduction pathways were seen in subjects vaccinated with poly-ICLC and in volunteers who had received the highly effective, replication-competent yellow fever vaccine. Furthermore, >90% of ovarian carcinoma patients immunized with poly-ICLC in combination with a NYES0-1 peptide vaccine (in addition to Montanide) showed induction of CD4+ and CD8+ T cell, as well as antibody responses to the peptide in a recent phase 1 study. At the same time, polyICLC has been extensively tested in more than 25 clinical trials to date and exhibited a relatively benign toxicity profile.

The application provides improved methods of prediction of peptides, such as mutated peptides, that can bind to HLA molecules of a high proportion of individuals. In particular embodiments, the application provides methods of identifying from a given set of neo-antigen comprising peptides the most suitable peptides for preparing an immunogenic composition for a subject, said method comprising selecting from set given set of peptides the plurality of peptides capable of binding an HLA protein of the subject, wherein said ability to bind an HLA protein is determined by analyzing the sequence of peptides with a machine which has been trained with peptide sequence databases corresponding to the specific HLA-binding peptides for each of the HLA-alleles of said subject. More particularly, the application provides methods of identifying from a given set of neo-antigen comprising peptides the most suitable peptides for preparing an immunogenic composition for a subject, said method comprising selecting from set given set of peptides the plurality of peptides determined as capable of binding an HLA protein of the subject, ability to bind an HLA protein is determined by analyzing the sequence of peptides with a machine which has been trained with a peptide sequence database obtained by carrying out the methods described herein above. Thus, in particular embodiments, the application provides methods of identifying a plurality of subject-specific peptides for preparing a subject-specific immunogenic composition, wherein the subject has a tumor and the subject-specific peptides are specific to the subject and the subject's tumor, said method comprising: whole genome or whole exome nucleic acid sequencing of a sample of the subject's tumor and a non-tumor sample of the subject; determining based on the whole genome or whole exome nucleic acid sequencing, non-silent mutations present in the genome of cancer cells of the subject but not in normal tissue from the subject, and the HLA genotype of the subject, wherein the non-silent mutations comprise a point, splice-site, frameshift, read-through or gene-fusion mutation; and selecting from the identified non-silent mutations the plurality of subject-specific peptides, each having a different tumor neo-epitope that is an epitope specific to the tumor of the subject and each being identified as capable of binding an HLA protein of the subject, as determined by analyzing the sequence of peptides derived from the non-silent mutations in the methods for predicting HLA binding described herein.

In particular embodiments, the methods are used to determine whether or not a peptide will bind to an HLA protein. In further embodiments, the methods provide a predictive score indicative of binding an HLA protein of the subject.

Thus, in particular embodiments, the application provides methods of identifying a plurality of subject-specific peptides for preparing a subject-specific immunogenic composition, said method comprising selecting a plurality of subject-specific peptides, each having a different tumor neo-epitope that is an epitope specific to the tumor of the subject and each having a predictive score indicative of binding an HLA protein of the subject, wherein said predictive score is determined by analyzing the sequence of peptides derived from the non-silent mutations by carrying out the method of predicting HLA-binding described herein.

In particular embodiments, the cell used in the method for determining HLA binding as described herein is an antigen-presenting cell.

Neoantigens

In certain embodiments, tumor antigens that bind to HLA alleles are identified or predicted. In certain embodiments, the tumor antigens are neoantigens. In a further aspect, the invention provides methods for identifying tumor neoantigen-comprising peptides, wherein the methods comprise identifying for a given HLA allele, the peptides binding said HLA allele in a tumor cell from a tumor of a patient.

As described herein, there is a large body of evidence in both animals and humans that mutated epitopes are effective in inducing an immune response and that cases of spontaneous tumor regression or long term survival correlate with CD8+ T cell responses to mutated epitopes (Buckwalter and Srivastava P K. "It is the antigen(s), stupid" and other lessons from over a decade of vaccine therapy of human cancer. Seminars in immunology 20:296-300 (2008); Karanikas et al, High frequency of cytolytic T lymphocytes directed against a tumor-specific mutated antigen detectable with HLA tetramers in the blood of a lung carcinoma patient with long survival. Cancer Res. 61:3718-3724 (2001); Lennerz et al, The response of autologous T cells to a human melanoma is dominated by mutated neoantigens. Proc Natl Acad Sci USA. 102: 16013 (2005)) and that "immunoediting" can be tracked to alterations in expression of dominant mutated antigens in mice and man (Matsushita et al, Cancer exome analysis reveals a T-cell-dependent mechanism of cancer immunoediting Nature 482:400 (2012); DuPage et al, Expression of tumor-specific antigens underlies cancer immunoediting Nature 482:405 (2012); and Sampson et al, Immunologic escape after prolonged progression-free survival with epidermal growth factor receptor variant III peptide vaccination in patients with newly diagnosed glioblastoma J Clin Oncol. 28:4722-4729 (2010)).

Sequencing technology has revealed that each tumor contains multiple, patient-specific mutations that alter the protein coding content of a gene. Such mutations create altered proteins, ranging from single amino acid changes (caused by missense mutations) to addition of long regions of novel amino acid sequence due to frame shifts, read-through of termination codons or translation of intron regions (novel open reading frame mutations; neoORFs). These mutated proteins are valuable targets for the host's immune response to the tumor as, unlike native proteins, they are not subject to the immune-dampening effects of self-tolerance. Therefore, mutated proteins are more likely to be immunogenic and are also more specific for the tumor cells compared to normal cells of the patient. The mutated proteins can be referred to as neoantigens. The term "neoantigen" or "neoantigenic" means a class of tumor antigens that arises from a tumor-specific mutation(s) which alters the amino acid sequence of genome encoded proteins.

Embodiments disclosed herein provide a method of identifying peptides, e.g., neoantigens, including, but not limited to novel unannotated open reading frames (nuORFs), that are capable of eliciting a cancer specific T cell response (see, e.g., WO2020131586A2). Genomic aberrations in cancer cells give rise to mutant peptides (neoantigens) displayed on the human leukocyte antigen (HLA) molecules and recognized by T cells, thus triggering an immune response against cancer cells. Patients vaccinated with neoantigen-based peptides display expanded neoantigen-specific T cells, suggesting that this could be a promising avenue for cancer treatment (Ott et al., An immunogenic personal neoantigen vaccine or patients with melanoma, Nature 2017 Jul 13; 547(7662):217-221; Sahin et al., 2017 Personalized RNA mutanome vaccines mobilize poly-specific therapeutic immunity against cancer", Nature, vol. 547, 2017, pages 222-226). Neoantigens are commonly predicted based on mutations detected by whole exome sequencing (WES). Their expression levels are estimated using mRNA sequencing (RNA-seq). Ribosome profiling (Ribo-seq) allows to monitor mRNA translation, and has been used to predict a plethora of translated novel unannotated ORFs (nuORFs) (Fields et al., 2015. A Regression-Based Analysis of Ribosome-Profiling Data Reveals a Conserved Complexity to Mammalian Translation, Mol Cell, vol. 60, pages 816-827; Ji et al., 2015. Many lncRNAs, 5'UTRs, and pseudogenes are translated and some are likely to express functional proteins, ELIFE, vol. 4). Ribo-seq analysis of human fibroblasts infected with HSV-1 and HCMV has identified nuORFs that contribute peptides presented on major histocompatibility complex class I (MHC I) (Erhard et al., 2018. Improved Ribo-seq enables identification of cryptic translation events, Nat. Methods, vol. 15, no. 5, pages 363-366).

The present invention provides for improved HLA epitope prediction, methods and products for use therein. Provided herein are methods and tools for improved HLA epitope prediction. These are of interest, for example, for use in the production of suitable neoantigen-comprising peptides as described further herein.

The prediction tools can be used to select subject specific peptides that are presented by a tumor for any neoplasia. By "neoplasia" is meant any disease that is caused by or results in inappropriately high levels of cell division, inappropriately low levels of apoptosis, or both. For example, cancer is an example of a neoplasia. Examples of cancers include, without limitation, leukemia (e.g., acute leukemia, acute lymphocytic leukemia, acute myelocytic leukemia, acute myeloblastic leukemia, acute promyelocytic leukemia, acute myelomonocytic leukemia, acute monocytic leukemia, acute erythroleukemia, chronic leukemia, chronic myelocytic leukemia, chronic lymphocytic leukemia), polycythemia vera, lymphoma (e.g., Hodgkin's disease, non-Hodgkin's disease), Waldenstrom's macroglobulinemia, heavy chain disease, and solid tumors such as sarcomas and carcinomas (e.g., fibrosarcoma, myxosarcoma, liposarcoma, chondrosarcoma, osteogenic sarcoma, chordoma, angiosarcoma, endotheliosarcoma, lymphangiosarcoma, lymphangioendotheliosarcoma, synovioma, mesothelioma, Ewing's tumor, leiomyosarcoma, rhabdomyosarcoma, colon carcinoma, pancreatic cancer, breast cancer, ovarian cancer, prostate cancer, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, bile duct carcinoma, choriocarcinoma, seminoma, embryonal carcinoma, Wilm's tumor, cervical cancer, uterine cancer, testicular cancer, lung carcinoma, small cell lung carcinoma, bladder carcinoma, epithelial carcinoma, glioma, astrocytoma, medulloblastoma, craniopharyngioma, ependymoma, pinealoma, hemangioblastoma, acoustic neuroma, oligodendroglioma, schwannoma, meningioma, melanoma, neuroblastoma, and retinoblastoma). Lymphoproliferative disorders are also considered to be proliferative diseases.

Autoimmune Diseases

In certain embodiments, self-antigen peptides that bind to HLA alleles are identified or predicted. In certain embodiments, the self-antigens are aberrantly targeted by the host immune system. As used throughout the present specification, the terms "autoimmune disease" or "autoimmune disorder" are used interchangeably refer to a diseases or disorders caused by an immune response against a self-tissue or tissue component (self-antigen) and include a self-antibody response and/or cell-mediated response. The terms encompass organ-specific autoimmune diseases, in which an autoimmune response is directed against a single tissue, as well as non-organ specific autoimmune diseases, in which an autoimmune response is directed against a component present in two or more, several or many organs throughout the body.

Examples of autoimmune diseases include but are not limited to acute disseminated encephalomyelitis (ADEM); Addison's disease; ankylosing spondylitis; antiphospholipid antibody syndrome (APS); aplastic anemia; autoimmune gastritis; autoimmune hepatitis; autoimmune thrombocytopenia; Behçet's disease; coeliac disease; dermatomyositis; diabetes mellitus type I; Goodpasture's syndrome; Graves' disease; Guillain-Barre syndrome (GBS); Hashimoto's disease; idiopathic thrombocytopenic purpura; inflammatory bowel disease (IBD) including Crohn's disease and ulcerative colitis; mixed connective tissue disease; multiple sclerosis (MS); myasthenia gravis; opsoclonus myoclonus syndrome (OMS); optic neuritis; Ord's thyroiditis; pemphigus; pernicious anaemia; polyarteritis nodosa; polymyositis; primary biliary cirrhosis; primary myxedema; psoriasis; rheumatic fever; rheumatoid arthritis; Reiter's syndrome; scleroderma; Sjogren's syndrome; systemic lupus erythematosus; Takayasu's arteritis; temporal arteritis; vitiligo; warm autoimmune hemolytic anemia; or Wegener's granulomatosis.

Infections

In certain embodiments, peptides arising from an infectious agent (e.g., virus, bacteria, or any pathogen) that bind to subject specific HLA alleles are identified or predicted. In certain embodiments, the infectious agent mutates to express peptides capable of binding different HLA-alleles. Thus, peptides for generating an immunological composition or vaccine require prediction of novel peptide binding to subject specific HLA alleles.

Examples of pathogenic bacteria include without limitation any one or more of (or any combination of) *Acinetobacter baumannii, Actinobacillus* sp., *Actinomycetes, Actinomyces* sp. (such as *Actinomyces israelii* and *Actinomyces naeslundii*), *Aeromonas* sp. (such as *Aeromonas hydrophila, Aeromonas veronii* biovar *sobria* (*Aeromonas sobria*), and *Aeromonas caviae*), *Anaplasma phagocytophilum, Anaplasma marginale, Alcaligenes xylosoxidans, Acinetobacter baumannii, Actinobacillus actinomycetemcomitans, Bacillus* sp. (such as *Bacillus anthracis, Bacillus cereus, Bacillus subtilis, Bacillus thuringiensis,* and *Bacillus stearothermophilus*), *Bacteroides* sp. (such as *Bacteroides fragilis*), *Bartonella* sp. (such as *Bartonella bacilliformis* and *Bartonella henselae*), *Bifidobacterium* sp., *Bordetella* sp. (such as *Bordetella pertussis, Bordetella parapertussis,* and *Bordetella bronchiseptica*), *Borrelia* sp. (such as *Borrelia recurrentis,* and *Borrelia burgdorferi*), *Brucella* sp. (such as *Brucella abortus, Brucella canis, Brucella melitensis* and *Brucella suis*), *Burkholderia* sp. (such as *Burkholderia pseudomallei* and *Burkholderia cepacia*), *Campylobacter* sp. (such as *Campylobacter jejuni, Campylobacter coli, Campylobacter lari* and *Campylobacter fetus*), *Capnocytophaga* sp., *Cardiobacterium hominis, Chlamydia trachomatis, Chlamydophila pneumoniae, Chlamydophila psittaci, Citrobacter* sp. *Coxiella burnetii, Corynebacterium* sp. (such as, *Corynebacterium diphtheriae, Corynebacterium jeikeium* and *Corynebacterium*), *Clostridium* sp. (such as *Clostridium perfringens, Clostridium difficile, Clostridium botulinum* and *Clostridium tetani*), *Eikenella corrodens, Enterobacter* sp. (such as *Enterobacter aerogenes, Enterobacter agglomerans, Enterobacter cloacae* and *Escherichia coli,* including opportunistic *Escherichia coli,* such as enterotoxigenic *E. coli,* enteroinvasive *E. coli,* enteropathogenic *E. coli,* enterohemorrhagic *E. coli,* enteroaggregative *E. coli* and uropathogenic *E. coli*) *Enterococcus* sp. (such as *Enterococcus faecalis* and *Enterococcus faecium*) *Ehrlichia* sp. (such as *Ehrlichia chaffeensis* and *Ehrlichia canis*), *Erysipelothrix rhusiopathiae, Eubacterium* sp., *Francisella tularensis, Fusobacterium nucleatum, Gardnerella vaginalis, Gemella morbillorum, Haemophilus* sp. (such as *Haemophilus influenzae, Haemophilus ducreyi, Haemophilus aegyptius, Haemophilus parainfluenzae, Haemophilus haemolyticus* and *Haemophilus parahaemolyticus*), *Helicobacter* sp. (such as *Helicobacter pylori, Helicobacter cinaedi* and *Helicobacter fennelliae*), *Kingella kingae, Klebsiella* sp. (such as *Klebsiella pneumoniae, Klebsiella granulomatis* and *Klebsiella oxytoca*), *Lactobacillus* sp., *Listeria monocytogenes, Leptospira interrogans, Legionella pneumophila, Leptospira interrogans, Peptostreptococcus* sp., *Mannheimia haemolytica, Moraxella catarrhalis, Morganella* sp., *Mobiluncus* sp., *Micrococcus* sp., *Mycobacterium* sp. (such as *Mycobacterium leprae, Mycobacterium tuberculosis, Mycobacterium paratuberculosis, Mycobacterium intracellulare, Mycobacterium avium, Mycobacterium bovis,* and *Mycobacterium marinum*), *Mycoplasma* sp. (such as *Mycoplasma pneumoniae, Mycoplasma hominis,* and *Mycoplasma genitalium*), *Nocardia* sp. (such as *Nocardia asteroides, Nocardia cyriacigeorgica* and *Nocardia brasiliensis*), *Neisseria* sp. (such as *Neisseria gonorrhoeae* and *Neisseria meningitidis*), *Pasteurella multocida, Plesiomonas shigelloides. Prevotella* sp., *Porphyromonas* sp., *Prevotella melaninogenica, Proteus* sp. (such as *Proteus vulgaris* and *Proteus mirabilis*), *Providencia* sp. (such as *Providencia alcalifaciens, Providencia rettgeri* and *Providencia stuartii*), *Pseudomonas aeruginosa, Propionibacterium acnes, Rhodococcus equi, Rickettsia* sp. (such as *Rickettsia rickettsii, Rickettsia akari* and *Rickettsia prowazekii, Orientia tsutsugamushi* (formerly: *Rickettsia tsutsugamushi*) and *Rickettsia typhi*), *Rhodococcus* sp., *Serratia marcescens, Stenotrophomonas maltophilia, Salmonella* sp. (such as *Salmonella enterica, Salmonella typhi, Salmonella paratyphi, Salmonella enteritidis, Salmonella choleraesuis* and *Salmonella typhimurium*), *Serratia* sp. (such as *Serratia marcescens* and *Serratia liquefaciens*), *Shigella* sp. (such as *Shigella dysenteriae, Shigella flexneri, Shigella boydii* and *Shigella sonnei*), *Staphylococcus* sp. (such as *Staphylococcus aureus, Staphylococcus epidermidis, Staphylococcus haemolyticus, Staphylococcus saprophyticus*), *Streptococcus* sp. (such as *Streptococcus pneumoniae* (for example chloramphenicol-resistant serotype 4 *Streptococcus pneumoniae,* spectinomycin-resistant serotype 6B *Streptococcus pneumoniae,* streptomycin-resistant serotype 9V *Streptococcus pneumoniae,* erythromycin-resistant serotype 14 *Streptococcus pneumoniae,* optochin-resistant serotype 14 *Streptococcus pneumoniae,* rifampicin-resistant serotype 18C *Streptococcus pneumoniae,* tetracycline-resistant serotype 19F *Streptococcus pneumoniae,* penicillin-resistant serotype 19F *Streptococcus pneumoniae,* and trimethoprim-resistant serotype 23F *Streptococcus pneumoniae,* chloramphenicol-resistant serotype 4 *Streptococcus pneumoniae,* spectinomycin-resistant serotype 6B *Streptococcus pneumoniae,* streptomycin-resistant serotype 9V *Streptococcus pneumoniae,* optochin-resistant serotype 14 *Streptococcus pneumoniae,* rifampicin-resistant serotype 18C *Streptococcus pneumo-* niae, penicillin-resistant serotype 19F *Streptococcus pneumoniae*, or trimethoprim-resistant serotype 23F *Streptococcus pneumoniae*), *Streptococcus agalactiae, Streptococcus mutans, Streptococcus pyogenes,* Group A streptococci, *Streptococcus pyogenes,* Group B streptococci, *Streptococcus agalactiae,* Group C streptococci, *Streptococcus anginosus, Streptococcus equisimilis,* Group D streptococci, *Streptococcus bovis,* Group F streptococci, and *Streptococcus anginosus* Group G streptococci), *Spirillum minus, Streptobacillus moniliformis, Treponema* sp. (such as *Treponema carateum, Treponema pertenue, Treponema pallidum* and *Treponema endemicum*), *Tropheryma whippelii, Ureaplasma urealyticum, Veillonella* sp., *Vibrio* sp. (such as *Vibrio cholerae, Vibrio parahemolyticus, Vibrio vulnificus, Vibrio parahaemolyticus, Vibrio vulnificus, Vibrio alginolyticus, Vibrio mimicus, Vibrio hollisae, Vibrio fluvialis, Vibrio metschnikovii, Vibrio damsela* and *Vibrio furnissii*), *Yersinia* sp. (such as *Yersinia enterocolitica, Yersinia pestis,* and *Yersinia pseudotuberculosis*) and *Xanthomonas maltophilia* among others.

Examples of fungi include without limitation any one or more of (or any combination of), *Aspergillus, Blastomyces, Candidiasis, Coccidioidomycosis, Cryptococcus neoformans, Cryptococcus gattii, Histoplasma, Mucormycosis, Pneumocystis, Sporothrix,* fungal eye infections ringwork, *Exserohilum,* and *Cladosporium.* In certain example embodiments, the fungus is a yeast. Examples of yeast include without limitation one or more of (or any combination of), *Aspergillus* species, a *Geotrichum* species, a *Saccharomyces* species, a *Hansenula* species, a *Candida* species, a *Kluyveromyces* species, a *Debaryomyces* species, a *Pichia* species, or combination thereof. In certain example embodiments, the fungus is a mold. Example molds include, but are not limited to, a *Penicillium* species, a *Cladosporium* species, a *Byssochlamys* species, or a combination thereof.

In certain example embodiments, the pathogen may be a virus. The virus may be a DNA virus, a RNA virus, or a retrovirus. Example of RNA viruses include one or more of (or any combination of) Coronaviridae virus, a Picornaviridae virus, a Caliciviridae virus, a Flaviviridae virus, a Togaviridae virus, a Bornaviridae, a Filoviridae, a Paramyxoviridae, a Pneumoviridae, a Rhabdoviridae, an Arenaviridae, a Bunyaviridae, an Orthomyxoviridae, or a Deltavirus. In certain example embodiments, the virus is Coronavirus, SARS, Poliovirus, Rhinovirus, Hepatitis A, Norwalk virus, Yellow fever virus, West Nile virus, Hepatitis C virus, Dengue fever virus, Zika virus, Rubella virus, Ross River virus, Sindbis virus, Chikungunya virus, Borna disease virus, Ebola virus, Marburg virus, Measles virus, Mumps virus, Nipah virus, Hendra virus, Newcastle disease virus, Human respiratory syncytial virus, Rabies virus, Lassa virus, Hantavirus, Crimean-Congo hemorrhagic fever virus, Influenza, or Hepatitis D virus.

In certain example embodiments, the virus may be a retrovirus. Example retroviruses include one or more of or any combination of viruses of the Genus Alpharetrovirus, Betaretrovirus, Gammaretrovirus, Deltaretrovirus, Epsilonretrovirus, Lentivirus, Spumavirus, or the Family Metaviridae, Pseudoviridae, and Retroviridae (including HIV), Hepadnaviridae (including Hepatitis B virus), and Caulimoviridae (including Cauliflower mosaic virus).

In certain example embodiments, the virus is a DNA virus. Example DNA viruses that include one or more of (or any combination of) viruses from the Family Myoviridae, Podoviridae, Siphoviridae, Alloherpesviridae, Herpesviridae (including human herpes virus, and Varicella Zoster virus), Maloca herpesviridae, Lipothrixviridae, Rudiviridae, Adenoviridae, Ampullaviridae, Ascoviridae, Asfarviridae (including African swine fever virus), Baculoviridae, Coronaviridae, Clavaviridae, Corticoviridae, Fusellovididae, Globuloviridae, Guttaviridae, Hytrosaviridae, Iridoviridae, Marseille viridae, Mimiviridae, Nudiviridae, Nimaviridae, Pandoraviridae, Papillomaviridae, Phycodnaviridae, Plasmaviridae, Polydnaviruses, Polyomaviridae (including Simian virus 40, JC virus, BK virus), Poxviridae (including Cowpox and smallpox), Sphaerolipoviridae, Tectiviridae, Turriviridae, Dinodnavirus, Salterprovirus, Rhinovirus, among others.

In certain example embodiments, the pathogen may be a protozoon. Examples of protozoa include without limitation any one or more of (or any combination of), Euglenozoa, Heterolobosea, Diplomonadida, Amoebozoa, *Blastocystis,* and Apicomplexa. Example Euglenozoa include, but are not limited to, *Trypanosoma cruzi* (Chagas disease), *T. brucei gambiense, T. brucei rhodesiense, Leishmania braziliensis, L. infantum, L. mexicana, L. major, L. tropica,* and *L. donovani.* Example Heterolobosea include, but are not limited to, *Naegleria fowleri.* Example Diplomonadida include, but are not limited to, Giardia intestinalis (*G. lamblia, G. duodenalis*). Example Amoebozoa include, but are not limited to, *Acanthamoeba castellanii, Balamuthia mandrillaris, Entamoeba histolytica.* Example *Blastocystis* include, but are not limited to, *Blastocystis hominis.* Example Apicomplexa include, but are not limited to, *Babesia microti, Cryptosporidium parvum, Cyclospora cayetanensis, Plasmodium falciparum, P. vivax, P. ovale, P. malariae,* and *Toxoplasma gondii.*

Therapeutic Compositions and Methods of Use
Vaccines and Immunological Compositions In certain embodiments, the peptides identified according to the present invention are used in a vaccine or immunological composition to treat any disease or condition described herein (e.g., tumor, autoimmunity, infection, transplant). The term "vaccine" or "immunological composition" are used interchangeably and are meant to refer in the present context to a pooled sample of one or more antigenic peptides, for example at least one, at least two, at least three, at least four, at least five, or more antigenic peptides. A "vaccine" is to be understood as including a protective vaccine, which is a composition for generating immunity for the prophylaxis and/or treatment of diseases (e.g., neoplasia/tumor). A "vaccine" is also to be understood as including a tolerizing vaccine, which is a composition for reducing immunity for the prophylaxis and/or treatment of diseases (e.g., autoimmune disease). A tolerizing vaccine may be formulated with antigenic epitopes specific for an allergen or for an autoimmunity antigen identified according to the present invention. A protective vaccine may be formulated with antigenic epitopes specific for a pathogen or for a cancer cell. Accordingly, vaccines are medicaments which comprise antigens and are intended to be used in humans or animals for generating specific defense and protective substance by vaccination. A "vaccine composition" can include a pharmaceutically acceptable excipient, carrier or diluent.

The vaccine may include one or more peptides identified according to the present invention. For example, 1 to 10 peptides. Ranges provided herein are understood to be shorthand for all of the values within the range. For example, a range of 1 to 50 is understood to include any number, combination of numbers, or sub-range from the group consisting of 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50. With respect to sub-ranges, "nested sub-ranges"

that extend from either end point of the range are specifically contemplated. For example, a nested sub-range of an exemplary range of 1 to 50 may comprise 1 to 10, 1 to 20, 1 to 30, and 1 to 40 in one direction, or 50 to 40, 50 to 30, 50 to 20, and 50 to 10 in the other direction.

As used herein, the terms "prevent," "preventing," "prevention," "prophylactic treatment," and the like, refer to reducing the probability of developing a disease or condition in a subject, who does not have, but is at risk of or susceptible to developing a disease or condition.

The vaccine of the present invention may ameliorate a disease as described herein. By "ameliorate" is meant decrease, suppress, attenuate, diminish, arrest, or stabilize the development or progression of a disease (e.g., a neoplasia, tumor, autoimmunity, infection, etc.).

The terms "treat," "treated," "treating," "treatment," and the like are meant to refer to reducing or ameliorating a disorder and/or symptoms associated therewith (e.g., a neoplasia or tumor). "Treating" may refer to administration of the therapy to a subject after the onset, or suspected onset, of a cancer. "Treating" includes the concepts of "alleviating", which refers to lessening the frequency of occurrence or recurrence, or the severity, of any symptoms or other ill effects related to a cancer and/or the side effects associated with cancer therapy. The term "treating" also encompasses the concept of "managing" which refers to reducing the severity of a particular disease or disorder in a patient or delaying its recurrence, e.g., lengthening the period of remission in a patient who had suffered from the disease. It is appreciated that, although not precluded, treating a disorder or condition does not require that the disorder, condition, or symptoms associated therewith be completely eliminated.

The term "therapeutic effect" refers to some extent of relief of one or more of the symptoms of a disorder (e.g., a neoplasia or tumor) or its associated pathology. "Therapeutically effective amount" as used herein refers to an amount of an agent which is effective, upon single or multiple dose administration to the cell or subject, in prolonging the survivability of the patient with such a disorder, reducing one or more signs or symptoms of the disorder, preventing or delaying, and the like beyond that expected in the absence of such treatment. "Therapeutically effective amount" is intended to qualify the amount required to achieve a therapeutic effect. A physician or veterinarian having ordinary skill in the art can readily determine and prescribe the "therapeutically effective amount" (e.g., ED50) of the pharmaceutical composition required. For example, the physician or veterinarian could start doses of the compounds of the invention employed in a pharmaceutical composition at levels lower than that required in order to achieve the desired therapeutic effect and gradually increase the dosage until the desired effect is achieved.

In certain embodiments, a protective vaccine is used to treat cancer. Additional examples of cancers and cancer conditions that can be treated with the therapy of this document include, but are not limited to a patient in need thereof that has been diagnosed as having cancer, or at risk of developing cancer. The subject may have a solid tumor such as breast, ovarian, prostate, lung, kidney, gastric, colon, testicular, head and neck, pancreas, brain, melanoma, and other tumors of tissue organs and hematological tumors, such as lymphomas and leukemias, including acute myelogenous leukemia, chronic myelogenous leukemia, chronic lymphocytic leukemia, T cell lymphocytic leukemia, and B cell lymphomas, tumors of the brain and central nervous system (e.g., tumors of the meninges, brain, spinal cord, cranial nerves and other parts of the CNS, such as glioblastomas or medulla blastomas); head and/or neck cancer, breast tumors, tumors of the circulatory system (e.g., heart, mediastinum and pleura, and other intrathoracic organs, vascular tumors, and tumor-associated vascular tissue); tumors of the blood and lymphatic system (e.g., Hodgkin's disease, Non-Hodgkin's disease lymphoma, Burkitt's lymphoma, AIDS-related lymphomas, malignant immunoproliferative diseases, multiple myeloma, and malignant plasma cell neoplasms, lymphoid leukemia, myeloid leukemia, acute or chronic lymphocytic leukemia, monocytic leukemia, other leukemias of specific cell type, leukemia of unspecified cell type, unspecified malignant neoplasms of lymphoid, hematopoietic and related tissues, such as diffuse large cell lymphoma, T cell lymphoma or cutaneous T cell lymphoma); tumors of the excretory system (e.g., kidney, renal pelvis, ureter, bladder, and other urinary organs); tumors of the gastrointestinal tract (e.g., esophagus, stomach, small intestine, colon, colorectal, rectosigmoid junction, rectum, anus, and anal canal); tumors involving the liver and intrahepatic bile ducts, gall bladder, and other parts of the biliary tract, pancreas, and other digestive organs; tumors of the oral cavity (e.g., lip, tongue, gum, floor of mouth, palate, parotid gland, salivary glands, tonsil, oropharynx, nasopharynx, pyriform sinus, hypopharynx, and other sites of the oral cavity); tumors of the reproductive system (e.g., vulva, vagina, Cervix uteri, uterus, ovary, and other sites associated with female genital organs, placenta, penis, prostate, testis, and other sites associated with male genital organs); tumors of the respiratory tract (e.g., nasal cavity, middle ear, accessory sinuses, larynx, trachea, bronchus and lung, such as small cell lung cancer and non-small cell lung cancer); tumors of the skeletal system (e.g., bone and articular cartilage of limbs, bone articular cartilage and other sites); tumors of the skin (e.g., malignant melanoma of the skin, non-melanoma skin cancer, basal cell carcinoma of skin, squamous cell carcinoma of skin, mesothelioma, Kaposi's sarcoma); and tumors involving other tissues including peripheral nerves and autonomic nervous system, connective and soft tissue, retroperitoneum and peritoneum, eye, thyroid, adrenal gland, and other endocrine glands and related structures, secondary and unspecified malignant neoplasms of lymph nodes, secondary malignant neoplasm of respiratory and digestive systems and secondary malignant neoplasm of other sites. Thus the population of subjects described herein may be suffering from one of the above cancer types. In other embodiments, the population of subjects may be all subjects suffering from solid tumors, or all subjects suffering from liquid tumors.

Of special interest is the treatment of Non-Hodgkin's Lymphoma (NHL), clear cell Renal Cell Carcinoma (ccRCC), metastatic melanoma, sarcoma, leukemia or a cancer of the bladder, colon, brain, breast, head and neck, endometrium, lung, ovary, pancreas or prostate. In certain embodiments, the melanoma is high risk melanoma.

Cancers that can be treated using the therapy described herein may include among others cases which are refractory to treatment with other chemotherapeutics. The term "refractory, as used herein refers to a cancer (and/or metastases thereof), which shows no or only weak antiproliferative response (e.g., no or only weak inhibition of tumor growth) after treatment with another chemotherapeutic agent. These are cancers that cannot be treated satisfactorily with other chemotherapeutics. Refractory cancers encompass not only (i) cancers where one or more chemotherapeutics have already failed during treatment of a patient, but also (ii) cancers that can be shown to be refractory by other means, e.g., biopsy and culture in the presence of chemotherapeutics.

The therapy described herein is also applicable to the treatment of patients in need thereof who have not been previously treated.

The therapy described herein is also applicable where the subject has no detectable neoplasia but is at high risk for disease recurrence.

Also of special interest is the treatment of patients in need thereof who have undergone Autologous Hematopoietic Stem Cell Transplant (AHSCT), and in particular patients who demonstrate residual disease after undergoing AHSCT. The post-AHSCT setting is characterized by a low volume of residual disease, the infusion of immune cells to a situation of homeostatic expansion, and the absence of any standard relapse-delaying therapy. These features provide a unique opportunity to use the claimed neoplastic vaccine or immunogenic composition compositions to delay disease relapse.

In certain embodiments, the vaccine as described herein can promote tolerance or dampen an inappropriate, unwanted, or undesirable immune response, thereby permitting treatment of autoimmune disease, as described herein, and/or conditions associated with transplants (e.g., graft vs. host disease). Immune tolerance, or immunological tolerance, or immunotolerance, is a state of unresponsiveness of the immune system to substances or tissue that have the capacity to elicit an immune response in given organism. Immune recognition of non-self-antigens typically complicates transplantation and engrafting of foreign tissue from an organism of the same species (allografts), resulting in graft reaction. In certain embodiments, a state of tolerance can be induced, either by previous exposure to the antigen of the donor in a manner that causes immune tolerance rather than sensitization in the recipient. Antigen-specific immune tolerance (ASI) is a promising approach to treat or prevent autoimmune disorders, however, there is a need to identify proper peptides (see, e.g., Shakya and Nandakumar, Antigen-Specific Tolerization and Targeted Delivery as Therapeutic Strategies for Autoimmune Diseases. Trends Biotechnol. 2018 July; 36(7):686-699; and Pozsgay et al., Antigen-specific immunotherapies in rheumatic diseases. Nat Rev Rheumatol. 2017 September; 13(9):525-537). In certain embodiments, approaches include the use of tolerizing peptides coupled to MHC constructs and/or nanocompounds, tolerizing dendritic cells (see, e.g., Wei et al., Development and Functional Characterization of Murine Tolerogenic Dendritic Cells. J Vis Exp. 2018 May 18; (135)), and antigen-specific vaccines.

The present invention is based, at least in part, on the ability to present the immune system of the patient with one or more HLA allele specific peptides. In certain embodiments, the immune system of the patient is presented with a pool of tumor specific neoantigens. The application further provides novel neoantigenic peptides identified by the methods provided herein. Accordingly, provided herein are immunogenic compositions comprising a peptide having a sequence selected from $XLXX_4XX_6X_7XX_9$ (SEQ ID NO:30); wherein one or more of $X_4$ is E or D, $X_6$ is L, V, or I, $X_7$ is I, V, or A, and X is L or V, and wherein X is any amino acid; $XLXDXXX_7XX_9$ (SEQ ID NO:31), wherein one or more of $X_7$ is L and $X_9$ is Y or F, and wherein X is any amino acid; $XX_2X_3X_4XXXXY$ (SEQ ID NO:32), wherein one or more of $X_2$ is T, S, or L, $X_3$ is D or E and $X_7$ is I, V, or A, and wherein X is any amino acid; $XLXXXX_6XXX_9$ (SEQ ID NO:33); wherein one or more of $X_6$ is L or V and $X_9$ is V or L, and wherein X is any amino acid; $XLXX_4XX_6XXX_9$ (SEQ ID NO:34), wherein one or more of $X_4$ is E or D, $X_6$ is L or V and $X_9$ is V or L, and wherein X is any amino acid; $XLDXXXXX_9$ (SEQ ID NO:35), wherein $X_9$ is L or V, and wherein X is any amino acid; $XXXXXXLXX_9$ (SEQ ID NO:36), wherein one or more of $X_2$ is L or V and $X_9$ is K, Y or R, and wherein X is any amino acid; $XiX_2XXXXXXR$ (SEQ ID NO:37), wherein one or more of $X_1$ is R or A and $X_2$ is V or L, and wherein X is any amino acid; $EX_2XXXXXXX_9$ (SEQ ID NO:38), wherein one or more of $X_2$ is V, T, or A and X is V or L, and wherein X is any amino acid; $XX_2XRXXXXX_9$ (SEQ ID NO:39), wherein one or more of $X_2$ is P or A and $X_9$ is Y, F, or L, and wherein X is any amino acid; $X_1EXXLXXXX_9$ (SEQ ID NO:40), wherein one or more of $X_1$ is A or E and $X_9$ is F, W, or L, and wherein X is any amino acid; $X_1EXXLXLXX_9$ (SEQ ID NO:41), wherein one or more of $X_1$ is A or E and $X_9$ is F, W, or L, and wherein X is any amino acid; $DX_2XXXXXXX_9$ (SEQ ID NO:42), wherein one or more of $X_2$ is P or A and $X_9$ is I, V, or L, and wherein X is any amino acid; and $X_1YXXXXXXX_9$ (SEQ ID NO:43), wherein one or more of $X_1$ is M, W, or V and $X_9$ is F or L, and wherein X is any amino acid.

Producing Antigenic Peptides

One of skill in the art from this disclosure and the knowledge in the art will appreciate that there are a variety of ways in which to produce such tumor specific neoantigens or any other antigens. In general, such tumor specific neoantigens or antigens may be produced either in vitro or in vivo. Tumor specific neoantigens or antigens may be produced in vitro as peptides or polypeptides, which may then be formulated into a neoplasia vaccine or immunogenic composition and administered to a subject. As described in further detail herein, such in vitro production may occur by a variety of methods known to one of skill in the art such as, for example, peptide synthesis or expression of a peptide/polypeptide from a DNA or RNA molecule in any of a variety of bacterial, eukaryotic, or viral recombinant expression systems, followed by purification of the expressed peptide/polypeptide. Alternatively, tumor specific neoantigens or antigens may be produced in vivo by introducing molecules (e.g., DNA, RNA, viral expression systems, and the like) that encode tumor specific neoantigens or antigens into a subject, whereupon the encoded tumor specific neoantigens or antigens are expressed. The methods of in vitro and in vivo production of neoantigens or antigens is also further described herein as it relates to pharmaceutical compositions and methods of delivery of the therapy. By an isolated "polypeptide" or "peptide" is meant a polypeptide that has been separated from components that naturally accompany it. Typically, the polypeptide is isolated when it is at least 60%, by weight, free from the proteins and naturally-occurring organic molecules with which it is naturally associated. Preferably, the preparation is at least 75%, more preferably at least 90%, and most preferably at least 99%, by weight, a polypeptide. An isolated polypeptide may be obtained, for example, by extraction from a natural source, by expression of a recombinant nucleic acid encoding such a polypeptide; or by chemically synthesizing the protein. Purity can be measured by any appropriate method, for example, column chromatography, polyacrylamide gel electrophoresis, or by HPLC analysis.

In certain embodiments, the present invention includes modified neoantigenic or antigenic peptides. As used herein in reference to peptides, the terms "modified", "modification" and the like refer to one or more changes that enhance a desired property of the antigenic peptide, where the change does not alter the primary amino acid sequence of the antigenic peptide. "Modification" includes a covalent chemical modification that does not alter the primary amino acid sequence of the neoantigenic peptide itself. Such desired properties include, for example, prolonging the in vivo half-life, increasing the stability, reducing the clearance, altering the immunogenicity or allergenicity, enabling the raising of particular antibodies, cellular targeting, antigen uptake, antigen processing, MHC affinity, MHC stability, or antigen presentation. Changes to an antigenic peptide that may be carried out include, but are not limited to, conjugation to a carrier protein, conjugation to a ligand, conjugation to an antibody, PEGylation, polysialylation HESylation, recombinant PEG mimetics, Fc fusion, albumin fusion, nanoparticle attachment, nanoparticulate encapsulation, cholesterol fusion, iron fusion, acylation, amidation, glycosylation, side chain oxidation, phosphorylation, biotinylation, the addition of a surface active material, the addition of amino acid mimetics, or the addition of unnatural amino acids. Modified peptides also include analogs. By "analog" is meant a molecule that is not identical, but has analogous functional or structural features. For example, a tumor specific neo-antigen polypeptide analog retains the biological activity of a corresponding naturally-occurring tumor specific neo-antigen polypeptide, while having certain biochemical modifications that enhance the analog's function relative to a naturally-occurring polypeptide. Such biochemical modifications could increase the analog's protease resistance, membrane permeability, or half-life, without altering, for example, ligand binding. An analog may include an unnatural amino acid.

The recitation of a listing of chemical groups in any definition of a variable herein includes definitions of that variable as any single group or combination of listed groups. The recitation of an embodiment for a variable or aspect herein includes that embodiment as any single embodiment or in combination with any other embodiments or portions thereof.

Modified peptides may include a spacer or a linker. The terms "spacer" or "linker" as used in reference to a fusion protein refers to a peptide that joins the proteins comprising a fusion protein. Generally, a spacer has no specific biological activity other than to join or to preserve some minimum distance or other spatial relationship between the proteins or RNA sequences. However, in certain embodiments, the constituent amino acids of a spacer may be selected to influence some property of the molecule such as the folding, net charge, or hydrophobicity of the molecule.

Suitable linkers for use in an embodiment of the present invention are well known to those of skill in the art and include, but are not limited to, straight or branched-chain carbon linkers, heterocyclic carbon linkers, or peptide linkers. The linker is used to separate two neoantigenic peptides by a distance sufficient to ensure that, in a preferred embodiment, each neoantigenic peptide properly folds. Preferred peptide linker sequences adopt a flexible extended conformation and do not exhibit a propensity for developing an ordered secondary structure. Typical amino acids in flexible protein regions include Gly, Asn and Ser. Virtually any permutation of amino acid sequences containing Gly, Asn and Ser would be expected to satisfy the above criteria for a linker sequence. Other near neutral amino acids, such as Thr and Ala, also may be used in the linker sequence. Still other amino acid sequences that may be used as linkers are disclosed in Maratea et al. (1985), Gene 40: 39-46; Murphy et al. (1986) Proc. Nat'l. Acad. Sci. USA 83: 8258-62; U.S. Pat. Nos. 4,935,233; and 4,751,180.

The clinical effectiveness of protein therapeutics is often limited by short plasma half-life and susceptibility to protease degradation. Studies of various therapeutic proteins (e.g., filgrastim) have shown that such difficulties may be overcome by various modifications, including conjugating or linking the polypeptide sequence to any of a variety of non-proteinaceous polymers, e.g., polyethylene glycol (PEG), polypropylene glycol, or polyoxyalkylenes (see, for example, typically via a linking moiety covalently bound to both the protein and the nonproteinaceous polymer, e.g., a PEG). Such PEG-conjugated biomolecules have been shown to possess clinically useful properties, including better physical and thermal stability, protection against susceptibility to enzymatic degradation, increased solubility, longer in vivo circulating half-life and decreased clearance, reduced immunogenicity and antigenicity, and reduced toxicity.

PEGs suitable for conjugation to a polypeptide sequence are generally soluble in water at room temperature, and have the general formula $R(O-CH_2-CH_2)_nO-R$, where R is hydrogen or a protective group such as an alkyl or an alkanol group, and where n is an integer from 1 to 1000. When R is a protective group, it generally has from 1 to 8 carbons. The PEG conjugated to the polypeptide sequence can be linear or branched. Branched PEG derivatives, "star-PEGs" and multi-armed PEGs are contemplated by the present disclosure. A molecular weight of the PEG used in the present disclosure is not restricted to any particular range, but certain embodiments have a molecular weight between 500 and 20,000 while other embodiments have a molecular weight between 4,000 and 10,000. The present disclosure also contemplates compositions of conjugates wherein the PEGs have different n values and thus the various different PEGs are present in specific ratios. For example, some compositions comprise a mixture of conjugates where n=1, 2, 3 and 4. In some compositions, the percentage of conjugates where n=1 is 18-25%, the percentage of conjugates where n=2 is 50-66%, the percentage of conjugates where n=3 is 12-16%, and the percentage of conjugates where n=4 is up to 5%. Such compositions can be produced by reaction conditions and purification methods know in the art. For example, cation exchange chromatography may be used to separate conjugates, and a fraction is then identified which contains the conjugate having, for example, the desired number of PEGs attached, purified free from unmodified protein sequences and from conjugates having other numbers of PEGs attached.

PEG may be bound to a polypeptide of the present disclosure via a terminal reactive group (a "spacer"). The spacer is, for example, a terminal reactive group which mediates a bond between the free amino or carboxyl groups of one or more of the polypeptide sequences and polyethylene glycol. The PEG having the spacer which may be bound to the free amino group includes N-hydroxysuccinimide polyethylene glycol which may be prepared by activating succinic acid ester of polyethylene glycol with N-hydroxysuccinimide. Another activated polyethylene glycol which may be bound to a free amino group is 2,4-bis(0-methoxypolyethyleneglycol)-6-chloro-s-triazine which may be prepared by reacting polyethylene glycol monomethyl ether with cyanuric chloride. The activated polyethylene glycol which is bound to the free carboxyl group includes polyoxyethylenediamine.

Conjugation of one or more of the polypeptide sequences of the present disclosure to PEG having a spacer may be carried out by various conventional methods. For example, the conjugation reaction can be carried out in solution at a pH of from 5 to 10, at temperature from 4° C. to room temperature, for 30 minutes to 20 hours, utilizing a molar ratio of reagent to protein of from 4:1 to 30:1. Reaction conditions may be selected to direct the reaction towards producing predominantly a desired degree of substitution. In general, low temperature, low pH (e.g., pH=5), and short reaction time tend to decrease the number of PEGs attached, whereas high temperature, neutral to high pH (e.g., pH>7), and longer reaction time tend to increase the number of PEGs attached. Various means known in the art may be used to terminate the reaction. In some embodiments the reaction is terminated by acidifying the reaction mixture and freezing at, e.g., −20° C.

The present disclosure also contemplates the use of PEG Mimetics. Recombinant PEG mimetics have been developed that retain the attributes of PEG (e.g., enhanced serum half-life) while conferring several additional advantageous properties. By way of example, simple polypeptide chains (comprising, for example, Ala, Glu, Gly, Pro, Ser and Thr) capable of forming an extended conformation similar to PEG can be produced recombinantly already fused to the peptide or protein drug of interest (e.g., Amunix' XTEN technology; Mountain View, CA). This obviates the need for an additional conjugation step during the manufacturing process. Moreover, established molecular biology techniques enable control of the side chain composition of the polypeptide chains, allowing optimization of immunogenicity and manufacturing properties.

For purposes of the present disclosure, "glycosylation" is meant to broadly refer to the enzymatic process that attaches glycans to proteins, lipids or other organic molecules. The use of the term "glycosylation" in conjunction with the present disclosure is generally intended to mean adding or deleting one or more carbohydrate moieties (either by removing the underlying glycosylation site or by deleting the glycosylation by chemical and/or enzymatic means), and/or adding one or more glycosylation sites that may or may not be present in the native sequence. In addition, the phrase includes qualitative changes in the glycosylation of the native proteins involving a change in the nature and proportions of the various carbohydrate moieties present. Glycosylation can dramatically affect the physical properties of proteins and can also be important in protein stability, secretion, and subcellular localization. Proper glycosylation can be essential for biological activity. In fact, some genes from eucaryotic organisms, when expressed in bacteria (e.g., *E. coli*) which lack cellular processes for glycosylating proteins, yield proteins that are recovered with little or no activity by virtue of their lack of glycosylation.

Addition of glycosylation sites can be accomplished by altering the amino acid sequence. The alteration to the polypeptide may be made, for example, by the addition of, or substitution by, one or more serine or threonine residues (for O-linked glycosylation sites) or asparagine residues (for N-linked glycosylation sites). The structures of N-linked and O-linked oligosaccharides and the sugar residues found in each type may be different. One type of sugar that is commonly found on both is N-acetylneuraminic acid (hereafter referred to as sialic acid). Sialic acid is usually the terminal residue of both N-linked and O-linked oligosaccharides and, by virtue of its negative charge, may confer acidic properties to the glycoprotein. A particular embodiment of the present disclosure comprises the generation and use of N-glycosylation variants.

The polypeptide sequences of the present disclosure may optionally be altered through changes at the DNA level, particularly by mutating the DNA encoding the polypeptide at preselected bases such that codons are generated that will translate into the desired amino acids. Another means of increasing the number of carbohydrate moieties on the polypeptide is by chemical or enzymatic coupling of glycosides to the polypeptide.

Removal of carbohydrates may be accomplished chemically or enzymatically, or by substitution of codons encoding amino acid residues that are glycosylated. Chemical deglycosylation techniques are known, and enzymatic cleavage of carbohydrate moieties on polypeptides can be achieved by the use of a variety of endo- and exo-glycosidases.

Dihydrofolate reductase (DHFR)—deficient Chinese Hamster Ovary (CHO) cells are a commonly used host cell for the production of recombinant glycoproteins. These cells do not express the enzyme beta-galactoside alpha-2,6-sialyltransferase and therefore do not add sialic acid in the alpha-2,6 linkage to N-linked oligosaccharides of glycoproteins produced in these cells.

The present disclosure also contemplates the use of polysialylation, the conjugation of peptides and proteins to the naturally occurring, biodegradable a-(2→8) linked polysialic acid ("PSA") in order to improve their stability and in vivo pharmacokinetics. PSA is a biodegradable, non-toxic natural polymer that is highly hydrophilic, giving it a high apparent molecular weight in the blood which increases its serum half-life. In addition, polysialylation of a range of peptide and protein therapeutics has led to markedly reduced proteolysis, retention of activity in vivo activity, and reduction in immunogenicity and antigenicity (see, e.g., G. Gregoriadis et al., Int. J. Pharmaceutics 300(1-2): 125-30). As with modifications with other conjugates (e.g., PEG), various techniques for site-specific polysialylation are available (see, e.g., T. Lindhout et al., PNAS 108(18)7397-7402 (2011)).

Additional suitable components and molecules for conjugation include, for example, thyroglobulin; albumins such as human serum albumin (HAS); tetanus toxoid; Diphtheria toxoid; polyamino acids such as poly(D-lysine:D-glutamic acid); VP6 polypeptides of rotaviruses; influenza virus hemagglutinin, influenza virus nucleoprotein; Keyhole Limpet Hemocyanin (KLH); and hepatitis B virus core protein and surface antigen; or any combination of the foregoing.

Fusion of albumin to one or more polypeptides of the present disclosure can, for example, be achieved by genetic manipulation, such that the DNA coding for HSA, or a fragment thereof, is joined to the DNA coding for the one or more polypeptide sequences. Thereafter, a suitable host can be transformed or transfected with the fused nucleotide sequences in the form of, for example, a suitable plasmid, so as to express a fusion polypeptide. The expression may be effected in vitro from, for example, prokaryotic or eukaryotic cells, or in vivo from, for example, a transgenic organism. In some embodiments of the present disclosure, the expression of the fusion protein is performed in mammalian cell lines, for example, CHO cell lines. Transformation is used broadly herein to refer to the genetic alteration of a cell resulting from the direct uptake, incorporation and expression of exogenous genetic material (exogenous DNA) from its surroundings and taken up through the cell membrane(s). Transformation occurs naturally in some species of bacteria, but it can also be effected by artificial means in other cells.

Furthermore, albumin itself may be modified to extend its circulating half-life. Fusion of the modified albumin to one or more Polypeptides can be attained by the genetic manipulation techniques described above or by chemical conjugation; the resulting fusion molecule has a half-life that exceeds that of fusions with non-modified albumin. (See WO2011/051489).

Several albumin—binding strategies have been developed as alternatives for direct fusion, including albumin binding through a conjugated fatty acid chain (acylation). Because serum albumin is a transport protein for fatty acids, these natural ligands with albumin-binding activity have been used for half-life extension of small protein therapeutics. For example, insulin detemir (LEVEMIR), an approved product for diabetes, comprises a myristyl chain conjugated to a genetically-modified insulin, resulting in a long-acting insulin analog.

Another type of modification is to conjugate (e.g., link) one or more additional components or molecules at the N- and/or C-terminus of a polypeptide sequence, such as another protein (e.g., a protein having an amino acid sequence heterologous to the subject protein), or a carrier molecule. Thus, an exemplary polypeptide sequence can be provided as a conjugate with another component or molecule. A conjugate modification may result in a polypeptide sequence that retains activity with an additional or complementary function or activity of the second molecule. For example, a polypeptide sequence may be conjugated to a molecule, e.g., to facilitate solubility, storage, in vivo or shelf half-life or stability, reduction in immunogenicity, delayed or controlled release in vivo, etc. Other functions or activities include a conjugate that reduces toxicity relative to an unconjugated polypeptide sequence, a conjugate that targets a type of cell or organ more efficiently than an unconjugated polypeptide sequence, or a drug to further counter the causes or effects associated with a disorder or disease as set forth herein (e.g., diabetes).

A Polypeptide may also be conjugated to large, slowly metabolized macromolecules such as proteins; polysaccharides, such as sepharose, agarose, cellulose, cellulose beads; polymeric amino acids such as polyglutamic acid, polylysine; amino acid copolymers; inactivated virus particles; inactivated bacterial toxins such as toxoid from diphtheria, tetanus, cholera, leukotoxin molecules; inactivated bacteria; and dendritic cells.

Additional candidate components and molecules for conjugation include those suitable for isolation or purification. Particular non-limiting examples include binding molecules, such as biotin (biotin-avidin specific binding pair), an antibody, a receptor, a ligand, a lectin, or molecules that comprise a solid support, including, for example, plastic or polystyrene beads, plates or beads, magnetic beads, test strips, and membranes.

Purification methods such as cation exchange chromatography may be used to separate conjugates by charge difference, which effectively separates conjugates into their various molecular weights. For example, the cation exchange column can be loaded and then washed with ~20 mM sodium acetate, pH ~4, and then eluted with a linear (0 M to 0.5 M) NaCl gradient buffered at a pH from about 3 to 5.5, e.g., at pH ~4.5. The content of the fractions obtained by cation exchange chromatography may be identified by molecular weight using conventional methods, for example, mass spectroscopy, SDS-PAGE, or other known methods for separating molecular entities by molecular weight.

In certain embodiments, the amino- or carboxyl-terminus of a polypeptide sequence of the present disclosure can be fused with an immunoglobulin Fc region (e.g., human Fc) to form a fusion conjugate (or fusion molecule). Fc fusion conjugates have been shown to increase the systemic half-life of biopharmaceuticals, and thus the biopharmaceutical product may require less frequent administration. Fc binds to the neonatal Fc receptor (FcRn) in endothelial cells that line the blood vessels, and, upon binding, the Fc fusion molecule is protected from degradation and re-released into the circulation, keeping the molecule in circulation longer. This Fc binding is believed to be the mechanism by which endogenous IgG retains its long plasma half-life. More recent Fc-fusion technology links a single copy of a biopharmaceutical to the Fc region of an antibody to optimize the pharmacokinetic and pharmacodynamic properties of the biopharmaceutical as compared to traditional Fc-fusion conjugates.

The present disclosure contemplates the use of other modifications, currently known or developed in the future, of the Polypeptides to improve one or more properties. One such method for prolonging the circulation half-life, increasing the stability, reducing the clearance, or altering the immunogenicity or allergenicity of a polypeptide of the present disclosure involves modification of the polypeptide sequences by hesylation, which utilizes hydroxyethyl starch derivatives linked to other molecules in order to modify the molecule's characteristics. Various aspects of hesylation are described in, for example, U.S. Patent Appln. Nos. 2007/0134197 and 2006/0258607.

In Vitro Peptide/Polypeptide Synthesis

Proteins or peptides may be made by any technique known to those of skill in the art, including the expression of proteins, polypeptides or peptides through standard molecular biological techniques, the isolation of proteins or peptides from natural sources, in vitro translation, or the chemical synthesis of proteins or peptides. The nucleotide and protein, polypeptide and peptide sequences corresponding to various genes have been previously disclosed, and may be found at computerized databases known to those of ordinary skill in the art. One such database is the National Center for Biotechnology Information's Genbank and GenPept databases located at the National Institutes of Health website. The coding regions for known genes may be amplified and/or expressed using the techniques disclosed herein or as would be known to those of ordinary skill in the art. Alternatively, various commercial preparations of proteins, polypeptides and peptides are known to those of skill in the art.

Peptides can be readily synthesized chemically utilizing reagents that are free of contaminating bacterial or animal substances (Merrifield R B: Solid phase peptide synthesis. I. The synthesis of a tetrapeptide. J. Am. Chem. Soc. 85:2149-54, 1963). In certain embodiments, neoantigenic peptides are prepared by (1) parallel solid-phase synthesis on multichannel instruments using uniform synthesis and cleavage conditions; (2) purification over a RP-HPLC column with column stripping; and re-washing, but not replacement, between peptides; followed by (3) analysis with a limited set of the most informative assays. The Good Manufacturing Practices (GMP) footprint can be defined around the set of peptides for an individual patient, thus requiring suite changeover procedures only between syntheses of peptides for different patients.

Alternatively, a nucleic acid (e.g., a polynucleotide) encoding a neoantigenic peptide of the invention may be used to produce the neoantigenic peptide in vitro. The polynucleotide may be, e.g., DNA, cDNA, PNA, CNA, RNA, either single- and/or double-stranded, or native or stabilized forms of polynucleotides, such as e.g. polynucleotides with a phosphorothioate backbone, or combinations thereof and it may or may not contain introns so long as it codes for the peptide. In one embodiment in vitro translation is used to produce the peptide. Many exemplary systems exist that one skilled in the art could utilize (e.g., Retic Lysate IVT Kit, Life Technologies, Waltham, MA).

An expression vector capable of expressing a polypeptide can also be prepared. Expression vectors for different cell types are well known in the art and can be selected without undue experimentation. Generally, the DNA is inserted into an expression vector, such as a plasmid, in proper orientation and correct reading frame for expression. If necessary, the DNA may be linked to the appropriate transcriptional and translational regulatory control nucleotide sequences recognized by the desired host (e.g., bacteria), although such controls are generally available in the expression vector. The vector is then introduced into the host bacteria for cloning using standard techniques (see, e.g., Sambrook et al. (1989) Molecular Cloning, A Laboratory Manual, Cold Spring Harbor Laboratory, Cold Spring Harbor, N.Y.).

Expression vectors comprising the isolated polynucleotides, as well as host cells containing the expression vectors, are also contemplated. The neoantigenic peptides may be provided in the form of RNA or cDNA molecules encoding the desired neoantigenic peptides. One or more neoantigenic peptides of the invention may be encoded by a single expression vector.

The term "polynucleotide encoding a polypeptide" encompasses a polynucleotide which includes only coding sequences for the polypeptide as well as a polynucleotide which includes additional coding and/or non-coding sequences. Polynucleotides can be in the form of RNA or in the form of DNA. DNA includes cDNA, genomic DNA, and synthetic DNA; and can be double-stranded or single-stranded, and if single stranded can be the coding strand or non-coding (anti-sense) strand.

In embodiments, the polynucleotides may comprise the coding sequence for the tumor specific neoantigenic peptide fused in the same reading frame to a polynucleotide which aids, for example, in expression and/or secretion of a polypeptide from a host cell (e.g., a leader sequence which functions as a secretory sequence for controlling transport of a polypeptide from the cell). The polypeptide having a leader sequence is a preprotein and can have the leader sequence cleaved by the host cell to form the mature form of the polypeptide.

In embodiments, the polynucleotides can comprise the coding sequence for the tumor specific neoantigenic peptide fused in the same reading frame to a marker sequence that allows, for example, for purification of the encoded polypeptide, which may then be incorporated into the personalized neoplasia vaccine or immunogenic composition. For example, the marker sequence can be a hexa-histidine tag supplied by a pQE-9 vector to provide for purification of the mature polypeptide fused to the marker in the case of a bacterial host, or the marker sequence can be a hemagglutinin (HA) tag derived from the influenza hemagglutinin protein when a mammalian host (e.g., COS-7 cells) is used. Additional tags include, but are not limited to, Calmodulin tags, FLAG tags, Myc tags, S tags, SBP tags, Softag 1, Softag 3, V5 tag, Xpress tag, Isopeptag, SpyTag, Biotin Carboxyl Carrier Protein (BCCP) tags, GST tags, fluorescent protein tags (e.g., green fluorescent protein tags), maltose binding protein tags, Nus tags, Strep-tag, thioredoxin tag, TC tag, Ty tag, and the like.

In embodiments, the polynucleotides may comprise the coding sequence for one or more of the tumor specific neoantigenic peptides fused in the same reading frame to create a single concatamerized neoantigenic peptide construct capable of producing multiple neoantigenic peptides.

In certain embodiments, isolated nucleic acid molecules having a nucleotide sequence at least 60% identical, at least 65% identical, at least 70% identical, at least 75% identical, at least 80% identical, at least 85% identical, at least 90% identical, at least 95% identical, or at least 96%, 97%, 98% or 99% identical to a polynucleotide encoding a tumor specific neoantigenic peptide of the present invention, can be provided. By a polynucleotide having a nucleotide sequence at least, for example, 95% "identical" to a reference nucleotide sequence is intended that the nucleotide sequence of the polynucleotide is identical to the reference sequence except that the polynucleotide sequence can include up to five point mutations per each 100 nucleotides of the reference nucleotide sequence. In other words, to obtain a polynucleotide having a nucleotide sequence at least 95% identical to a reference nucleotide sequence, up to 5% of the nucleotides in the reference sequence can be deleted or substituted with another nucleotide, or a number of nucleotides up to 5% of the total nucleotides in the reference sequence can be inserted into the reference sequence. These mutations of the reference sequence can occur at the amino- or carboxy-terminal positions of the reference nucleotide sequence or anywhere between those terminal positions, interspersed either individually among nucleotides in the reference sequence or in one or more contiguous groups within the reference sequence.

As a practical matter, whether any particular nucleic acid molecule is at least 80% identical, at least 85% identical, at least 90% identical, and in some embodiments, at least 95%, 96%, 97%, 98%, or 99% identical to a reference sequence can be determined conventionally using known computer programs such as the Bestfit program (Wisconsin Sequence Analysis Package, Version 8 for Unix, Genetics Computer Group, University Research Park, 575 Science Drive, Madison, WI 53711). Bestfit uses the local homology algorithm of Smith and Waterman, Advances in Applied Mathematics 2:482-489 (1981), to find the best segment of homology between two sequences. When using Bestfit or any other sequence alignment program to determine whether a particular sequence is, for instance, 95% identical to a reference sequence according to the present invention, the parameters are set such that the percentage of identity is calculated over the full length of the reference nucleotide sequence and that gaps in homology of up to 5%>of the total number of nucleotides in the reference sequence are allowed.

The isolated tumor specific neoantigenic peptides described herein can be produced in vitro (e.g., in the laboratory) by any suitable method known in the art. Such methods range from direct protein synthetic methods to constructing a DNA sequence encoding isolated polypeptide sequences and expressing those sequences in a suitable transformed host. In some embodiments, a DNA sequence is constructed using recombinant technology by isolating or synthesizing a DNA sequence encoding a wild-type protein of interest. Optionally, the sequence can be mutagenized by site-specific mutagenesis to provide functional analogs thereof. See, e.g. Zoeller et al., Proc. Nat'l. Acad. Sci. USA 81:5662-5066 (1984) and U.S. Pat. No. 4,588,585.

In embodiments, a DNA sequence encoding a polypeptide of interest would be constructed by chemical synthesis using an oligonucleotide synthesizer. Such oligonucleotides can be designed based on the amino acid sequence of the desired polypeptide and selecting those codons that are favored in the host cell in which the recombinant polypeptide of interest is produced. Standard methods can be applied to synthesize an isolated polynucleotide sequence encoding an isolated polypeptide of interest. For example, a complete amino acid sequence can be used to construct a back-translated gene. Further, a DNA oligomer containing a nucleotide sequence coding for the particular isolated polypeptide can be synthesized. For example, several small oligonucleotides coding for portions of the desired polypeptide can be synthesized and then ligated. The individual oligonucleotides typically contain 5' or 3' overhangs for complementary assembly.

Once assembled (e.g., by synthesis, site-directed mutagenesis, or another method), the polynucleotide sequences encoding a particular isolated polypeptide of interest is inserted into an expression vector and optionally operatively linked to an expression control sequence appropriate for expression of the protein in a desired host. Proper assembly can be confirmed by nucleotide sequencing, restriction mapping, and expression of a biologically active polypeptide in a suitable host. As well known in the art, in order to obtain high expression levels of a transfected gene in a host, the gene can be operatively linked to transcriptional and translational expression control sequences that are functional in the chosen expression host.

Recombinant expression vectors may be used to amplify and express DNA encoding the tumor specific neoantigenic peptides. Recombinant expression vectors are replicable DNA constructs which have synthetic or cDNA-derived DNA fragments encoding a tumor specific neoantigenic peptide or a bioequivalent analog operatively linked to suitable transcriptional or translational regulatory elements derived from mammalian, microbial, viral or insect genes. A transcriptional unit generally comprises an assembly of (1) a genetic element or elements having a regulatory role in gene expression, for example, transcriptional promoters or enhancers, (2) a structural or coding sequence which is transcribed into mRNA and translated into protein, and (3) appropriate transcription and translation initiation and termination sequences, as described in detail herein. Such regulatory elements can include an operator sequence to control transcription. The ability to replicate in a host, usually conferred by an origin of replication, and a selection gene to facilitate recognition of transformants can additionally be incorporated. DNA regions are operatively linked when they are functionally related to each other. For example, DNA for a signal peptide (secretory leader) is operatively linked to DNA for a polypeptide if it is expressed as a precursor which participates in the secretion of the polypeptide; a promoter is operatively linked to a coding sequence if it controls the transcription of the sequence; or a ribosome binding site is operatively linked to a coding sequence if it is positioned so as to permit translation. Generally, operatively linked means contiguous, and in the case of secretory leaders, means contiguous and in reading frame. Structural elements intended for use in yeast expression systems include a leader sequence enabling extracellular secretion of translated protein by a host cell. Alternatively, where recombinant protein is expressed without a leader or transport sequence, it can include an N-terminal methionine residue. This residue can optionally be subsequently cleaved from the expressed recombinant protein to provide a final product.

Useful expression vectors for eukaryotic hosts, especially mammals or humans include, for example, vectors comprising expression control sequences from SV40, bovine papilloma virus, adenovirus and cytomegalovirus. Useful expression vectors for bacterial hosts include known bacterial plasmids, such as plasmids from *Escherichia coli*, including pCR 1, pBR322, pMB9 and their derivatives, wider host range plasmids, such as Ml 3 and filamentous single-stranded DNA phages.

Suitable host cells for expression of a polypeptide include prokaryotes, yeast, insect or higher eukaryotic cells under the control of appropriate promoters. Prokaryotes include gram negative or gram positive organisms, for example *E. coli* or bacilli. Higher eukaryotic cells include established cell lines of mammalian origin. Cell-free translation systems could also be employed. Appropriate cloning and expression vectors for use with bacterial, fungal, yeast, and mammalian cellular hosts are well known in the art (see Pouwels et al., Cloning Vectors: A Laboratory Manual, Elsevier, N.Y., 1985).

Various mammalian or insect cell culture systems are also advantageously employed to express recombinant protein. Expression of recombinant proteins in mammalian cells can be performed because such proteins are generally correctly folded, appropriately modified and completely functional. Examples of suitable mammalian host cell lines include the COS-7 lines of monkey kidney cells, described by Gluzman (Cell 23: 175, 1981), and other cell lines capable of expressing an appropriate vector including, for example, L cells, C127, 3T3, Chinese hamster ovary (CHO), 293, HeLa and BHK cell lines. Mammalian expression vectors can comprise nontranscribed elements such as an origin of replication, a suitable promoter and enhancer linked to the gene to be expressed, and other 5' or 3' flanking nontranscribed sequences, and 5' or 3' nontranslated sequences, such as necessary ribosome binding sites, a polyadenylation site, splice donor and acceptor sites, and transcriptional termination sequences. Baculovirus systems for production of heterologous proteins in insect cells are reviewed by Luckow and Summers, Bio/Technology 6:47 (1988).

The proteins produced by a transformed host can be purified according to any suitable method. Such standard methods include chromatography (e.g., ion exchange, affinity and sizing column chromatography, and the like), centrifugation, differential solubility, or by any other standard technique for protein purification. Affinity tags such as hexahistidine, maltose binding domain, influenza coat sequence, glutathione-S-transferase, and the like can be attached to the protein to allow easy purification by passage over an appropriate affinity column. Isolated proteins can also be physically characterized using such techniques as proteolysis, nuclear magnetic resonance and x-ray crystallography.

For example, supernatants from systems which secrete recombinant protein into culture media can be first concentrated using a commercially available protein concentration filter, for example, an Amicon or Millipore Pellicon ultrafiltration unit. Following the concentration step, the concentrate can be applied to a suitable purification matrix. Alternatively, an anion exchange resin can be employed, for example, a matrix or substrate having pendant diethylaminoethyl (DEAE) groups. The matrices can be acrylamide, agarose, dextran, cellulose or other types commonly employed in protein purification. Alternatively, a cation exchange step can be employed. Suitable cation exchangers include various insoluble matrices comprising sulfopropyl or carboxymethyl groups. Finally, one or more reversed-phase high performance liquid chromatography (RP-ffPLC) steps employing hydrophobic RP-FTPLC media, e.g., silica gel having pendant methyl or other aliphatic groups, can be employed to further purify a cancer stem cell protein-Fc composition. Some or all of the foregoing purification steps, in various combinations, can also be employed to provide a homogeneous recombinant protein. Recombinant protein produced in bacterial culture can be isolated, for example, by initial extraction from cell pellets, followed by one or more concentration, salting-out, aqueous ion exchange or size exclusion chromatography steps. High performance liquid chromatography (HPLC) can be employed for final purification steps. Microbial cells employed in expression of a recombinant protein can be disrupted by any convenient method, including freeze-thaw cycling, sonication, mechanical disruption, or use of cell lysing agents.

In Vivo Peptide/Polypeptide Synthesis

The present invention also contemplates the use of nucleic acid molecules as vehicles for delivering neoantigenic peptides/polypeptides to the subject in need thereof, in vivo, in the form of, e.g., DNA/RNA vaccines (see, e.g., WO2012/159643, and WO2012/159754, hereby incorporated by reference in their entirety).

In one embodiment antigens may be administered to a patient in need thereof by use of a plasmid. These are plasmids which usually consist of a strong viral promoter to drive the in vivo transcription and translation of the gene (or complementary DNA) of interest (Mor, et al., (1995), The Journal of Immunology 155 (4): 2039-2046). Intron A may sometimes be included to improve mRNA stability and hence increase protein expression (Leitner et al. (1997), The Journal of Immunology 159 (12): 6112-6119). Plasmids also include a strong polyadenylation/transcriptional termination signal, such as bovine growth hormone or rabbit beta-globulin polyadenylation sequences (Alarcon et al., (1999), Adv. Parasitol. Advances in Parasitology 42: 343-410; Robinson et al., (2000). Adv. Virus Res. Advances in Virus Research 55: 1-74; Bohm et al., (1996). Journal of Immunological Methods 193 (1): 29-40.). Multi cistronic vectors are sometimes constructed to express more than one immunogen, or to express an immunogen and an immunostimulatory protein (Lewis et al., (1999). Advances in Virus Research (Academic Press) 54: 129-88).

Because the plasmid is the "vehicle" from which the immunogen is expressed, optimising vector design for maximal protein expression is essential (Lewis et al., (1999). Advances in Virus Research (Academic Press) 54: 129-88). One way of enhancing protein expression is by optimising the codon usage of pathogenic mRNAs for eukaryotic cells. Another consideration is the choice of promoter. Such promoters may be the SV40 promoter or Rous Sarcoma Virus (RSV). Plasmids may be introduced into animal tissues by a number of different methods. The two most popular approaches are injection of DNA in saline, using a standard hypodermic needle, and gene gun delivery. A schematic outline of the construction of a DNA vaccine plasmid and its subsequent delivery by these two methods into a host is illustrated at Scientific American (Weiner et al., (1999) Scientific American 281 (1): 34-41). Injection in saline is normally conducted intramuscularly (EVI) in skeletal muscle, or intradermally (ID), with DNA being delivered to the extracellular spaces. This can be assisted by electroporation by temporarily damaging muscle fibres with myotoxins such as bupivacaine; or by using hypertonic solutions of saline or sucrose (Alarcon et al., (1999). Adv. Parasitol. Advances in Parasitology 42: 343-410). Immune responses to this method of delivery can be affected by many factors, including needle type, needle alignment, speed of injection, volume of injection, muscle type, and age, sex and physiological condition of the animal being injected (Alarcon et al., (1999). Adv. Parasitol. Advances in Parasitology 42: 343-410).

Gene gun delivery, the other commonly used method of delivery, ballistically accelerates plasmid DNA (pDNA) that has been adsorbed onto gold or tungsten microparticles into the target cells, using compressed helium as an accelerant (Alarcon et al., (1999). Adv. Parasitol. Advances in Parasitology 42: 343-410; Lewis et al., (1999). Advances in Virus Research (Academic Press) 54: 129-88).

Alternative delivery methods may include aerosol instillation of naked DNA on mucosal surfaces, such as the nasal and lung mucosa, (Lewis et al., (1999). Advances in Virus Research (Academic Press) 54: 129-88) and topical administration of pDNA to the eye and vaginal mucosa (Lewis et al., (1999) Advances in Virus Research (Academic Press) 54: 129-88). Mucosal surface delivery has also been achieved using cationic liposome-DNA preparations, biodegradable microspheres, attenuated *Shigella* or *Listeria* vectors for oral administration to the intestinal mucosa, and recombinant adenovirus vectors. DNA or RNA may also be delivered to cells following mild mechanical disruption of the cell membrane, temporarily permeabilizing the cells. Such a mild mechanical disruption of the membrane can be accomplished by gently forcing cells through a small aperture (Ex vivo Cytosolic Delivery of Functional Macromolecules to Immune Cells, Sharei et al, PLOS ONE|DOI: 10.1371/journal.pone.Ol 18803 Apr. 13, 2015).

The method of delivery determines the dose of DNA required to raise an effective immune response. Saline injections require variable amounts of DNA, from 10 µg-1 mg, whereas gene gun deliveries require 100 to 1000 times less DNA than intramuscular saline injection to raise an effective immune response. Generally, 0.2 µg-20 µg are required, although quantities as low as 16 ng have been reported. These quantities vary from species to species, with mice, for example, requiring approximately 10 times less DNA than primates. Saline injections require more DNA because the DNA is delivered to the extracellular spaces of the target tissue (normally muscle), where it has to overcome physical barriers (such as the basal lamina and large amounts of connective tissue, to mention a few) before it is taken up by the cells, while gene gun deliveries bombard DNA directly into the cells, resulting in less "wastage" (See e.g., Sedegah et al., (1994). Proceedings of the National Academy of Sciences of the United States of America 91 (21): 9866-9870; Daheshia et al., (1997). The Journal of Immunology 159 (4): 1945-1952; Chen et al., (1998). The Journal of Immunology 160 (5): 2425-2432; Sizemore (1995) Science 270 (5234): 299-302; Fynan et al., (1993) Proc. Natl. Acad. Sci. U.S.A. 90 (24): 11478-82).

In one embodiment, a neoplasia vaccine or immunogenic composition may include separate DNA plasmids encoding, for example, one or more neoantigenic peptides/polypeptides as identified in according to the invention. As discussed herein, the exact choice of expression vectors can depend upon the peptide/polypeptides to be expressed, and is well within the skill of the ordinary artisan. The expected persistence of the DNA constructs (e.g., in an episomal, non-replicating, non-integrated form in the muscle cells) is expected to provide an increased duration of protection.

One or more antigenic peptides of the invention may be encoded and expressed in vivo using a viral based system (e.g., an adenovirus system, an adeno associated virus (AAV) vector, a poxvirus, or a lentivirus). In one embodiment, the neoplasia vaccine or immunogenic composition may include a viral based vector for use in a human patient in need thereof, such as, for example, an adenovirus (see, e.g., Baden et al. First-in-human evaluation of the safety and immunogenicity of a recombinant adenovirus serotype 26

HIV-1 Env vaccine (IPCAVD 001). J Infect Dis. 2013 Jan. 15; 207(2):240-7, hereby incorporated by reference in its entirety). Plasmids that can be used for adeno associated virus, adenovirus, and lentivirus delivery have been described previously (see e.g., U.S. Pat. Nos. 6,955,808 and 6,943,019, and U.S. Patent application No. 20080254008, hereby incorporated by reference). The peptides and polypeptides of the invention can also be expressed by a vector, e.g., a nucleic acid molecule as herein-discussed, e.g., RNA or a DNA plasmid, a viral vector such as a poxvirus, e.g., orthopox virus, avipox virus, or adenovirus, AAV or lentivirus. This approach involves the use of a vector to express nucleotide sequences that encode the peptide of the invention. Upon introduction into an acutely or chronically infected host or into a noninfected host, the vector expresses the immunogenic peptide, and thereby elicits a host CTL response.

Among vectors that may be used in the practice of the invention, integration in the host genome of a cell is possible with retrovirus gene transfer methods, often resulting in long term expression of the inserted transgene. In a preferred embodiment the retrovirus is a lentivirus. Additionally, high transduction efficiencies have been observed in many different cell types and target tissues. The tropism of a retrovirus can be altered by incorporating foreign envelope proteins, expanding the potential target population of target cells. A retrovirus can also be engineered to allow for conditional expression of the inserted transgene, such that only certain cell types are infected by the lentivirus. Cell type specific promoters can be used to target expression in specific cell types. Lentiviral vectors are retroviral vectors (and hence both lentiviral and retroviral vectors may be used in the practice of the invention). Moreover, lentiviral vectors are preferred as they are able to transduce or infect non-dividing cells and typically produce high viral titers. Selection of a retroviral gene transfer system may therefore depend on the target tissue. Retroviral vectors are comprised of cis-acting long terminal repeats with packaging capacity for up to 6-10 kb of foreign sequence. The minimum cis-acting LTRs are sufficient for replication and packaging of the vectors, which are then used to integrate the desired nucleic acid into the target cell to provide permanent expression. Widely used retroviral vectors that may be used in the practice of the invention include those based upon murine leukemia virus (MuLV), gibbon ape leukemia virus (GaLV), Simian Immuno deficiency virus (SIV), human immuno deficiency virus (HIV), and combinations thereof (see, e.g., Buchscher et al., (1992) J. Virol. 66:2731-2739; Johann et al., (1992) J. Virol. 66: 1635-1640; Sommnerfelt et al., (1990) Virol. 176:58-59; Wilson et al., (1998) J. Virol. 63:2374-2378; Miller et al., (1991) J. Virol. 65:2220-2224; PCT/US94/05700).

Also useful in the practice of the invention is a minimal non-primate lentiviral vector, such as a lentiviral vector based on the equine infectious anemia virus (EIAV) (see, e.g., Balagaan, (2006) J Gene Med; 8: 275-285, Published online 21 Nov. 2005 in Wiley InterScience (www.interscience.wiley.com). DOI: 10.1002/jgm.845). The vectors may have cytomegalovirus (CMV) promoter driving expression of the target gene. Accordingly, the invention contemplates amongst vector(s) useful in the practice of the invention: viral vectors, including retroviral vectors and lentiviral vectors.

Lentiviral vectors have been disclosed as in the treatment for Parkinson's Disease, see, e.g., US Patent Publication No. 20120295960 and U.S. Pat. Nos. 7,303,910 and 7,351,585. Lentiviral vectors have also been disclosed for delivery to the Brain, see, e.g., US Patent Publication Nos. US20110293571; US20040013648, US20070025970, US20090111106 and U.S. Pat. No. 7,259,015. In another embodiment lentiviral vectors are used to deliver vectors to the brain of those being treated for a disease.

As to lentivirus vector systems useful in the practice of the invention, mention is made of U.S. Pat. Nos. 6,428,953, 6,165,782, 6,013,516, 5,994,136, 6,312,682, and 7,198,784, and documents cited therein.

In an embodiment herein the delivery is via an lentivirus. Zou et al. administered about 10 µ[|$]$¨$$[|$]$¨ AÄ[|$] $¨gi of a recombinant lentivirus having a titer of $1 \times 10^9$ transducing units (TU)/ml by an intrathecal catheter. These sort of dosages can be adapted or extrapolated to use of a retroviral or lentiviral vector in the present invention. For transduction in tissues such as the brain, it is necessary to use very small volumes, so the viral preparation is concentrated by ultracentrifugation. The resulting preparation should have at least $10^8$ TU/ml, preferably from $10^8$ to $10^9$ TU/ml, more preferably at least $10^9$ TU/ml. Other methods of concentration such as ultrafiltration or binding to and elution from a matrix may be used.

In other embodiments the amount of lentivirus administered may be $1.\times.10^5$ or about $1.\times.10^5$ plaque forming units (PFU), $5.\times.10^5$ or about $5.\times.10^5$ PFU, $1.\times.10^6$ or about $1.\times 10^6$ PFU, $5.\times.10^6$ or about $5.\times.10^6$ PFU, $1.\times.10^7$ or about $1.\times.10^7$ PFU, $5.\times.10^7$ or about $5.\times.10^7$ PFU, $1.\times.10^8$ or about $1.\times.10^8$ PFU, $5.\times.10^8$ or about $5.\times.10^8$ PFU, $1.\times.10^9$ or about $1.\times.10^9$ PFU, $5.\times.10^9$ or about $5.\times.10^9$ PFU, $1.\times.10^{10}$ or about $1.\times.10^{10}$ PFU or $5.\times.10^{10}$ or about $5.\times.10^{10}$ PFU as total single dosage for an average human of 75 kg or adjusted for the weight and size and species of the subject. One of skill in the art can determine suitable dosage. Suitable dosages for a virus can be determined empirically. Also useful in the practice of the invention is an adenovirus vector. One advantage is the ability of recombinant adenoviruses to efficiently transfer and express recombinant genes in a variety of mammalian cells and tissues in vitro and in vivo, resulting in the high expression of the transferred nucleic acids. Further, the ability to productively infect quiescent cells, expands the utility of recombinant adenoviral vectors. In addition, high expression levels ensure that the products of the nucleic acids will be expressed to sufficient levels to generate an immune response (see e.g., U.S. Pat. No. 7,029,848, hereby incorporated by reference).

As to adenovirus vectors useful in the practice of the invention, mention is made of U.S. Pat. No. 6,955,808. The adenovirus vector used can be selected from the group consisting of the Ad5, Ad35, Adl 1, C6, and C7 vectors. The sequence of the Adenovirus 5 ("Ad5") genome has been published. (Chroboczek, J., Bieber, F., and Jacrot, B. (1992) The Sequence of the Genome of Adenovirus Type 5 and Its Comparison with the Genome of Adenovirus Type 2, Virology 186, 280-285; the contents if which is hereby incorporated by reference). Ad35 vectors are described in U.S. Pat. Nos. 6,974,695, 6,913,922, and 6,869,794. Adl 1 vectors are described in U.S. Pat. No. 6,913,922. C6 adenovirus vectors are described in U.S. Pat. Nos. 6,780,407; 6,537,594; 6,309, 647; 6,265, 189; 6,156,567; 6,090,393; 5,942,235 and 5,833, 975. C7 vectors are described in U.S. Pat. No. 6,277,558. Adenovirus vectors that are El-defective or deleted, E3-defective or deleted, and/or E4-defective or deleted may also be used. Certain adenoviruses having mutations in the E1 region have improved safety margin because E1-defective adenovirus mutants are replication-defective in non-permissive cells, or, at the very least, are highly attenuated. Adenoviruses having mutations in the E3 region may have enhanced the immunogenicity by disrupting the mechanism whereby adenovirus down-regulates MHC class I molecules. Adenoviruses having E4 mutations may have reduced immunogenicity of the adenovirus vector because of suppression of late gene expression. Such vectors may be particularly useful when repeated re-vaccination utilizing the same vector is desired. Adenovirus vectors that are deleted or mutated in E1, E3, E4, E1 and E3, and E1 and E4 can be used in accordance with the present invention. Furthermore, "gutless" adenovirus vectors, in which all viral genes are deleted, can also be used in accordance with the present invention. Such vectors require a helper virus for their replication and require a special human 293 cell line expressing both E1 a and Cre, a condition that does not exist in natural environment. Such "gutless" vectors are non-immunogenic and thus the vectors may be inoculated multiple times for re-vaccination. The "gutless" adenovirus vectors can be used for insertion of heterologous inserts/genes such as the transgenes of the present invention, and can even be used for co-delivery of a large number of heterologous inserts/genes.

In an embodiment herein the delivery is via an adenovirus, which may be at a single booster dose containing at least $1\times10^5$ particles (also referred to as particle units, pu) of adenoviral vector. In an embodiment herein, the dose preferably is at least about $1\times10^6$ particles (for example, about $1\times10^6$-$1\times10^{12}$ particles), more preferably at least about $1\times10^7$ particles, more preferably at least about $1\times10^8$ particles (e.g., about $1\times10^8$-$1\times10^{11}$ particles or about $1\times10^8$-$1\times10^{12}$ particles), and most preferably at least about $1\times10^9$ particles (e.g., about $1\times10^9$-$1\times10^{10}$ particles or about $1\times10^9$-$1\times10^{12}$ particles), or even at least about $1\times10^{10}$ particles (e.g., about $1\times10^{10}$-$1\times10^{12}$ particles) of the adenoviral vector. Alternatively, the dose comprises no more than about $1\times10^{14}$ particles, preferably no more than about $1\times10^{11}$ particles, even more preferably no more than about $1\times10^{12}$ particles, even more preferably no more than about $1\times10^{11}$ particles, and most preferably no more than about $1\times10^{10}$ particles (e.g., no more than about $1\times10^9$ articles). Thus, the dose may contain a single dose of adenoviral vector with, for example, about $1\times10^6$ particle units (pu), about $2\times10^6$ pu, about $4\times10^6$ pu, about $1\times10^7$ pu, about $2\times10$ pu, about $4\times10$ pu, about $1\times10$ pu, about $2\times10$ pu, about $4\times10$ pu, about $1\times10^9$ pu, about $2\times10^9$ pu, about $4\times10^9$ pu, about $1\times10^{10}$ pu, about $2\times10^{10}$ pu, about $4\times10^{10}$ pu, about $1\times10^{11}$ pu, about $2\times10^{11}$ pu, about $4\times10^{11}$ pu, about $1\times10^{12}$ pu, about $2\times10^{12}$ pu, or about $4\times10^{12}$ pu of adenoviral vector. See, for example, the adenoviral vectors in U.S. Pat. No. 8,454,972 B2 to Nabel, et. al., granted on Jun. 4, 2013; incorporated by reference herein, and the dosages at col 29, lines 36-58 thereof. In an embodiment herein, the adenovirus is delivered via multiple doses.

In terms of in vivo delivery, AAV is advantageous over other viral vectors due to low toxicity and low probability of causing insertional mutagenesis because it doesn't integrate into the host genome. AAV has a packaging limit of 4.5 or 4.75 Kb. Constructs larger than 4.5 or 4.75 Kb result in significantly reduced virus production. There are many promoters that can be used to drive nucleic acid molecule expression. AAV ITR can serve as a promoter and is advantageous for eliminating the need for an additional promoter element. For ubiquitous expression, the following promoters can be used: CMV, CAG, CBh, PGK, SV40, Ferritin heavy or light chains, etc. For brain expression, the following promoters can be used: Synapsin1 for all neurons, CaMKIIalpha for excitatory neurons, GAD67 or GAD65 or VGAT for GABAergic neurons, etc. Promoters used to drive RNA synthesis can include: Pol III promoters such as U6 or H1. The use of a Pol II promoter and intronic cassettes can be used to express guide RNA (gRNA).

With regard to AAV vectors useful in the practice of the invention, mention is made of U.S. Pat. Nos. 5,658,785, 7,115,391, 7,172,893, 6,953,690, 6,936,466, 6,924,128, 6,893,865, 6,793,926, 6,537,540, 6,475,769 and 6,258,595, and documents cited therein.

As to AAV, the AAV can be AAV1, AAV2, AAV5 or any combination thereof. One can select the AAV with regard to the cells to be targeted; e.g., one can select AAV serotypes 1, 2, 5 or a hybrid capsid AAV1, AAV2, AAV5 or any combination thereof for targeting brain or neuronal cells; and one can select AAV4 for targeting cardiac tissue. AAV8 is useful for delivery to the liver. The above promoters and vectors are preferred individually.

In an embodiment herein, the delivery is via an AAV. A therapeutically effective dosage for in vivo delivery of the AAV to a human is believed to be in the range of from about 20 to about 50 ml of saline solution containing from about $1\times10^{10}$ to about $1\times10^{50}$ functional AAV/ml solution. The dosage may be adjusted to balance the therapeutic benefit against any side effects. In an embodiment herein, the AAV dose is generally in the range of concentrations from about $1\times10$ to $1\times10$ genomes AAV, from about $1\times10$ to $1\times10$ genomes AAV, from about $1\times10^{10}$ to about $1\times10^{16}$ genomes, or about $1\times10^{11}$ to about $1\times10^{16}$ genomes AAV. A human dosage may be about $1\times10^{13}$ genomes AAV. Such concentrations may be delivered in from about 0.001 ml to about 100 ml, about 0.05 to about 50 ml, or about 10 to about 25 ml of a carrier solution. In a preferred embodiment, AAV is used with a titer of about $2\times10^{13}$ viral genomes/milliliter, and each of the striatal hemispheres of a mouse receives one 500 nanoliter injection. Other effective dosages can be readily established by one of ordinary skill in the art through routine trials establishing dose response curves. See, for example, U.S. Pat. No. 8,404,658 B2 to Hajjar, et al., granted on Mar. 26, 2013, at col. 27, lines 45-60.

In another embodiment effectively activating a cellular immune response for a neoplasia vaccine or immunogenic composition can be achieved by expressing the relevant antigens in a vaccine or immunogenic composition in a non-pathogenic microorganism. Well-known examples of such microorganisms are *Mycobacterium bovis* BCG, *Salmonella* and *Pseudomonas* (See, U.S. Pat. No. 6,991,797, hereby incorporated by reference in its entirety). In another embodiment a Poxvirus is used in the neoplasia vaccine or immunogenic composition. These include orthopoxvirus, avipox, vaccinia, MVA, NYVAC, canarypox, ALVAC, fowlpox, TROVAC, etc. (see e.g., Verardi et al., Hum Vaccin Immunother. 2012 July; 8(7):961-70; and Moss, Vaccine. 2013; 31(39): 4220-4222). Poxvirus expression vectors were described in 1982 and quickly became widely used for vaccine development as well as research in numerous fields. Advantages of the vectors include simple construction, ability to accommodate large amounts of foreign DNA and high expression levels.

Information concerning poxviruses that may be used in the practice of the invention, such as Chordopoxvirinae subfamily poxviruses (poxviruses of vertebrates), for instance, orthopoxviruses and avipoxviruses, e.g., vaccinia virus (e.g., Wyeth Strain, WR Strain (e.g., ATCC® VR-1354), Copenhagen Strain, NYVAC, NYVAC. 1, NYVAC.2, MVA, MVA-BN), canarypox virus (e.g., Wheatley C93 Strain, ALVAC), fowlpox virus (e.g., FP9 Strain, Webster Strain, TROVAC), dovepox, pigeonpox, quailpox, and raccoon pox, inter alia, synthetic or non-naturally occurring recombinants thereof, uses thereof, and methods for making and using such recombinants may be found in scientific and patent literature, such as: U.S. Pat. Nos. 4,603,112, 4,769,330, 5,110,587, 5,174,993, 5,364,773, 5,762,938, 5,494,807, 5,766,597, 7,767,449, 6,780,407, 6,537,594, 6,265,189, 6,214,353, 6,130,066, 6,004,777, 5,990,091, 5,942,235, 5,833,975, 5,766,597, 5,756, 101, 7,045,313, 6,780,417, 8,470,598, 8,372,622, 8,268,329, 8,268,325, 8,236,560, 8,163,293, 7,964,398, 7,964,396, 7,964,395, 7,939,086, 7,923,017, 7,897,156, 7,892,533, 7,628,980, 7,459,270, 7,445,924, 7,384,644, 7,335,364, 7,189,536, 7,097,842, 6,913,752, 6,761,893, 6,682,743, 5,770,212, 5,766,882, and 5,989,562, and Panicali, D. Proc. Natl. Acad. Sci. 1982; 79; 4927-493, Panicali D. Proc. Natl. Acad. Sci. 1983; 80(17): 5364-8, Mackett, M. Proc. Natl. Acad. Sci. 1982; 79: 7415-7419, Smith G L. Proc. Natl. Acad. Sci. 1983; 80(23): 7155-9, Smith G L. Nature 1983; 302: 490-5, Sullivan V J. Gen. Vir. 1987; 68: 2587-98, Perkus M Journal of Leukocyte Biology 1995; 58: 1-13, Yilma T D. Vaccine 1989; 7: 484-485, Brochier B. Nature 1991; 354: 520-22, Wiktor, T J. Proc. Natl Acd. Sci. 1984; 81: 7194-8, Rupprecht, C E. Proc. Natl Acd. Sci. 1986; 83: 7947-50, Poulet, H Vaccine 2007; 25(July): 5606-12, Weyer J. Vaccine 2009; 27(November): 7198-201, Buller, R M Nature 1985; 317(6040): 813-5, Buller R M. J. Virol. 1988; 62(3):866-74, Flexner, C. Nature 1987; 330(6145): 259-62, Shida, H. J. Virol. 1988; 62(12): 4474-80, Kotwal, G J. J. Virol. 1989; 63(2): 600-6, Child, S J. Virology 1990; 174(2): 625-9, Mayr A. Zentralbl Bakteriol 1978; 167(5,6): 375-9, Antoine G. Virology. 1998; 244(2): 365-96, Wyatt, L S. Virology 1998; 251(2): 334-42, Sancho, M C. J. Virol. 2002; 76(16); 8313-34, Gallego-Gomez, J C. J. Virol. 2003; 77(19); 10606-22, Goebel S J. Virology 1990; (a,b) 179: 247-66, Tartaglia, J. Virol. 1992; 188(1): 217-32, Najera J L. J. Virol. 2006; 80(12): 6033-47, Najera, J L. J. Virol. 2006; 80: 6033-6047, Gomez, C E. J. Gen. Virol. 2007; 88: 2473-78, Mooij, P. Jour. Of Virol. 2008; 82: 2975-2988, Gomez, C E. Curr. Gene Ther. 2011; 11: 189-217, Cox, W. Virology 1993; 195: 845-50, Perkus, M. Jour. Of Leukocyte Biology 1995; 58: 1-13, Blanchard T J. J Gen Virology 1998; 79(5): 1159-67, Amara R. Science 2001; 292: 69-74, Hel, Z., J. Immunol. 2001; 167: 7180-9, Gherardi M M. J. Virol. 2003; 77: 7048-57, Didierlaurent, A. Vaccine 2004; 22: 3395-3403, Bissht H. Proc. Nat. Aca. Sci. 2004; 101: 6641-46, McCurdy L H. Clin. Inf. Dis 2004; 38: 1749-53, Earl P L. Nature 2004; 428: 182-85, Chen Z. J. Virol. 2005; 79: 2678-2688, Najera J L. J. Virol. 2006; 80(12): 6033-47, Nam J H. Acta. Virol. 2007; 51: 125-30, Antonis A F. Vaccine 2007; 25: 4818-4827, B Weyer J. Vaccine 2007; 25: 4213-22, Ferrier-Rembert A. Vaccine 2008; 26(14): 1794-804, Corbett M. Proc. Natl. Acad. Sci. 2008; 105(6): 2046-51, Kaufman H L., J. Clin. Oncol. 2004; 22: 2122-32, Amato, R J. Clin. Cancer Res. 2008; 14(22): 7504-10, Dreicer R. Invest New Drugs 2009; 27(4): 379-86, Kantoff P W. J. Clin. Oncol. 2010, 28, 1099-1 105, Amato R J. J. Clin. Can. Res. 2010; 16(22): 5539-47, Kim, D W. Hum. Vaccine. 2010; 6: 784-791, Oudard, S. Cancer Immunol. Immunother. 2011; 60: 261-71, Wyatt, L S. Aids Res. Hum. Retroviruses. 2004; 20: 645-53, Gomez, C E. Virus Research 2004; 105: 11-22, Webster, D P. Proc. Natl. Acad. Sci. 2005; 102: 4836-4, Huang, X. Vaccine 2007; 25: 8874-84, Gomez, C E. Vaccine 2007a; 25: 2863-85, Esteban M. Hum. Vaccine 2009; 5: 867-871, Gomez, C E. Curr. Gene therapy 2008; 8(2): 97-120, Whelan, K T. Plos one 2009; 4(6): 5934, Scriba, T J. Eur. Jour. Immuno. 2010; 40(1): 279-90, Corbett, M. Proc. Natl. Acad. Sci. 2008; 105: 2046-2051, Midgley, C M. J. Gen. Virol. 2008; 89: 2992-97, Von Krempelhuber, A. Vaccine 2010; 28: 1209-16, Perreau, M. J. Of Virol. 2011; October: 9854-62, Pantaleo, G. Curr Opin HIV-AIDS. 2010; 5: 391-396, each of which is incorporated herein by reference.

In another embodiment the vaccinia virus is used in the neoplasia vaccine or immunogenic composition to express a neoantigen. (Rolph et al., Recombinant viruses as vaccines and immunological tools. Curr Opin Immunol 9:517-524, 1997). The recombinant vaccinia virus is able to replicate within the cytoplasm of the infected host cell and the polypeptide of interest can therefore induce an immune response. Moreover, Poxviruses have been widely used as vaccine or immunogenic composition vectors because of their ability to target encoded antigens for processing by the major histocompatibility complex class I pathway by directly infecting immune cells, in particular antigen-presenting cells, but also due to their ability to self-adjuvant.

In another embodiment ALVAC is used as a vector in a neoplasia vaccine or immunogenic composition. ALVAC is a canarypox virus that can be modified to express foreign transgenes and has been used as a method for vaccination against both prokaryotic and eukaryotic antigens (Horig H, Lee D S, Conkright W, et al. Phase I clinical trial of a recombinant canarypoxvirus (ALVAC) vaccine expressing human carcinoembryonic antigen and the B7.1 co-stimulatory molecule. Cancer Immunol Immunother 2000; 49:504-14; von Mehren M, Arlen P, Tsang K Y, et al. Pilot study of a dual gene recombinant avipox vaccine containing both carcinoembryonic antigen (CEA) and B7.1 transgenes in patients with recurrent CEA-expressing adenocarcinomas. Clin Cancer Res 2000; 6:2219-28; Musey L, Ding Y, Elizaga M, et al. HIV-1 vaccination administered intramuscularly can induce both systemic and mucosal T cell immunity in HIV-1-uninfected individuals. J Immunol 2003; 171: 1094-101; Paoletti E. Applications of pox virus vectors to vaccination: an update. Proc Natl Acad Sci USA 1996; 93: 11349-53; U.S. Pat. No. 7,255,862). In a phase I clinical trial, an ALVAC virus expressing the tumor antigen CEA showed an excellent safety profile and resulted in increased CEA-specific T cell responses in selected patients; objective clinical responses, however, were not observed (Marshall J L, Hawkins M J, Tsang K Y, et al. Phase I study in cancer patients of a replication-defective avipox recombinant vaccine that expresses human carcinoembryonic antigen. J Clin Oncol 1999; 17:332-7).

In another embodiment a Modified Vaccinia Ankara (MVA) virus may be used as a viral vector for a neoantigen vaccine or immunogenic composition. MVA is a member of the Orthopoxvirus family and has been generated by about 570 serial passages on chicken embryo fibroblasts of the Ankara strain of Vaccinia virus (CVA) (for review see Mayr, A., et al., Infection 3, 6-14, 1975). As a consequence of these passages, the resulting MVA virus contains 31 kilobases less genomic information compared to CVA, and is highly host-cell restricted (Meyer, H. et al., J. Gen. Virol. 72, 1031-1038, 1991). MVA is characterized by its extreme attenuation, namely, by a diminished virulence or infectious ability, but still holds an excellent immunogenicity. When tested in a variety of animal models, MVA was proven to be avirulent, even in immuno-suppressed individuals. Moreover, MVA-BN®-HER2 is a candidate immunotherapy designed for the treatment of HER-2-positive breast cancer and is currently in clinical trials. (Mandl et al., Cancer Immunol Immunother. January 2012; 61(1): 19-29). Methods to make and use recombinant MVA has been described (e.g., see U.S. Pat. Nos. 8,309,098 and 5, 185,146 hereby incorporated in its entirety).

In another embodiment the modified Copenhagen strain of vaccinia virus, NYVAC and NYVAC variations are used as a vector (see U.S. Pat. No. 7,255,862; PCT WO 95/30018; U.S. Pat. Nos. 5,364,773 and 5,494,807, hereby incorporated by reference in its entirety).

In one embodiment recombinant viral particles of the vaccine or immunogenic composition are administered to patients in need thereof. Dosages of expressed neoantigen can range from a few to a few hundred micrograms, e.g., 5 to 500 µg. The vaccine or immunogenic composition can be administered in any suitable amount to achieve expression at these dosage levels. The viral particles can be administered to a patient in need thereof or transfected into cells in an amount of about at least $10^{3.5}$ pfu; thus, the viral particles are preferably administered to a patient in need thereof or infected or transfected into cells in at least about $10^4$ pfu to about $10^6$ pfu; however, a patient in need thereof can be administered at least about $10^7$ pfu such that a more preferred amount for administration can be at least about $10^7$ pfu to about $10^9$ pfu. Doses as to NYVAC are applicable as to ALVAC, MVA, MVA-BN, and avipoxes, such as canarypox and fowlpox.

Vaccine or Immunogenic Composition Adjuvant

Effective vaccine or immunogenic compositions advantageously include a strong adjuvant to initiate an immune response. As described herein, poly-ICLC, an agonist of TLR3 and the RNA helicase-domains of MDA5 and RIG3, has shown several desirable properties for a vaccine or immunogenic composition adjuvant. These properties include the induction of local and systemic activation of immune cells in vivo, production of stimulatory chemokines and cytokines, and stimulation of antigen-presentation by DCs. Furthermore, poly-ICLC can induce durable CD4+ and CD8+ responses in humans. Importantly, striking similarities in the upregulation of transcriptional and signal transduction pathways were seen in subjects vaccinated with poly-ICLC and in volunteers who had received the highly effective, replication-competent yellow fever vaccine. Furthermore, >90% of ovarian carcinoma patients immunized with poly-ICLC in combination with a NY-ESO-1 peptide vaccine (in addition to Montanide) showed induction of CD4+ and CD8+ T cell, as well as antibody responses to the peptide in a recent phase 1 study. At the same time, poly-ICLC has been extensively tested in more than 25 clinical trials to date and exhibited a relatively benign toxicity profile. In addition to a powerful and specific immunogen the neoantigen peptides may be combined with an adjuvant (e.g., poly-ICLC) or another anti-neoplastic agent. Without being bound by theory, these neoantigens are expected to bypass central thymic tolerance (thus allowing stronger anti-tumor T cell response), while reducing the potential for autoimmunity (e.g., by avoiding targeting of normal self-antigens). An effective immune response advantageously includes a strong adjuvant to activate the immune system (Speiser and Romero, Molecularly defined vaccines for cancer immunotherapy, and protective T cell immunity Seminars in Immunol 22: 144 (2010)). For example, Toll-like receptors (TLRs) have emerged as powerful sensors of microbial and viral pathogen "danger signals", effectively inducing the innate immune system, and in turn, the adaptive immune system (Bhardwaj and Gnjatic, TLR AGONISTS: Are They Good Adjuvants?Cancer J. 16:382-391 (2010)). Among the TLR agonists, poly-ICLC (a synthetic double-stranded RNA mimic) is one of the most potent activators of myeloid-derived dendritic cells. In a human volunteer study, poly-ICLC has been shown to be safe and to induce a gene expression profile in peripheral blood cells comparable to that induced by one of the most potent live attenuated viral vaccines, the yellow fever vaccine YF-17D (Caskey et al, Synthetic double-stranded RNA induces innate immune responses similar to a live viral vaccine in humans J Exp Med 208:2357 (2011)). In a preferred embodiment Hiltonol®, a GMP preparation of poly-ICLC prepared by Oncovir, Inc, is utilized as the adjuvant. In other embodiments, other adjuvants described herein are envisioned. For instance oil-in-water, water-in-oil or multiphasic W/O/W; see, e.g., U.S. Pat. No. 7,608,279 and Aucouturier et al, Vaccine 19 (2001), 2666-2672, and documents cited therein.

Pharmaceutical Compositions/Methods of Delivery

The present invention is also directed to pharmaceutical compositions comprising an effective amount of one or more antigenic peptides as described herein (including a pharmaceutically acceptable salt, thereof), optionally in combination with a pharmaceutically acceptable carrier, excipient or additive.

The term "pharmaceutically acceptable" refers to approved or approvable by a regulatory agency of the Federal or a state government or listed in the U.S. Pharmacopeia or other generally recognized pharmacopeia for use in animals, including humans.

A "pharmaceutically acceptable excipient, carrier or diluent" refers to an excipient, carrier or diluent that can be administered to a subject, together with an agent, and which does not destroy the pharmacological activity thereof and is nontoxic when administered in doses sufficient to deliver a therapeutic amount of the agent.

A "pharmaceutically acceptable salt" of pooled tumor specific neoantigens as recited herein may be an acid or base salt that is generally considered in the art to be suitable for use in contact with the tissues of human beings or animals without excessive toxicity, irritation, allergic response, or other problem or complication. Such salts include mineral and organic acid salts of basic residues such as amines, as well as alkali or organic salts of acidic residues such as carboxylic acids. Specific pharmaceutical salts include, but are not limited to, salts of acids such as hydrochloric, phosphoric, hydrobromic, malic, glycolic, fumaric, sulfuric, sulfamic, sulfanilic, formic, toluenesulfonic, methanesulfonic, benzene sulfonic, ethane disulfonic, 2-hydroxyethylsulfonic, nitric, benzoic, 2-acetoxybenzoic, citric, tartaric, lactic, stearic, salicylic, glutamic, ascorbic, pamoic, succinic, fumaric, maleic, propionic, hydroxymaleic, hydroiodic, phenylacetic, alkanoic such as acetic, HOOC—(CH2)n-COOH where n is 0-4, and the like. Similarly, pharmaceutically acceptable cations include, but are not limited to sodium, potassium, calcium, aluminum, lithium and ammonium. Those of ordinary skill in the art will recognize from this disclosure and the knowledge in the art that further pharmaceutically acceptable salts for the pooled tumor specific neoantigens provided herein, including those listed by Remington's Pharmaceutical Sciences, 17th ed., Mack Publishing Company, Easton, PA, p. 1418 (1985). In general, a pharmaceutically acceptable acid or base salt can be synthesized from a parent compound that contains a basic or acidic moiety by any conventional chemical method. Briefly, such salts can be prepared by reacting the free acid or base forms of these compounds with a stoichiometric amount of the appropriate base or acid in an appropriate solvent.

When administered as a combination, the therapeutic agents (i.e. the neoantigenic peptides) can be formulated as separate compositions that are given at the same time or different times, or the therapeutic agents can be given as a single composition.

The compositions may be administered once daily, twice daily, once every two days, once every three days, once every four days, once every five days, once every six days, once every seven days, once every two weeks, once every three weeks, once every four weeks, once every two months, once every six months, or once per year. The dosing interval can be adjusted according to the needs of individual patients. For longer intervals of administration, extended release or depot formulations can be used.

The compositions of the invention can be used to treat diseases and disease conditions that are acute, and may also be used for treatment of chronic conditions. In particular, the compositions of the invention are used in methods to treat or prevent a neoplasia. In certain embodiments, the compounds of the invention are administered for time periods exceeding two weeks, three weeks, one month, two months, three months, four months, five months, six months, one year, two years, three years, four years, or five years, ten years, or fifteen years; or for example, any time period range in days, months or years in which the low end of the range is any time period between 14 days and 15 years and the upper end of the range is between 15 days and 20 years (e.g., 4 weeks and 15 years, 6 months and 20 years). In some cases, it may be advantageous for the compounds of the invention to be administered for the remainder of the patient's life. In preferred embodiments, the patient is monitored to check the progression of the disease or disorder, and the dose is adjusted accordingly. In preferred embodiments, treatment according to the invention is effective for at least two weeks, three weeks, one month, two months, three months, four months, five months, six months, one year, two years, three years, four years, or five years, ten years, fifteen years, twenty years, or for the remainder of the subject's life.

Surgical resection uses surgery to remove abnormal tissue in cancer, such as mediastinal, neurogenic, or germ cell tumors, or thymoma. In certain embodiments, administration of the composition is initiated following tumor resection. In other embodiments, administration of the neoplasia vaccine or immunogenic composition is initiated 1, 2, 3, 4, 5, 6, 7, 8, 9, 10, 11, 12, 13, 14, 15 or more weeks after tumor resection. Preferably, administration of the neoplasia vaccine or immunogenic composition is initiated 4, 5, 6, 7, 8, 9, 10, 11 or 12 weeks after tumor resection.

In certain embodiments, the vaccine of the present invention is administered to a subject one or more times. In certain embodiments, a subject is primed with a vaccine and then boosted after the initial vaccination. The term "prime/boost" or "prime/boost dosing regimen" is meant to refer to the successive administrations of a vaccine or immunogenic or immunological compositions. The priming administration (priming) is the administration of a first vaccine or immunogenic or immunological composition type and may comprise one, two or more administrations. The boost administration is the second administration of a vaccine or immunogenic or immunological composition type and may comprise one, two or more administrations, and, for instance, may comprise or consist essentially of annual administrations. In certain embodiments, administration of the neoplasia vaccine or immunogenic composition is in a prime/boost dosing regimen.

In certain embodiments, administration of the neoplasia vaccine or immunogenic composition is in a prime/boost dosing regimen, for example administration of the neoplasia vaccine or immunogenic composition at weeks 1, 2, 3 or 4 as a prime and administration of the neoplasia vaccine or immunogenic composition is at months 2, 3 or 4 as a boost. In another embodiment heterologous prime-boost strategies are used to elicit a greater cytotoxic T cell response (see Schneider et al., Induction of CD8+ T cells using heterologous prime-boost immunisation strategies, Immunological Reviews Volume 170, Issue 1, pages 29-38, August 1999). In another embodiment DNA encoding neoantigens is used to prime followed by a protein boost. In another embodiment protein is used to prime followed by boosting with a virus encoding the neoantigen. In another embodiment a virus encoding the neoantigen is used to prime and another virus is used to boost. In another embodiment protein is used to prime and DNA is used to boost. In a preferred embodiment a DNA vaccine or immunogenic composition is used to prime a T cell response and a recombinant viral vaccine or immunogenic composition is used to boost the response. In another preferred embodiment a viral vaccine or immunogenic composition is coadministered with a protein or DNA vaccine or immunogenic composition to act as an adjuvant for the protein or DNA vaccine or immunogenic composition. The patient can then be boosted with either the viral vaccine or immunogenic composition, protein, or DNA vaccine or immunogenic composition (see Hutchings et al., Combination of protein and viral vaccines induces potent cellular and humoral immune responses and enhanced protection from murine malaria challenge. Infect Immun. 2007 December; 75(12):5819-26. Epub 2007 Oct. 1). The pharmaceutical compositions can be processed in accordance with conventional methods of pharmacy to produce medicinal agents for administration to patients in need thereof, including humans and other mammals.

Modifications of the neoantigenic peptides can affect the solubility, bioavailability and rate of metabolism of the peptides, thus providing control over the delivery of the active species. Solubility can be assessed by preparing the neoantigenic peptide and testing according to known methods well within the routine practitioner's skill in the art.

In certain embodiments of the pharmaceutical composition the pharmaceutically acceptable carrier comprises water. In certain embodiments, the pharmaceutically acceptable carrier further comprises dextrose. In certain embodiments, the pharmaceutically acceptable carrier further comprises dimethylsulfoxide. In certain embodiments, the pharmaceutical composition further comprises an immunomodulator or adjuvant. In certain embodiments, the immunomodulator or adjuvant is selected from the group consisting of poly-ICLC, STING agonist, 1018 ISS, aluminum salts, Amplivax, AS15, BCG, CP-870,893, CpG7909, CyaA, dSLEVI, GM-CSF, IC30, IC31, Imiquimod, ImuFact FMP321, IS Patch, ISS, ISCOMATRLX, JuvImmune, LipoVac, MF59, monophosphoryl lipid A, Montanide IMS 1312, Montanide ISA 206, Montanide ISA 50V, Montanide ISA-51, OK-432, OM-174, OM-197-MP-EC, ONTAK, PEPTEL, vector system, PLGA microparticles, resiquimod, SRL172, Virosomes and other Virus-like particles, YF-17D, VEGF trap, R848, beta-glucan, Pam3Cys, and Aquila's QS21 stimulon. In certain embodiments, the immunomodulator or adjuvant comprises poly-ICLC.

Xanthenone derivatives such as, for example, Vadimezan or AsA404 (also known as 5,6-dimethylaxanthenone-4-acetic acid (DMXAA)), may also be used as adjuvants according to embodiments of the invention. Alternatively, such derivatives may also be administered in parallel to the vaccine or immunogenic composition of the invention, for example via systemic or intratumoral delivery, to stimulate immunity at the tumor site. Without being bound by theory, it is believed that such xanthenone derivatives act by stimulating interferon (IFN) production via the stimulator of IFN gene (ISTING) receptor (see e.g., Conlon et al. (2013)

Mouse, but not Human STING, Binds and Signals in Response to the Vascular Disrupting Agent 5,6-Dimethyl-xanthenone-4-Acetic Acid, Journal of Immunology, 190: 5216-25 and Kim et al. (2013) Anticancer Flavonoids are Mouse-Selective STING Agonists, 8: 1396-1401). The vaccine or immunological composition may also include an adjuvant compound chosen from the acrylic or methacrylic polymers and the copolymers of maleic anhydride and an alkenyl derivative. It is in particular a polymer of acrylic or methacrylic acid cross-linked with a polyalkenyl ether of a sugar or polyalcohol (carbomer), in particular cross-linked with an allyl sucrose or with allylpentaerythritol. It may also be a copolymer of maleic anhydride and ethylene cross-linked, for example, with divinyl ether (see U.S. Pat. No. 6,713,068 hereby incorporated by reference in its entirety).

In certain embodiments, the pH modifier can stabilize the adjuvant or immunomodulator as described herein.

In certain embodiments, a pharmaceutical composition comprises: one to five peptides, dimethylsulfoxide (DMSO), dextrose, water, succinate, poly I: poly C, poly-L-lysine, carboxymethylcellulose, and chloride. In certain embodiments, each of the one to five peptides is present at a concentration of 300 µg/ml. In certain embodiments, the pharmaceutical composition comprises <3% DMSO by volume. In certain embodiments, the pharmaceutical composition comprises 3.6-3.7% dextrose in water. In certain embodiments, the pharmaceutical composition comprises 3.6-3.7 mM succinate (e.g., as sodium succinate) or a salt thereof. In certain embodiments, the pharmaceutical composition comprises 0.5 mg/ml poly I: poly C. In certain embodiments, the pharmaceutical composition comprises 0.375 mg/ml poly-L-Lysine. In certain embodiments, the pharmaceutical composition comprises 1.25 mg/ml sodium carboxymethylcellulose. In certain embodiments, the pharmaceutical composition comprises 0.225% sodium chloride.

Pharmaceutical compositions comprise the herein-described tumor specific neoantigenic peptides in a therapeutically effective amount for treating diseases and conditions (e.g., a neoplasia/tumor), which have been described herein, optionally in combination with a pharmaceutically acceptable additive, carrier and/or excipient. One of ordinary skill in the art from this disclosure and the knowledge in the art will recognize that a therapeutically effective amount of one of more compounds according to the present invention may vary with the condition to be treated, its severity, the treatment regimen to be employed, the pharmacokinetics of the agent used, as well as the patient (animal or human) treated.

To prepare the pharmaceutical compositions according to the present invention, a therapeutically effective amount of one or more of the compounds according to the present invention is preferably intimately admixed with a pharmaceutically acceptable carrier according to conventional pharmaceutical compounding techniques to produce a dose. A carrier may take a wide variety of forms depending on the form of preparation desired for administration, e.g., ocular, oral, topical or parenteral, including gels, creams ointments, lotions and time released implantable preparations, among numerous others. In preparing pharmaceutical compositions in oral dosage form, any of the usual pharmaceutical media may be used. Thus, for liquid oral preparations such as suspensions, elixirs and solutions, suitable carriers and additives including water, glycols, oils, alcohols, flavoring agents, preservatives, coloring agents and the like may be used. For solid oral preparations such as powders, tablets, capsules, and for solid preparations such as suppositories, suitable carriers and additives including starches, sugar carriers, such as dextrose, mannitol, lactose and related carriers, diluents, granulating agents, lubricants, binders, disintegrating agents and the like may be used. If desired, the tablets or capsules may be enteric-coated or sustained release by standard techniques.

The active compound is included in the pharmaceutically acceptable carrier or diluent in an amount sufficient to deliver to a patient a therapeutically effective amount for the desired indication, without causing serious toxic effects in the patient treated.

Oral compositions generally include an inert diluent or an edible carrier. They may be enclosed in gelatin capsules or compressed into tablets. For the purpose of oral therapeutic administration, the active compound or its prodrug derivative can be incorporated with excipients and used in the form of tablets, troches, or capsules. Pharmaceutically compatible binding agents, and/or adjuvant materials can be included as part of the composition.

The tablets, pills, capsules, troches and the like can contain any of the following ingredients, or compounds of a similar nature: a binder such as microcrystalline cellulose, gum tragacanth or gelatin; an excipient such as starch or lactose, a dispersing agent such as alginic acid or corn starch; a lubricant such as magnesium stearate; a glidant such as colloidal silicon dioxide; a sweetening agent such as sucrose or saccharin; or a flavoring agent such as peppermint, methyl salicylate, or orange flavoring. When the dosage unit form is a capsule, it can contain, in addition to material herein discussed, a liquid carrier such as a fatty oil. In addition, dosage unit forms can contain various other materials which modify the physical form of the dosage unit, for example, coatings of sugar, shellac, or enteric agents. Formulations of the present invention suitable for oral administration may be presented as discrete units such as capsules, cachets or tablets each containing a predetermined amount of the active ingredient; as a powder or granules; as a solution or a suspension in an aqueous liquid or a non-aqueous liquid; or as an oil-in-water liquid emulsion or a water-in-oil emulsion and as a bolus, etc.

A tablet may be made by compression or molding, optionally with one or more accessory ingredients. Compressed tablets may be prepared by compressing in a suitable machine the active ingredient in a free-flowing form such as a powder or granules, optionally mixed with a binder, lubricant, inert diluent, preservative, surface-active or dispersing agent. Molded tablets may be made by molding in a suitable machine a mixture of the powdered compound moistened with an inert liquid diluent. The tablets optionally may be coated or scored and may be formulated so as to provide slow or controlled release of the active ingredient therein.

Methods of formulating such slow or controlled release compositions of pharmaceutically active ingredients, are known in the art and described in several issued U.S. patents, some of which include, but are not limited to, U.S. Pat. Nos. 3,870,790; 4,226,859; 4,369,172; 4,842,866 and 5,705,190, the disclosures of which are incorporated herein by reference in their entireties. Coatings can be used for delivery of compounds to the intestine (see, e.g., U.S. Pat. Nos. 6,638,534, 5,541,171, 5,217,720, and 6,569,457, and references cited therein).

The active compound or pharmaceutically acceptable salt thereof may also be administered as a component of an elixir, suspension, syrup, wafer, chewing gum or the like. A syrup may contain, in addition to the active compounds, sucrose or fructose as a sweetening agent and certain preservatives, dyes and colorings and flavors.

Solutions or suspensions used for ocular, parenteral, intradermal, subcutaneous, or topical application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates; and agents for the adjustment of tonicity such as sodium chloride or dextrose. In certain embodiments, the pharmaceutically acceptable carrier is an aqueous solvent, i.e., a solvent comprising water, optionally with additional co-solvents. Exemplary pharmaceutically acceptable carriers include water, buffer solutions in water (such as phosphate-buffered saline (PBS), and 5% dextrose in water (D5W)). In certain embodiments, the aqueous solvent further comprises dimethyl sulfoxide (DMSO), e.g., in an amount of about 1-4%, or 1-3%. In certain embodiments, the pharmaceutically acceptable carrier is isotonic (i.e., has substantially the same osmotic pressure as a body fluid such as plasma).

In one embodiment, the active compounds are prepared with carriers that protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, polylactic acid, and polylactic-co-glycolic acid (PLGA). Methods for preparation of such formulations are within the ambit of the skilled artisan in view of this disclosure and the knowledge in the art.

A skilled artisan from this disclosure and the knowledge in the art recognizes that in addition to tablets, other dosage forms can be formulated to provide slow or controlled release of the active ingredient. Such dosage forms include, but are not limited to, capsules, granulations and gel-caps.

Liposomal suspensions may also be pharmaceutically acceptable carriers. These may be prepared according to methods known to those skilled in the art. For example, liposomal formulations may be prepared by dissolving appropriate lipid(s) in an inorganic solvent that is then evaporated, leaving behind a thin film of dried lipid on the surface of the container. An aqueous solution of the active compound are then introduced into the container. The container is then swirled by hand to free lipid material from the sides of the container and to disperse lipid aggregates, thereby forming the liposomal suspension. Other methods of preparation well known by those of ordinary skill may also be used in this aspect of the present invention.

The formulations may conveniently be presented in unit dosage form and may be prepared by conventional pharmaceutical techniques. Such techniques include the step of bringing into association the active ingredient and the pharmaceutical carrier(s) or excipient(s). In general, the formulations are prepared by uniformly and intimately bringing into association the active ingredient with liquid carriers or finely divided solid carriers or both, and then, if necessary, shaping the product.

Formulations and compositions suitable for topical administration in the mouth include lozenges comprising the ingredients in a flavored basis, usually sucrose and acacia or tragacanth; pastilles comprising the active ingredient in an inert basis such as gelatin and glycerin, or sucrose and acacia; and mouthwashes comprising the ingredient to be administered in a suitable liquid carrier.

Formulations suitable for topical administration to the skin may be presented as ointments, creams, gels and pastes comprising the ingredient to be administered in a pharmaceutical acceptable carrier. A preferred topical delivery system is a transdermal patch containing the ingredient to be administered.

Formulations for rectal administration may be presented as a suppository with a suitable base comprising, for example, cocoa butter or a salicylate.

Formulations suitable for nasal administration, wherein the carrier is a solid, include a coarse powder having a particle size, for example, in the range of 20 to 500 microns which is administered in the manner in which snuff is administered, i.e., by rapid inhalation through the nasal passage from a container of the powder held close up to the nose. Suitable formulations, wherein the carrier is a liquid, for administration, as for example, a nasal spray or as nasal drops, include aqueous or oily solutions of the active ingredient.

Formulations suitable for vaginal administration may be presented as pessaries, tampons, creams, gels, pastes, foams or spray formulations containing in addition to the active ingredient such carriers as are known in the art to be appropriate.

The parenteral preparation can be enclosed in ampoules, disposable syringes or multiple dose vials made of glass or plastic. If administered intravenously, preferred carriers include, for example, physiological saline or phosphate buffered saline (PBS).

For parenteral formulations, the carrier usually comprises sterile water or aqueous sodium chloride solution, though other ingredients including those which aid dispersion may be included. Of course, where sterile water is to be used and maintained as sterile, the compositions and carriers are also sterilized. Injectable suspensions may also be prepared, in which case appropriate liquid carriers, suspending agents and the like may be employed. Formulations suitable for parenteral administration include aqueous and non-aqueous sterile injection solutions which may contain antioxidants, buffers, bacteriostats and solutes which render the formulation isotonic with the blood of the intended recipient; and aqueous and non-aqueous sterile suspensions which may include suspending agents and thickening agents. The formulations may be presented in unit-dose or multi-dose containers, for example, sealed ampules and vials, and may be stored in a freeze-dried (lyophilized) condition requiring only the addition of the sterile liquid carrier, for example, water for injections, immediately prior to use. Extemporaneous injection solutions and suspensions may be prepared from sterile powders, granules and tablets of the kind previously described.

Administration of the active compound may range from continuous (intravenous drip) to several oral administrations per day (for example, Q.I.D.) and may include oral, topical, eye or ocular, parenteral, intramuscular, intravenous, subcutaneous, transdermal (which may include a penetration enhancement agent), buccal and suppository administration, among other routes of administration, including through an eye or ocular route.

The neoplasia vaccine or immunogenic composition, and any additional agents, may be administered by injection, orally, parenterally, by inhalation spray, rectally, vaginally, or topically in dosage unit formulations containing conventional pharmaceutically acceptable carriers, adjuvants, and vehicles. The term parenteral as used herein includes, into a lymph node or nodes, subcutaneous, intravenous, intramuscular, intrasternal, infusion techniques, intraperitoneally, eye or ocular, intravitreal, intrabuccal, transdermal, intranasal, into the brain, including intracranial and intradural, into the joints, including ankles, knees, hips, shoulders, elbows, wrists, directly into tumors, and the like, and in suppository form.

In certain embodiments, the vaccine or immunogenic composition is administered intravenously or subcutaneously. Various techniques can be used for providing the subject compositions at the site of interest, such as injection, use of catheters, trocars, projectiles, pluronic gel, stents, sustained drug release polymers or other device which provides for internal access. Where an organ or tissue is accessible because of removal from the patient, such organ or tissue may be bathed in a medium containing the subject compositions, the subject compositions may be painted onto the organ, or may be applied in any convenient way.

The tumor specific neoantigenic peptides may be administered through a device suitable for the controlled and sustained release of a composition effective in obtaining a desired local or systemic physiological or pharmacological effect. The method includes positioning the sustained released drug delivery system at an area wherein release of the agent is desired and allowing the agent to pass through the device to the desired area of treatment.

The tumor specific neoantigenic peptides may be utilized in combination with at least one known other therapeutic agent, or a pharmaceutically acceptable salt of said agent. Examples of known therapeutic agents which can be used for combination therapy include, but are not limited to, corticosteroids (e.g., cortisone, prednisone, dexamethasone), non-steroidal anti-inflammatory drugs (NSAIDS) (e.g., ibuprofen, celecoxib, aspirin, indomethacin, naproxen), alkylating agents such as busulfan, cis-platin, mitomycin C, and carboplatin; antimitotic agents such as colchicine, vinblastine, paclitaxel, and docetaxel; topo I inhibitors such as camptothecin and topotecan; topo II inhibitors such as doxorubicin and etoposide; and/or RNA/DNA antimetabolites such as 5-azacytidine, 5-fluorouracil and methotrexate; DNA antimetabolites such as 5-fluoro-2'-deoxy-uridine, ara-C, hydroxyurea and thioguanine; antibodies such as HERCEPTIN and RITUXAN.

It should be understood that in addition to the ingredients particularly mentioned herein, the formulations of the present invention may include other agents conventional in the art having regard to the type of formulation in question, for example, those suitable for oral administration may include flavoring agents.

Pharmaceutically acceptable salt forms may be the preferred chemical form of compounds according to the present invention for inclusion in pharmaceutical compositions according to the present invention.

The present compounds or their derivatives, including prodrug forms of these agents, can be provided in the form of pharmaceutically acceptable salts. As used herein, the term pharmaceutically acceptable salts or complexes refers to appropriate salts or complexes of the active compounds according to the present invention which retain the desired biological activity of the parent compound and exhibit limited toxicological effects to normal cells. Nonlimiting examples of such salts are (a) acid addition salts formed with inorganic acids (for example, hydrochloric acid, hydrobromic acid, sulfuric acid, phosphoric acid, nitric acid, and the like), and salts formed with organic acids such as acetic acid, oxalic acid, tartaric acid, succinic acid, malic acid, ascorbic acid, benzoic acid, tannic acid, pamoic acid, alginic acid, and polyglutamic acid, among others; (b) base addition salts formed with metal cations such as zinc, calcium, sodium, potassium, and the like, among numerous others.

The compounds herein are commercially available or can be synthesized. As can be appreciated by the skilled artisan, further methods of synthesizing the compounds of the formulae herein is evident to those of ordinary skill in the art. Additionally, the various synthetic steps may be performed in an alternate sequence or order to give the desired compounds. Synthetic chemistry transformations and protecting group methodologies (protection and deprotection) useful in synthesizing the compounds described herein are known in the art and include, for example, those such as described in R. Larock, Comprehensive Organic Transformations, 2nd. Ed., Wiley-VCH Publishers (1999); T. W. Greene and P. G. M. Wuts, Protective Groups in Organic Synthesis, 3rd. Ed., John Wiley and Sons (1999); L. Fieser and M. Fieser, Fieser and Fieser's Reagents for Organic Synthesis, John Wiley and Sons (1999); and L. Paquette, ed., Encyclopedia of Reagents for Organic Synthesis, John Wiley and Sons (1995), and subsequent editions thereof.

The additional agents that may be included with the tumor specific neo-antigenic peptides of this invention may contain one or more asymmetric centers and thus occur as racemates and racemic mixtures, single enantiomers, individual diastereomers and diastereomeric mixtures. All such isomeric forms of these compounds are expressly included in the present invention. The compounds of this invention may also be represented in multiple tautomeric forms, in such instances, the invention expressly includes all tautomeric forms of the compounds described herein (e.g., alkylation of a ring system may result in alkylation at multiple sites, the invention expressly includes all such reaction products). All such isomeric forms of such compounds are expressly included in the present invention. All crystal forms of the compounds described herein are expressly included in the present invention.

Dosage. When the agents described herein are administered as pharmaceuticals to humans or animals, they can be given per se or as a pharmaceutical composition containing active ingredient in combination with a pharmaceutically acceptable carrier, excipient, or diluent.

Actual dosage levels and time course of administration of the active ingredients in the pharmaceutical compositions of the invention can be varied so as to obtain an amount of the active ingredient which is effective to achieve the desired therapeutic response for a particular patient, composition, and mode of administration, without being toxic to the patient. Generally, agents or pharmaceutical compositions of the invention are administered in an amount sufficient to reduce or eliminate symptoms associated with neoplasia, e.g. cancer or tumors.

A preferred dose of an agent is the maximum that a patient can tolerate and not develop serious or unacceptable side effects. Exemplary dose ranges include 0.01 mg to 250 mg per day, 0.01 mg to 100 mg per day, 1 mg to 100 mg per day, 10 mg to 100 mg per day, 1 mg to 10 mg per day, and 0.01 mg to 10 mg per day. A preferred dose of an agent is the maximum that a patient can tolerate and not develop serious or unacceptable side effects. In embodiments, the agent is administered at a concentration of about 10 micrograms to about 100 mg per kilogram of body weight per day, about 0.1 to about 10 mg/kg per day, or about 1.0 mg to about 10 mg/kg of body weight per day.

In embodiments, the pharmaceutical composition comprises an agent in an amount ranging between 1 and 10 mg, such as 1, 2, 3, 4, 5, 6, 7, 8, 9, or 10 mg.

In embodiments, the therapeutically effective dosage produces a serum concentration of an agent of from about 0.1 ng/ml to about 50-100 mg/ml. The pharmaceutical compositions 5 typically should provide a dosage of from about 0.001 mg to about 2000 mg of compound per kilogram of body weight per day. For example, dosages for systemic administration to a human patient can range from 1-10 mg/kg, 20-80 mg/kg, 5-50 mg/kg, 75-150 mg/kg, 100-500 mg/kg, 250-750 mg/kg, 500-1000 mg/kg, 1-10 mg/kg, 5-50 mg/kg, 25-75 mg/kg, 50-100 mg/kg, 100-250 mg/kg, 50-100 mg/kg, 250-500 mg/kg, 500-750 mg/kg, 750-1000 mg/kg, 1000-1500 mg/kg, 10 1500-2000 mg/kg, 5 mg/kg, 20 mg/kg, 50 mg/kg, 100 mg/kg, 500 mg/kg, 1000 mg/kg, 1500 mg/kg, or 2000 mg/kg. Pharmaceutical dosage unit forms are prepared to provide from about 1 mg to about 5000 mg, for example from about 100 to about 2500 mg of the compound or a combination of essential ingredients per dosage unit form.

In embodiments, about 50 nM to about 1 μM of an agent is administered to a subject. In related embodiments, about 50-100 nM, 50-250 nM, 100-500 nM, 250-500 nM, 250-750 nM, 500-750 nM, 500 nM to 1 μM, or 750 nM to 1 μM of an agent is administered to a subject.

Determination of an effective amount is well within the capability of those skilled in the art, especially in light of the detailed disclosure provided herein. Generally, an efficacious or effective amount of an agent is determined by first administering a low dose of the agent(s) and then incrementally increasing the administered dose or dosages until a desired effect (e.g., reduce or eliminate symptoms associated with viral infection or autoimmune disease) is observed in the treated subject, with minimal or acceptable toxic side effects. Applicable methods for determining an appropriate dose and dosing schedule for administration of a pharmaceutical composition of the present invention are described, for example, in Goodman and Gilman's The Pharmacological Basis of Therapeutics, Goodman et al., eds., 11th Edition, McGraw-Hill 2005, and Remington: The Science and Practice of Pharmacy, 20th and 21st Editions, Gennaro and University of the Sciences in Philadelphia, Eds., Lippincott Williams & Wilkins (2003 and 2005), each of which is hereby incorporated by reference.

Preferred unit dosage formulations are those containing a daily dose or unit, daily sub-dose, as herein discussed, or an appropriate fraction thereof, of the administered ingredient.

The dosage regimen for treating a disorder or a disease with the tumor specific neoantigenic peptides of this invention and/or compositions of this invention is based on a variety of factors, including the type of disease, the age, weight, sex, medical condition of the patient, the severity of the condition, the route of administration, and the particular compound employed. Thus, the dosage regimen may vary widely, but can be determined routinely using standard methods.

The amounts and dosage regimens administered to a subject can depend on a number of factors, such as the mode of administration, the nature of the condition being treated, the body weight of the subject being treated and the judgment of the prescribing physician; all such factors being within the ambit of the skilled artisan from this disclosure and the knowledge in the art.

The amount of compound included within therapeutically active formulations according to the present invention is an effective amount for treating the disease or condition. In general, a therapeutically effective amount of the present preferred compound in dosage form usually ranges from slightly less than about 0.025 mg/kg/day to about 2.5 g/kg/day, preferably about 0.1 mg/kg/day to about 100 mg/kg/day of the patient or considerably more, depending upon the compound used, the condition or infection treated and the route of administration, although exceptions to this dosage range may be contemplated by the present invention. In its most preferred form, compounds according to the present invention are administered in amounts ranging from about 1 mg/kg/day to about 100 mg/kg/day. The dosage of the compound can depend on the condition being treated, the particular compound, and other clinical factors such as weight and condition of the patient and the route of administration of the compound. It is to be understood that the present invention has application for both human and veterinary use.

For oral administration to humans, a dosage of between approximately 0.1 to 100 mg/kg/day, preferably between approximately 1 and 100 mg/kg/day, is generally sufficient.

Where drug delivery is systemic rather than topical, this dosage range generally produces effective blood level concentrations of active compound ranging from less than about 0.04 to about 400 micrograms/cc or more of blood in the patient. The compound is conveniently administered in any suitable unit dosage form, including but not limited to one containing 0.001 to 3000 mg, preferably 0.05 to 500 mg of active ingredient per unit dosage form. An oral dosage of 10-250 mg is usually convenient.

According to certain exemplary embodiments, the vaccine or immunogenic composition is administered at a dose of about 10 μg to 1 mg per neoantigenic peptide. According to certain exemplary embodiments, the vaccine or immunogenic composition is administered at an average weekly dose level of about 10 μg to 2000 μg per neoantigenic peptide.

The concentration of active compound in the drug composition will depend on absorption, distribution, inactivation, and excretion rates of the drug as well as other factors known to those of skill in the art. It is to be noted that dosage values will also vary with the severity of the condition to be alleviated. It is to be further understood that for any particular subject, specific dosage regimens should be adjusted over time according to the individual need and the professional judgment of the person administering or supervising the administration of the compositions, and that the concentration ranges set forth herein are exemplary only and are not intended to limit the scope or practice of the claimed composition. The active ingredient may be administered at once, or may be divided into a number of smaller doses to be administered at varying intervals of time.

The invention provides for pharmaceutical compositions containing at least one tumor specific neoantigen described herein. In embodiments, the pharmaceutical compositions contain a pharmaceutically acceptable carrier, excipient, or diluent, which includes any pharmaceutical agent that does not itself induce the production of an immune response harmful to a subject receiving the composition, and which may be administered without undue toxicity. As used herein, the term "pharmaceutically acceptable" means being approved by a regulatory agency of the Federal or a state government or listed in the U.S. Pharmacopia, European Pharmacopia or other generally recognized pharmacopia for use in mammals, and more particularly in humans. These compositions can be useful for treating and/or preventing viral infection and/or autoimmune disease.

A thorough discussion of pharmaceutically acceptable carriers, diluents, and other excipients is presented in Remington's Pharmaceutical Sciences (17th ed., Mack Publishing Company) and Remington: The Science and Practice of Pharmacy (21st ed., Lippincott Williams & Wilkins), which are hereby incorporated by reference. The formulation of the pharmaceutical composition should suit the mode of administration. In embodiments, the pharmaceutical composition is suitable for administration to humans, and can be sterile, non-particulate and/or non-pyrogenic.

Pharmaceutically acceptable carriers, excipients, or diluents include, but are not limited, to saline, buffered saline, dextrose, water, glycerol, ethanol, sterile isotonic aqueous buffer, and combinations thereof.

Wetting agents, emulsifiers and lubricants, such as sodium lauryl sulfate and magnesium stearate, as well as coloring agents, release agents, coating agents, sweetening, flavoring and perfuming agents, preservatives, and antioxidants can also be present in the compositions.

Examples of pharmaceutically-acceptable antioxidants include, but are not limited to: (1) water soluble antioxidants, such as ascorbic acid, cysteine hydrochloride, sodium bisulfate, sodium metabi sulfite, sodium sulfite and the like; (2) oil-soluble antioxidants, such as ascorbyl palmitate, butylated hydroxyanisole (BHA), butylated hydroxytoluene (BHT), lecithin, propyl gallate, alpha-tocopherol, and the like; and (3) metal chelating agents, such as citric acid, ethylenediamine tetraacetic acid (EDTA), sorbitol, tartaric acid, phosphoric acid, and the like.

In embodiments, the pharmaceutical composition is provided in a solid form, such as a lyophilized powder suitable for reconstitution, a liquid solution, suspension, emulsion, tablet, pill, capsule, sustained release formulation, or powder.

In embodiments, the pharmaceutical composition is supplied in liquid form, for example, in a sealed container indicating the quantity and concentration of the active ingredient in the pharmaceutical composition. In related embodiments, the liquid form of the pharmaceutical composition is supplied in a hermetically sealed container. Methods for formulating the pharmaceutical compositions of the present invention are conventional and well known in the art (see Remington and Remington's). One of skill in the art can readily formulate a pharmaceutical composition having the desired characteristics (e.g., route of administration, biosafety, and release profile).

Methods for preparing the pharmaceutical compositions include the step of bringing into association the active ingredient with a pharmaceutically acceptable carrier and, optionally, one or more accessory ingredients. The pharmaceutical compositions can be prepared by uniformly and intimately bringing into association the active ingredient with liquid carriers, or finely divided solid carriers, or both, and then, if necessary, shaping the product. Additional methodology for preparing the pharmaceutical compositions, including the preparation of multilayer dosage forms, are described in Ansel's Pharmaceutical Dosage Forms and Drug Delivery Systems (9th ed., Lippincott Williams & Wilkins), which is hereby incorporated by reference.

Pharmaceutical compositions suitable for oral administration can be in the form of capsules, cachets, pills, tablets, lozenges (using a flavored basis, usually sucrose and acacia or tragacanth), powders, granules, or as a solution or a suspension in an aqueous or non-aqueous liquid, or as an oil-in-water or water-in-oil liquid emulsion, or as an elixir or syrup, or as pastilles (using an inert base, such as gelatin and glycerin, or sucrose and acacia) and/or as mouth washes and the like, each containing a predetermined amount of a compound(s) described herein, a derivative thereof, or a pharmaceutically acceptable salt or prodrug thereof as the active ingredient(s). The active ingredient can also be administered as a bolus, electuary, or paste.

In solid dosage forms for oral administration (e.g., capsules, tablets, pills, dragees, powders, granules and the like), the active ingredient is mixed with one or more pharmaceutically acceptable carriers, excipients, or diluents, such as sodium citrate or dicalcium phosphate, and/or any of the following: (1) fillers or extenders, such as starches, lactose, sucrose, glucose, mannitol, and/or silicic acid; (2) binders, such as, for example, carboxymethylcellulose, alginates, gelatin, polyvinyl pyrrolidone, sucrose and/or acacia; (3) humectants, such as glycerol; (4) disintegrating agents, such as agar-agar, calcium carbonate, potato or tapioca starch, alginic acid, certain silicates, and sodium carbonate; (5) solution retarding agents, such as paraffin; (6) absorption accelerators, such as quaternary ammonium compounds; (7) wetting agents, such as, for example, acetyl alcohol and glycerol monostearate; (8) absorbents, such as kaolin and bentonite clay; (9) lubricants, such a talc, calcium stearate, magnesium stearate, solid polyethylene glycols, sodium lauryl sulfate, and mixtures thereof; and (10) coloring agents. In the case of capsules, tablets, and pills, the pharmaceutical compositions can also comprise buffering agents. Solid compositions of a similar type can also be prepared using fillers in soft and hard-filled gelatin capsules, and excipients such as lactose or milk sugars, as well as high molecular weight polyethylene glycols and the like.

A tablet can be made by compression or molding, optionally with one or more accessory ingredients. Compressed tablets can be prepared using binders (for example, gelatin or hydroxypropylmethyl cellulose), lubricants, inert diluents, preservatives, disintegrants (for example, sodium starch glycolate or cross-linked sodium carboxymethyl cellulose), surface-actives, and/or dispersing agents. Molded tablets can be made by molding in a suitable machine a mixture of the powdered active ingredient moistened with an inert liquid diluent.

The tablets and other solid dosage forms, such as dragees, capsules, pills, and granules, can optionally be scored or prepared with coatings and shells, such as enteric coatings and other coatings well known in the art.

In some embodiments, in order to prolong the effect of an active ingredient, it is desirable to slow the absorption of the compound from subcutaneous or intramuscular injection. This can be accomplished by the use of a liquid suspension of crystalline or amorphous material having poor water solubility. The rate of absorption of the active ingredient then depends upon its rate of dissolution which, in turn, can depend upon crystal size and crystalline form. Alternatively, delayed absorption of a parenterally-administered active ingredient is accomplished by dissolving or suspending the compound in an oil vehicle. In addition, prolonged absorption of the injectable pharmaceutical form can be brought about by the inclusion of agents that delay absorption such as aluminum monostearate and gelatin.

Controlled release parenteral compositions can be in form of aqueous suspensions, microspheres, microcapsules, magnetic microspheres, oil solutions, oil suspensions, emulsions, or the active ingredient can be incorporated in biocompatible carrier(s), liposomes, nanoparticles, implants or infusion devices.

Materials for use in the preparation of microspheres and/or microcapsules include biodegradable/bioerodible polymers such as polyglactin, poly-(isobutyl cyanoacrylate), poly(2-hydroxyethyl-L-glutamine) and poly(lactic acid). Biocompatible carriers which can be used when formulating a controlled release parenteral formulation include carbohydrates such as dextrans, proteins such as albumin, lipoproteins or antibodies.

Materials for use in implants can be non-biodegradable, e.g., polydimethylsiloxane, or biodegradable such as, e.g., poly(caprolactone), poly(lactic acid), poly(glycolic acid) or poly(ortho esters).

In embodiments, the active ingredient(s) are administered by aerosol. This is accomplished by preparing an aqueous aerosol, liposomal preparation, or solid particles containing the compound. A nonaqueous (e.g., fluorocarbon propellant) suspension can be used. The pharmaceutical composition can also be administered using a sonic nebulizer, which would minimize exposing the agent to shear, which can result in degradation of the compound.

Ordinarily, an aqueous aerosol is made by formulating an aqueous solution or suspension of the active ingredient(s) together with conventional pharmaceutically-acceptable carriers and stabilizers. The carriers and stabilizers vary with the requirements of the particular compound, but typically include nonionic surfactants (Tweens, Pluronics, or polyethylene glycol), innocuous proteins like serum albumin, sorbitan esters, oleic acid, lecithin, amino acids such as glycine, buffers, salts, sugars or sugar alcohols. Aerosols generally are prepared from isotonic solutions.

Dosage forms for topical or transdermal administration of an active ingredient(s) includes powders, sprays, ointments, pastes, creams, lotions, gels, solutions, patches and inhalants. The active ingredient(s) can be mixed under sterile conditions with a pharmaceutically acceptable carrier, and with any preservatives, buffers, or propellants as appropriate.

Transdermal patches suitable for use in the present invention are disclosed in Transdermal Drug Delivery: Developmental Issues and Research Initiatives (Marcel Dekker Inc., 1989) and U.S. Pat. Nos. 4,743,249, 4,906,169, 5,198,223, 4,816,540, 5,422,119, 5,023,084, which are hereby incorporated by reference. The transdermal patch can also be any transdermal patch well known in the art, including transscrotal patches. Pharmaceutical compositions in such transdermal patches can contain one or more absorption enhancers or skin permeation enhancers well known in the art (see, e.g., U.S. Pat. Nos. 4,379,454 and 4,973,468, which are hereby incorporated by reference). Transdermal therapeutic systems for use in the present invention can be based on iontophoresis, diffusion, or a combination of these two effects. Transdermal patches have the added advantage of providing controlled delivery of active ingredient(s) to the body. Such dosage forms can be made by dissolving or dispersing the active ingredient(s) in a proper medium. Absorption enhancers can also be used to increase the flux of the active ingredient across the skin. The rate of such flux can be controlled by either providing a rate controlling membrane or dispersing the active ingredient(s) in a polymer matrix or gel.

Such pharmaceutical compositions can be in the form of creams, ointments, lotions, liniments, gels, hydrogels, solutions, suspensions, sticks, sprays, pastes, plasters and other kinds of transdermal drug delivery systems. The compositions can also include pharmaceutically acceptable carriers or excipients such as emulsifying agents, antioxidants, buffering agents, preservatives, humectants, penetration enhancers, chelating agents, gel-forming agents, ointment bases, perfumes, and skin protective agents.

Examples of emulsifying agents include, but are not limited to, naturally occurring gums, e.g. gum acacia or gum tragacanth, naturally occurring phosphatides, e.g. soybean lecithin and sorbitan monooleate derivatives.

Examples of antioxidants include, but are not limited to, butylated hydroxy anisole (BHA), ascorbic acid and derivatives thereof, tocopherol and derivatives thereof, and cysteine.

Examples of preservatives include, but are not limited to, parabens, such as methyl or propyl p-hydroxybenzoate and benzalkonium chloride.

Examples of humectants include, but are not limited to, glycerin, propylene glycol, sorbitol and urea.

Examples of penetration enhancers include, but are not limited to, propylene glycol, DMSO, triethanolamine, N,N-dimethylacetamide, N,N-dimethylformamide, 2-pyrrolidone and derivatives thereof, tetrahydrofurfuryl alcohol, propylene glycol, diethylene glycol monoethyl or monomethyl ether with propylene glycol monolaurate or methyl laurate, eucalyptol, lecithin, TRANSCUTOL, and AZO E.

Examples of chelating agents include, but are not limited to, sodium EDTA, citric acid and phosphoric acid.

Examples of gel forming agents include, but are not limited to, Carbopol, cellulose derivatives, bentonite, alginates, gelatin and polyvinylpyrrolidone. In addition to the active ingredient(s), the ointments, pastes, creams, and gels of the present invention can contain excipients, such as animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays can contain excipients such as lactose, talc, silicic acid, aluminum hydroxide, calcium silicates and polyamide powder, or mixtures of these substances. Sprays can additionally contain customary propellants, such as chlorofluorohydrocarbons, and volatile unsubstituted hydrocarbons, such as butane and propane.

Injectable depot forms are made by forming microcapsule matrices of compound(s) of the invention in biodegradable polymers such as polylactide-polyglycolide. Depending on the ratio of compound to polymer, and the nature of the particular polymer employed, the rate of compound release can be controlled. Examples of other biodegradable polymers include poly(orthoesters) and poly(anhydrides). Depot injectable formulations are also prepared by entrapping the drug in liposomes or microemulsions which are compatible with body tissue.

Subcutaneous implants are well known in the art and are suitable for use in the present invention. Subcutaneous implantation methods are preferably non-irritating and mechanically resilient. The implants can be of matrix type, of reservoir type, or hybrids thereof. In matrix type devices, the carrier material can be porous or non-porous, solid or semi-solid, and permeable or impermeable to the active compound or compounds. The carrier material can be biodegradable or may slowly erode after administration. In some instances, the matrix is non-degradable but instead relies on the diffusion of the active compound through the matrix for the carrier material to degrade. Alternative subcutaneous implant methods utilize reservoir devices where the active compound or compounds are surrounded by a rate controlling membrane, e.g., a membrane independent of component concentration (possessing zero-order kinetics). Devices consisting of a matrix surrounded by a rate controlling membrane also suitable for use.

Both reservoir and matrix type devices can contain materials such as polydimethylsiloxane, such as SILASTIC, or other silicone rubbers. Matrix materials can be insoluble polypropylene, polyethylene, polyvinyl chloride, ethylvinyl acetate, polystyrene and polymethacrylate, as well as glycerol esters of the glycerol palmitostearate, glycerol stearate, and glycerol behenate type. Materials can be hydrophobic or hydrophilic polymers and optionally contain solubilizing agents. Subcutaneous implant devices can be slow-release capsules made with any suitable polymer, e.g., as described in U.S. Pat. Nos. 5,035,891 and 4,210,644, which are hereby incorporated by reference.

In general, at least four different approaches are applicable in order to provide rate control over the release and transdermal permeation of a drug compound. These approaches are: membrane-moderated systems, adhesive diffusion-controlled systems, matrix dispersion-type systems and microreservoir systems. It is appreciated that a controlled release percutaneous and/or topical composition can be obtained by using a suitable mixture of these approaches.

In a membrane-moderated system, the active ingredient is present in a reservoir which is totally encapsulated in a shallow compartment molded from a drug-impermeable laminate, such as a metallic plastic laminate, and a rate-controlling polymeric membrane such as a microporous or a non-porous polymeric membrane, e.g., ethylene-vinyl acetate copolymer. The active ingredient is released through the rate controlling polymeric membrane. In the drug reservoir, the active ingredient can either be dispersed in a solid polymer matrix or suspended in an unleachable, viscous liquid medium such as silicone fluid. On the external surface of the polymeric membrane, a thin layer of an adhesive polymer is applied to achieve an intimate contact of the transdermal system with the skin surface. The adhesive polymer is preferably a polymer which is hypoallergenic and compatible with the active drug substance.

In an adhesive diffusion-controlled system, a reservoir of the active ingredient is formed by directly dispersing the active ingredient in an adhesive polymer and then by, e.g., solvent casting, spreading the adhesive containing the active ingredient onto a flat sheet of substantially drug-impermeable metallic plastic backing to form a thin drug reservoir layer.

A matrix dispersion-type system is characterized in that a reservoir of the active ingredient is formed by substantially homogeneously dispersing the active ingredient in a hydrophilic or lipophilic polymer matrix. The drug-containing polymer is then molded into disc with a substantially well-defined surface area and controlled thickness. The adhesive polymer is spread along the circumference to form a strip of adhesive around the disc.

A microreservoir system can be considered as a combination of the reservoir and matrix dispersion type systems. In this case, the reservoir of the active substance is formed by first suspending the drug solids in an aqueous solution of water-soluble polymer and then dispersing the drug suspension in a lipophilic polymer to form a multiplicity of unleachable, microscopic spheres of drug reservoirs.

Any of the herein-described controlled release, extended release, and sustained release compositions can be formulated to release the active ingredient in about 30 minutes to about 1 week, in about 30 minutes to about 72 hours, in about 30 minutes to 24 hours, in about 30 minutes to 12 hours, in about 30 minutes to 6 hours, in about 30 minutes to 4 hours, and in about 3 hours to 10 hours. In embodiments, an effective concentration of the active ingredient(s) is sustained in a subject for 4 hours, 6 hours, 8 hours, 10 hours, 12 hours, 16 hours, 24 hours, 48 hours, 72 hours, or more after administration of the pharmaceutical compositions to the subject.

Vaccine or immunogenic compositions. The present invention is directed in some aspects to pharmaceutical compositions suitable for the prevention or treatment of cancer. In one embodiment, the composition comprises at least an immunogenic composition, e.g., a neoplasia vaccine or immunogenic composition capable of raising a specific T cell response. The neoplasia vaccine or immunogenic composition comprises neoantigenic peptides and/or neoantigenic polypeptides corresponding to tumor specific neoantigens as described herein.

A suitable neoplasia vaccine or immunogenic composition can preferably contain a plurality of tumor specific neoantigenic peptides. In an embodiment, the vaccine or immunogenic composition can include between 1 and 100 sets of peptides, more preferably between 1 and 50 such peptides, even more preferably between 10 and 30 sets peptides, even more preferably between 15 and 25 peptides. According to another preferred embodiment, the vaccine or immunogenic composition can include at least one peptides, more preferably 2, 3, 4, or 5 peptides. In certain embodiments, the vaccine or immunogenic composition can comprise 5, 6, 7, 8, 9, 10, 11, 12, 13, 14, 15, 16, 17, 18, 19, 20, 21, 22, 23, 24, 25, 26, 27, 28, 29, or 30 different peptides.

The optimum amount of each peptide to be included in the vaccine or immunogenic composition and the optimum dosing regimen can be determined by one skilled in the art without undue experimentation. For example, the peptide or its variant may be prepared for intravenous (i.v.) injection, sub-cutaneous (s.c.) injection, intradermal (i.d.) injection, intraperitoneal (i.p.) injection, intramuscular (i.m.) injection. Preferred methods of peptide injection include s.c, i.d., i.p., i.m., and i.v. Preferred methods of DNA injection include i.d., i.m., s.c, i.p. and i.v. For example, doses of between 1 and 500 mg 50 µg and 1.5 mg, preferably 10 µg to 500 µg, of peptide or DNA may be given and can depend from the respective peptide or DNA. Doses of this range were successfully used in previous trials (Brunsvig P F, et al., Cancer Immunol Immunother. 2006; 55(12): 1553-1564; M. Staehler, et al., ASCO meeting 2007; Abstract No 3017). Other methods of administration of the vaccine or immunogenic composition are known to those skilled in the art.

In one embodiment of the present invention the different tumor specific neoantigenic peptides and/or polypeptides are selected for use in the neoplasia vaccine or immunogenic composition so as to maximize the likelihood of generating an immune attack against the neoplasias/tumors in a high proportion of subjects in the population. Without being bound by theory, it is believed that the inclusion of a diversity of tumor specific neoantigenic peptides can generate a broad scale immune attack against a neoplasia/tumor. In one embodiment, the selected tumor specific neoantigenic peptides/polypeptides are encoded by missense mutations. In a second embodiment, the selected tumor specific neoantigenic peptides/polypeptides are encoded by a combination of missense mutations and neoORF mutations. In a third embodiment, the selected tumor specific neoantigenic peptides/polypeptides are encoded by neoORF mutations.

In one embodiment in which the selected tumor specific neoantigenic peptides/polypeptides are encoded by missense mutations, the peptides and/or polypeptides are chosen based on their capability to associate with the MHC molecules of a high proportion of subjects in the population. Peptides/polypeptides derived from neoOR mutations can also be selected on the basis of their capability to associate with the MHC molecules of the patient population.

The vaccine or immunogenic composition is capable of raising a specific cytotoxic T-cells response and/or a specific helper T cell response.

The vaccine or immunogenic composition can further comprise an adjuvant and/or a carrier. Examples of useful adjuvants and carriers are given herein. The peptides and/or polypeptides in the composition can be associated with a carrier such as, e.g., a protein or an antigen-presenting cell such as e.g. a dendritic cell (DC) capable of presenting the peptide to a T cell. Adjuvants are any substance whose admixture into the vaccine or immunogenic composition increases or otherwise modifies the immune response to the mutant peptide. Carriers are scaffold structures, for example a polypeptide or a polysaccharide, to which the neoantigenic peptides, is capable of being associated. Optionally, adjuvants are conjugated covalently or non-covalently to the peptides or polypeptides of the invention.

The ability of an adjuvant to increase the immune response to an antigen is typically manifested by a significant increase in immune-mediated reaction, or reduction in disease symptoms. For example, an increase in humoral immunity is typically manifested by a significant increase in the titer of antibodies raised to the antigen, and an increase in T cell activity is typically manifested in increased cell proliferation, or cellular cytotoxicity, or cytokine secretion. An adjuvant may also alter an immune response, for example, by changing a primarily humoral or Th2 response into a primarily cellular, or Th1 response.

Suitable adjuvants include, but are not limited to 1018 ISS, aluminum salts, Amplivax, AS15, BCG, CP-870,893, CpG7909, CyaA, dSLEVI, GM-CSF, IC30, IC31, Imiquimod, ImuFact FMP321, IS Patch, ISS, ISCOMATRIX, Juvlmmune, LipoVac, MF59, monophosphoryl lipid A, Montanide FMS 1312, Montanide ISA 206, Montanide ISA 50V, Montanide ISA-51, OK-432, OM-174, OM-197-MP-EC, ONTAK, PEPTEL. vector system, PLG microparticles, resiquimod, SRL172, Virosomes and other Virus-like particles, YF-17D, VEGF trap, R848, beta-glucan, Pam3Cys, Aquila's QS21 stimulon (Aquila Biotech, Worcester, Mass., USA) which is derived from saponin, mycobacterial extracts and synthetic bacterial cell wall mimics, and other proprietary adjuvants such as Ribi's Detox. Quil or Superfos. Several immunological adjuvants (e.g., MF59) specific for dendritic cells and their preparation have been described previously (Dupuis M, et al., Cell Immunol. 1998; 186(1): 18-27; Allison A C; Dev Biol Stand. 1998; 92:3-11). Also cytokines may be used. Several cytokines have been directly linked to influencing dendritic cell migration to lymphoid tissues (e.g., TNF-alpha), accelerating the maturation of dendritic cells into efficient antigen-presenting cells for T-lymphocytes (e.g., GM-CSF, IL-1 and IL-4) (U.S. Pat. No. 5,849,589, specifically incorporated herein by reference in its entirety) and acting as immunoadjuvants (e.g., IL-12) (Gabrilovich D I, et al., J Immunother Emphasis Tumor Immunol. 1996 (6):414-418).

Toll like receptors (TLRs) may also be used as adjuvants, and are important members of the family of pattern recognition receptors (PRRs) which recognize conserved motifs shared by many micro-organisms, termed "pathogen-associated molecular patterns" (PAMPS). Recognition of these "danger signals" activates multiple elements of the innate and adaptive immune system. TLRs are expressed by cells of the innate and adaptive immune systems such as dendritic cells (DCs), macrophages, T and B cells, mast cells, and granulocytes and are localized in different cellular compartments, such as the plasma membrane, lysosomes, endosomes, and endolysosomes. Different TLRs recognize distinct PAMPS. For example, TLR4 is activated by LPS contained in bacterial cell walls, TLR9 is activated by unmethylated bacterial or viral CpG DNA, and TLR3 is activated by double stranded RNA. TLR ligand binding leads to the activation of one or more intracellular signaling pathways, ultimately resulting in the production of many key molecules associated with inflammation and immunity (particularly the transcription factor NF-κB and the Type-I interferons). TLR mediated DC activation leads to enhanced DC activation, phagocytosis, upregulation of activation and co-stimulation markers such as CD80, CD83, and CD86, expression of CCR7 allowing migration of DC to draining lymph nodes and facilitating antigen presentation to T cells, as well as increased secretion of cytokines such as type I interferons, IL-12, and IL-6. All of these downstream events are critical for the induction of an adaptive immune response.

Among the most promising cancer vaccine or immunogenic composition adjuvants currently in clinical development are the TLR9 agonist CpG and the synthetic double-stranded RNA (dsRNA) TLR3 ligand poly-ICLC. In preclinical studies poly-ICLC appears to be the most potent TLR adjuvant when compared to LPS and CpG due to its induction of pro-inflammatory cytokines and lack of stimulation of IL-10, as well as maintenance of high levels of co-stimulatory molecules in DCsl. Furthermore, poly-ICLC was recently directly compared to CpG in non-human primates (rhesus macaques) as adjuvant for a protein vaccine or immunogenic composition consisting of human papillomavirus (HPV)16 capsomers (Stahl-Hennig C, Eisenblatter M, Jasny E, et al. Synthetic double-stranded RNAs are adjuvants for the induction of T helper 1 and humoral immune responses to human papillomavirus in rhesus macaques. PLoS pathogens. April 2009; 5(4)).

CpG immuno stimulatory oligonucleotides have also been reported to enhance the effects of adjuvants in a vaccine or immunogenic composition setting. Without being bound by theory, CpG oligonucleotides act by activating the innate (non-adaptive) immune system via Toll-like receptors (TLR), mainly TLR9. CpG triggered TLR9 activation enhances antigen-specific humoral and cellular responses to a wide variety of antigens, including peptide or protein antigens, live or killed viruses, dendritic cell vaccines, autologous cellular vaccines and polysaccharide conjugates in both prophylactic and therapeutic vaccines. More importantly, it enhances dendritic cell maturation and differentiation, resulting in enhanced activation of Th1 cells and strong cytotoxic T-lymphocyte (CTL) generation, even in the absence of CD4 T cell help. The Th1 bias induced by TLR9 stimulation is maintained even in the presence of vaccine adjuvants such as alum or incomplete Freund's adjuvant (IF A) that normally promote a Th2 bias. CpG oligonucleotides show even greater adjuvant activity when formulated or co-administered with other adjuvants or in formulations such as microparticles, nano particles, lipid emulsions or similar formulations, which are especially necessary for inducing a strong response when the antigen is relatively weak. They also accelerate the immune response and enabled the antigen doses to be reduced by approximately two orders of magnitude, with comparable antibody responses to the full-dose vaccine without CpG in some experiments (Arthur M. Krieg, Nature Reviews, Drug Discovery, 5, Jun. 2006, 471-484). U.S. Pat. No. 6,406,705 B1 describes the combined use of CpG oligonucleotides, non-nucleic acid adjuvants and an antigen to induce an antigen-specific immune response. A commercially available CpG TLR9 antagonist is dSLEVI (double Stem Loop Immunomodulator) by Mologen (Berlin, GERMANY), which is a preferred component of the pharmaceutical composition of the present invention. Other TLR binding molecules such as RNA binding TLR 7, TLR 8 and/or TLR 9 may also be used.

Other examples of useful adjuvants include, but are not limited to, chemically modified CpGs (e.g. CpR, Idera), Poly(I:C)(e.g. polyi:CI2U), non-CpG bacterial DNA or RNA as well as immunoactive small molecules and antibodies such as cyclophosphamide, sunitinib, bevacizumab, celebrex, NCX-4016, sildenafil, tadalafil, vardenafil, sorafenib, XL-999, CP-547632, pazopanib, ZD2171, AZD2171, ipilimumab, tremelimumab, and SC58175, which may act therapeutically and/or as an adjuvant. The amounts and concentrations of adjuvants and additives useful in the context of the present invention can readily be determined by the skilled artisan without undue experimentation. Additional adjuvants include colony-stimulating factors, such as Granulocyte Macrophage Colony Stimulating Factor (GM-CSF, sargramostim).

Poly-ICLC is a synthetically prepared double-stranded RNA consisting of polyI and polyC strands of average length of about 5000 nucleotides, which has been stabilized to thermal denaturation and hydrolysis by serum nucleases by the addition of polylysine and carboxymethylcellulose. The compound activates TLR3 and the RNA helicase-domain of MDA5, both members of the PAMP family, leading to DC and natural killer (NK) cell activation and production of a "natural mix" of type I interferons, cytokines, and chemokines. Furthermore, poly-ICLC exerts a more direct, broad host-targeted anti-infectious and possibly antitumor effect mediated by the two IFN-inducible nuclear enzyme systems, the 2'5'-OAS and the Pl/eIF2a kinase, also known as the PKR (4-6), as well as RIG-I helicase and MDA5.

In rodents and non-human primates, poly-ICLC was shown to enhance T cell responses to viral antigens, cross-priming, and the induction of tumor-, virus-, and autoantigen-specific CD8+ T cells. In a recent study in non-human primates, poly-ICLC was found to be essential for the generation of antibody responses and T cell immunity to DC targeted or non-targeted HIV Gag p24 protein, emphasizing its effectiveness as a vaccine adjuvant.

In human subjects, transcriptional analysis of serial whole blood samples revealed similar gene expression profiles among the 8 healthy human volunteers receiving one single s.c. administration of poly-ICLC and differential expression of up to 212 genes between these 8 subjects versus 4 subjects receiving placebo. Remarkably, comparison of the poly-ICLC gene expression data to previous data from volunteers immunized with the highly effective yellow fever vaccine YF17D showed that a large number of transcriptional and signal transduction canonical pathways, including those of the innate immune system, were similarly upregulated at peak time points.

More recently, an immunologic analysis was reported on patients with ovarian, fallopian tube, and primary peritoneal cancer in second or third complete clinical remission who were treated on a phase 1 study of subcutaneous vaccination with synthetic overlapping long peptides (OLP) from the cancer testis antigen NY-ESO-1 alone or with Montanide-ISA-51, or with 1.4 mg poly-ICLC and Montanide. The generation of NY-ESO-1-specific CD4+ and CD8+ T cell and antibody responses were markedly enhanced with the addition of poly-ICLC and Montanide compared to OLP alone or OLP and Montanide.

A vaccine or immunogenic composition according to the present invention may comprise more than one different adjuvant. Furthermore, the invention encompasses a therapeutic composition comprising any adjuvant substance including any of those herein discussed. It is also contemplated that the peptide or polypeptide, and the adjuvant can be administered separately in any appropriate sequence. A carrier may be present independently of an adjuvant. The carrier may be covalently linked to the antigen. A carrier can also be added to the antigen by inserting DNA encoding the carrier in frame with DNA encoding the antigen. The function of a carrier can for example be to confer stability, to increase the biological activity, or to increase serum half-life. Extension of the half-life can help to reduce the number of applications and to lower doses, thus are beneficial for therapeutic but also economic reasons. Furthermore, a carrier may aid presenting peptides to T cells. The carrier may be any suitable carrier known to the person skilled in the art, for example a protein or an antigen presenting cell. A carrier protein could be but is not limited to keyhole limpet hemocyanin, serum proteins such as transferrin, bovine serum albumin, human serum albumin, thyroglobulin or ovalbumin, immunoglobulins, or hormones, such as insulin or palmitic acid. For immunization of humans, the carrier may be a physiologically acceptable carrier acceptable to humans and safe. However, tetanus toxoid and/or diptheria toxoid are suitable carriers in one embodiment of the invention. Alternatively, the carrier may be dextrans for example sepharose.

Cytotoxic T cells (CTLs) recognize an antigen in the form of a peptide bound to an MHC molecule rather than the intact foreign antigen itself. The MHC molecule itself is located at the cell surface of an antigen presenting cell. Thus, an activation of CTLs is only possible if a trimeric complex of peptide antigen, MHC molecule, and APC is present. Correspondingly, it may enhance the immune response if not only the peptide is used for activation of CTLs, but if additionally APCs with the respective MHC molecule are added. Therefore, in some embodiments the vaccine or immunogenic composition according to the present invention additionally contains at least one antigen presenting cell.

The antigen-presenting cell (or stimulator cell) typically has an MHC class I or II molecule on its surface, and in one embodiment is substantially incapable of itself loading the MHC class I or II molecule with the selected antigen. As is described in more detail herein, the MHC class I or II molecule may readily be loaded with the selected antigen in vitro.

CD8+ cell activity may be augmented through the use of CD4+ cells. The identification of CD4 T+ cell epitopes for tumor antigens has attracted interest because many immune based therapies against cancer may be more effective if both CD8+ and CD4+T lymphocytes are used to target a patient's tumor. CD4+ cells are capable of enhancing CD8 T cell responses. Many studies in animal models have clearly demonstrated better results when both CD4+ and CD8+ T cells participate in anti-tumor responses (see e.g., Nishimura et al. (1999) Distinct role of antigen-specific T helper type 1 (TH1) and Th2 cells in tumor eradication in vivo. J Ex Med 190:617-27). Universal CD4+ T cell epitopes have been identified that are applicable to developing therapies against different types of cancer (see e.g., Kobayashi et al. (2008) Current Opinion in Immunology 20:221-27). For example, an HLA-DR restricted helper peptide from tetanus toxoid was used in melanoma vaccines to activate CD4+ T cells non-specifically (see e.g., Slingluff et al. (2007) Immunologic and Clinical Outcomes of a Randomized Phase II Trial of Two Multipeptide Vaccines for Melanoma in the Adjuvant Setting, Clinical Cancer Research 13(21):6386-

95). It is contemplated within the scope of the invention that such CD4+ cells may be applicable at three levels that vary in their tumor specificity: 1) a broad level in which universal CD4+ epitopes (e.g., tetanus toxoid) may be used to augment CD8+ cells; 2) an intermediate level in which native, tumor-associated CD4+ epitopes may be used to augment CD8+ cells; and 3) a patient specific level in which neoantigen CD4+ epitopes may be used to augment CD8+ cells in a patient specific manner. Although current algorithms for predicting CD4 epitopes are limited in accuracy, it is a reasonable expectation that many long peptides containing predicted CD8 neoepitopes will also include CD4 epitopes. CD4 epitopes are longer than CD8 epitopes and typically are 10-12 amino acids in length although some can be longer (Kreiter et al, Mutant MHC Class II epitopes drive therapeutic immune responses to cancer, Nature (2015)). Thus, the neoantigen epitopes described herein, either in the form of long peptides (>25 amino acids) or nucleic acids encoding such long peptides, may also boost CD4 responses in a tumor and patient-specific manner (level (3) above).

CD8+ cell immunity may also be generated with neoantigen loaded dendritic cell (DC) vaccine. DCs are potent antigen-presenting cells that initiate T cell immunity and can be used as cancer vaccines when loaded with one or more peptides of interest, for example, by direct peptide injection. For example, patients that were newly diagnosed with metastatic melanoma were shown to be immunized against 3 HLA-A*0201-restricted gplOO melanoma antigen-derived peptides with autologous peptide pulsed CD40L/IFN-g-activated mature DCs via an IL-12p70-producing patient DC vaccine (see e.g., Carreno et al (2013) L-12p70-producing patient DC vaccine elicits Tel-polarized immunity, Journal of Clinical Investigation, 123(8):3383-94 and Ali et al. (2009) In situ regulation of DC subsets and T cells mediates tumor regression in mice, Cancer Immunotherapy, 1(8): 1-10). It is contemplated within the scope of the invention that neoantigen loaded DCs may be prepared using the synthetic TLR 3 agonist Polyinosinic-Polycytidylic Acid-poly-L-lysine Carboxymethylcellulose (Poly-ICLC) to stimulate the DCs. Poly-ICLC is a potent individual maturation stimulus for human DCs as assessed by an upregulation of CD83 and CD86, induction of interleukin-12 (IL-12), tumor necrosis factor (TNF), interferon gamma-induced protein 10 (IP-10), interleukin 1 (IL-1), and type I interferons (IFN), and minimal interleukin 10 (IL-10) production. DCs may be differentiated from frozen peripheral blood mononuclear cells (PBMCs) obtained by leukapheresis, while PBMCs may be isolated by Ficoll gradient centrifugation and frozen in aliquots.

Illustratively, the following 7 day activation protocol may be used. Day 1 PBMCs are thawed and plated onto tissue culture flasks to select for monocytes which adhere to the plastic surface after 1-2 hr incubation at 37° C. in the tissue culture incubator. After incubation, the lymphocytes are washed off and the adherent monocytes are cultured for 5 days in the presence of interleukin-4 (IL-4) and granulocyte macrophage-colony stimulating factor (GM-CSF) to differentiate to immature DCs. On Day 6, immature DCs are pulsed with the keyhole limpet hemocyanin (KLH) protein which serves as a control for the quality of the vaccine and may boost the immunogenicity of the vaccine. The DCs are stimulated to mature, loaded with peptide antigens, and incubated overnight. On Day 7, the cells are washed, and frozen in 1 ml aliquots containing 4-20×10(6) cells using a controlled-rate freezer. Lot release testing for the batches of DCs may be performed to meet minimum specifications before the DCs are injected into patients (see e.g., Sabado et al. (2013) Preparation of tumor antigen-loaded mature dendritic cells for immunotherapy, J. Vis Exp. August 1; (78). doi: 10.3791/50085).

A DC vaccine may be incorporated into a scaffold system to facilitate delivery to a patient. Therapeutic treatment of a patients neoplasia with a DC vaccine may utilize a biomaterial system that releases factors that recruit host dendritic cells into the device, differentiates the resident, immature DCs by locally presenting adjuvants (e.g., danger signals) while releasing antigen, and promotes the release of activated, antigen loaded DCs to the lymph nodes (or desired site of action) where the DCs may interact with T cells to generate a potent cytotoxic T lymphocyte response to the cancer neoantigens. Implantable biomaterials may be used to generate a potent cytotoxic T lymphocyte response against a neoplasia in a patient specific manner. The biomaterial-resident dendritic cells may then be activated by exposing them to danger signals mimicking infection, in concert with release of antigen from the biomaterial. The activated dendritic cells then migrate from the biomaterials to lymph nodes to induce a cytotoxic T effector response. This approach has previously been demonstrated to lead to regression of established melanoma in preclinical studies using a lysate prepared from tumor biopsies (see e.g., Ali et al. (2209) In situ regulation of DC subsets and T cells mediates tumor regression in mice, Cancer Immunotherapy 1(8): 1-10; Ali et al. (2009) Infection-mimicking materials to program dendritic cells in situ. Nat Mater 8: 151-8), and such a vaccine is currently being tested in a Phase I clinical trial recently initiated at the Dana-Farber Cancer Institute. This approach has also been shown to lead to regression of glioblastoma, as well as the induction of a potent memory response to prevent relapse, using the C6 rat glioma model.24 in the current proposal. The ability of such an implantable, biomatrix vaccine delivery scaffold to amplify and sustain tumor specific dendritic cell activation may lead to more robust anti-tumor immunosensitization than can be achieved by traditional subcutaneous or intra-nodal vaccine administrations.

The present invention may include any method for loading a neoantigenic peptide onto a dendritic cell. One such method applicable to the present invention is a microfluidic intracellular delivery system. Such systems cause temporary membrane disruption by rapid mechanical deformation of human and mouse immune cells, thus allowing the intracellular delivery of biomolecules (Sharei et al., 2015, PLOS ONE).

Preferably, the antigen presenting cells are dendritic cells. Suitably, the dendritic cells are autologous dendritic cells that are pulsed with the neoantigenic peptide. The peptide may be any suitable peptide that gives rise to an appropriate T cell response. T cell therapy using autologous dendritic cells pulsed with peptides from a tumor associated antigen is disclosed in Murphy et al. (1996) The Prostate 29, 371-380 and Tjua et al. (1997) The Prostate 32, 272-278. In certain embodiments the dendritic cells are targeted using CD141, DEC205, or XCR1 markers. CD141+XCR1+DCs were identified as a subset that may be better suited to the induction of anti-tumor responses (Bachem et al., J. Exp. Med. 207, 1273-1281 (2010); Crozat et al., J. Exp. Med. 207, 1283-1292 (2010); and Gallois & Bhardwaj, Nature Med. 16, 854-856 (2010)).

Thus, in one embodiment of the present invention the vaccine or immunogenic composition containing at least one antigen presenting cell is pulsed or loaded with one or more peptides of the present invention. Alternatively, peripheral blood mononuclear cells (PBMCs) isolated from a patient may be loaded with peptides ex vivo and injected back into the patient. As an alternative the antigen presenting cell comprises an expression construct encoding a peptide of the present invention. The polynucleotide may be any suitable polynucleotide and it is preferred that it is capable of transducing the dendritic cell, thus resulting in the presentation of a peptide and induction of immunity.

The inventive pharmaceutical composition may be compiled so that the selection, number and/or amount of peptides present in the composition covers a high proportion of subjects in the population. The selection may be dependent on the specific type of cancer, the status of the disease, earlier treatment regimens, and, of course, the HLA-haplotypes present in the patient population.

Pharmaceutical compositions comprising the peptide of the invention may be administered to an individual already suffering from cancer. In therapeutic applications, compositions are administered to a patient in an amount sufficient to elicit an effective CTL response to the tumor antigen and to cure or at least partially arrest symptoms and/or complications. An amount adequate to accomplish this is defined as "therapeutically effective dose." Amounts effective for this use can depend on, e.g., the peptide composition, the manner of administration, the stage and severity of the disease being treated, the weight and general state of health of the patient, and the judgment of the prescribing physician, but generally range for the initial immunization (that is for therapeutic or prophylactic administration) from about 1.0 µg to about 50,000 µg of peptide for a 70 kg patient, followed by boosting dosages or from about 1.0 µg to about 10,000 µg of peptide pursuant to a boosting regimen over weeks to months depending upon the patient's response and condition and possibly by measuring specific CTL activity in the patient's blood. It should be kept in mind that the peptide and compositions of the present invention may generally be employed in serious disease states, that is, life-threatening or potentially life threatening situations, especially when the cancer has metastasized. For therapeutic use, administration should begin as soon as possible after the detection or surgical removal of tumors. This is followed by boosting doses until at least symptoms are substantially abated and for a period thereafter.

The pharmaceutical compositions (e.g., vaccine compositions) for therapeutic treatment are intended for parenteral, topical, nasal, oral or local administration. Preferably, the pharmaceutical compositions are administered parenterally, e.g., intravenously, subcutaneously, intradermally, or intramuscularly. The compositions may be administered at the site of surgical excision to induce a local immune response to the tumor. The invention provides compositions for parenteral administration which comprise a solution of the peptides and vaccine or immunogenic compositions are dissolved or suspended in an acceptable carrier, preferably an aqueous carrier. A variety of aqueous carriers may be used, e.g., water, buffered water, 0.9% saline, 0.3% glycine, hyaluronic acid and the like. These compositions may be sterilized by conventional, well known sterilization techniques, or may be sterile filtered. The resulting aqueous solutions may be packaged for use as is, or lyophilized, the lyophilized preparation being combined with a sterile solution prior to administration. The compositions may contain pharmaceutically acceptable auxiliary substances as required to approximate physiological conditions, such as pH adjusting and buffering agents, tonicity adjusting agents, wetting agents and the like, for example, sodium acetate, sodium lactate, sodium chloride, potassium chloride, calcium chloride, sorbitan monolaurate, triethanolamine oleate, etc.

A liposome suspension containing a peptide may be administered intravenously, locally, topically, etc. in a dose which varies according to, inter alia, the manner of administration, the peptide being delivered, and the stage of the disease being treated. For targeting to the immune cells, a ligand, such as, e.g., antibodies or fragments thereof specific for cell surface determinants of the desired immune system cells, can be incorporated into the liposome.

For solid compositions, conventional or nanoparticle nontoxic solid carriers may be used which include, for example, pharmaceutical grades of mannitol, lactose, starch, magnesium stearate, sodium saccharin, talcum, cellulose, glucose, sucrose, magnesium carbonate, and the like. For oral administration, a pharmaceutically acceptable nontoxic composition is formed by incorporating any of the normally employed excipients, such as those carriers previously listed, and generally 10-95% of active ingredient, that is, one or more peptides of the invention, and more preferably at a concentration of 25%-75%.

For aerosol administration, the immunogenic peptides are preferably supplied in finely divided form along with a surfactant and propellant. Typical percentages of peptides are 0.01%-20% by weight, preferably 1%-10%. The surfactant can, of course, be nontoxic, and preferably soluble in the propellant. Representative of such agents are the esters or partial esters of fatty acids containing from 6 to 22 carbon atoms, such as caproic, octanoic, lauric, palmitic, stearic, linoleic, linolenic, olesteric and oleic acids with an aliphatic polyhydric alcohol or its cyclic anhydride. Mixed esters, such as mixed or natural glycerides may be employed. The surfactant may constitute 0.1%-20% by weight of the composition, preferably 0.25-5%. The balance of the composition is ordinarily propellant. A carrier can also be included as desired, as with, e.g., lecithin for intranasal delivery.

The peptides and polypeptides of the invention can be readily synthesized chemically utilizing reagents that are free of contaminating bacterial or animal substances (Merrifield R B: Solid phase peptide synthesis. I. The synthesis of a tetrapeptide. J. Am. Chem. Soc. 85:2149-54, 1963).

The peptides and polypeptides of the invention can also be expressed by a vector, e.g., a nucleic acid molecule as herein-discussed, e.g., RNA or a DNA plasmid, a viral vector such as a poxvirus, e.g., orthopox virus, avipox virus, or adenovirus, AAV or lentivirus. This approach involves the use of a vector to express nucleotide sequences that encode the peptide of the invention. Upon introduction into an acutely or chronically infected host or into a noninfected host, the vector expresses the immunogenic peptide, and thereby elicits a host CTL response.

For therapeutic or immunization purposes, nucleic acids encoding the peptide of the invention and optionally one or more of the peptides described herein can also be administered to the patient. A number of methods are conveniently used to deliver the nucleic acids to the patient. For instance, the nucleic acid can be delivered directly, as "naked DNA". This approach is described, for instance, in Wolff et al., Science 247: 1465-1468 (1990) as well as U.S. Pat. Nos. 5,580,859 and 5,589,466. The nucleic acids can also be administered using ballistic delivery as described, for instance, in U.S. Pat. No. 5,204,253. Particles comprised solely of DNA can be administered. Alternatively, DNA can be adhered to particles, such as gold particles. Generally, a plasmid for a vaccine or immunological composition can comprise DNA encoding an antigen (e.g., one or more neoantigens) operatively linked to regulatory sequences which control expression or expression and secretion of the antigen from a host cell, e.g., a mammalian cell; for instance, from upstream to downstream, DNA for a promoter, such as a mammalian virus promoter (e.g., a CMV promoter such as an hCMV or mCMV promoter, e.g., an early-intermediate promoter, or an SV40 promoter-see documents cited or incorporated herein for useful promoters), DNA for a eukaryotic leader peptide for secretion (e.g., tissue plasminogen activator), DNA for the neoantigen(s), and DNA encoding a terminator (e.g., the 3' UTR transcriptional terminator from the gene encoding Bovine Growth Hormone or bGH polyA). A composition can contain more than one plasmid or vector, whereby each vector contains and expresses a different neoantigen. Mention is also made of Wasmoen U.S. Pat. No. 5,849,303, and Dale U.S. Pat. No. 5,811,104, whose text may be useful. DNA or DNA plasmid formulations can be formulated with or inside cationic lipids; and, as to cationic lipids, as well as adjuvants, mention is also made of Loosmore U.S. Patent Application 2003/0104008. Also, teachings in Audonnet U.S. Pat. Nos. 6,228,846 and 6,159,477 may be relied upon for DNA plasmid teachings that can be employed in constructing and using DNA plasmids that contain and express in vivo.

The nucleic acids can also be delivered complexed to cationic compounds, such as cationic lipids. Lipid-mediated gene delivery methods are described, for instance, in W01996/18372; WO 1993/24640; Mannino & Gould-Fogerite, BioTechniques 6(7): 682-691 (1988); U.S. Pat. No. 5,279,833; WO 1991/06309; and Feigner et al., Proc. Natl. Acad. Sci. USA 84: 7413-7414 (1987).

RNA encoding the peptide of interest (e.g., mRNA) can also be used for delivery (see, e.g., Kiken et al, 2011; Su et al, 2011; see also U.S. Pat. No. 8,278,036; Halabi et al. J Clin Oncol (2003) 21: 1232-1237; Petsch et al, Nature Biotechnology 2012 Dec. 7; 30(12): 1210-6).

Viral vectors as described herein can also be used to deliver the neoantigenic peptides of the invention. Vectors can be administered so as to have in vivo expression and response akin to doses and/or responses elicited by antigen administration.

A preferred means of administering nucleic acids encoding the peptide of the invention uses minigene constructs encoding multiple epitopes. To create a DNA sequence encoding the selected CTL epitopes (minigene) for expression in human cells, the amino acid sequences of the epitopes are reverse translated. A human codon usage table is used to guide the codon choice for each amino acid. These epitope-encoding DNA sequences are directly adjoined, creating a continuous polypeptide sequence. To optimize expression and/or immunogenicity, additional elements can be incorporated into the minigene design. Examples of amino acid sequence that could be reverse translated and included in the minigene sequence include: helper T lymphocyte, epitopes, a leader (signal) sequence, and an endoplasmic reticulum retention signal. In addition, MHC presentation of CTL epitopes may be improved by including synthetic (e.g. poly-alanine) or naturally-occurring flanking sequences adjacent to the CTL epitopes.

The minigene sequence is converted to DNA by assembling oligonucleotides that encode the plus and minus strands of the minigene. Overlapping oligonucleotides (30-100 bases long) are synthesized, phosphorylated, purified and annealed under appropriate conditions using well known techniques. The ends of the oligonucleotides are joined using T4 DNA ligase. This synthetic minigene, encoding the CTL epitope polypeptide, can then cloned into a desired expression vector.

Standard regulatory sequences well known to those of skill in the art are included in the vector to ensure expression in the target cells. Several vector elements are required: a promoter with a down-stream cloning site for minigene insertion; a polyadenylation signal for efficient transcription termination; an E. coli origin of replication; and an E. coli selectable marker (e.g. ampicillin or kanamycin resistance). Numerous promoters can be used for this purpose, e.g., the human cytomegalovirus (hCMV) promoter. See, U.S. Pat. Nos. 5,580,859 and 5,589,466 for other suitable promoter sequences.

Additional vector modifications may be desired to optimize minigene expression and immunogenicity. In some cases, introns are required for efficient gene expression, and one or more synthetic or naturally-occurring introns could be incorporated into the transcribed region of the minigene. The inclusion of mRNA stabilization sequences can also be considered for increasing minigene expression. It has recently been proposed that immuno stimulatory sequences (ISSs or CpGs) play a role in the immunogenicity of DNA' vaccines. These sequences could be included in the vector, outside the minigene coding sequence, if found to enhance immunogenicity.

In some embodiments, a bicistronic expression vector, to allow production of the minigene-encoded epitopes and a second protein included to enhance or decrease immunogenicity can be used. Examples of proteins or polypeptides that could beneficially enhance the immune response if co-expressed include cytokines (e.g., IL2, IL12, GM-CSF), cytokine-inducing molecules (e.g. LeIF) or costimulatory molecules. Helper (HTL) epitopes could be joined to intracellular targeting signals and expressed separately from the CTL epitopes. This would allow direction of the HTL epitopes to a cell compartment different than the CTL epitopes. If required, this could facilitate more efficient entry of HTL epitopes into the MHC class II pathway, thereby improving CTL induction. In contrast to CTL induction, specifically decreasing the immune response by co-expression of immunosuppressive molecules (e.g. TGF-β) may be beneficial in certain diseases.

Once an expression vector is selected, the minigene is cloned into the polylinker region downstream of the promoter. This plasmid is transformed into an appropriate E. coli strain, and DNA is prepared using standard techniques. The orientation and DNA sequence of the minigene, as well as all other elements included in the vector, are confirmed using restriction mapping and DNA sequence analysis. Bacterial cells harboring the correct plasmid can be stored as a master cell bank and a working cell bank.

Purified plasmid DNA can be prepared for injection using a variety of formulations. The simplest of these is reconstitution of lyophilized DNA in sterile phosphate-buffer saline (PBS). A variety of methods have been described, and new techniques may become available. As noted herein, nucleic acids are conveniently formulated with cationic lipids. In addition, glycolipids, fusogenic liposomes, peptides and compounds referred to collectively as protective, interactive, non-condensing (PINC) could also be complexed to purified plasmid DNA to influence variables such as stability, intramuscular dispersion, or trafficking to specific organs or cell types.

Target cell sensitization can be used as a functional assay for expression and MHC class I presentation of minigene-encoded CTL epitopes. The plasmid DNA is introduced into a mammalian cell line that is suitable as a target for standard CTL chromium release assays. The transfection method used is dependent on the final formulation. Electroporation can be used for "naked" DNA, whereas cationic lipids allow direct in vitro transfection. A plasmid expressing green fluorescent protein (GFP) can be co-transfected to allow enrichment of transfected cells using fluorescence activated cell sorting (FACS). These cells are then chromium-51 labeled and used as target cells for epitope-specific CTL lines. Cytolysis, detected by 51 Cr release, indicates production of MHC presentation of mini gene-encoded CTL epitopes.

In vivo immunogenicity is a second approach for functional testing of minigene DNA formulations. Transgenic mice expressing appropriate human MHC molecules are immunized with the DNA product. The dose and route of administration are formulation dependent (e.g. FM for DNA in PBS, IP for lipid-complexed DNA). Twenty-one days after immunization, splenocytes are harvested and restimulated for 1 week in the presence of peptides encoding each epitope being tested. These effector cells (CTLs) are assayed for cytolysis of peptide-loaded, chromium-51 labeled target cells using standard techniques. Lysis of target cells sensitized by MHC loading of peptides corresponding to minigene-encoded epitopes demonstrates DNA vaccine function for in vivo induction of CTLs.

Peptides may be used to elicit CTL ex vivo, as well. The resulting CTL, can be used to treat chronic tumors in patients in need thereof that do not respond to other conventional forms of therapy, or does not respond to a peptide vaccine approach of therapy. Ex vivo CTL responses to a particular tumor antigen are induced by incubating in tissue culture the patient's CTL precursor cells (CTLp) together with a source of antigen-presenting cells (APC) and the appropriate peptide. After an appropriate incubation time (typically 1-4 weeks), in which the CTLp are activated and mature and expand into effector CTL, the cells are infused back into the patient, where they destroy their specific target cell (i.e., a tumor cell). In order to optimize the in vitro conditions for the generation of specific cytotoxic T cells, the culture of stimulator cells are maintained in an appropriate serum-free medium.

Prior to incubation of the stimulator cells with the cells to be activated, e.g., precursor CD8+ cells, an amount of antigenic peptide is added to the stimulator cell culture, of sufficient quantity to become loaded onto the human Class I molecules to be expressed on the surface of the stimulator cells. In the present invention, a sufficient amount of peptide is an amount that allows about 200, and preferably 200 or more, human Class I MHC molecules loaded with peptide to be expressed on the surface of each stimulator cell. Preferably, the stimulator cells are incubated with >2 μg/ml peptide. For example, the stimulator cells are incubated with >3, 4, 5, 10, 15, or more g/ml peptide.

Resting or precursor CD8+ cells are then incubated in culture with the appropriate stimulator cells for a time period sufficient to activate the CD8+ cells. Preferably, the CD8+ cells are activated in an antigen-specific manner. The ratio of resting or precursor CD8+(effector) cells to stimulator cells may vary from individual to individual and may further depend upon variables such as the amenability of an individual's lymphocytes to culturing conditions and the nature and severity of the disease condition or other condition for which the within-described treatment modality is used. Preferably, however, the lymphocyte: stimulator cell ratio is in the range of about 30:1 to 300:1. The effector/stimulator culture may be maintained for as long a time as is necessary to stimulate a therapeutically useable or effective number of CD8+ cells.

The induction of CTL in vitro requires the specific recognition of peptides that are bound to allele specific MHC class I molecules on APC. The number of specific MHC/peptide complexes per APC is crucial for the stimulation of CTL, particularly in primary immune responses. While small amounts of peptide/MHC complexes per cell are sufficient to render a cell susceptible to lysis by CTL, or to stimulate a secondary CTL response, the successful activation of a CTL precursor (pCTL) during primary response requires a significantly higher number of MHC/peptide complexes. Peptide loading of empty major histocompatability complex molecules on cells allows the induction of primary cytotoxic T lymphocyte responses.

Since mutant cell lines do not exist for every human MHC allele, it is advantageous to use a technique to remove endogenous MHC-associated peptides from the surface of APC, followed by loading the resulting empty MHC molecules with the immunogenic peptides of interest. The use of non-transformed (non-tumorigenic), noninfected cells, and preferably, autologous cells of patients as APC is desirable for the design of CTL induction protocols directed towards development of ex vivo CTL therapies. This application discloses methods for stripping the endogenous MHC-associated peptides from the surface of APC followed by the loading of desired peptides.

A stable MHC class I molecule is a trimeric complex formed of the following elements: 1) a peptide usually of 8-10 residues, 2) a transmembrane heavy polymorphic protein chain which bears the peptide-binding site in its a1 and a2 domains, and 3) a non-covalently associated non-polymorphic light chain, p2microglobuiin. Removing the bound peptides and/or dissociating the p2microglobulin from the complex renders the MHC class I molecules nonfunctional and unstable, resulting in rapid degradation. All MHC class I molecules isolated from PBMCs have endogenous peptides bound to them. Therefore, the first step is to remove all endogenous peptides bound to MHC class I molecules on the APC without causing their degradation before exogenous peptides can be added to them.

Two possible ways to free up MHC class I molecules of bound peptides include lowering the culture temperature from 37° C. to 26° C. overnight to destabilize p2microglobulin and stripping the endogenous peptides from the cell using a mild acid treatment. The methods release previously bound peptides into the extracellular environment allowing new exogenous peptides to bind to the empty class I molecules. The cold-temperature incubation method enables exogenous peptides to bind efficiently to the MHC complex, but requires an overnight incubation at 26° C. which may slow the cell's metabolic rate. It is also likely that cells not actively synthesizing MHC molecules (e.g., resting PBMC) would not produce high amounts of empty surface MHC molecules by the cold temperature procedure.

Harsh acid stripping involves extraction of the peptides with trifluoroacetic acid, pH 2, or acid denaturation of the immunoaffinity purified class I-peptide complexes. These methods are not feasible for CTL induction, since it is important to remove the endogenous peptides while preserving APC viability and an optimal metabolic state which is critical for antigen presentation. Mild acid solutions of pH 3 such as glycine or citrate-phosphate buffers have been used to identify endogenous peptides and to identify tumor associated T cell epitopes. The treatment is especially effective, in that only the MHC class I molecules are destabilized (and associated peptides released), while other surface antigens remain intact, including MHC class II molecules. Most importantly, treatment of cells with the mild acid solutions do not affect the cell's viability or metabolic state. The mild acid treatment is rapid since the stripping of the endogenous peptides occurs in two minutes at 4° C. and the APC is ready to perform its function after the appropriate peptides are loaded. The technique is utilized herein to make peptide-specific APCs for the generation of primary antigen-specific CTL. The resulting APC are efficient in inducing peptide-specific CD8+CTL.

Activated CD8+ cells may be effectively separated from the stimulator cells using one of a variety of known methods. For example, monoclonal antibodies specific for the stimulator cells, for the peptides loaded onto the stimulator cells, or for the CD8+ cells (or a segment thereof) may be utilized to bind their appropriate complementary ligand. Antibody-tagged molecules may then be extracted from the stimulator-effector cell admixture via appropriate means, e.g., via well-known immunoprecipitation or immunoassay methods.

Effective, cytotoxic amounts of the activated CD8+ cells can vary between in vitro and in vivo uses, as well as with the amount and type of cells that are the ultimate target of these killer cells. The amount can also vary depending on the condition of the patient and should be determined via consideration of all appropriate factors by the practitioner. Preferably, however, about $1 \times 10^6$ to about $1 \times 10^{12}$, more preferably about $1 \times 10^8$ to about $1 \times 10^{11}$, and even more preferably, about $1 \times 10^9$ to about $1 \times 10^{10}$ activated CD8+ cells are utilized for adult humans, compared to about $5 \times 10^6$-$5 \times 10^7$ cells used in mice.

Preferably, as discussed herein, the activated CD 8+ cells are harvested from the cell culture prior to administration of the CD8+ cells to the individual being treated. It is important to note, however, that unlike other present and proposed treatment modalities, the present method uses a cell culture system that is not tumorigenic. Therefore, if complete separation of stimulator cells and activated CD8+ cells are not achieved, there is no inherent danger known to be associated with the administration of a small number of stimulator cells, whereas administration of mammalian tumor-promoting cells may be extremely hazardous.

Methods of re-introducing cellular components are known in the art and include procedures such as those exemplified in U.S. Pat. No. 4,844,893 to Honsik, et al. and U.S. Pat. No. 4,690,915 to Rosenberg. For example, administration of activated CD8+ cells via intravenous infusion is appropriate.

The practice of the present invention employs, unless otherwise indicated, conventional techniques of molecular biology (including recombinant techniques), microbiology, cell biology, biochemistry and immunology, which are well within the purview of the skilled artisan. Such techniques are explained fully in the literature, such as, "Molecular Cloning: A Laboratory Manual", second edition (Sambrook, 1989); "Oligonucleotide Synthesis" (Gait, 1984); "Animal Cell Culture" (Freshney, 1987); "Methods in Enzymology" "Handbook of Experimental Immunology" (Wei, 1996); "Gene Transfer Vectors for Mammalian Cells" (Miller and Calos, 1987); "Current Protocols in Molecular Biology" (Ausubel, 1987); "PCR: The Polymerase Chain Reaction", (Mullis, 1994); "Current Protocols in Immunology" (Coligan, 1991). These techniques are applicable to the production of the polynucleotides and polypeptides of the invention, and, as such, may be considered in making and practicing the invention. Particularly useful techniques for particular embodiments are discussed in the sections that follow.

The present invention provides methods of inducing a neoplasia/tumor specific immune response in a subject, vaccinating against a neoplasia/tumor, treating, alleviating a symptom of cancer, preventing or treating an infection, treating an autoimmune disease, or preventing transplant rejection in a subject by administering the subject a plurality of antigenic peptides or composition of the invention. According to the invention, the herein-described vaccine or immunogenic composition may be used for a patient that has been diagnosed as having cancer, or at risk of developing cancer.

The claimed combination of the invention is administered in an amount sufficient to induce a CTL response.

Any compositions or methods provided herein can be combined with one or more of any of the other compositions and methods provided herein.

The tumor specific neoantigen peptides and pharmaceutical compositions described herein can also be administered in a combination therapy with another agent, for example a therapeutic agent. By "agent" is meant any small molecule chemical compound, antibody, nucleic acid molecule, or polypeptide, or fragments thereof. In certain embodiments, the additional agents can be, but are not limited to, chemotherapeutic agents, anti-angiogenesis agents and agents that reduce immune-suppression.

"Combination therapy" is intended to embrace administration of therapeutic agents (e.g. neoantigenic peptides described herein) in a sequential manner, that is, wherein each therapeutic agent is administered at a different time, as well as administration of these therapeutic agents, or at least two of the therapeutic agents, in a substantially simultaneous manner. Substantially simultaneous administration can be accomplished, for example, by administering to the subject a single capsule having a fixed ratio of each therapeutic agent or in multiple, single capsules for each of the therapeutic agents. For example, one combination of the present invention may comprise a pooled sample of neoantigenic peptides administered at the same or different times, or they can be formulated as a single, co-formulated pharmaceutical composition comprising the peptides. As another example, a combination of the present invention (e.g., a pooled sample of tumor specific neoantigens) may be formulated as separate pharmaceutical compositions that can be administered at the same or different time. As used herein, the term "simultaneously" is meant to refer to administration of one or more agents at the same time. For example, in certain embodiments, the neoantigenic peptides are administered simultaneously. Simultaneously includes administration contemporaneously, that is during the same period of time. In certain embodiments, the one or more agents are administered simultaneously in the same hour, or simultaneously in the same day. Sequential or substantially simultaneous administration of each therapeutic agent can be effected by any appropriate route including, but not limited to, oral routes, intravenous routes, sub-cutaneous routes, intramuscular routes, direct absorption through mucous membrane tissues (e.g., nasal, mouth, vaginal, and rectal), and ocular routes (e.g., intravitreal, intraocular, etc.). The therapeutic agents can be administered by the same route or by different routes. For example, one component of a particular combination may be administered by intravenous injection while the other component(s) of the combination may be administered orally. The components may be administered in any therapeutically effective sequence. The phrase "combination" embraces groups of compounds or non-drug therapies useful as part of a combination therapy.

The neoplasia vaccine or immunogenic composition can be administered before, during, or after administration of the additional agent. In embodiments, the neoplasia vaccine or immunogenic composition is administered before the first administration of the additional agent. In other embodiments, the neoplasia vaccine or immunogenic composition is administered after the first administration of the additional therapeutic agent (e.g., 1, 2, 3, 4, 5, 6, 7, 8, 9, 10, 11, 12, 13, 14 days or more). In embodiments, the neoplasia vaccine or immunogenic composition is administered simultaneously with the first administration of the additional therapeutic agent.

The therapeutic agent is for example, a chemotherapeutic or biotherapeutic agent, radiation, or immunotherapy. Any suitable therapeutic treatment for a particular cancer may be administered. Examples of chemotherapeutic and biotherapeutic agents include, but are not limited to, an angiogenesis inhibitor, such as hydroxyangiostatin Kl-3, DL-a-Difluorom ethyl—ornithine, endostatin, fumagillin, genistein, minocycline, staurosporine, and thalidomide; a DNA intercaltor/ cross-linker, such as Bleomycin, Carboplatin, Carmustine, Chlorambucil, Cyclophosphamide, cis-Diammineplatinum (II) dichloride (Cisplatin), Melphalan, Mitoxantrone, and Oxaliplatin; a DNA synthesis inhibitor, such as (±)-Amethopterin (Methotrexate), 3-Amino-1,2,4-benzotriazine 1,4-di oxide, Aminopterin, Cytosine β-D-arabinofuranoside, 5-Fluoro-5'-deoxyuridine, 5-Fluorouracil, Ganciclovir, Hydroxyurea, and Mitomycin C; a DNA-RNA transcription regulator, such as Actinomycin D, Daunorubicin, Doxorubicin, Homoharringtonine, and Idarubicin; an enzyme inhibitor, such as S(+)-Camptothecin, Curcumin, (−)-Deguelin, 5,6-Dichlorobenzimidazole I-β-D-ribofuranoside, Etoposide, Formestane, Fostriecin, Hispidin, 2-Imino-l-imidazoli-dineacetic acid (Cyclocreatine), Mevinolin, Trichostatin A, Tyrphostin AG 34, and Tyrphostin AG 879; a gene regulator, such as 5-Aza-2'-deoxycytidine, 5-Azacytidine, Cholecalciferol (Vitamin D3), 4-Hydroxytamoxifen, Melatonin, Mifepristone, Raloxifene, all trans-Retinal (Vitamin A aldehyde), Retinoic acid all trans (Vitamin A acid), 9-cis-Retinoic Acid, 13-cis-Retinoic acid, Retinol (Vitamin A), Tamoxifen, and Troglitazone; a microtubule inhibitor, such as Colchicine, docetaxel, Dolastatin 15, Nocodazole, Paclitaxel, Podophyllotoxin, Rhizoxin, Vinblastine, Vincristine, Vindesine, and Vinorelbine (Navelbine); and an unclassified therapeutic agent, such as 17-(Allylamino)-17-demethoxygeldanamycin, 4-Amino-1,8-naphthalimide, Apigenin, Brefeldin A, Cimetidine, Dichloromethylene-diphosphonic acid, Leuprolide (Leuprorelin), Luteinizing Hormone-Releasing Hormone, Pifithrin-a, Rapamycin, Sex hormone-binding globulin, Thapsigargin, and Urinary trypsin inhibitor fragment (Bikunin). The therapeutic agent may be altretamine, amifostine, asparaginase, capecitabine, cladribine, cisapride, cytarabine, dacarbazine (DTIC), dactinomycin, dronabinol, epoetin alpha, filgrastim, fludarabine, gemcitabine, granisetron, ifosfamide, irinotecan, lansoprazole, levamisole, leucovorin, megestrol, mesna, metoclopramide, mitotane, omeprazole, ondansetron, pilocarpine, prochlorperazine, or topotecan hydrochloride. The therapeutic agent may be a monoclonal antibody or small molecule such as rituximab (Rituxan®), alemtuzumab (Campath®), Bevacizumab (Avastin®), Cetuximab (Erbitux®), panitumumab (Vectibix®), and trastuzumab (Herceptin®), Vemurafenib (Zelboraf®) imatinib mesylate (Gleevec®), erlotinib (Tarceva®), gefitinib (Iressa®), Vismodegib (Erivedge™), 90Y-ibritumomab tiuxetan, 131I-tositumomab, ado-trastuzumab emtansine, lapatinib (Tykerb®), pertuzumab (Perjeta™), ado-trastuzumab emtansine (Kadcyla™) regorafenib (Stivarga®), sunitinib (Sutent®), Denosumab (Xgeva®), sorafenib (Nexavar®), pazopanib (Votrient®), axitinib (Inlyta®), dasatinib (Sprycel®), nilotinib (Tasigna®), bosutinib (Bosulif®), ofatumumab (Arzerra®), obinutuzumab (Gazyva™), ibrutinib (Imbruvica™) idelalisib (Zydelig®), crizotinib (Xalkori®), erlotinib (Tarceva®), afatinib dimaleate (Gilotrif®), ceritinib (LDK378/Zykadia), Tositumomab and 131I-tositumomab (Bexxar®), ibritumomab tiuxetan (Zevalin®), brentuximab vedotin (Adcetris®), bortezomib (Velcade®), siltuximab (Sylvant™), trametinib (Mekinist®), dabrafenib (Tafinlar®), pembrolizumab (Keytruda®), carfilzomib (Kyprolis®), Ramucirumab (Cyramza™), Cabozantinib (Cometriq™), vandetanib (Caprelsa®), Optionally, the therapeutic agent is a neoantigen. The therapeutic agent may be a cytokine such as interferons (INFs), interleukins (TLs), or hematopoietic growth factors. The therapeutic agent may be INF-α, IL-2, Aldesleukin, IL-2, Erythropoietin, Granulocyte-macrophage colony-stimulating factor (GM-CSF) or granulocyte colony-stimulating factor. The therapeutic agent may be a targeted therapy such as toremifene (Fareston®), fulvestrant (Faslodex®), anastrozole (Arimidex®), exemestane (Aromasin®), letrozole (Femara®), ziv-aflibercept (Zaltrap®), Alitretinoin (Panretin®), temsirolimus (Torisel®), Tretinoin (Vesanoid®), denileukin diftitox (Ontak®), vorinostat (Zolinza®), romidepsin (Istodax®), bexarotene (Targretin®), pralatrexate (Folotyn®), lenalidomide (Revlimid®), belinostat (Beleodaq™), lenaliomide (Revlimid®), pomalidomide (Pomalyst®), Cabazitaxel (Jevtana®), enzalutamide (Xtandi®), abiraterone acetate (Zytiga®), radium 223 chloride (Xofigo®), or everolimus (Afinitor®). Additionally, the therapeutic agent may be an epigenetic targeted drug such as FIDAC inhibitors, kinase inhibitors, DNA methyltransferase inhibitors, histone demethylase inhibitors, or histone methylation inhibitors. The epigenetic drugs may be Azacitidine (Vidaza), Decitabine (Dacogen), Vorinostat (Zolinza), Romidepsin (Istodax), or Ruxolitinib (Jakafi). For prostate cancer treatment, a preferred chemotherapeutic agent with which anti-CTLA-4 can be combined is paclitaxel (TAXOL).

In certain embodiments, the one or more additional agents are one or more anti-glucocorticoid-induced tumor necrosis factor family receptor (GITR) agonistic antibodies. GITR is a costimulatory molecule for T lymphocytes, modulates innate and adaptive immune system and has been found to participate in a variety of immune responses and inflammatory processes. GITR was originally described by Nocentini et al. after being cloned from dexamethasone-treated murine T cell hybridomas (Nocentini et al. Proc Natl Acad Sci USA 94:6216-6221.1997). Unlike CD28 and CTLA-4, GITR has a very low basal expression on naive CD4+ and CD8+ T cells (Ronchetti et al. Eur J Immunol 34:613-622. 2004). The observation that GITR stimulation has immunostimulatory effects in vitro and induced autoimmunity in vivo prompted the investigation of the antitumor potency of triggering this pathway. A review of Modulation Of Ctla 4 And Gitr For Cancer Immunotherapy can be found in Cancer Immunology and Immunotherapy (Avogadri et al. Current Topics in Microbiology and Immunology 344. 2011). Other agents that can contribute to relief of immune suppression include checkpoint inhibitors targeted at another member of the CD28/CTLA4 Ig superfamily such as BTLA, LAG3, ICOS, PDL1 or KIR (Page et a, Annual Review of Medicine 65:27 (2014)). In further additional embodiments, the checkpoint inhibitor is targeted at a member of the TNFR superfamily such as CD40, OX40, CD 137, GITR, CD27 or TEVI-3. In some cases targeting a checkpoint inhibitor is accomplished with an inhibitory antibody or similar molecule. In other cases, it is accomplished with an agonist for the target; examples of this class include the stimulatory targets OX40 and GITR.

In certain embodiments, the one or more additional agents are synergistic in that they increase immunogenicity after treatment. In one embodiment, the additional agent allows for lower toxicity and/or lower discomfort due to lower doses of the additional therapeutic agents or any components of the combination therapy described herein. In another embodiment the additional agent results in longer lifespan due to increased effectiveness of the combination therapy described herein. Chemotherapeutic treatments that enhance the immunological response in a patient have been reviewed (Zitvogel et al., Immunological aspects of cancer chemotherapy. Nat Rev Immunol. 2008 January; 8(1):59-73). Additionally, chemotherapeutic agents can be administered safely with immunotherapy without inhibiting vaccine specific T cell responses (Perez et al., A new era in anticancer peptide vaccines. Cancer May 2010). In one embodiment, the additional agent is administered to increase the efficacy of the therapy described herein. In one embodiment the additional agent is a chemotherapy treatment. In one embodiment, low doses of chemotherapy potentiate delayed-type hypersensitivity (DTH) responses. In one embodiment, the chemotherapy agent targets regulatory T cells. In one embodiment, cyclophosphamide is the therapeutic agent. In one embodiment cyclophosphamide is administered prior to vaccination. In one embodiment, cyclophosphamide is administered as a single dose before vaccination (Walter et al., Multipeptide immune response to cancer vaccine IMA901 after single-dose cyclophosphamide associates with longer patient survival. Nature Medicine; 18:8 2012). In another embodiment, cyclophosphamide is administered according to a metronomic program, where a daily dose is administered for one month (Ghiringhelli et al., Metronomic cyclophosphamide regimen selectively depletes CD4+CD25+ regulatory T cells and restores T and NK effector functions in end stage cancer patients. Cancer Immunol Immunother 2007 56:641-648). In another embodiment, taxanes are administered before vaccination to enhance T-cell and NK-cell functions (Zitvogel et al., 2008, Nat. Rev. Immunol., 8(1):59-73). In another embodiment a low dose of a chemotherapeutic agent is administered with the therapy described herein. In one embodiment the chemotherapeutic agent is estramustine. In one embodiment the cancer is hormone resistant prostate cancer. A >50% decrease in serum prostate specific antigen (PSA) was seen in 8.7% of advanced hormone refractory prostate cancer patients by personalized vaccination alone, whereas such a decrease was seen in 54% of patients when the personalized vaccination was combined with a low dose of estramustine (Itoh et al., Personalized peptide vaccines: A new therapeutic modality for cancer. Cancer Sci 2006; 97: 970-976). In another embodiment glucocorticoids are administered with or before the therapy described herein (Zitvogel et al., 2008, Nat. Rev. Immunol., 8(1):59-73). In another embodiment glucocorticoids are administered after the therapy described herein. In another embodiment Gemcitabine is administered before, simultaneously, or after the therapy described herein to enhance the frequency of tumor specific CTL precursors (Zitvogel et al., 2008, Nat. Rev. Immunol., 8(1):59-73). In another embodiment 5-fluorouracil is administered with the therapy described herein as synergistic effects were seen with a peptide based vaccine (Zitvogel et al., 2008, Nat. Rev. Immunol., 8(1):59-73). In another embodiment an inhibitor of Braf, such as Vemurafenib, is used as an additional agent. Braf inhibition has been shown to be associated with an increase in melanoma antigen expression and T cell infiltrate and a decrease in immunosuppressive cytokines in tumors of treated patients (Frederick et al., BRAF inhibition is associated with enhanced melanoma antigen expression and a more favorable tumor microenvironment in patients with metastatic melanoma. Clin Cancer Res. 2013; 19: 1225-1231). In another embodiment an inhibitor of tyrosine kinases is used as an additional agent. In one embodiment the tyrosine kinase inhibitor is used before vaccination with the therapy described herein. In one embodiment the tyrosine kinase inhibitor is used simultaneously with the therapy described herein. In another embodiment the tyrosine kinase inhibitor is used to create a more immune permissive environment. In another embodiment the tyrosine kinase inhibitor is sunitinib or imatinib mesylate. It has previously been shown that favorable outcomes could be achieved with sequential administration of continuous daily dosing of sunitinib and recombinant vaccine (Farsaci et al., Consequence of dose scheduling of sunitinib on host immune response elements and vaccine combination therapy. Int J Cancer; 130: 1948-1959). Sunitinib has also been shown to reverse type-1 immune suppression using a daily dose of 50 mg/day (Finke et al., Sunitinib Reverses Type-1 Immune Suppression and Decreases T-Regulatory Cells in Renal Cell Carcinoma Patients. Clin Cancer Res 2008; 14(20)). In another embodiment targeted therapies are administered in combination with the therapy described herein. Doses of targeted therapies has been described previously (Alvarez, Present and future evolution of advanced breast cancer therapy. Breast Cancer Research 2010, 12(Suppl 2):S1). In another embodiment temozolomide is administered with the therapy described herein. In one embodiment temozolomide is administered at 200 mg/day for 5 days every fourth week of a combination therapy with the therapy described herein. Results of a similar strategy have been shown to have low toxicity (Kyte et al., Tel om erase Peptide Vaccination Combined with Temozolomide: A Clinical Trial in Stage IV Melanoma Patients. Clin Cancer Res; 17(13) 2011). In another embodiment the therapy is administered with an additional therapeutic agent that results in lymphopenia. In one embodiment the additional agent is temozolomide. An immune response can still be induced under these conditions (Sampson et al., Greater chemotherapy-induced lymphopenia enhances tumor-specific immune responses that eliminate EGFRvIII-expressing tumor cells in patients with glioblastoma. Neuro-Oncology 13(3):324-333, 2011).

Patients in need thereof may receive a series of priming vaccinations with a mixture of tumor-specific peptides. Additionally, over a 4 week period the priming may be followed by two boosts during a maintenance phase. All vaccinations are subcutaneously delivered. The vaccine or immunogenic composition is evaluated for safety, tolerability, immune response and clinical effect in patients and for feasibility of producing vaccine or immunogenic composition and successfully initiating vaccination within an appropriate time frame. The first cohort can consist of 5 patients, and after safety is adequately demonstrated, an additional cohort of 10 patients may be enrolled. Peripheral blood is extensively monitored for peptide-specific T cell responses and patients are followed for up to two years to assess disease recurrence.

Administering a combination therapy consistent with standard of care. In another aspect, the therapy described herein provides selecting the appropriate point to administer a combination therapy in relation to and within the standard of care for the cancer being treated for a patient in need thereof. The studies described herein show that the combination therapy can be effectively administered even within the standard of care that includes surgery, radiation, or chemotherapy. The standards of care for the most common cancers can be found on the website of National Cancer Institute (www.cancer.gov/cancertopics). The standard of care is the current treatment that is accepted by medical experts as a proper treatment for a certain type of disease and that is widely used by healthcare professionals. Standard or care is also called best practice, standard medical care, and standard therapy. Standards of Care for cancer generally include surgery, lymph node removal, radiation, chemotherapy, targeted therapies, antibodies targeting the tumor, and immunotherapy. Immunotherapy can include checkpoint blockers (CBP), chimeric antigen receptors (CARs), and adoptive T cell therapy. The combination therapy described herein can be incorporated within the standard of care. The combination therapy described herein may also be administered where the standard of care has changed due to advances in medicine.

Incorporation of the combination therapy described herein may depend on a treatment step in the standard of care that can lead to activation of the immune system. Treatment steps that can activate and function synergistically with the combination therapy have been described herein. The therapy can be advantageously administered simultaneously or after a treatment that activates the immune system.

Incorporation of the combination therapy described herein may depend on a treatment step in the standard of care that causes the immune system to be suppressed. Such treatment steps may include irradiation, high doses of alkylating agents and/or methotrexate, steroids such as glucoteroids, surgery, such as to remove the lymph nodes, imatinib mesylate, high doses of T F, and taxanes (Zitvogel et al., 2008, Nat. Rev. Immunol., 8(1):59-73). The combination therapy may be administered before such steps or may be administered after.

In one embodiment the combination therapy may be administered after bone marrow transplants and peripheral blood stem cell transplantation. Bone marrow transplantation and peripheral blood stem cell transplantation are procedures that restore stem cells that were destroyed by high doses of chemotherapy and/or radiation therapy. After being treated with high-dose anticancer drugs and/or radiation, the patient receives harvested stem cells, which travel to the bone marrow and begin to produce new blood cells. A "mini-transplant" uses lower, less toxic doses of chemotherapy and/or radiation to prepare the patient for transplant. A "tandem transplant" involves two sequential courses of high-dose chemotherapy and stem cell transplant. In autologous transplants, patients receive their own stem cells. In syngeneic transplants, patients receive stem cells from their identical twin. In allogeneic transplants, patients receive stem cells from their brother, sister, or parent. A person who is not related to the patient (an unrelated donor) also may be used. In some types of leukemia, the graft-versus-tumor (GVT) effect that occurs after allogeneic BMT and PBSCT is crucial to the effectiveness of the treatment. GVT occurs when white blood cells from the donor (the graft) identify the cancer cells that remain in the patient's body after the chemotherapy and/or radiation therapy (the tumor) as foreign and attack them. Immunotherapy with the combination therapy described herein can take advantage of this by vaccinating after a transplant. Additionally, the transferred cells may be presented with neoantigens of the combination therapy described herein before transplantation.

In one embodiment the combination therapy is administered to a patient in need thereof with a cancer that requires surgery. In one embodiment the combination therapy described herein is administered to a patient in need thereof in a cancer where the standard of care is primarily surgery followed by treatment to remove possible micro-metastases, such as breast cancer. Breast cancer is commonly treated by various combinations of surgery, radiation therapy, chemotherapy, and hormone therapy based on the stage and grade of the cancer. Adjuvant therapy for breast cancer is any treatment given after primary therapy to increase the chance of long-term survival. Neoadjuvant therapy is treatment given before primary therapy. Adjuvant therapy for breast cancer is any treatment given after primary therapy to increase the chance of long-term disease-free survival. Primary therapy is the main treatment used to reduce or eliminate the cancer. Primary therapy for breast cancer usually includes surgery, a mastectomy (removal of the breast) or a lumpectomy (surgery to remove the tumor and a small amount of normal tissue around it; a type of breast-conserving surgery). During either type of surgery, one or more nearby lymph nodes are also removed to see if cancer cells have spread to the lymphatic system. When a woman has breast-conserving surgery, primary therapy almost always includes radiation therapy. Even in early-stage breast cancer, cells may break away from the primary tumor and spread to other parts of the body (metastasize). Therefore, doctors give adjuvant therapy to kill any cancer cells that may have spread, even if they cannot be detected by imaging or laboratory tests.

In one embodiment the combination therapy is administered consistent with the standard of care for Ductal carcinoma in situ (DCIS). The standard of care for this breast cancer type is: 1. Breast-conserving surgery and radiation therapy with or without tamoxifen; 2. Total mastectomy with or without tamoxifen; 3. Breast-conserving surgery without radiation therapy. The combination therapy may be administered before breast conserving surgery or total mastectomy to shrink the tumor before surgery. In another embodiment the combination therapy can be administered as an adjuvant therapy to remove any remaining cancer cells.

In another embodiment patients diagnosed with stage I, II, IIIA, and Operable IIIC breast cancer are treated with the combination therapy as described herein. The standard of care for this breast cancer type is: 1. Local-regional treatment: Breast-conserving therapy (lumpectomy, breast radiation, and surgical staging of the axilla), Modified radical mastectomy (removal of the entire breast with level I-II axillary dissection) with or without breast reconstruction, Sentinel node biopsy. 2. Adjuvant radiation therapy postmastectomy in axillary node-positive tumors: For one to three nodes: unclear role for regional radiation (infra/supraclavicular nodes, internal mammary nodes, axillary nodes, and chest wall). For more than four nodes or extranodal involvement: regional radiation is advised. 3. Adjuvant systemic therapy. In one embodiment the combination therapy is administered as a neoadjuvant therapy to shrink the tumor. In another embodiment the combination is administered as an adjuvant systemic therapy.

In another embodiment patients diagnosed with inoperable stage IIIB or IIIC or inflammatory breast cancer are treated with the combination therapy as described herein. The standard of care for this breast cancer type is: 1. Multimodality therapy delivered with curative intent is the standard of care for patients with clinical stage IIIB disease.

2. Initial surgery is generally limited to biopsy to permit the determination of histology, estrogen-receptor (ER) and progesterone-receptor (PR) levels, and human epidermal growth factor receptor 2 (HER2/neu) overexpression. Initial treatment with anthracycline-based chemotherapy and/or taxane-based therapy is standard. For patients who respond to neoadjuvant chemotherapy, local therapy may consist of total mastectomy with axillary lymph node dissection followed by postoperative radiation therapy to the chest wall and regional lymphatics. Breast-conserving therapy can be considered in patients with a good partial or complete response to neoadjuvant chemotherapy. Subsequent systemic therapy may consist of further chemotherapy. Hormone therapy should be administered to patients whose tumors are ER-positive or unknown. All patients should be considered candidates for clinical trials to evaluate the most appropriate fashion in which to administer the various components of multimodality regimens.

In one embodiment the combination therapy is administered as part of the various components of multimodality regimens. In another embodiment the combination therapy is administered before, simultaneously with, or after the multimodality regimens. In another embodiment the combination therapy is administered based on synergism between the modalities. In another embodiment the combination therapy is administered after treatment with anthracycline-based chemotherapy and/or taxane-based therapy (Zitvogel et al., 2008, Nat. Rev. Immunol., 8(1):59-73). Treatment after administering the combination therapy may negatively affect dividing effector T cells. The combination therapy may also be administered after radiation.

In another embodiment the combination therapy described herein is used in the treatment in a cancer where the standard of care is primarily not surgery and is primarily based on systemic treatments, such as Chronic Lymphocytic Leukemia (CLL).

In another embodiment patients diagnosed with stage I, II, III, and IV Chronic Lymphocytic Leukemia are treated with the combination therapy as described herein. The standard of care for this cancer type is: 1. Observation in asymptomatic or minimally affected patients, 2. Rituximab, 3. Ofatumumab, 4. Oral alkylating agents with or without corticosteroids, 5. Fludarabine, 2-chlorodeoxyadenosine, or pentostatin, 6. Bendamustine, 7. Lenalidomide and 8. Combination chemotherapy. Combination chemotherapy regimens include the following: Fludarabine plus cyclophosphamide plus rituximab. o Fludarabine plus rituximab as seen in the CLB-9712 and CLB-9011 trials, o Fludarabine plus cyclophosphamide versus fludarabine plus cyclophosphamide plus rituximab, Pentostatin plus cyclophosphamide plus rituximab as seen in the MAYO-MC0183 trial, for example, Ofatumumab plus fludarabine plus cyclophosphamide, CVP: cyclophosphamide plus vincristine plus prednisone, CHOP: cyclophosphamide plus doxorubicin plus vincristine plus prednisone, Fludarabine plus cyclophosphamide versus fludarabine as seen in the E2997 trial [NCT00003764] and the LRF-CLL4 trial, for example, Fludarabine plus chlorambucil as seen in the CLB-9011 trial, for example. 9. Involved-field radiation therapy. 10. Alemtuzumab 11. Bone marrow and peripheral stem cell transplantations are under clinical evaluation. 12. Ibrutinib.

In one embodiment the combination therapy is administered before, simultaneously with or after treatment with Rituximab or Ofatumumab. As these are monoclonal antibodies that target B-cells, treatment with the combination therapy may be synergistic. In another embodiment the combination therapy is administered after treatment with oral alkylating agents with or without corticosteroids, and Fludarabine, 2-chlorodeoxyadenosine, or pentostatin, as these treatments may negatively affect the immune system if administered before. In one embodiment bendamustine is administered with the combination therapy in low doses based on the results for prostate cancer described herein. In one embodiment the combination therapy is administered after treatment with bendamustine.

In another embodiment, therapies targeted to specific recurrent mutations in genes that include extracellular domains are used in the treatment of a patient in need thereof suffering from cancer. The genes may advantageously be well-expressed genes. Well expressed may be expressed in "transcripts per million" (TPM). A TPM greater than 100 is considered well expressed. Well expressed genes may be FGFR3, ERBB3, EGFR, MUC4, PDGFRA, MMP12, TMEM52, and PODXL. The therapies may be a ligand capable of binding to an extracellular neoantigen epitope. Such ligands are well known in the art and may include therapeutic antibodies or fragments thereof, antibody-drug conjugates, engineered T cells, or aptamers. Engineered T cells may be chimeric antigen receptors (CARs). Antibodies may be fully humanized, humanized, or chimeric. The antibody fragments may be a nanobody, Fab, Fab', (Fab')2, Fv, ScFv, diabody, triabody, tetrabody, Bis-scFv, minibody, Fab2, or Fab3 fragment. Antibodies may be developed against tumor-specific neoepitopes using known methods in the art.

Adoptive Cell Transfer (ACT)

In certain embodiments, immune cells specific to an identified antigenic peptide that binds to a subject specific HLA allele is used in treatment. For example, CD8+ T cells that express a TCR or CAR specific for the peptide, or dendritic cells that are loaded with one or more peptides are transferred to a subject in need thereof. As used herein, "ACT", "adoptive cell therapy" and "adoptive cell transfer" may be used interchangeably. In certain embodiments, Adoptive cell therapy (ACT) can refer to the transfer of cells to a patient with the goal of transferring the functionality and characteristics into the new host by engraftment of the cells (see, e.g., Mettananda et al., Editing an α-globin enhancer in primary human hematopoietic stem cells as a treatment for β-thalassemia, Nat Commun. 2017 Sep. 4; 8(1):424). As used herein, the term "engraft" or "engraftment" refers to the process of cell incorporation into a tissue of interest in vivo through contact with existing cells of the tissue. Adoptive cell therapy (ACT) can refer to the transfer of cells, most commonly immune-derived cells, back into the same patient or into a new recipient host with the goal of transferring the immunologic functionality and characteristics into the new host. If possible, use of autologous cells helps the recipient by minimizing GVHD issues. The adoptive transfer of autologous tumor infiltrating lymphocytes (TIL) (Besser et al., (2010) Clin. Cancer Res 16 (9) 2646-55; Dudley et al., (2002) Science 298 (5594): 850-4; and Dudley et al., (2005) Journal of Clinical Oncology 23 (10): 2346-57.) or genetically re-directed peripheral blood mononuclear cells (Johnson et al., (2009) Blood 114 (3): 535-46; and Morgan et al., (2006) Science 314(5796) 126-9) has been used to successfully treat patients with advanced solid tumors, including melanoma and colorectal carcinoma, as well as patients with CD19-expressing hematologic malignancies (Kalos et al., (2011) Science Translational Medicine 3 (95): 95ra73). In certain embodiments, allogenic cells immune cells are transferred (see, e.g., Ren et al., (2017) Clin Cancer Res 23 (9) 2255-2266). As described further herein, allogenic cells can be edited to reduce alloreactivity and prevent graft-versushost disease. Thus, use of allogenic cells allows for cells to be obtained from healthy donors and prepared for use in patients as opposed to preparing autologous cells from a patient after diagnosis.

Aspects of the invention involve the adoptive transfer of immune system cells, such as T cells, specific for selected antigens, such as tumor associated antigens or tumor specific neoantigens (see, e.g., Maus et al., 2014, Adoptive Immunotherapy for Cancer or Viruses, Annual Review of Immunology, Vol. 32: 189-225; Rosenberg and Restifo, 2015, Adoptive cell transfer as personalized immunotherapy for human cancer, Science Vol. 348 no. 6230 pp. 62-68; Restifo et al., 2015, Adoptive immunotherapy for cancer: harnessing the T cell response. Nat. Rev. Immunol. 12(4): 269-281; and Jenson and Riddell, 2014, Design and implementation of adoptive therapy with chimeric antigen receptor-modified T cells. Immunol Rev. 257(1): 127-144; and Rajasagi et al., 2014, Systematic identification of personal tumor-specific neoantigens in chronic lymphocytic leukemia. Blood. 2014 Jul. 17; 124(3):453-62).

In certain embodiments, an antigen to be targeted in adoptive cell therapy (such as particularly CAR or TCR T cell therapy) of a disease (such as particularly of tumor or cancer) is a tumor-specific antigen (TSA).

In certain embodiments, an antigen to be targeted in adoptive cell therapy (such as particularly CAR or TCR T cell therapy) of a disease (such as particularly of tumor or cancer) is a neoantigen.

In certain embodiments, an antigen to be targeted in adoptive cell therapy (such as particularly CAR or TCR T cell therapy) of a disease (such as particularly of tumor or cancer) is a tumor-associated antigen (TAA).

Various strategies may for example be employed to genetically modify T cells by altering the specificity of the T cell receptor (TCR) for example by introducing new TCR a and R chains with selected peptide specificity (see U.S. Pat. No. 8,697,854; PCT Patent Publications: WO2003020763, WO2004033685, WO2004044004, WO2005114215, WO2006000830, WO2008038002, WO2008039818, WO2004074322, WO2005113595, WO2006125962, WO2013166321, WO2013039889, WO2014018863, WO2014083173; U.S. Pat. No. 8,088, 379).

As an alternative to, or addition to, TCR modifications, chimeric antigen receptors (CARs) may be used in order to generate immunoresponsive cells, such as T cells, specific for selected targets, such as malignant cells, with a wide variety of receptor chimera constructs having been described (see U.S. Pat. Nos. 5,843,728; 5,851,828; 5,912,170; 6,004, 811; 6,284,240; 6,392,013; 6,410,014; 6,753,162; 8,211, 422; and, PCT Publication WO9215322).

In general, CARs are comprised of an extracellular domain, a transmembrane domain, and an intracellular domain, wherein the extracellular domain comprises an antigen-binding domain that is specific for a predetermined target. While the antigen-binding domain of a CAR is often an antibody or antibody fragment (e.g., a single chain variable fragment, scFv), the binding domain is not particularly limited so long as it results in specific recognition of a target. For example, in some embodiments, the antigen-binding domain may comprise a receptor, such that the CAR is capable of binding to the ligand of the receptor. Alternatively, the antigen-binding domain may comprise a ligand, such that the CAR is capable of binding the endogenous receptor of that ligand.

The antigen-binding domain of a CAR is generally separated from the transmembrane domain by a hinge or spacer. The spacer is also not particularly limited, and it is designed to provide the CAR with flexibility. For example, a spacer domain may comprise a portion of a human Fc domain, including a portion of the CH3 domain, or the hinge region of any immunoglobulin, such as IgA, IgD, IgE, IgG, or IgM, or variants thereof. Furthermore, the hinge region may be modified so as to prevent off-target binding by FcRs or other potential interfering objects. For example, the hinge may comprise an IgG4 Fc domain with or without a S228P, L235E, and/or N297Q mutation (according to Kabat numbering) in order to decrease binding to FcRs. Additional spacers/hinges include, but are not limited to, CD4, CD8, and CD28 hinge regions.

The transmembrane domain of a CAR may be derived either from a natural or from a synthetic source. Where the source is natural, the domain may be derived from any membrane bound or transmembrane protein. Transmembrane regions of particular use in this disclosure may be derived from CD8, CD28, CD3, CD45, CD4, CD5, CDS, CD9, CD 16, CD22, CD33, CD37, CD64, CD80, CD86, CD 134, CD137, CD 154, TCR. Alternatively, the transmembrane domain may be synthetic, in which case it will comprise predominantly hydrophobic residues such as leucine and valine. Preferably a triplet of phenylalanine, tryptophan and valine will be found at each end of a synthetic transmembrane domain. Optionally, a short oligo- or polypeptide linker, preferably between 2 and 10 amino acids in length may form the linkage between the transmembrane domain and the cytoplasmic signaling domain of the CAR. A glycine-serine doublet provides a particularly suitable linker.

Alternative CAR constructs may be characterized as belonging to successive generations. First-generation CARs typically consist of a single-chain variable fragment of an antibody specific for an antigen, for example comprising a VL linked to a VH of a specific antibody, linked by a flexible linker, for example by a CD8a hinge domain and a CD8a transmembrane domain, to the transmembrane and intracellular signaling domains of either CD3ζ or FcRγ (scFv-CD3ζ or scFv-FcRγ; see U.S. Pat. Nos. 7,741,465; 5,912,172; 5,906,936). Second-generation CARs incorporate the intracellular domains of one or more costimulatory molecules, such as CD28, OX40 (CD134), or 4-1BB (CD137) within the endodomain (for example scFv-CD28/OX40/4-1BB-CD3ζ; see U.S. Pat. Nos. 8,911,993; 8,916,381; 8,975,071; 9,101,584; 9,102,760; 9,102,761). Third-generation CARs include a combination of costimulatory endodomains, such a CD3ζ-chain, CD97, GDI la-CD18, CD2, ICOS, CD27, CD154, CDS, OX40, 4-1BB, CD2, CD7, LIGHT, LFA-1, NKG2C, B7-H3, CD30, CD40, PD-1, or CD28 signaling domains (for example scFv-CD28-4-1BB-CD3ζ or scFv-CD28-OX40-CD3ζ; see U.S. Pat. Nos. 8,906,682; 8,399, 645; 5,686,281; PCT Publication No. WO2014134165; PCT Publication No. WO2012079000). In certain embodiments, the primary signaling domain comprises a functional signaling domain of a protein selected from the group consisting of CD3 zeta, CD3 gamma, CD3 delta, CD3 epsilon, common FcR gamma (FCERIG), FcR beta (Fc Epsilon Rib), CD79a, CD79b, Fc gamma RIIa, DAP10, and DAP12. In certain preferred embodiments, the primary signaling domain comprises a functional signaling domain of CD3ζ or FcRγ. In certain embodiments, the one or more costimulatory signaling domains comprise a functional signaling domain of a protein selected, each independently, from the group consisting of: CD27, CD28, 4-1BB (CD137), OX40, CD30, CD40, PD-1, ICOS, lymphocyte function-associated antigen-1 (LFA-1), CD2, CD7, LIGHT, NKG2C, B7-H3, a ligand that specifically binds with CD83, CDS, ICAM-1, GITR, BAFFR, HVEM (LIGHTR), SLAMF7, NKp80 (KLRF1), CD160, CD19, CD4, CD8 alpha, CD8 beta, IL2R beta, IL2R gamma, IL7R alpha, ITGA4, VLA1, CD49a, ITGA4, IA4, CD49D, ITGA6, VLA-6, CD49f, ITGAD, CD11d, ITGAE, CD103, ITGAL, CD11a, LFA-1, ITGAM, CD11b, ITGAX, CD11c, ITGB1, CD29, ITGB2, CD18, ITGB7, TNFR2, TRANCE/RANKL, DNAM1 (CD226), SLAMF4 (CD244, 2B4), CD84, CD96 (Tactile), CEACAM1, CRTAM, Ly9 (CD229), CD160 (BY55), PSGL1, CD100 (SEMA4D), CD69, SLAMF6 (NTB-A, Lyl08), SLAM (SLAMFI, CD150, IPO-3), BLAME (SLAMF8), SELPLG (CD162), LTBR, LAT, GADS, SLP-76, PAG/Cbp, NKp44, NKp30, NKp46, and NKG2D. In certain embodiments, the one or more costimulatory signaling domains comprise a functional signaling domain of a protein selected, each independently, from the group consisting of: 4-1BB, CD27, and CD28. In certain embodiments, a chimeric antigen receptor may have the design as described in U.S. Pat. No. 7,446,190, comprising an intracellular domain of CD3ζ chain (such as amino acid residues 52-163 of the human CD3 zeta chain, as shown in SEQ ID NO: 14 of U.S. Pat. No. 7,446,190), a signaling region from CD28 and an antigen-binding element (or portion or domain; such as scFv). The CD28 portion, when between the zeta chain portion and the antigen-binding element, may suitably include the transmembrane and signaling domains of CD28 (such as amino acid residues 114-220 of SEQ ID NO: 10, full sequence shown in SEQ ID NO: 6 of U.S. Pat. No. 7,446,190; these can include the following portion of CD28 as set forth in Genbank identifier NM_006139 (sequence version 1, 2 or 3): IEVMYPPPYLD-NEKSNGTIIHVKGKHLCPSPLFPGPSKPFWVLVVVGGV-LACYSLLVTVA FIIFWVRSKRSRLLHSDYMNMTPRRPGPTRKHYQPY-APPRDFAAYRS (SEQ ID NO: 173478)). Alternatively, when the zeta sequence lies between the CD28 sequence and the antigen-binding element, intracellular domain of CD28 can be used alone (such as amino sequence set forth in SEQ ID NO: 9 of U.S. Pat. No. 7,446,190). Hence, certain embodiments employ a CAR comprising (a) a zeta chain portion comprising the intracellular domain of human CD3ζ chain, (b) a costimulatory signaling region, and (c) an antigen-binding element (or portion or domain), wherein the costimulatory signaling region comprises the amino acid sequence encoded by SEQ ID NO: 6 of U.S. Pat. No. 7,446,190.

Alternatively, costimulation may be orchestrated by expressing CARs in antigen-specific T cells, chosen so as to be activated and expanded following engagement of their native αβTCR, for example by antigen on professional antigen-presenting cells, with attendant costimulation. In addition, additional engineered receptors may be provided on the immunoresponsive cells, for example to improve targeting of a T cell attack and/or minimize side effects.

By means of an example and without limitation, Kochenderfer et al., (2009) J Immunother. 32 (7): 689-702 described anti-CD19 chimeric antigen receptors (CAR). FMC63-28Z CAR contained a single chain variable region moiety (scFv) recognizing CD19 derived from the FMC63 mouse hybridoma (described in Nicholson et al., (1997) Molecular Immunology 34: 1157-1165), a portion of the human CD28 molecule, and the intracellular component of the human TCR-ζ molecule. FMC63-CD828BBZ CAR contained the FMC63 scFv, the hinge and transmembrane regions of the CD8 molecule, the cytoplasmic portions of CD28 and 4-1BB, and the cytoplasmic component of the TCR-ζ molecule. The exact sequence of the CD28 molecule included in the FMC63-28Z CAR corresponded to Genbank identifier NM_006139; the sequence included all amino acids starting with the amino acid sequence IEVMYPPPY (SEQ ID NO: 173479) and continuing all the way to the carboxy-terminus of the protein. To encode the anti-CD19 scFv component of the vector, the authors designed a DNA sequence which was based on a portion of a previously published CAR (Cooper et al., (2003) Blood 101: 1637-1644). This sequence encoded the following components in frame from the 5' end to the 3' end: an XhoI site, the human granulocyte-macrophage colony-stimulating factor (GM-CSF) receptor α-chain signal sequence, the FMC63 light chain variable region (as in Nicholson et al., supra), a linker peptide (as in Cooper et al., supra), the FMC63 heavy chain variable region (as in Nicholson et al., supra), and a NotI site. A plasmid encoding this sequence was digested with XhoI and NotI. To form the MSGV-FMC63-28Z retroviral vector, the XhoI and NotI-digested fragment encoding the FMC63 scFv was ligated into a second XhoI and NotI-digested fragment that encoded the MSGV retroviral backbone (as in Hughes et al., (2005) Human Gene Therapy 16: 457-472) as well as part of the extracellular portion of human CD28, the entire transmembrane and cytoplasmic portion of human CD28, and the cytoplasmic portion of the human TCR-ζ molecule (as in Maher et al., 2002) Nature Biotechnology 20: 70-75). The FMC63-28Z CAR is included in the KTE-C19 (axicabtagene ciloleucel) anti-CD19 CAR-T therapy product in development by Kite Pharma, Inc. for the treatment of inter alia patients with relapsed/refractory aggressive B-cell non-Hodgkin lymphoma (NHL). Accordingly, in certain embodiments, cells intended for adoptive cell therapies, more particularly immunoresponsive cells such as T cells, may express the FMC63-28Z CAR as described by Kochenderfer et al. (supra). Hence, in certain embodiments, cells intended for adoptive cell therapies, more particularly immunoresponsive cells such as T cells, may comprise a CAR comprising an extracellular antigen-binding element (or portion or domain; such as scFv) that specifically binds to an antigen, an intracellular signaling domain comprising an intracellular domain of a CD3ζ chain, and a costimulatory signaling region comprising a signaling domain of CD28. Preferably, the CD28 amino acid sequence is as set forth in Genbank identifier NM_006139 (sequence version 1, 2 or 3) starting with the amino acid sequence IEVMYPPPY (SEQ ID NO: 173479) and continuing all the way to the carboxy-terminus of the protein. The sequence is reproduced herein: IEVMYPPPYLD-NEKSNGTIIHVKGKHLCPSPLFPGPSKPFWVLVVVGGV-LACYSLLVTVA FIIFWVRSKRSRLLHSDYMNMT-PRRPGPTRKHYQPYAPPRDFAAYRS (SEQ ID NO: 173478). Preferably, the antigen is CD19, more preferably the antigen-binding element is an anti-CD19 scFv, even more preferably the anti-CD19 scFv as described by Kochenderfer et al. (supra).

Additional anti-CD19 CARs are further described in WO2015187528. More particularly Example 1 and Table 1 of WO2015187528, incorporated by reference herein, demonstrate the generation of anti-CD19 CARs based on a fully human anti-CD19 monoclonal antibody (47G4, as described in US20100104509) and murine anti-CD19 monoclonal antibody (as described in Nicholson et al. and explained above). Various combinations of a signal sequence (human CD8-alpha or GM-CSF receptor), extracellular and transmembrane regions (human CD8-alpha) and intracellular T cell signaling domains (CD28-CD3ζ; 4-1BB-CD3ζ; CD27-

CD3ζ; CD28-CD27-CD3ζ, 4-1BB-CD27-CD3ζ; CD27-4-1BB-CD3ζ; CD28-CD27-FcεRI gamma chain; or CD28-FcεRI gamma chain) were disclosed. Hence, in certain embodiments, cells intended for adoptive cell therapies, more particularly immunoresponsive cells such as T cells, may comprise a CAR comprising an extracellular antigen-binding element that specifically binds to an antigen, an extracellular and transmembrane region as set forth in Table 1 of WO2015187528 and an intracellular T cell signaling domain as set forth in Table 1 of WO2015187528. Preferably, the antigen is CD19, more preferably the antigen-binding element is an anti-CD19 scFv, even more preferably the mouse or human anti-CD19 scFv as described in Example 1 of WO2015187528. In certain embodiments, the CAR comprises, consists essentially of or consists of an amino acid sequence of SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, or SEQ ID NO: 13 as set forth in Table 1 of WO2015187528.

By means of an example and without limitation, chimeric antigen receptor that recognizes the CD70 antigen is described in WO2012058460A2 (see also, Park et al., CD70 as a target for chimeric antigen receptor T cells in head and neck squamous cell carcinoma, Oral Oncol. 2018 March; 78:145-150; and Jin et al., CD70, a novel target of CAR T cell therapy for gliomas, Neuro Oncol. 2018 Jan. 10; 20(1): 55-65). CD70 is expressed by diffuse large B-cell and follicular lymphoma and also by the malignant cells of Hodgkins lymphoma, Waldenstrom's macroglobulinemia and multiple myeloma, and by HTLV-1- and EBV-associated malignancies. (Agathanggelou et al. Am. J. Pathol. 1995; 147: 1152-1160; Hunter et al., Blood 2004; 104:4881. 26; Lens et al., J Immunol. 2005; 174:6212-6219; Baba et al., J Virol. 2008; 82:3843-3852.) In addition, CD70 is expressed by non-hematological malignancies such as renal cell carcinoma and glioblastoma. (Junker et al., J Urol. 2005; 173:2150-2153; Chahlavi et al., Cancer Res 2005; 65:5428-5438) Physiologically, CD70 expression is transient and restricted to a subset of highly activated T, B, and dendritic cells.

By means of an example and without limitation, chimeric antigen receptor that recognizes BCMA has been described (see, e.g., US20160046724A1; WO2016014789A2; WO2017211900A1; WO2015158671A1; US20180085444A1; WO2018028647A1; US20170283504A1; and WO2013154760A1).

In certain embodiments, the immune cell may, in addition to a CAR or exogenous TCR as described herein, further comprise a chimeric inhibitory receptor (inhibitory CAR) that specifically binds to a second target antigen and is capable of inducing an inhibitory or immunosuppressive or repressive signal to the cell upon recognition of the second target antigen. In certain embodiments, the chimeric inhibitory receptor comprises an extracellular antigen-binding element (or portion or domain) configured to specifically bind to a target antigen, a transmembrane domain, and an intracellular immunosuppressive or repressive signaling domain. In certain embodiments, the second target antigen is an antigen that is not expressed on the surface of a cancer cell or infected cell or the expression of which is downregulated on a cancer cell or an infected cell. In certain embodiments, the second target antigen is an MHC-class I molecule. In certain embodiments, the intracellular signaling domain comprises a functional signaling portion of an immune checkpoint molecule, such as for example PD-1 or CTLA4. Advantageously, the inclusion of such inhibitory CAR reduces the chance of the engineered immune cells attacking non-target (e.g., non-cancer) tissues.

Alternatively, T cells expressing CARs may be further modified to reduce or eliminate expression of endogenous TCRs in order to reduce off-target effects. Reduction or elimination of endogenous TCRs can reduce off-target effects and increase the effectiveness of the T cells (U.S. Pat. No. 9,181,527). T cells stably lacking expression of a functional TCR may be produced using a variety of approaches. T cells internalize, sort, and degrade the entire T cell receptor as a complex, with a half-life of about 10 hours in resting T cells and 3 hours in stimulated T cells (von Essen, M. et al. 2004. J. Immunol. 173:384-393). Proper functioning of the TCR complex requires the proper stoichiometric ratio of the proteins that compose the TCR complex. TCR function also requires two functioning TCR zeta proteins with ITAM motifs. The activation of the TCR upon engagement of its MHC-peptide ligand requires the engagement of several TCRs on the same T cell, which all must signal properly. Thus, if a TCR complex is destabilized with proteins that do not associate properly or cannot signal optimally, the T cell will not become activated sufficiently to begin a cellular response.

Accordingly, in some embodiments, TCR expression may eliminated using RNA interference (e.g., shRNA, siRNA, miRNA, etc.), CRISPR, or other methods that target the nucleic acids encoding specific TCRs (e.g., TCR-α and TCR-β) and/or CD3 chains in primary T cells. By blocking expression of one or more of these proteins, the T cell will no longer produce one or more of the key components of the TCR complex, thereby destabilizing the TCR complex and preventing cell surface expression of a functional TCR.

In some instances, CAR may also comprise a switch mechanism for controlling expression and/or activation of the CAR. For example, a CAR may comprise an extracellular, transmembrane, and intracellular domain, in which the extracellular domain comprises a target-specific binding element that comprises a label, binding domain, or tag that is specific for a molecule other than the target antigen that is expressed on or by a target cell. In such embodiments, the specificity of the CAR is provided by a second construct that comprises a target antigen binding domain (e.g., an scFv or a bispecific antibody that is specific for both the target antigen and the label or tag on the CAR) and a domain that is recognized by or binds to the label, binding domain, or tag on the CAR. See, e.g., WO 2013/044225, WO 2016/000304, WO 2015/057834, WO 2015/057852, WO 2016/070061, U.S. Pat. No. 9,233,125, US 2016/0129109. In this way, a T cell that expresses the CAR can be administered to a subject, but the CAR cannot bind its target antigen until the second composition comprising an antigen-specific binding domain is administered.

Alternative switch mechanisms include CARs that require multimerization in order to activate their signaling function (see, e.g., US 2015/0368342, US 2016/0175359, US 2015/0368360) and/or an exogenous signal, such as a small molecule drug (US 2016/0166613, Yung et al., Science, 2015), in order to elicit a T cell response. Some CARs may also comprise a "suicide switch" to induce cell death of the CAR T cells following treatment (Buddee et al., PLoS One, 2013) or to downregulate expression of the CAR following binding to the target antigen (WO 2016/011210).

Alternative techniques may be used to transform target immunoresponsive cells, such as protoplast fusion, lipofection, transfection or electroporation. A wide variety of vectors may be used, such as retroviral vectors, lentiviral vectors, adenoviral vectors, adeno-associated viral vectors, plasmids or transposons, such as a Sleeping Beauty transposon (see U.S. Pat. Nos. 6,489,458; 7,148,203; 7,160,682; 7,985,739; 8,227,432), may be used to introduce CARs, for example using 2nd generation antigen-specific CARs signaling through CD3ζ and either CD28 or CD137. Viral vectors may for example include vectors based on HIV, SV40, EBV, HSV or BPV.

Cells that are targeted for transformation may for example include T cells, Natural Killer (NK) cells, cytotoxic T lymphocytes (CTL), regulatory T cells, human embryonic stem cells, tumor-infiltrating lymphocytes (TIL) or a pluripotent stem cell from which lymphoid cells may be differentiated. T cells expressing a desired CAR may for example be selected through co-culture with γ-irradiated activating and propagating cells (AaPC), which co-express the cancer antigen and co-stimulatory molecules. The engineered CAR T cells may be expanded, for example by co-culture on AaPC in presence of soluble factors, such as IL-2 and IL-21. This expansion may for example be carried out so as to provide memory CAR+ T cells (which may for example be assayed by non-enzymatic digital array and/or multi-panel flow cytometry). In this way, CAR T cells may be provided that have specific cytotoxic activity against antigen-bearing tumors (optionally in conjunction with production of desired chemokines such as interferon-γ). CAR T cells of this kind may for example be used in animal models, for example to treat tumor xenografts.

In certain embodiments, ACT includes co-transferring CD4+Th1 cells and CD8+CTLs to induce a synergistic antitumour response (see, e.g., Li et al., Adoptive cell therapy with CD4+T helper 1 cells and CD8+ cytotoxic T cells enhances complete rejection of an established tumour, leading to generation of endogenous memory responses to non-targeted tumour epitopes. Clin Transl Immunology. 2017 October; 6(10): e160).

In certain embodiments, Th17 cells are transferred to a subject in need thereof. Th17 cells have been reported to directly eradicate melanoma tumors in mice to a greater extent than Th1 cells (Muranski P, et al., Tumor-specific Th17-polarized cells eradicate large established melanoma. Blood. 2008 Jul. 15; 112(2):362-73; and Martin-Orozco N, et al., T helper 17 cells promote cytotoxic T cell activation in tumor immunity. Immunity. 2009 Nov. 20; 31(5):787-98). Those studies involved an adoptive T cell transfer (ACT) therapy approach, which takes advantage of CD4+ T cells that express a TCR recognizing tyrosinase tumor antigen. Exploitation of the TCR leads to rapid expansion of Th17 populations to large numbers ex vivo for reinfusion into the autologous tumor-bearing hosts.

In certain embodiments, ACT may include autologous iPSC-based vaccines, such as irradiated iPSCs in autologous anti-tumor vaccines (see e.g., Kooreman, Nigel G. et al., Autologous iPSC-Based Vaccines Elicit Anti-tumor Responses In vivo, Cell Stem Cell 22, 1-13, 2018, doi.org/10.1016/j.stem.2018.01.016).

Unlike T cell receptors (TCRs) that are MHC restricted, CARs can potentially bind any cell surface-expressed antigen and can thus be more universally used to treat patients (see Irving et al., Engineering Chimeric Antigen Receptor T-Cells for Racing in Solid Tumors: Don't Forget the Fuel, Front. Immunol., 3 Apr. 2017, doi.org/10.3389/fimmu.2017.00267). In certain embodiments, in the absence of endogenous T cell infiltrate (e.g., due to aberrant antigen processing and presentation), which precludes the use of TIL therapy and immune checkpoint blockade, the transfer of CAR T cells may be used to treat patients (see, e.g., Hinrichs C S, Rosenberg S A. Exploiting the curative potential of adoptive T-cell therapy for cancer. Immunol Rev (2014) 257(1):56-71. doi:10.1111/imr.12132).

Approaches such as the foregoing may be adapted to provide methods of treating and/or increasing survival of a subject having a disease, such as a neoplasia, for example by administering an effective amount of an immunoresponsive cell comprising an antigen recognizing receptor that binds a selected antigen, wherein the binding activates the immunoresponsive cell, thereby treating or preventing the disease (such as a neoplasia, a pathogen infection, an autoimmune disorder, or an allogeneic transplant reaction).

In certain embodiments, the treatment can be administered after lymphodepleting pretreatment in the form of chemotherapy (typically a combination of cyclophosphamide and fludarabine) or radiation therapy. Initial studies in ACT had short lived responses and the transferred cells did not persist in vivo for very long (Houot et al., T-cell-based immunotherapy: adoptive cell transfer and checkpoint inhibition. Cancer Immunol Res (2015) 3(10):1115-22; and Kamta et al., Advancing Cancer Therapy with Present and Emerging Immuno-Oncology Approaches. Front. Oncol. (2017) 7:64). Immune suppressor cells like Tregs and MDSCs may attenuate the activity of transferred cells by outcompeting them for the necessary cytokines. Not being bound by a theory lymphodepleting pretreatment may eliminate the suppressor cells allowing the TILs to persist.

In one embodiment, the treatment can be administrated into patients undergoing an immunosuppressive treatment (e.g., glucocorticoid treatment). The cells or population of cells, may be made resistant to at least one immunosuppressive agent due to the inactivation of a gene encoding a receptor for such immunosuppressive agent. In certain embodiments, the immunosuppressive treatment provides for the selection and expansion of the immunoresponsive T cells within the patient.

In certain embodiments, the treatment can be administered before primary treatment (e.g., surgery or radiation therapy) to shrink a tumor before the primary treatment. In another embodiment, the treatment can be administered after primary treatment to remove any remaining cancer cells.

In certain embodiments, immunometabolic barriers can be targeted therapeutically prior to and/or during ACT to enhance responses to ACT or CAR T cell therapy and to support endogenous immunity (see, e.g., Irving et al., Engineering Chimeric Antigen Receptor T-Cells for Racing in Solid Tumors: Don't Forget the Fuel, Front. Immunol., 3 Apr. 2017, doi.org/10.3389/fimmu.2017.00267).

The administration of cells or population of cells, such as immune system cells or cell populations, such as more particularly immunoresponsive cells or cell populations, as disclosed herein may be carried out in any convenient manner, including by aerosol inhalation, injection, ingestion, transfusion, implantation or transplantation. The cells or population of cells may be administered to a patient subcutaneously, intradermally, intratumorally, intranodally, intramedullary, intramuscularly, intrathecally, by intravenous or intralymphatic injection, or intraperitoneally. In some embodiments, the disclosed CARs may be delivered or administered into a cavity formed by the resection of tumor tissue (i.e. intracavity delivery) or directly into a tumor prior to resection (i.e. intratumoral delivery). In one embodiment, the cell compositions of the present invention are preferably administered by intravenous injection.

The administration of the cells or population of cells can consist of the administration of $10^4$-$10^9$ cells per kg body weight, preferably $10^5$ to $10^6$ cells/kg body weight including all integer values of cell numbers within those ranges.

Dosing in CAR T cell therapies may for example involve administration of from $10^6$ to $10^9$ cells/kg, with or without a course of lymphodepletion, for example with cyclophosphamide. The cells or population of cells can be administrated in one or more doses. In another embodiment, the effective amount of cells are administrated as a single dose. In another embodiment, the effective amount of cells are administrated as more than one dose over a period time. Timing of administration is within the judgment of managing physician and depends on the clinical condition of the patient. The cells or population of cells may be obtained from any source, such as a blood bank or a donor. While individual needs vary, determination of optimal ranges of effective amounts of a given cell type for a particular disease or conditions are within the skill of one in the art. An effective amount means an amount which provides a therapeutic or prophylactic benefit. The dosage administrated will be dependent upon the age, health and weight of the recipient, kind of concurrent treatment, if any, frequency of treatment and the nature of the effect desired.

In another embodiment, the effective amount of cells or composition comprising those cells are administrated parenterally. The administration can be an intravenous administration. The administration can be directly done by injection within a tumor.

To guard against possible adverse reactions, engineered immunoresponsive cells may be equipped with a transgenic safety switch, in the form of a transgene that renders the cells vulnerable to exposure to a specific signal. For example, the herpes simplex viral thymidine kinase (TK) gene may be used in this way, for example by introduction into allogeneic T lymphocytes used as donor lymphocyte infusions following stem cell transplantation (Greco, et al., Improving the safety of cell therapy with the TK-suicide gene. Front. Pharmacol. 2015; 6: 95). In such cells, administration of a nucleoside prodrug such as ganciclovir or acyclovir causes cell death. Alternative safety switch constructs include inducible caspase 9, for example triggered by administration of a small-molecule dimerizer that brings together two nonfunctional icasp9 molecules to form the active enzyme. A wide variety of alternative approaches to implementing cellular proliferation controls have been described (see U.S. Patent Publication No. 20130071414; PCT Patent Publication No. WO2011146862; PCT Patent Publication WO2014011987; PCT Patent Publication WO2013040371; Zhou et al. BLOOD, 2014, 123/25:3895-3905; Di Stasi et al., The New England Journal of Medicine 2011; 365:1673-1683; Sadelain M, The New England Journal of Medicine 2011; 365:1735-173; Ramos et al., Stem Cells 28(6):1107-15 (2010)).

In a further refinement of adoptive therapies, genome editing may be used to tailor immunoresponsive cells to alternative implementations, for example providing edited CAR T cells (see Poirot et al., 2015, Multiplex genome edited T-cell manufacturing platform for "off-the-shelf" adoptive T-cell immunotherapies, Cancer Res 75 (18): 3853; Ren et al., 2017, Multiplex genome editing to generate universal CAR T cells resistant to PD1 inhibition, Clin Cancer Res. 2017 May 1; 23(9):2255-2266. doi: 10.1158/1078-0432.CCR-16-1300. Epub 2016 Nov. 4; Qasim et al., 2017, Molecular remission of infant B-ALL after infusion of universal TALEN gene-edited CAR T cells, Sci Transl Med. 2017 Jan. 25; 9(374); Legut, et al., 2018, CRISPR-mediated TCR replacement generates superior anticancer transgenic T cells. Blood, 131(3), 311-322; and Georgiadis et al., Long Terminal Repeat CRISPR-CAR-Coupled "Universal" T Cells Mediate Potent Anti-leukemic Effects, Molecular Therapy, In Press, Corrected Proof, Available online 6 Mar. 2018). Cells may be edited using any CRISPR system and method of use thereof as described herein. CRISPR systems may be delivered to an immune cell by any method described herein. In preferred embodiments, cells are edited ex vivo and transferred to a subject in need thereof. Immunoresponsive cells, CAR T cells or any cells used for adoptive cell transfer may be edited. Editing may be performed for example to insert or knock-in an exogenous gene, such as an exogenous gene encoding a CAR or a TCR, at a preselected locus in a cell (e.g. TRAC locus); to eliminate potential alloreactive T cell receptors (TCR) or to prevent inappropriate pairing between endogenous and exogenous TCR chains, such as to knock-out or knock-down expression of an endogenous TCR in a cell; to disrupt the target of a chemotherapeutic agent in a cell; to block an immune checkpoint, such as to knock-out or knock-down expression of an immune checkpoint protein or receptor in a cell; to knock-out or knock-down expression of other gene or genes in a cell, the reduced expression or lack of expression of which can enhance the efficacy of adoptive therapies using the cell; to knock-out or knock-down expression of an endogenous gene in a cell, said endogenous gene encoding an antigen targeted by an exogenous CAR or TCR; to knock-out or knock-down expression of one or more IHC constituent proteins in a cell; to activate a T cell; to modulate cells such that the cells are resistant to exhaustion or dysfunction; and/or increase the differentiation and/or proliferation of functionally exhausted or dysfunctional CD8+ T cells (see PCT Patent Publications: WO2013176915, WO2014059173, WO2014172606, WO2014184744, and WO2014191128).

In certain embodiments, editing may result in inactivation of a gene. By inactivating a gene, it is intended that the gene of interest is not expressed in a functional protein form. In a particular embodiment, the CRISPR system specifically catalyzes cleavage in one targeted gene thereby inactivating said targeted gene. The nucleic acid strand breaks caused are commonly repaired through the distinct mechanisms of homologous recombination or non-homologous end joining (NHEJ). However, NHEJ is an imperfect repair process that often results in changes to the DNA sequence at the site of the cleavage. Repair via non-homologous end joining (NHEJ) often results in small insertions or deletions (Indel) and can be used for the creation of specific gene knockouts. Cells in which a cleavage induced mutagenesis event has occurred can be identified and/or selected by well-known methods in the art. In certain embodiments, homology directed repair (HDR) is used to concurrently inactivate a gene (e.g., TRAC) and insert an endogenous TCR or CAR into the inactivated locus.

Hence, in certain embodiments, editing of cells (such as by CRISPR/Cas), particularly cells intended for adoptive cell therapies, more particularly immunoresponsive cells such as T cells, may be performed to insert or knock-in an exogenous gene, such as an exogenous gene encoding a CAR or a TCR, at a preselected locus in a cell. Conventionally, nucleic acid molecules encoding CARs or TCRs are transfected or transduced to cells using randomly integrating vectors, which, depending on the site of integration, may lead to clonal expansion, oncogenic transformation, variegated transgene expression and/or transcriptional silencing of the transgene. Directing of transgene(s) to a specific locus in a cell can minimize or avoid such risks and advantageously provide for uniform expression of the transgene(s) by the cells. Without limitation, suitable 'safe harbor' loci for directed transgene integration include CCR5 or AAVS1.

Homology-directed repair (HDR) strategies are known and described elsewhere in this specification allowing to insert transgenes into desired loci (e.g., TRAC locus).

Further suitable loci for insertion of transgenes, in particular CAR or exogenous TCR transgenes, include without limitation loci comprising genes coding for constituents of endogenous T cell receptor, such as T cell receptor alpha locus (TRA) or T cell receptor beta locus (TRB), for example T cell receptor alpha constant (TRAC) locus, T cell receptor beta constant 1 (TRBC1) locus or T cell receptor beta constant 2 (TRBC1) locus. Advantageously, insertion of a transgene into such locus can simultaneously achieve expression of the transgene, potentially controlled by the endogenous promoter, and knock-out expression of the endogenous TCR. This approach has been exemplified in Eyquem et al., (2017) Nature 543: 113-117, wherein the authors used CRISPR/Cas9 gene editing to knock-in a DNA molecule encoding a CD19-specific CAR into the TRAC locus downstream of the endogenous promoter; the CAR-T cells obtained by CRISPR were significantly superior in terms of reduced tonic CAR signaling and exhaustion.

T cell receptors (TCR) are cell surface receptors that participate in the activation of T cells in response to the presentation of antigen. The TCR is generally made from two chains, a and 3, which assemble to form a heterodimer and associates with the CD3-transducing subunits to form the T cell receptor complex present on the cell surface. Each a and p chain of the TCR consists of an immunoglobulin-like N-terminal variable (V) and constant (C) region, a hydrophobic transmembrane domain, and a short cytoplasmic region. As for immunoglobulin molecules, the variable region of the a and p chains are generated by V(D)J recombination, creating a large diversity of antigen specificities within the population of T cells. However, in contrast to immunoglobulins that recognize intact antigen, T cells are activated by processed peptide fragments in association with an MHC molecule, introducing an extra dimension to antigen recognition by T cells, known as MHC restriction. Recognition of MHC disparities between the donor and recipient through the T cell receptor leads to T cell proliferation and the potential development of graft versus host disease (GVHD). The inactivation of TCRα or TCRβ can result in the elimination of the TCR from the surface of T cells preventing recognition of alloantigen and thus GVHD. However, TCR disruption generally results in the elimination of the CD3 signaling component and alters the means of further T cell expansion.

Hence, in certain embodiments, editing of cells (such as by CRISPR/Cas), particularly cells intended for adoptive cell therapies, more particularly immunoresponsive cells such as T cells, may be performed to knock-out or knock-down expression of an endogenous TCR in a cell. For example, NHEJ-based or HDR-based gene editing approaches can be employed to disrupt the endogenous TCR alpha and/or beta chain genes. For example, gene editing system or systems, such as CRISPR/Cas system or systems, can be designed to target a sequence found within the TCR beta chain conserved between the beta 1 and beta 2 constant region genes (TRBC1 and TRBC2) and/or to target the constant region of the TCR alpha chain (TRAC) gene.

Allogeneic cells are rapidly rejected by the host immune system. It has been demonstrated that, allogeneic leukocytes present in non-irradiated blood products will persist for no more than 5 to 6 days (Boni, Muranski et al. 2008 Blood 1; 112(12):4746-54). Thus, to prevent rejection of allogeneic cells, the host's immune system usually has to be suppressed to some extent. However, in the case of adoptive cell transfer the use of immunosuppressive drugs also have a detrimental effect on the introduced therapeutic T cells. Therefore, to effectively use an adoptive immunotherapy approach in these conditions, the introduced cells would need to be resistant to the immunosuppressive treatment. Thus, in a particular embodiment, the present invention further comprises a step of modifying T cells to make them resistant to an immunosuppressive agent, preferably by inactivating at least one gene encoding a target for an immunosuppressive agent. An immunosuppressive agent is an agent that suppresses immune function by one of several mechanisms of action. An immunosuppressive agent can be, but is not limited to a calcineurin inhibitor, a target of rapamycin, an interleukin-2 receptor α-chain blocker, an inhibitor of inosine monophosphate dehydrogenase, an inhibitor of dihydrofolic acid reductase, a corticosteroid or an immunosuppressive antimetabolite. The present invention allows conferring immunosuppressive resistance to T cells for immunotherapy by inactivating the target of the immunosuppressive agent in T cells. As non-limiting examples, targets for an immunosuppressive agent can be a receptor for an immunosuppressive agent such as: CD52, glucocorticoid receptor (GR), a FKBP family gene member and a cyclophilin family gene member.

In certain embodiments, editing of cells (such as by CRISPR/Cas), particularly cells intended for adoptive cell therapies, more particularly immunoresponsive cells such as T cells, may be performed to block an immune checkpoint, such as to knock-out or knock-down expression of an immune checkpoint protein or receptor in a cell. Immune checkpoints are inhibitory pathways that slow down or stop immune reactions and prevent excessive tissue damage from uncontrolled activity of immune cells. In certain embodiments, the immune checkpoint targeted is the programmed death-1 (PD-1 or CD279) gene (PDCD1). In other embodiments, the immune checkpoint targeted is cytotoxic T-lymphocyte-associated antigen (CTLA-4). In additional embodiments, the immune checkpoint targeted is another member of the CD28 and CTLA4 Ig superfamily such as BTLA, LAG3, ICOS, PDL1 or KIR. In further additional embodiments, the immune checkpoint targeted is a member of the TNFR superfamily such as CD40, OX40, CD137, GITR, CD27 or TIM-3.

Additional immune checkpoints include Src homology 2 domain-containing protein tyrosine phosphatase 1 (SHP-1) (Watson H A, et al., SHP-1: the next checkpoint target for cancer immunotherapy?Biochem Soc Trans. 2016 Apr. 15; 44(2):356-62). SHP-1 is a widely expressed inhibitory protein tyrosine phosphatase (PTP). In T cells, it is a negative regulator of antigen-dependent activation and proliferation. It is a cytosolic protein, and therefore not amenable to antibody-mediated therapies, but its role in activation and proliferation makes it an attractive target for genetic manipulation in adoptive transfer strategies, such as chimeric antigen receptor (CAR) T cells. Immune checkpoints may also include T cell immunoreceptor with Ig and ITIM domains (TIGIT/Vstm3/WUCAM/VSIG9) and VISTA (Le Mercier I, et al., (2015) Beyond CTLA-4 and PD-1, the generation Z of negative checkpoint regulators. Front. Immunol. 6:418).

WO2014172606 relates to the use of MT1 and/or MT2 inhibitors to increase proliferation and/or activity of exhausted CD8+ T cells and to decrease CD8+ T cell exhaustion (e.g., decrease functionally exhausted or unresponsive CD8+ immune cells). In certain embodiments, metallothioneins are targeted by gene editing in adoptively transferred T cells.

In certain embodiments, targets of gene editing may be at least one targeted locus involved in the expression of an immune checkpoint protein. Such targets may include, but are not limited to CTLA4, PPP2CA, PPP2CB, PTPN6, PTPN22, PDCD1, ICOS (CD278), PDL1, KIR, LAG3, HAVCR2, BTLA, CD160, TIGIT, CD96, CRTAM, LAIR1, SIGLEC7, SIGLEC9, CD244 (2B4), TNFRSF10B, TNFRSF10A, CASP8, CASP10, CASP3, CASP6, CASP7, FADD, FAS, TGFBRII, TGFRBRI, SMAD2, SMAD3, SMAD4, SMAD10, SKI, SKIL, TGIF1, IL10RA, IL10RB, HMOX2, IL6R, IL6ST, EIF2AK4, CSK, PAG1, SIT1, FOXP3, PRDM1, BATF, VISTA, GUCY1A2, GUCY1A3, GUCY1B2, GUCY1B3, MT1, MT2, CD40, OX40, CD137, GITR, CD27, SHP-1, TIM-3, CEACAM-1, CEACAM-3, or CEACAM-5. In preferred embodiments, the gene locus involved in the expression of PD-1 or CTLA-4 genes is targeted. In other preferred embodiments, combinations of genes are targeted, such as but not limited to PD-1 and TIGIT.

By means of an example and without limitation, WO2016196388 concerns an engineered T cell comprising (a) a genetically engineered antigen receptor that specifically binds to an antigen, which receptor may be a CAR; and (b) a disrupted gene encoding a PD-L1, an agent for disruption of a gene encoding a PD-L1, and/or disruption of a gene encoding PD-L1, wherein the disruption of the gene may be mediated by a gene editing nuclease, a zinc finger nuclease (ZFN), CRISPR/Cas9 and/or TALEN. WO2015142675 relates to immune effector cells comprising a CAR in combination with an agent (such as CRISPR, TALEN or ZFN) that increases the efficacy of the immune effector cells in the treatment of cancer, wherein the agent may inhibit an immune inhibitory molecule, such as PD1, PD-L1, CTLA-4, TIM-3, LAG-3, VISTA, BTLA, TIGIT, LAIR1, CD160, 2B4, TGFR beta, CEACAM-1, CEACAM-3, or CEACAM-5. Ren et al., (2017) Clin Cancer Res 23 (9) 2255-2266 performed lentiviral delivery of CAR and electro-transfer of Cas9 mRNA and gRNAs targeting endogenous TCR, β-2 microglobulin (B2M) and PD1 simultaneously, to generate gene-disrupted allogeneic CAR T cells deficient of TCR, HLA class I molecule and PD1.

In certain embodiments, cells may be engineered to express a CAR, wherein expression and/or function of methylcytosine dioxygenase genes (TET1, TET2 and/or TET3) in the cells has been reduced or eliminated, such as by CRISPR, ZNF or TALEN (for example, as described in WO201704916).

In certain embodiments, editing of cells (such as by CRISPR/Cas), particularly cells intended for adoptive cell therapies, more particularly immunoresponsive cells such as T cells, may be performed to knock-out or knock-down expression of an endogenous gene in a cell, said endogenous gene encoding an antigen targeted by an exogenous CAR or TCR, thereby reducing the likelihood of targeting of the engineered cells. In certain embodiments, the targeted antigen may be one or more antigen selected from the group consisting of CD38, CD138, CS-1, CD33, CD26, CD30, CD53, CD92, CD100, CD148, CD150, CD200, CD261, CD262, CD362, human telomerase reverse transcriptase (hTERT), survivin, mouse double minute 2 homolog (MDM2), cytochrome P450 1B1 (CYP1B), HER2/neu, Wilms' tumor gene 1 (WT1), livin, alphafetoprotein (AFP), carcinoembryonic antigen (CEA), mucin 16 (MUC16), MUC1, prostate-specific membrane antigen (PSMA), p53, cyclin (D1), B cell maturation antigen (BCMA), transmembrane activator and CAML Interactor (TACI), and B-cell activating factor receptor (BAFF-R) (for example, as described in WO2016011210 and WO2017011804).

In certain embodiments, editing of cells (such as by CRISPR/Cas), particularly cells intended for adoptive cell therapies, more particularly immunoresponsive cells such as T cells, may be performed to knock-out or knock-down expression of one or more MHC constituent proteins, such as one or more HLA proteins and/or beta-2 microglobulin (B2M), in a cell, whereby rejection of non-autologous (e.g., allogeneic) cells by the recipient's immune system can be reduced or avoided. In preferred embodiments, one or more HLA class I proteins, such as HLA-A, B and/or C, and/or B2M may be knocked-out or knocked-down. Preferably, B2M may be knocked-out or knocked-down. By means of an example, Ren et al., (2017) Clin Cancer Res 23 (9) 2255-2266 performed lentiviral delivery of CAR and electro-transfer of Cas9 mRNA and gRNAs targeting endogenous TCR, β-2 microglobulin (B2M) and PD1 simultaneously, to generate gene-disrupted allogeneic CAR T cells deficient of TCR, HLA class I molecule and PD1.

In other embodiments, at least two genes are edited. Pairs of genes may include, but are not limited to PD1 and TCRα, PD1 and TCRβ, CTLA-4 and TCRα, CTLA-4 and TCRβ, LAG3 and TCRα, LAG3 and TCRβ, Tim3 and TCRα, Tim3 and TCRβ, BTLA and TCRα, BTLA and TCRβ, BY55 and TCRα, BY55 and TCRβ, TIGIT and TCRα, TIGIT and TCRβ, B7H5 and TCRα, B7H5 and TCRβ, LAIR1 and TCRα, LAIR1 and TCRβ, SIGLEC10 and TCRα, SIGLEC10 and TCRβ, 2B4 and TCRα, 2B4 and TCRβ, B2M and TCRα, B2M and TCRβ.

In certain embodiments, a cell may be multiply edited (multiplex genome editing) as taught herein to (1) knock-out or knock-down expression of an endogenous TCR (for example, TRBC1, TRBC2 and/or TRAC), (2) knock-out or knock-down expression of an immune checkpoint protein or receptor (for example PD1, PD-L1 and/or CTLA4); and (3) knock-out or knock-down expression of one or more MHC constituent proteins (for example, HLA-A, B and/or C, and/or B2M, preferably B2M).

Whether prior to or after genetic modification of the T cells, the T cells can be activated and expanded generally using methods as described, for example, in U.S. Pat. Nos. 6,352,694; 6,534,055; 6,905,680; 5,858,358; 6,887,466; 6,905,681; 7,144,575; 7,232,566; 7,175,843; 5,883,223; 6,905,874; 6,797,514; 6,867,041; and 7,572,631. T cells can be expanded in vitro or in vivo.

Immune cells may be obtained using any method known in the art. In one embodiment, allogenic T cells may be obtained from healthy subjects. In one embodiment T cells that have infiltrated a tumor are isolated. T cells may be removed during surgery. T cells may be isolated after removal of tumor tissue by biopsy. T cells may be isolated by any means known in the art. In one embodiment, T cells are obtained by apheresis. In one embodiment, the method may comprise obtaining a bulk population of T cells from a tumor sample by any suitable method known in the art. For example, a bulk population of T cells can be obtained from a tumor sample by dissociating the tumor sample into a cell suspension from which specific cell populations can be selected. Suitable methods of obtaining a bulk population of T cells may include, but are not limited to, any one or more of mechanically dissociating (e.g., mincing) the tumor, enzymatically dissociating (e.g., digesting) the tumor, and aspiration (e.g., as with a needle).

The bulk population of T cells obtained from a tumor sample may comprise any suitable type of T cell. Preferably, the bulk population of T cells obtained from a tumor sample comprises tumor infiltrating lymphocytes (TILs).

The tumor sample may be obtained from any mammal. Unless stated otherwise, as used herein, the term "mammal" refers to any mammal including, but not limited to, mammals of the order Lagomorpha, such as rabbits; the order Carnivora, including Felines (cats) and Canines (dogs); the order Artiodactyla, including Bovines (cows) and Swines (pigs); or of the order Perissodactyla, including Equines (horses). The mammals may be non-human primates, e.g., of the order Primates, Ceboids, or Simoids (monkeys) or of the order Anthropoids (humans and apes). In some embodiments, the mammal may be a mammal of the order Rodentia, such as mice and hamsters. Preferably, the mammal is a non-human primate or a human. An especially preferred mammal is the human.

T cells can be obtained from a number of sources, including peripheral blood mononuclear cells (PBMC), bone marrow, lymph node tissue, spleen tissue, and tumors. In certain embodiments of the present invention, T cells can be obtained from a unit of blood collected from a subject using any number of techniques known to the skilled artisan, such as Ficoll separation. In one preferred embodiment, cells from the circulating blood of an individual are obtained by apheresis or leukapheresis. The apheresis product typically contains lymphocytes, including T cells, monocytes, granulocytes, B cells, other nucleated white blood cells, red blood cells, and platelets. In one embodiment, the cells collected by apheresis may be washed to remove the plasma fraction and to place the cells in an appropriate buffer or media for subsequent processing steps. In one embodiment of the invention, the cells are washed with phosphate buffered saline (PBS). In an alternative embodiment, the wash solution lacks calcium and may lack magnesium or may lack many if not all divalent cations. Initial activation steps in the absence of calcium lead to magnified activation. As those of ordinary skill in the art would readily appreciate a washing step may be accomplished by methods known to those in the art, such as by using a semi-automated "flow-through" centrifuge (for example, the Cobe 2991 cell processor) according to the manufacturer's instructions. After washing, the cells may be resuspended in a variety of biocompatible buffers, such as, for example, Ca-free, Mg-free PBS. Alternatively, the undesirable components of the apheresis sample may be removed and the cells directly resuspended in culture media.

In another embodiment, T cells are isolated from peripheral blood lymphocytes by lysing the red blood cells and depleting the monocytes, for example, by centrifugation through a PERCOLL™ gradient. A specific subpopulation of T cells, such as CD28+, CD4+, CDC, CD45RA+, and CD45RO+ T cells, can be further isolated by positive or negative selection techniques. For example, in one preferred embodiment, T cells are isolated by incubation with anti-CD3/anti-CD28 (i.e., 3×28)-conjugated beads, such as DYNABEADS® M-450 CD3/CD28 T, or XCYTE DYNABEADS™ for a time period sufficient for positive selection of the desired T cells. In one embodiment, the time period is about 30 minutes. In a further embodiment, the time period ranges from 30 minutes to 36 hours or longer and all integer values there between. In a further embodiment, the time period is at least 1, 2, 3, 4, 5, or 6 hours. In yet another preferred embodiment, the time period is 10 to 24 hours. In one preferred embodiment, the incubation time period is 24 hours. For isolation of T cells from patients with leukemia, use of longer incubation times, such as 24 hours, can increase cell yield. Longer incubation times may be used to isolate T cells in any situation where there are few T cells as compared to other cell types, such in isolating tumor infiltrating lymphocytes (TIL) from tumor tissue or from immunocompromised individuals. Further, use of longer incubation times can increase the efficiency of capture of CD8+ T cells.

Enrichment of a T cell population by negative selection can be accomplished with a combination of antibodies directed to surface markers unique to the negatively selected cells. A preferred method is cell sorting and/or selection via negative magnetic immunoadherence or flow cytometry that uses a cocktail of monoclonal antibodies directed to cell surface markers present on the cells negatively selected. For example, to enrich for CD4+ cells by negative selection, a monoclonal antibody cocktail typically includes antibodies to CD14, CD20, CD11b, CD16, HLA-DR, and CD8.

Further, monocyte populations (i.e., CD14+ cells) may be depleted from blood preparations by a variety of methodologies, including anti-CD14 coated beads or columns, or utilization of the phagocytotic activity of these cells to facilitate removal. Accordingly, in one embodiment, the invention uses paramagnetic particles of a size sufficient to be engulfed by phagocytotic monocytes. In certain embodiments, the paramagnetic particles are commercially available beads, for example, those produced by Life Technologies under the trade name Dynabeads™. In one embodiment, other non-specific cells are removed by coating the paramagnetic particles with "irrelevant" proteins (e.g., serum proteins or antibodies). Irrelevant proteins and antibodies include those proteins and antibodies or fragments thereof that do not specifically target the T cells to be isolated. In certain embodiments, the irrelevant beads include beads coated with sheep anti-mouse antibodies, goat anti-mouse antibodies, and human serum albumin.

In brief, such depletion of monocytes is performed by preincubating T cells isolated from whole blood, apheresed peripheral blood, or tumors with one or more varieties of irrelevant or non-antibody coupled paramagnetic particles at any amount that allows for removal of monocytes (approximately a 20:1 bead:cell ratio) for about 30 minutes to 2 hours at 22 to 37 degrees C., followed by magnetic removal of cells which have attached to or engulfed the paramagnetic particles. Such separation can be performed using standard methods available in the art. For example, any magnetic separation methodology may be used including a variety of which are commercially available, (e.g., DYNAL® Magnetic Particle Concentrator (DYNAL MPC®)). Assurance of requisite depletion can be monitored by a variety of methodologies known to those of ordinary skill in the art, including flow cytometric analysis of CD14 positive cells, before and after depletion.

For isolation of a desired population of cells by positive or negative selection, the concentration of cells and surface (e.g., particles such as beads) can be varied. In certain embodiments, it may be desirable to significantly decrease the volume in which beads and cells are mixed together (i.e., increase the concentration of cells), to ensure maximum contact of cells and beads. For example, in one embodiment, a concentration of 2 billion cells/ml is used. In one embodiment, a concentration of 1 billion cells/ml is used. In a further embodiment, greater than 100 million cells/ml is used. In a further embodiment, a concentration of cells of 10, 15, 20, 25, 30, 35, 40, 45, or 50 million cells/ml is used. In yet another embodiment, a concentration of cells from 75, 80, 85, 90, 95, or 100 million cells/ml is used. In further embodiments, concentrations of 125 or 150 million cells/ml can be used. Using high concentrations can result in increased cell yield, cell activation, and cell expansion. Further, use of high cell concentrations allows more efficient capture of cells that may weakly express target antigens of interest, such as CD28-negative T cells, or from samples where there are many tumor cells present (i.e., leukemic blood, tumor tissue, etc). Such populations of cells may have therapeutic value and would be desirable to obtain. For example, using high concentration of cells allows more efficient selection of CD8+ T cells that normally have weaker CD28 expression.

In a related embodiment, it may be desirable to use lower concentrations of cells. By significantly diluting the mixture of T cells and surface (e.g., particles such as beads), interactions between the particles and cells is minimized. This selects for cells that express high amounts of desired antigens to be bound to the particles. For example, CD4+ T cells express higher levels of CD28 and are more efficiently captured than CD8+ T cells in dilute concentrations. In one embodiment, the concentration of cells used is 5×10$^6$/ml. In other embodiments, the concentration used can be from about 1×10$^5$/ml to 1×10$^6$/ml, and any integer value in between.

T cells can also be frozen. Wishing not to be bound by theory, the freeze and subsequent thaw step provides a more uniform product by removing granulocytes and to some extent monocytes in the cell population. After a washing step to remove plasma and platelets, the cells may be suspended in a freezing solution. While many freezing solutions and parameters are known in the art and will be useful in this context, one method involves using PBS containing 20% DMSO and 8% human serum albumin, or other suitable cell freezing media, the cells then are frozen to −80° C. at a rate of 1° per minute and stored in the vapor phase of a liquid nitrogen storage tank. Other methods of controlled freezing may be used as well as uncontrolled freezing immediately at −20° C. or in liquid nitrogen.

T cells for use in the present invention may also be antigen-specific T cells. For example, tumor-specific T cells can be used. In certain embodiments, antigen-specific T cells can be isolated from a patient of interest, such as a patient afflicted with a cancer or an infectious disease. In one embodiment, neoepitopes are determined for a subject and T cells specific to these antigens are isolated. Antigen-specific cells for use in expansion may also be generated in vitro using any number of methods known in the art, for example, as described in U.S. Patent Publication No. US 20040224402 entitled, Generation and Isolation of Antigen-Specific T Cells, or in U.S. Pat. Nos. 6,040,177. Antigen-specific cells for use in the present invention may also be generated using any number of methods known in the art, for example, as described in Current Protocols in Immunology, or Current Protocols in Cell Biology, both published by John Wiley & Sons, Inc., Boston, Mass.

In a related embodiment, it may be desirable to sort or otherwise positively select (e.g. via magnetic selection) the antigen specific cells prior to or following one or two rounds of expansion. Sorting or positively selecting antigen-specific cells can be carried out using peptide-MHC tetramers (Altman, et al., Science. 1996 Oct. 4; 274(5284):94-6). In another embodiment, the adaptable tetramer technology approach is used (Andersen et al., 2012 Nat Protoc. 7:891-902). Tetramers are limited by the need to utilize predicted binding peptides based on prior hypotheses, and the restriction to specific HLAs. Peptide-MHC tetramers can be generated using techniques known in the art and can be made with any MHC molecule of interest and any antigen of interest as described herein. Specific epitopes to be used in this context can be identified using numerous assays known in the art. For example, the ability of a polypeptide to bind to MHC class I may be evaluated indirectly by monitoring the ability to promote incorporation of $^{125}$I labeled β2-microglobulin (β2m) into MHC class I/β2m/peptide heterotrimeric complexes (see Parker et al., J. Immunol. 152:163, 1994).

In one embodiment cells are directly labeled with an epitope-specific reagent for isolation by flow cytometry followed by characterization of phenotype and TCRs. In one embodiment, T cells are isolated by contacting with T cell specific antibodies. Sorting of antigen-specific T cells, or generally any cells of the present invention, can be carried out using any of a variety of commercially available cell sorters, including, but not limited to, MoFlo sorter (DakoCytomation, Fort Collins, Colo.), FACSAria™, FACSArray™, FACSVantage™, BD™ LSR II, and FACSCalibur™ (BD Biosciences, San Jose, Calif.).

In a preferred embodiment, the method comprises selecting cells that also express CD3. The method may comprise specifically selecting the cells in any suitable manner. Preferably, the selecting is carried out using flow cytometry. The flow cytometry may be carried out using any suitable method known in the art. The flow cytometry may employ any suitable antibodies and stains. Preferably, the antibody is chosen such that it specifically recognizes and binds to the particular biomarker being selected. For example, the specific selection of CD3, CD8, TIM-3, LAG-3, 4-1BB, or PD-1 may be carried out using anti-CD3, anti-CD8, anti-TIM-3, anti-LAG-3, anti-4-1BB, or anti-PD-1 antibodies, respectively. The antibody or antibodies may be conjugated to a bead (e.g., a magnetic bead) or to a fluorochrome. Preferably, the flow cytometry is fluorescence-activated cell sorting (FACS). TCRs expressed on T cells can be selected based on reactivity to autologous tumors. Additionally, T cells that are reactive to tumors can be selected for based on markers using the methods described in patent publication Nos. WO2014133567 and WO2014133568, herein incorporated by reference in their entirety. Additionally, activated T cells can be selected for based on surface expression of CD107a.

In one embodiment of the invention, the method further comprises expanding the numbers of T cells in the enriched cell population. Such methods are described in U.S. Pat. No. 8,637,307 and is herein incorporated by reference in its entirety. The numbers of T cells may be increased at least about 3-fold (or 4-, 5-, 6-, 7-, 8-, or 9-fold), more preferably at least about 10-fold (or 20-, 30-, 40-, 50-, 60-, 70-, 80-, or 90-fold), more preferably at least about 100-fold, more preferably at least about 1,000 fold, or most preferably at least about 100,000-fold. The numbers of T cells may be expanded using any suitable method known in the art. Exemplary methods of expanding the numbers of cells are described in patent publication No. WO 2003057171, U.S. Pat. No. 8,034,334, and U.S. Patent Application Publication No. 2012/0244133, each of which is incorporated herein by reference.

In one embodiment, ex vivo T cell expansion can be performed by isolation of T cells and subsequent stimulation or activation followed by further expansion. In one embodiment of the invention, the T cells may be stimulated or activated by a single agent. In another embodiment, T cells are stimulated or activated with two agents, one that induces a primary signal and a second that is a co-stimulatory signal. Ligands useful for stimulating a single signal or stimulating a primary signal and an accessory molecule that stimulates a second signal may be used in soluble form. Ligands may be attached to the surface of a cell, to an Engineered Multivalent Signaling Platform (EMSP), or immobilized on a surface. In a preferred embodiment both primary and secondary agents are co-immobilized on a surface, for example a bead or a cell. In one embodiment, the molecule providing the primary activation signal may be a CD3 ligand, and the co-stimulatory molecule may be a CD28 ligand or 4-1BB ligand.

In certain embodiments, T cells comprising a CAR or an exogenous TCR, may be manufactured as described in WO2015120096, by a method comprising: enriching a population of lymphocytes obtained from a donor subject; stimulating the population of lymphocytes with one or more T cell stimulating agents to produce a population of activated T cells, wherein the stimulation is performed in a closed system using serum-free culture medium; transducing the population of activated T cells with a viral vector comprising a nucleic acid molecule which encodes the CAR or TCR, using a single cycle transduction to produce a population of transduced T cells, wherein the transduction is performed in a closed system using serum-free culture medium; and expanding the population of transduced T cells for a predetermined time to produce a population of engineered T cells, wherein the expansion is performed in a closed system using serum-free culture medium. In certain embodiments, T cells comprising a CAR or an exogenous TCR, may be manufactured as described in WO2015120096, by a method comprising: obtaining a population of lymphocytes; stimulating the population of lymphocytes with one or more stimulating agents to produce a population of activated T cells, wherein the stimulation is performed in a closed system using serum-free culture medium; transducing the population of activated T cells with a viral vector comprising a nucleic acid molecule which encodes the CAR or TCR, using at least one cycle transduction to produce a population of transduced T cells, wherein the transduction is performed in a closed system using serum-free culture medium; and expanding the population of transduced T cells to produce a population of engineered T cells, wherein the expansion is performed in a closed system using serum-free culture medium. The predetermined time for expanding the population of transduced T cells may be 3 days. The time from enriching the population of lymphocytes to producing the engineered T cells may be 6 days. The closed system may be a closed bag system. Further provided is population of T cells comprising a CAR or an exogenous TCR obtainable or obtained by said method, and a pharmaceutical composition comprising such cells.

In certain embodiments, T cell maturation or differentiation in vitro may be delayed or inhibited by the method as described in WO2017070395, comprising contacting one or more T cells from a subject in need of a T cell therapy with an AKT inhibitor (such as, e.g., one or a combination of two or more AKT inhibitors disclosed in claim 8 of WO2017070395) and at least one of exogenous Interleukin-7 (IL-7) and exogenous Interleukin-15 (IL-15), wherein the resulting T cells exhibit delayed maturation or differentiation, and/or wherein the resulting T cells exhibit improved T cell function (such as, e.g., increased T cell proliferation; increased cytokine production; and/or increased cytolytic activity) relative to a T cell function of a T cell cultured in the absence of an AKT inhibitor.

In certain embodiments, a patient in need of a T cell therapy may be conditioned by a method as described in WO2016191756 comprising administering to the patient a dose of cyclophosphamide between 200 mg/m2/day and 2000 mg/m2/day and a dose of fludarabine between 20 mg/m2/day and 900 mg/m$^2$/day.

Vaccine or Immunogenic Composition Kits and Co-Packaging

In an aspect, the invention provides kits containing any one or more of the elements discussed herein to allow administration of the therapy. Elements may be provided individually or in combinations, and may be provided in any suitable container, such as a vial, a bottle, or a tube. In some embodiments, the kit includes instructions in one or more languages, for example in more than one language. In some embodiments, a kit comprises one or more reagents for use in a process utilizing one or more of the elements described herein. Reagents may be provided in any suitable container. For example, a kit may provide one or more delivery or storage buffers. Reagents may be provided in a form that is usable in a particular process, or in a form that requires addition of one or more other components before use (e.g. in concentrate or lyophilized form). A buffer can be any buffer, including but not limited to a sodium carbonate buffer, a sodium bicarbonate buffer, a borate buffer, a Tris buffer, a MOPS buffer, a HEPES buffer, and combinations thereof. In some embodiments, the buffer is alkaline. In some embodiments, the buffer has a pH from about 7 to about 10. In some embodiments, the kit comprises one or more of the vectors, proteins and/or one or more of the polynucleotides described herein. The kit may advantageously allow the provision of all elements of the systems of the invention. Kits can involve vector(s) and/or particle(s) and/or nanoparticle(s) containing or encoding RNA(s) for 1-50 or more neoantigen mutations to be administered to an animal, mammal, primate, rodent, etc., with such a kit including instructions for administering to such a eukaryote; and such a kit can optionally include any of the anti-cancer agents described herein. The kit may include any of the components above (e.g. vector(s) and/or particle(s) and/or nanoparticle(s) containing or encoding RNA(s) for 1-50 or more neoantigen mutations, neoantigen proteins or peptides) as well as instructions for use with any of the methods of the present invention. In one embodiment the kit contains at least one vial with an immunogenic composition or vaccine. In one embodiment the kit contains at least one vial with an immunogenic composition or vaccine and at least one vial with an anticancer agent. In one embodiment kits may comprise ready to use components that are mixed and ready to administer. In one aspect a kit contains a ready to use immunogenic or vaccine composition and a ready to use anti-cancer agent. The ready to use immunogenic or vaccine composition may comprise separate vials containing different pools of immunogenic compositions. The immunogenic compositions may comprise one vial containing a viral vector or DNA plasmid and the other vial may comprise immunogenic protein. The ready to use anticancer agent may comprise a cocktail of anticancer agents or a single anticancer agent. Separate vials may contain different anticancer agents. In another embodiment a kit may contain a ready to use anti-cancer agent and an immunogenic composition or vaccine in a ready to be reconstituted form. The immunogenic or vaccine composition may be freeze dried or lyophilized. The kit may comprise a separate vial with a reconstitution buffer that can be added to the lyophilized composition so that it is ready to administer. The buffer may advantageously comprise an adjuvant or emulsion according to the present invention. In another embodiment the kit may comprise a ready to reconstitute anticancer agent and a ready to reconstitute immunogenic composition or vaccine. In this aspect both may be lyophilized. In this aspect separate reconstitution buffers for each may be included in the kit. The buffer may advantageously comprise an adjuvant or emulsion according to the present invention. In another embodiment the kit may comprise single vials containing a dose of immunogenic composition and anti-cancer agent that are administered together. In another aspect multiple vials are included so that one vial is administered according to a treatment timeline. One vial may only contain the anti-cancer agent for one dose of treatment, another may contain both the anti-cancer agent and immunogenic composition for another dose of treatment, and one vial may only contain the immunogenic composition for yet another dose. In a further aspect the vials are labeled for their proper administration to a patient in need thereof. The immunogen or anti-cancer agents of any embodiment may be in a lyophilized form, a dried form or in aqueous solution as described herein. The immunogen may be a live attenuated virus, protein, or nucleic acid as described herein.

In one embodiment the anticancer agent is one that enhances the immune system to enhance the effectiveness of the immunogenic composition or vaccine. In a preferred embodiment the anti-cancer agent is a checkpoint inhibitor. In another embodiment the kit contains multiple vials of immunogenic compositions and anti-cancer agents to be administered at different time intervals along a treatment plan. In another embodiment the kit may comprise separate vials for an immunogenic composition for use in priming an immune response and another immunogenic composition to be used for boosting. In one aspect the priming immunogenic composition could be DNA or a viral vector and the boosting immunogenic composition may be protein. Either composition may be lyophilized or ready for administering. In another embodiment different cocktails of anti-cancer agents containing at least one anticancer agent are included in different vials for administration in a treatment plan.

Although the present invention and its advantages have been described in detail, it should be understood that various changes, substitutions and alterations can be made herein without departing from the spirit and scope of the invention as defined in the appended claims.

Further embodiments are illustrated in the following Examples which are given for illustrative purposes only and are not intended to limit the scope of the invention.

EXAMPLES

Example 1—Experimental Procedures

Cell Culture and HLA-Peptide Immunopurification. Applicants tested mono-allelic B cells generated by transduction of B721.221 cells with a retroviral vector coding a single class I HLA allele as described previously (Reche P A, Keskin D B, Hussey R E, Ancuta P, Gabuzda D, Reinherz E L. Elicitation from virus-naive individuals of cytotoxic T lymphocytes directed against conserved HIV-1 epitopes. Med Immunol. 2006; 5:1) (cells expressing HLA-A*02:01, -A*24:02, and -B*44:03 were purchased from the Fred Hutchinson Research Cell Bank, University of Washington; cells expressing HLA-A*03:01 were a gift from Dr. Marcus Altfeld and Dr. Wilfredo F. Garcia-Beltran, Ragon Institute; others were a gift from Dr. E. L. Reinherz, Dana Farber Cancer Institute). Cell lines were confirmed by standard molecular typing (Brigham and Women's Hospital Tissue Typing Laboratory). HLA-peptide immunopurifcation is described in the Supplemental Experimental Procedures of Abelin et al., Mass Spectrometry Profiling of HLA-Associated Peptidomes in Mono-allelic Cells Enables More Accurate Epitope Prediction. Immunity. 2017 Feb. 21; 46(2):315-326.

HLA-Peptide Sequencing by Tandem Mass Spectrometry. All nanoLC-ESI-MS/MS analyses employed the same LC separation conditions, instrument parameters, and data analytics described in the Supplemental Experimental Procedures of Abelin et al., Mass Spectrometry Profiling of HLA-Associated Peptidomes in Mono-allelic Cells Enables More Accurate Epitope Prediction. Immunity. 2017 Feb. 21; 46(2):315-326. The original mass spectra may be downloaded from MassIVE (massive.ucsd.edu) under the identifier MassIVE: MSV000080527. The data are directly accessible via ftp://massive.ucsd.edu/MSV000080527.

Sequence Properties of MS-Identified Peptides Compared to IEDB. A curated set of previously identified class I HLA-bound peptides was downloaded from the Immune Epitope Database (IEDB) at www.iedb.org/ (accessed on Oct. 26, 2015) (Vita R, Overton J A, Greenbaum J A, Ponomarenko J, Clark J D, Cantrell J R, Wheeler D K, Gabbard J L, Hix D, Sette A, Peters B. The immune epitope database (IEDB) 3.0. Nucleic Acids Res. 2015; 43:D405-D412). For each allele, IEDB peptides with a measured affinity <500 nM were compared to MS peptides in terms of their length and positional amino acid frequencies. In addition, a metric was defined for the pairwise "distance" between 9-mers (a Hamming distance calculated with an amino acid substitution matrix [Kim Y, Sidney J, Pinilla C, Sette A, Peters B. Derivation of an amino acid similarity matrix for peptide: MHC binding and its application as a Bayesian prior. BMC Bioinformatics. 2009; 10:394] and inversely weighted according to positional entropy) and used for clustering MS and IEDB peptides in a two-dimensional representation. A machine-learning approach (Supplemental Experimental Procedures of Abelin et al., Mass Spectrometry Profiling of HLA-Associated Peptidomes in Mono-allelic Cells Enables More Accurate Epitope Prediction. Immunity. 2017 Feb. 21; 46(2):315-326) identified peptides with motifs favored in the MS but that were poor-scoring according to NetMHCpan 2.8; the MHC-binding affinities for these peptides were determined by competitive binding per gel filtration protocol (Sidney J, Southwood S, Oseroff C, del Guercio M F, Sette A, Grey H M. Measurement of MHC/peptide interactions by gel filtration. Curr Protoc Immunol Chapter. 2001; 18:3).

Peptide Processing Analyses. For each MS hit, the upstream ten amino acids and downstream ten amino acids were determined. Sequence context was likewise determined for decoy peptides (100 per hit; selected randomly from the proteome and matched according to their first two and last two amino acids). Relative amino acid frequencies were determined at each position upstream and downstream of hits and decoys. Additional previously published MS datasets were analyzed in the same manner. For comparison, peptides with high and low NetChop scores (top 25% and bottom 25% of 1 million randomly selected sites in the genome) were compared, and the motif most favored by NetChop was derived.

Relationship between Expression and Affinity. RNA was isolated from B721.221 cells expressing HLA-A*29:02, B*51:01, B*54:01, and B*57:01 (RNeasy mini kit, QIAGEN), processed to cDNA (Nextera XT kit; Smart-seq2 protocol), sequenced (HiSeq2500, Rapid Run mode; 50 bp paired-end), and aligned (bowtie2-2.2.1 (Langmead B, Salzberg S L. Fast gapped-read alignment with Bowtie 2. Nat Methods. 2012; 9:357-359)); UCSC hg19 annotation). Applicants averaged transcript expression (RSEM-1.2.19

[Li B, Dewey C N. RSEM: Accurate transcript quantification from RNA-Seq data with or without a reference genome. BMC Bioinformatics. 2011; 12:323]; GEO: GSE93315) across the four cell lines and made adjustments by dropping non-coding transcripts and rescaling TPM values to sum to one million. Applicants determined expression of each peptide source protein by summing all transcripts containing the peptide.

Impact of Processing Pathways. MS peptides were compared to decoys (ten decoys per MS peptide; each from a different gene; matched per transcript expression) in terms of various features potentially related to peptide processing: UNIPROT localization (www.uniprot.org), distance from protein N terminus, source protein stability index (Guruprasad K, Reddy B V B, Pandit M W. Correlation between stability of a protein and its dipeptide composition: a novel approach for predicting in vivo stability of a protein from its primary sequence. Protein Eng. 1990; 4:155-161), intrinsically disordered sequence content (d2p2.pro) (Oates M E, Romero P, Ishida T, Ghalwash M, Mizianty M J, Xue B, Dosztinyi Z, Uversky V N, Obradovic Z, Kurgan L, et al. $D^2P^2$: Database of disordered protein predictions. Nucleic Acids Res. 2013; 41:D508-D516), count of known ubiquitination sites (Eichmann M, de Ru A, van Veelen P A, Peakman M, Kronenberg-Versteeg D. Identification and characterisation of peptide binding motifs of six autoimmune disease-associated human leukocyte antigen-class I molecules including HLA-B*39:06. Tissue Antigens. 2014; 84:378-388; Krönke J, Fink E C, Hollenbach P W, MacBeth K J, Hurst S N, Udeshi N D, Chamberlain P P, Mani D R, Man H W, Gandhi A K, et al. Lenalidomide induces ubiquitination and degradation of CK1α in del(5q) MDS. Nature. 2015; 523:183-188; Udeshi N D, Mani D R, Eisenhaure T, Mertins P, Jaffe J D, Clauser K R, Hacohen N, Carr S A. Methods for quantification of in vivo changes in protein ubiquitination following proteasome and deubiquitinase inhibition. Mol Cell Proteomics. 2012; 11:148-159), and physical interaction with known protein turnover regulators (Behrends C, Sowa M E, Gygi S P, Harper J W. Network organization of the human autophagy system. Nature. 2010; 466:68-76).

Development of New Epitope-Selection Algorithms. For each allele, Applicants trained neural-network classifiers (one hidden layer with 50 units) (by using Theano (Theano Development Team, 2016); 5-fold cross-validation) to differentiate MS 9-mers from random decoy 9-mers by using different input feature schemes: dummy encoding, BLOSUM62, PMBEC (Kim Y, Sidney J, Pinilla C, Sette A, Peters B. Derivation of an amino acid similarity matrix for peptide: MHC binding and its application as a Bayesian prior. BMC Bioinformatics. 2009; 10:394), biochemical properties (Bremel R D, Homan E J. An integrated approach to epitope analysis I: Dimensional reduction, visualization and prediction of MHC binding using amino acid principal components and regression approaches. Immunome Res. 2010; 6:7), and peptide-level features (Osorio D, Rondón-Villarreal P, Torres R. Peptides: Calculate indices and theoretical physicochemical properties of peptides and protein sequences. 2014 CRAN.R-project.org/package=Peptides. R Package Version 1.1.0); Applicants averaged the results of these models to obtain a single prediction (called MSIntrinsic). Applicants made a second prediction (MSIntrinsicEC) by adding expression and MS-trained cleavability. Applicants validated performance on external data by measuring PPV (fraction of true MS peptides among the top-scoring 0.1%, where decoys are present at 999:1). For multi-allelic datasets, the evaluation excluded any MS peptides that obviously belonged to an HLA-A or HLA-B allele other than the one in question (e.g., when predicting for A01:01 for a cell line with genotype A01:01/A02:01/B35:01/B44:02, Applicants excluded MS-observed peptides with NetMHCPan 2.8 scores worse than 1,000 nM for A01:01 and better than 150 nM for A02:01, B35:01, or B44:02).

Example 2—Improved Prediction of Endogenously Presented HLA Class I Epitopes in Human Tumors Based on 95 Mono-Allelic Peptidomes Antigen discovery is a high priority for developing cancer immunotherapies, but remains challenging because of inter-individual variation in tumor-specific antigens and rules of antigen presentation. To enable prediction of endogenous HLA-associated peptides across a large fraction of the human population, Applicants used mass spectrometry (MS) to profile >185,000 peptides eluted from 95 HLA-A, B, C and G mono-allelic cell lines. In addition to identifying canonical peptide motifs for each of these HLA alleles, Applicants found unique and shared binding submotifs across alleles, and distinct motifs associated with different peptide lengths. Based on the full dataset of peptides and quantitative gene expression, Applicants learned allele-and-length-specific and pan-allele-pan-length models that integrate transcript abundance and peptide processing. These models predicted endogenous HLA-associated ligands with a 2-fold improvement in positive predictive value compared to existing tools and correctly identified >75% of HLA-bound peptides that were observed experimentally in 11 patient tumor cell lines by MS. More accurate prediction of class I epitopes will enable antigen discovery in cancer as well as infections, autoimmunity and other immune-related conditions.

The HLA genes are the most polymorphic across the human population, with more than 16,200 distinct class I alleles as of May 2019 (Lefranc et al. 2015; Robinson et al. 2015). Short peptides (8-11mers) bound to the diverse array of class I HLA molecules (HLA-A, -B, —C, and -G) arise from endogenous or foreign proteins that are cleaved by the proteasome and peptidases of the endoplasmic reticulum prior to loading and display by surface HLA class I proteins to cytotoxic T cell lymphocytes (CTLs). Given the diversity in HLA binding, an important question is whether one can accurately predict if a peptide is presented by a specific HLA allele. The accuracy of computational models that predict binding between peptides and HLA alleles, especially HLA-A and -B alleles, has been improving (Jurtz et al. 2017; Abelin et al. 2017; O'Donnell et al. 2018; Gfeller et al. 2018; Bulik-Sullivan et al. 2018). In the field of cancer, these tools are now increasingly used in conjunction with next-generation DNA sequencing of tumors to identify immunogenic cancer neoantigens, which arise from tumor-specific somatic mutations. They have accelerated epitope discovery, as they enable experimental efforts to focus on a narrower list of epitopes with predicted high binding scores. However, even with widely used algorithms such as NetMHCpan (Jurtz et al. 2017; Nielsen and Andreatta 2016), the numbers of falsely discovered binders increase once the predicted binding affinity decreases (i.e. IC50>100 nM)(Rajasagi et al. 2014). Furthermore, while these algorithms are designed to predict the binding affinity of peptides to individual HLA molecules—the final step of antigen presentation, they do not account for intracellular availability of the peptide precursors or their processing by proteases. Finally, because previous research has focused exclusively on the few alleles highly expressed by Caucasian populations, existing algorithms have uneven accuracy in the prediction of epitopes binding to less common alleles in Caucasians, or those highly prevalent in other populations.

Detection and sequencing of HLA-binding peptides by liquid chromatography-tandem mass spectrometry (LC-MS/MS) has the unique advantage that information on endogenously processed and presented peptides from a cell can be directly learned. Characterization of HLA-bound peptides eluted from a limited set of cell lines engineered to express single HLA alleles could reveal novel allele-specific peptide motifs and be used to train predictive algorithms for endogenous allele-specific peptide presentation (Abelin et al. 2017). Here, Applicant greatly expanded the dataset and identified and characterized 186,464 eluted peptides from 95 HLA-A, -B, —C and -G alleles. Applicant included HLA-G peptidomes since this HLA was implicated in maternal-fetal tolerance and was also upregulated in many cancers (de Kruijf et al. 2010; Zhang et al. 2017). Altogether, these data provided the opportunity to compare peptide length preferences, and the spectrum of distinct and shared submotifs across HLA class I alleles, revealing the diversity and complexity of endogenous HLA ligands. Using this information, Applicant trained novel allele-and-length-specific and pan-allele-pan-length predictors, which identified 2-fold more peptides than conventional prediction tools, when evaluating peptides directly detected by MS from 11 patient-derived tumor cell lines generated from diverse malignancies. The datasets of HLA-binding peptides from mono-allelic cells and patient-derived tumors, as well as the prediction models and interactive web tools are all made publicly available.

Results

Figure 32A:
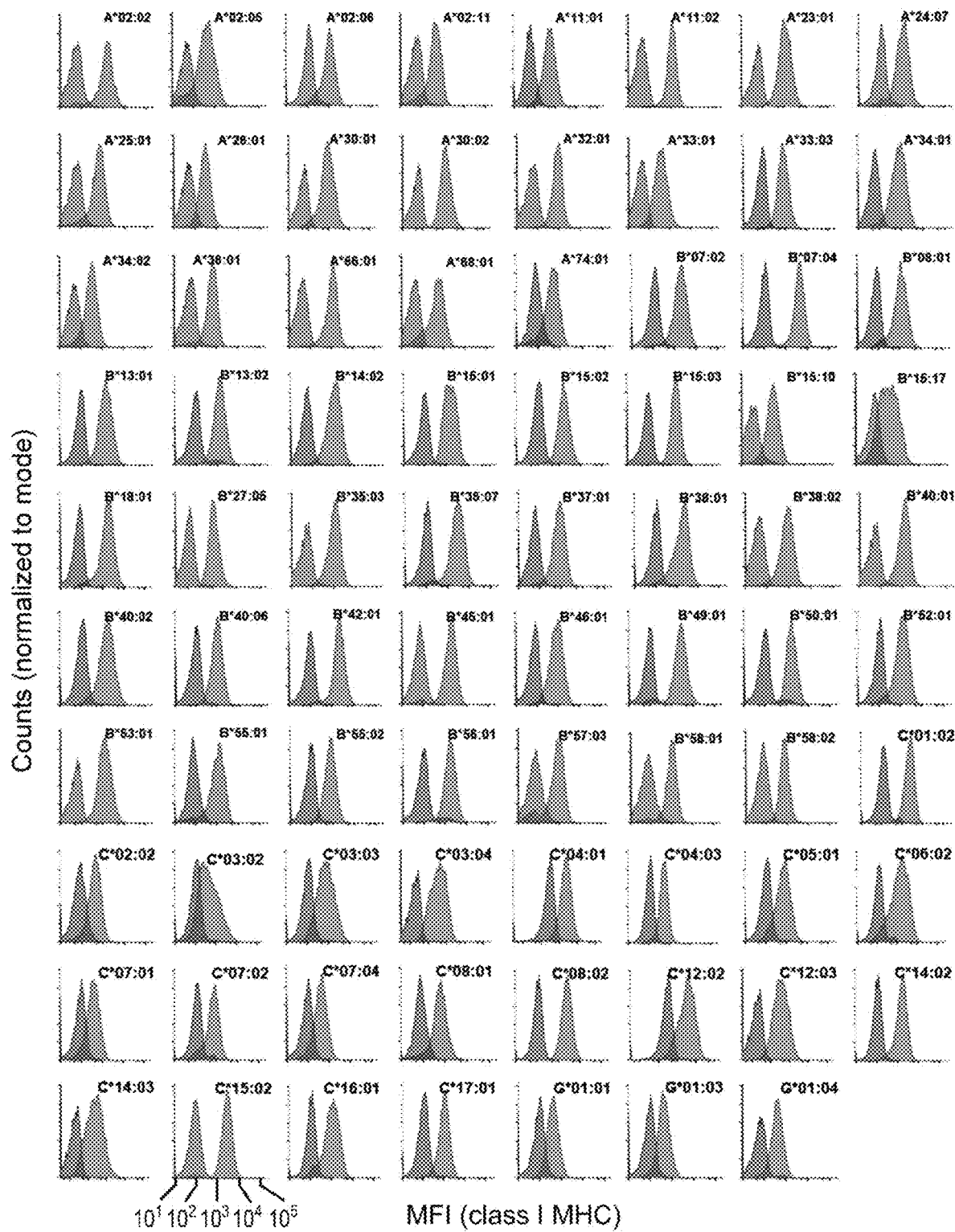
FIGS. 32A-32N—FIG. 32A) Mean Fluorescence Intensity (MFI) plots confirming expression of 76 newly generated mono-allelic cell lines.

Systematic LC-MS/MS Profiling of HLA Class I Ligands from Mono-Allelic Cell Lines Applicant engineered 79 cell lines expressing a single HLA class I allele by stably transfecting individual HLA-A, -B, —C, or -G alleles into the HLA-null B721.221 cell line (FIG. 26A), adding to the 16 lines (Abelin et al. 2017). Surface expression of the alleles was confirmed by flow cytometric detection (FIG. 26B; FIG. 32A). Altogether, the collection of 95 cell lines (31 HLA-A, 40 HLA-B, 21 HLA-C and 3 HLA-G) covered at least one allele in 95% of individuals worldwide for each HLA-A, -B and for HLA-C alleles, respectively (FIG. 26C)(Dawson et al. 2001; Gragert et al. 2013; Solberg et al. 2008).

Figures 32B, 32C, 32D, 32E:
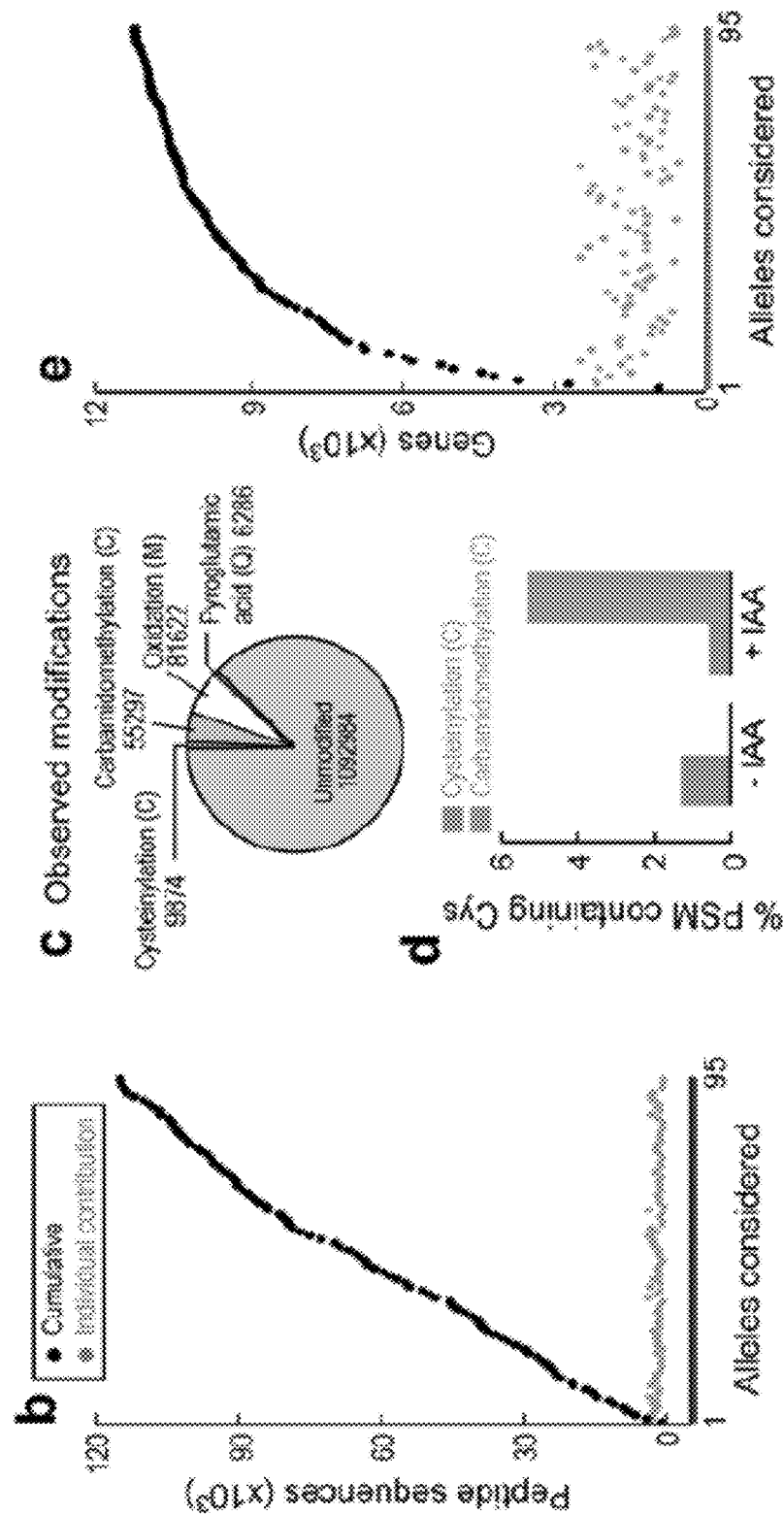
FIG. 32B) Each allele adds unique peptide sequences to the total immunopeptidome (black), number of individual peptide identifications are similar across alleles (blue).
FIG. 32C) Only a small fraction of identified peptides was discovered with a modification (cysteinylation (C), carbamidomethylation (C), oxidation (M) or pyroglutamic acid (Q)).
FIG. 32D) Addition of iodoacetamide (IAA) in the lysis buffer increases recovery of cysteine containing HLA peptides.
FIG. 32E) Number of genes presented by HLA peptides increases with additional allotypes.
Figures 32F, 32G:
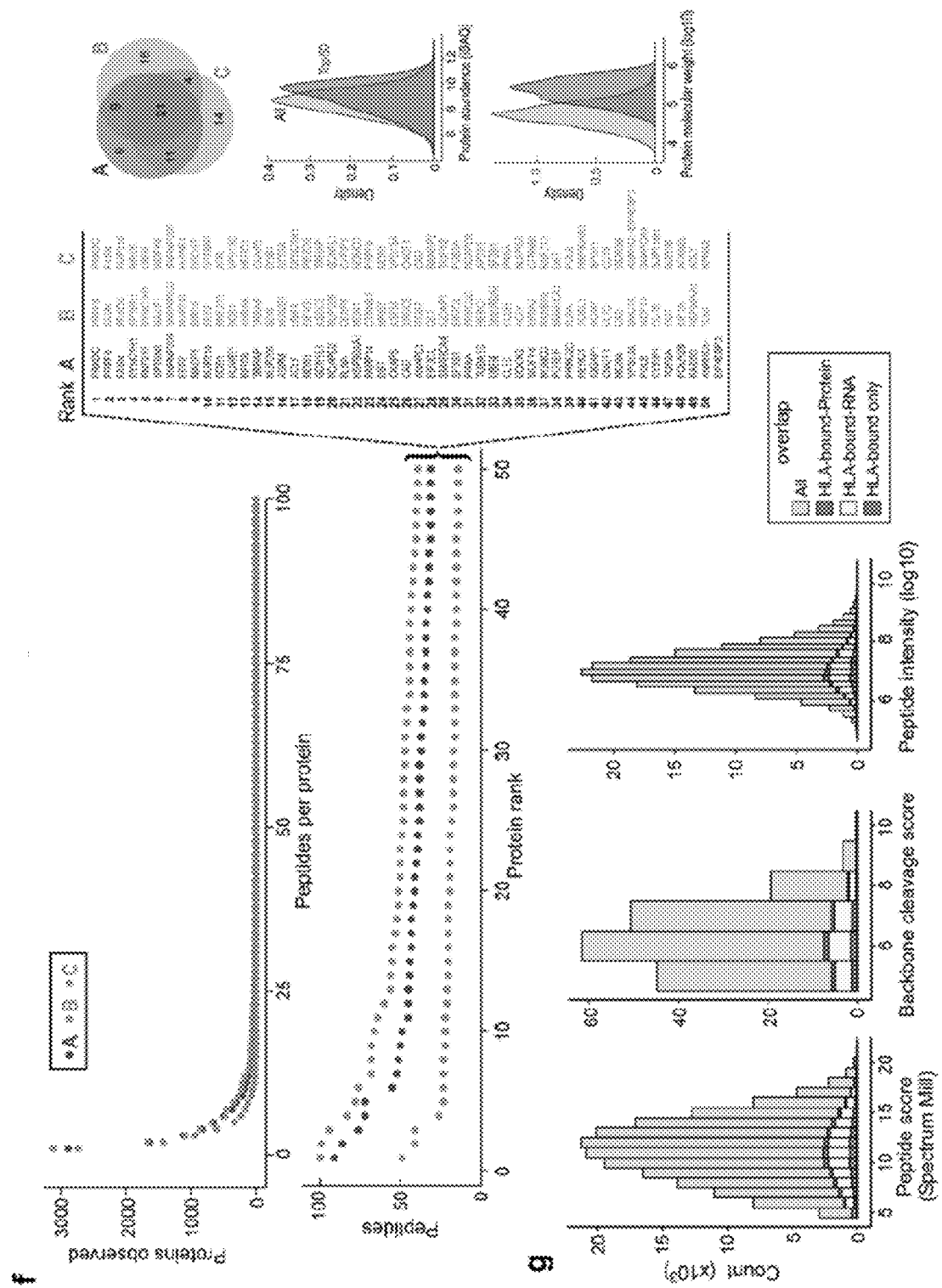
FIG. 32F) Most genes are covered by one or 2 peptide sequences only. Ranked by number of peptides for each protein starting with the most frequently observed gene, the top 50 proteins per HLA-type are similar between A-, B-, and C-alleles and derived from large and abundant proteins.
FIG. 32G) Peptides from genes only identified in HLA experiments show same scores, backbone cleavage scores and intensity distribution as peptides from genes overlapping to RNA and Proteome.
Figures 32H, 32M, 32N:
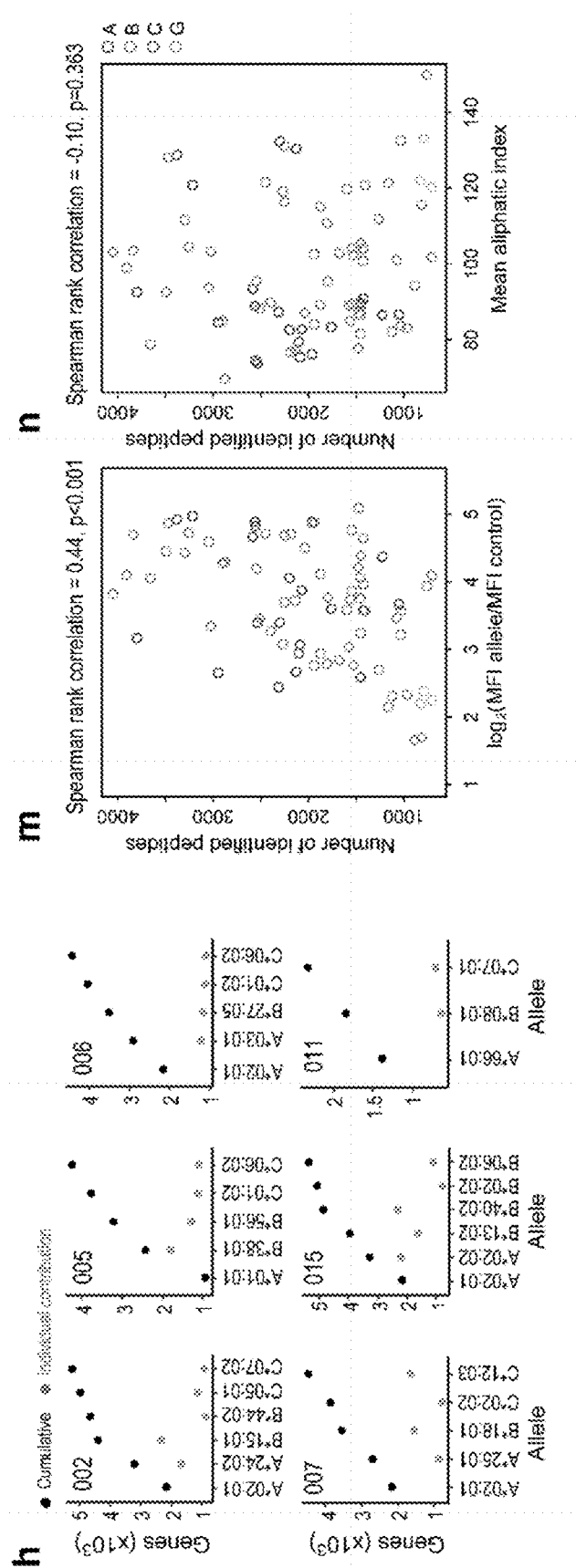
FIG. 32H) Antigens of up to 5000 genes can be presented by 6 alleles, HLA phenotypes reflect those of melanoma patients used in this and other studies (Ott et al. 2017).
FIG. 32M) Surface expression of single alleles measured by flow cytometry correlated weakly with number of identified peptides.
Figure 32I:
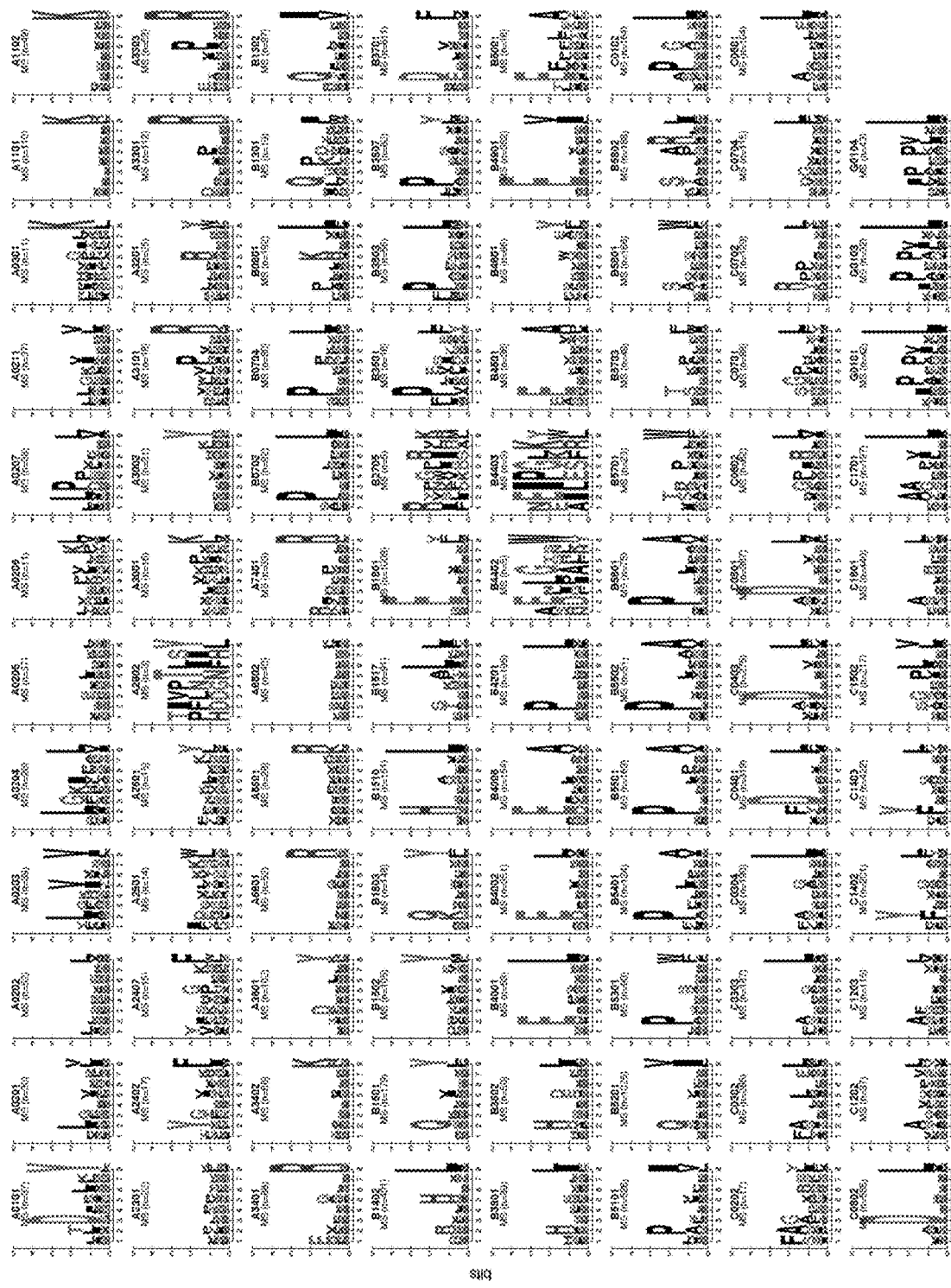
FIG. 32I) Logo plots per peptide length (8-11 mers) for 95 alleles using MS data.
Figure 32I:
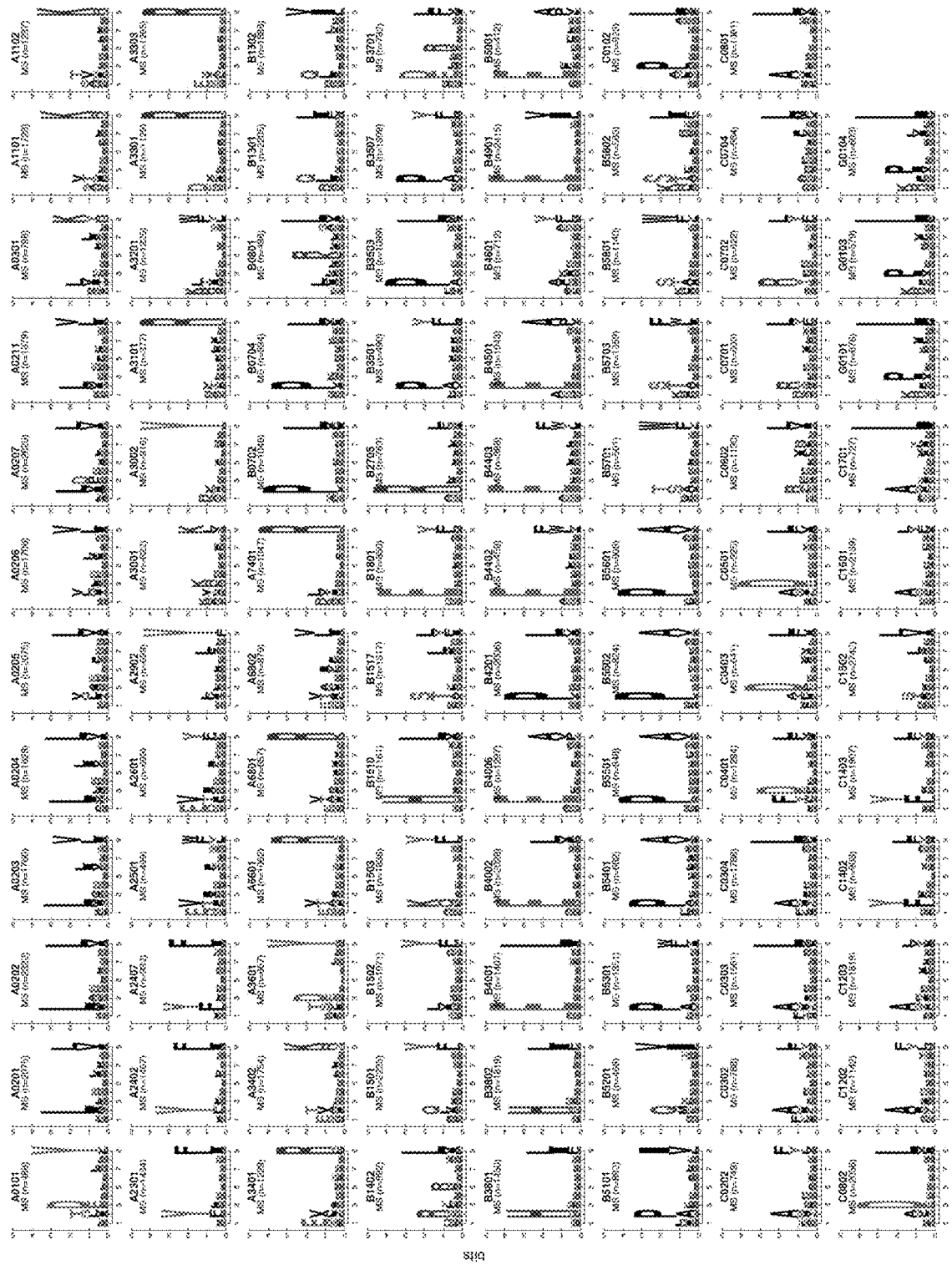
Figure 32I:
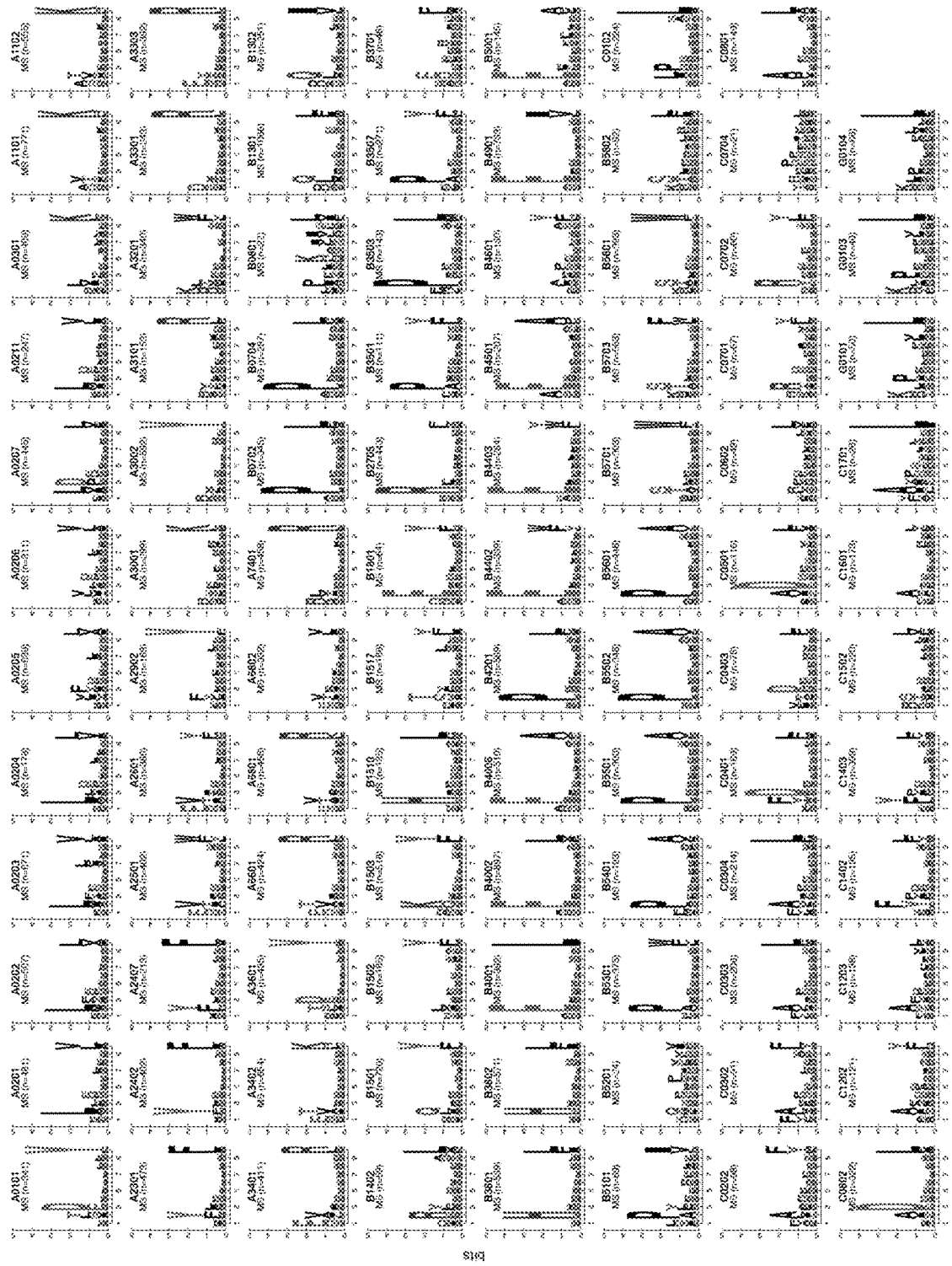
Figure 32I:
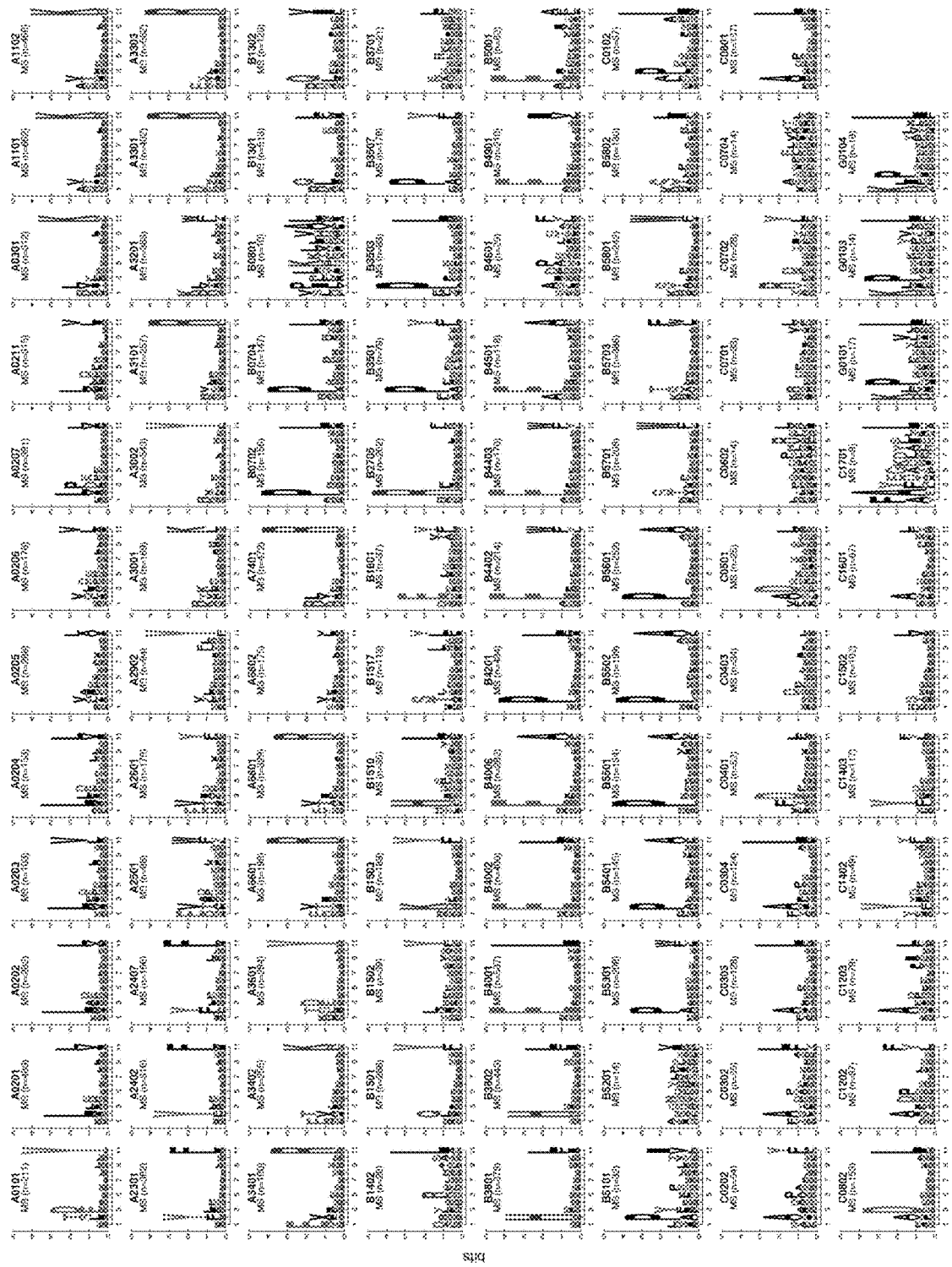
Figure 32J:
FIG. 32J) Logo plots per peptide length (8-11 mers) for 95 alleles as available in IEDB.
Figure 32J:
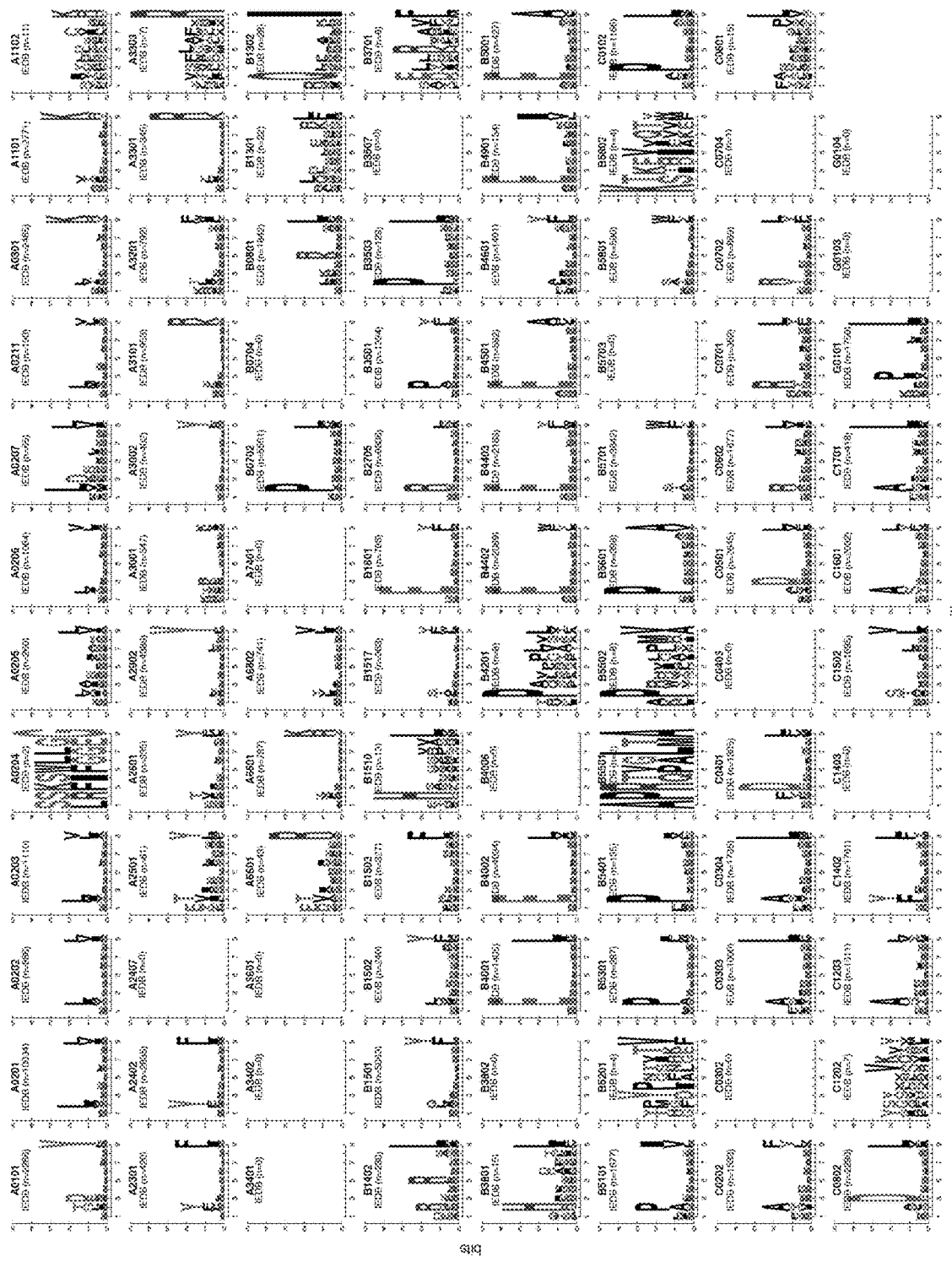
Figure 32J:
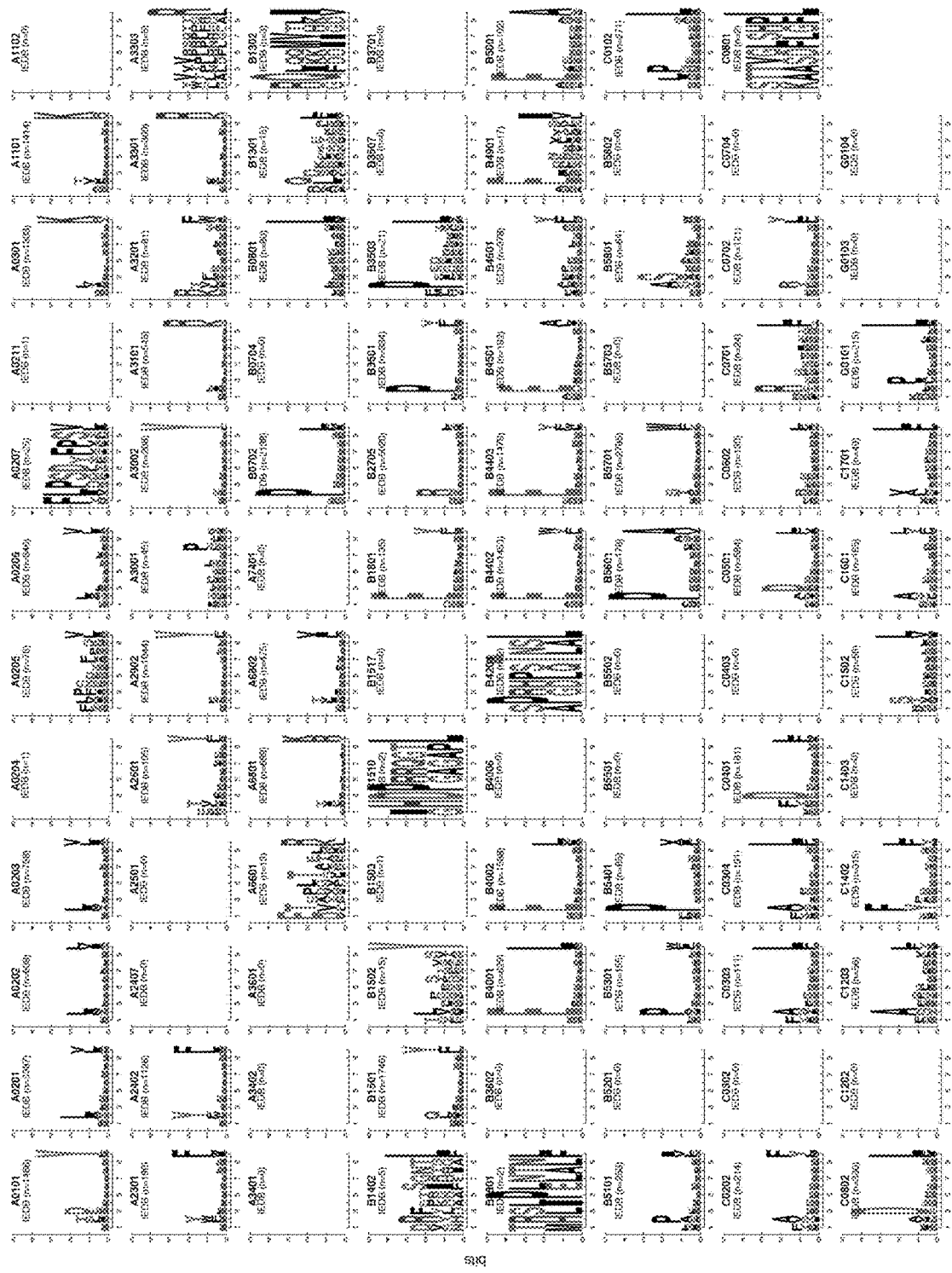
Figure 32J:
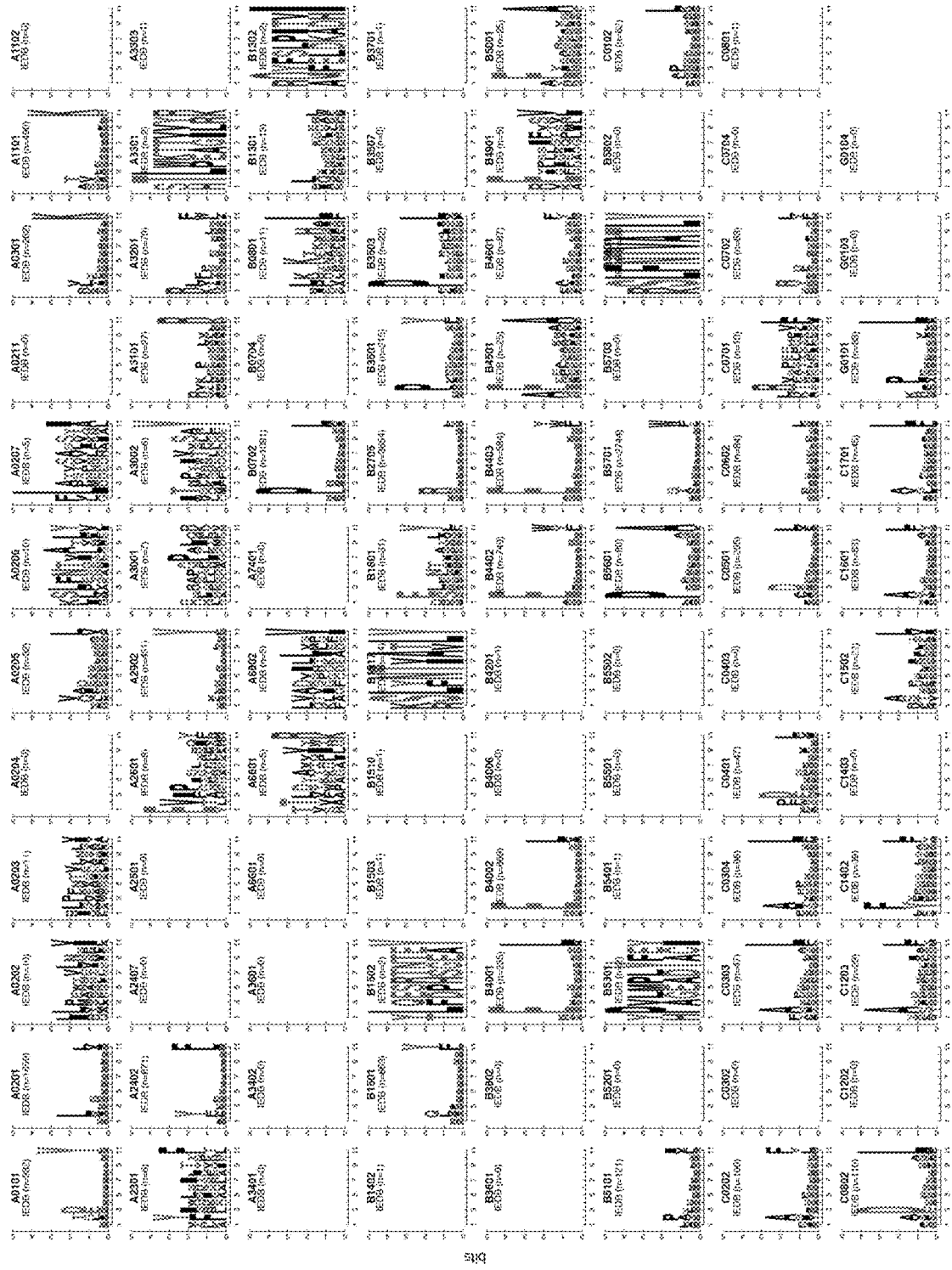

HLA-bound peptides for each engineered cell line were isolated by HLA immunopurification, analyzed by high-resolution LC-MS/MS and sequences identified by a 'no-enzyme' specificity database search at 1% FDR. Applicant identified a median of 1860 peptides per allele (range 692-4,033), or a total of 186,464 peptides across the 95 alleles after excluding non-specifically bound peptides (see, e.g., A*01:01 (SEQ ID Nos: 44-1120); A*02:01 (SEQ ID Nos: 1121-4202); A*02:02 (SEQ ID Nos: 4203-7373); A*02:03 (SEQ ID Nos: 7374-9953); A*02:04 (SEQ ID Nos: 9954-11940); A*02:05 (SEQ ID Nos: 11941-14981); A*02:06 (SEQ ID Nos: 14982-17191); A*02:07 (SEQ ID Nos: 117192-20710); A*02:11 (SEQ ID Nos: 20711-22696); A*03:01 (SEQ ID Nos: 22697-24233); A*11:01 (SEQ ID Nos: 24234-27505); A*11:02 (SEQ ID Nos: 27506-29812); A*23:01 (SEQ ID Nos: 29813-32133); A*24:02 (SEQ ID Nos: 32134-34347); A*24:07 (SEQ ID Nos: 34348-35681); A*25:01 (SEQ ID Nos: 35682-36682); A*26:01 (SEQ ID Nos: 36683-37957); A*29:02 (SEQ ID Nos: 37958-38921); A*30:01 (SEQ ID Nos: 38922-40029); A*30:02 (SEQ ID Nos: 40030-42114); A*31:01 (SEQ ID Nos: 42115-42919); A*32:01 (SEQ ID Nos: 42920-44874); A*33:01 (SEQ ID Nos: 44875-46761); A*33:03 (SEQ ID Nos: 46762-49053); A*34:01 (SEQ ID Nos: 49054-50948); A*34:02 (SEQ ID Nos: 50949-53677); A*36:01 (SEQ ID Nos: 53678-55165); A*66:01 (SEQ ID Nos: 55166-56901); A*68:01 (SEQ ID Nos: 56902-58374); A*68:02 (SEQ ID Nos: 58375-59804); A*74:01 (SEQ ID Nos: 59805-61821); B*07:02 (SEQ ID Nos: 61822-63473); B*07:04 (SEQ ID Nos: 63474-64885); B*08:01 (SEQ ID Nos: 64886-65609); B*13:01 (SEQ ID Nos: 65610-69419); B*13:02 (SEQ ID Nos: 69420-71587); B*14:02 (SEQ ID Nos: 71588-72970); B*15:01 (SEQ ID Nos: 72971-76378); B*15:02 (SEQ ID Nos: 76379-77762); B*15:03 (SEQ ID Nos: 77763-80458); B*15:10 (SEQ ID Nos: 80459-81940); B*15:17 (SEQ ID Nos: 81941-83632); B*18:01 (SEQ ID Nos: 83633-85593); B*27.05 (SEQ ID Nos: 85594-87076); B*35:01 (SEQ ID Nos: 87077-87772); B*35:03 (SEQ ID Nos: 87773-89157); B*35:07 (SEQ ID Nos: 89158-90977); B*37:01 (SEQ ID Nos: 90978-92452); B*38:01 (SEQ ID Nos: 92453-94858); B*38:02 (SEQ ID Nos: 94859-97742); B*40:01 (SEQ ID Nos: 97743-100731); B*40:02 (SEQ ID Nos: 100732-104409); B*40:06 (SEQ ID Nos: 104410-106653); B*42:01 (SEQ ID Nos: 106612-019885); B*44:02 (SEQ ID Nos: 109886-110903); B*44:03 (SEQ ID Nos: 110904-111749); B*45:01 (SEQ ID Nos: 111750-113153); B*46:01 (SEQ ID Nos: 113154-114113); B*49:01 (SEQ ID Nos: 114114-117833); B*50:01 (SEQ ID Nos: 117834-118468); B*51:01 (SEQ ID Nos: 118469-119991); B*52:01 (SEQ ID Nos: 119992-121525); B*53:01 (SEQ ID Nos: 121526-123560); 54:01 (SEQ ID Nos: 123561-124684); B*55:01 (SEQ ID Nos: 124685-126136); B*55:02 (SEQ ID Nos: 126137-127557); B*56:01 (SEQ ID Nos: 127558-129239); B*57:01 (SEQ ID Nos: 129240-130274); B*57:03 (SEQ ID Nos: 130275-132636); B*58:01 (SEQ ID Nos: 132637-134577); B*58:02 (SEQ ID Nos: 134578-135530); C*01:02 (SEQ ID Nos: 135531-136878); C*02:02 (SEQ ID Nos: 136879-137802); C*03:02 (SEQ ID Nos: 137803-138984); C*03:03 (SEQ ID Nos: 138985-141074); C*03:04 (SEQ ID Nos: 141075-143394); C*04:01 (SEQ ID Nos: 143395-145236); C*04:03 (SEQ ID Nos: 145237-146269); C*05:01 (SEQ ID Nos: 146270-147708); C*06:02 (SEQ ID Nos: 147709-149028); C*07:01 (SEQ ID Nos: 149029-149822); C*07:02 (SEQ ID Nos: 149823-150900); C*07:04 (SEQ ID Nos: 150901-151615); C*08:01 (SEQ ID Nos: 151616-153388); C*08:02 (SEQ ID Nos: 153389-156499); C*12:02 (SEQ ID Nos: 156500-157889); C*12:03 (SEQ ID Nos: 157890-160043); C*14:02 (SEQ ID Nos: 160044-161408); C*14:03 (SEQ ID Nos: 161409-164186); C*15:02 (SEQ ID Nos: 164187-167475); C*16:01 (SEQ ID Nos: 167476-170317); C*17:01 (SEQ ID Nos: 170318-171281); G*01:01 (SEQ ID Nos: 171282-172073); G*01:03 (SEQ ID Nos: 172074-172742) and G*01:04 (SEQ ID Nos: 172743-173477); and FIG. 32B), and covering more peptides containing cysteine by adding carbamidomethylation of cysteine into the sample processing workflow. Most of the observed modifications, representing 12% of total identified peptides, could be explained by sample processing artifacts such as oxidation of methionine (FIGS. 32C-32D). The HLA-bound peptides Applicant identified mapped to 10,649 human genes (with >2 HLA-associated peptides per gene), which represent 91% of human gene products detected by LC-MS/MS in an extensively fractionated proteome of the B721.221 cell line (with >2 unique peptides per gene), and 89% of transcribed genes (with >2 transcripts per million (TPM) from RNA-seq) (FIG. 26C; FIG. 32E). While the majority of proteins were represented by more than one HLA peptide, the top 50 most frequently detected proteins in the proteome analysis were large, highly abundant, and consistently observed as eluted peptides across HLA-A, -B, and —C alleles (FIG. 32F). Notably, 1,517 genes represented by HLA-bound peptides were not detected in either of the two expression data sets, suggesting they had very low RNA and protein levels. The respective peptides are reliable identifications because they had peptide identification metrics comparable to the rest of the dataset (FIG. 32G). Subsetting the dataset of peptides to sets of 6 alleles matched to patient-derived melanoma cell lines (Ott et al. 2017) usually recovered 4,000-5,000 genes (FIG. 32H). Applicant concluded that all expressed proteins could undergo processing and presentation by HLA class I molecules, a far higher proportion than previously appreciated (Pearson et al. 2016).

Figure 1:
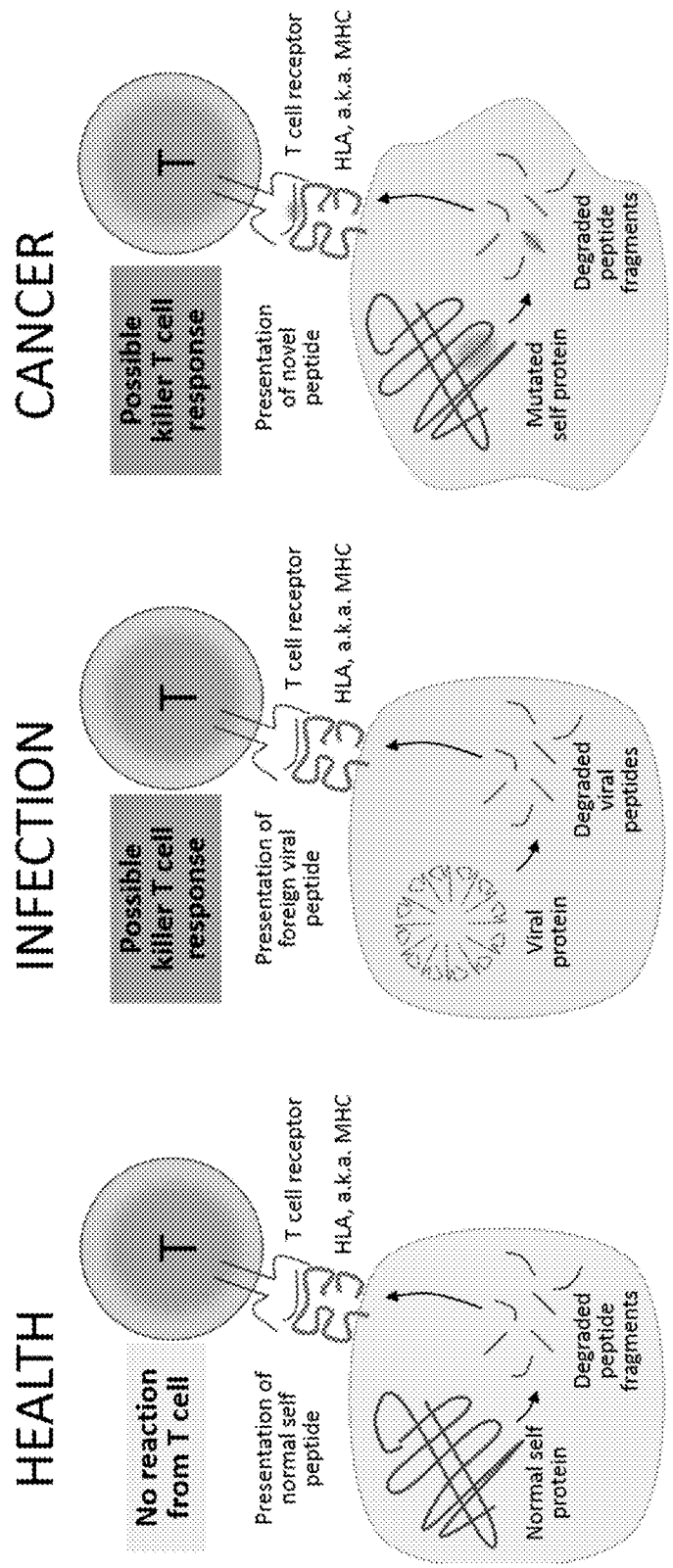
FIG. 1—The human immune system recognizes non-self antigens (e.g. viral or mutated peptides) presented on MHC class I molecules and elicits an immune response upon T cell receptor recognition.
Figure 2:
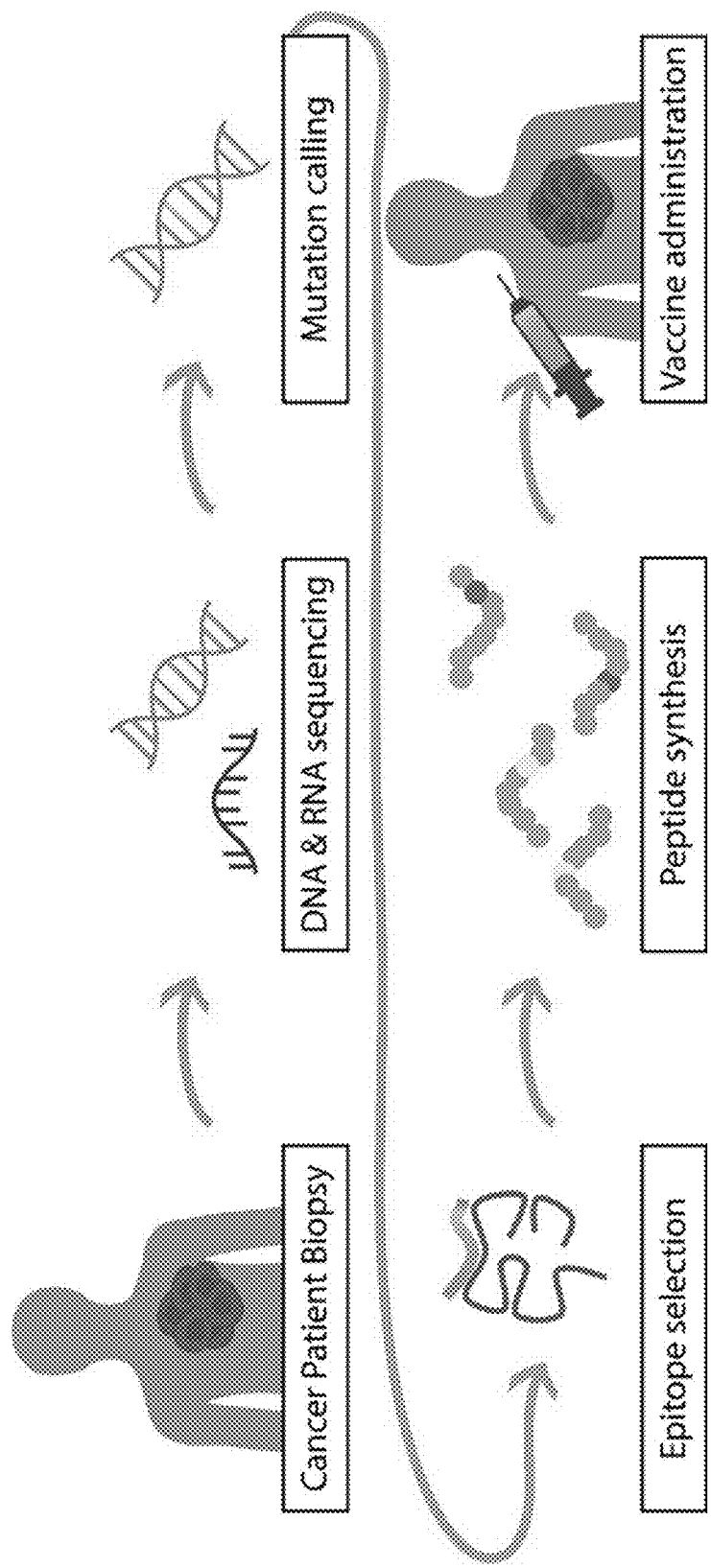
FIG. 2—Cancer vaccine therapeutic workflow. Tumor specific mutations that give rise to protein coding changes are identified and evaluated for their likelihood to produce HLA-binding neoantigens. Selected candidates are synthesized and administered as a vaccine. Tumor-specific antigens can be used to design a personalized cancer vaccine that potentiates a tumor-specific immune response.
Figure 3:
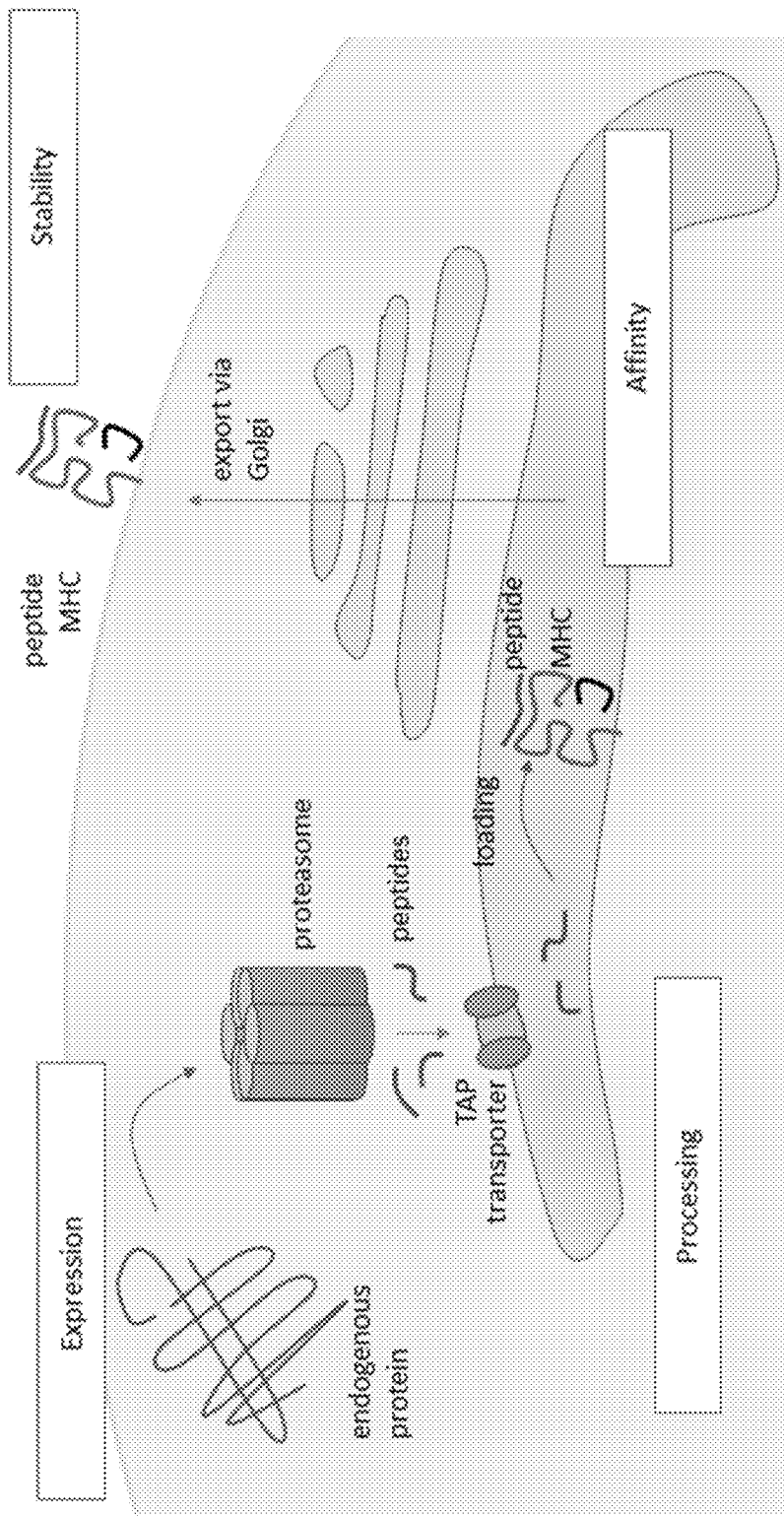
FIG. 3—Intracellular proteins are processed into peptides by the proteasome, transported into the ER and loaded onto MHC molecules. Peptide-MHC complexes are shuttled to the cell surface for T cell recognition. Thus, many endogenous processing steps contribute to peptide presentation.
Figure 4:
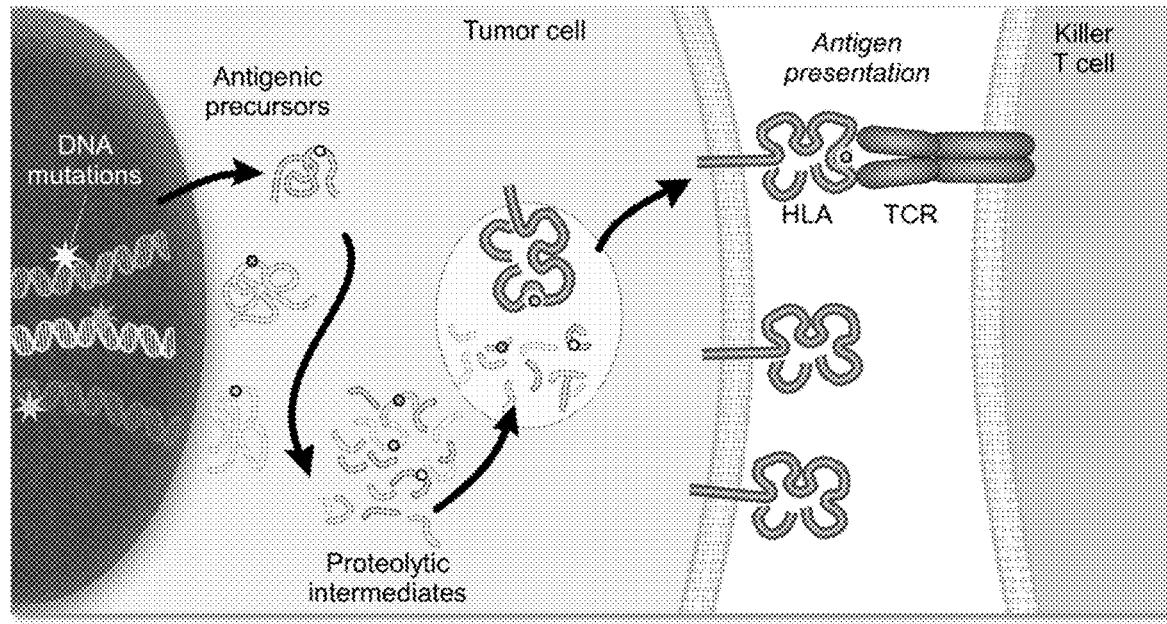
FIG. 4—Disease-specific mutations have the potential to generate neoantigens. Current neoantigen prediction models NetMHCpan solely based on binding affinity. MS provides a platform to better understand rules of antigen processing and presentation. See, e.g., Purroy N et al., Cold Spring Harb Perspect Med 2017.
Figure 5:
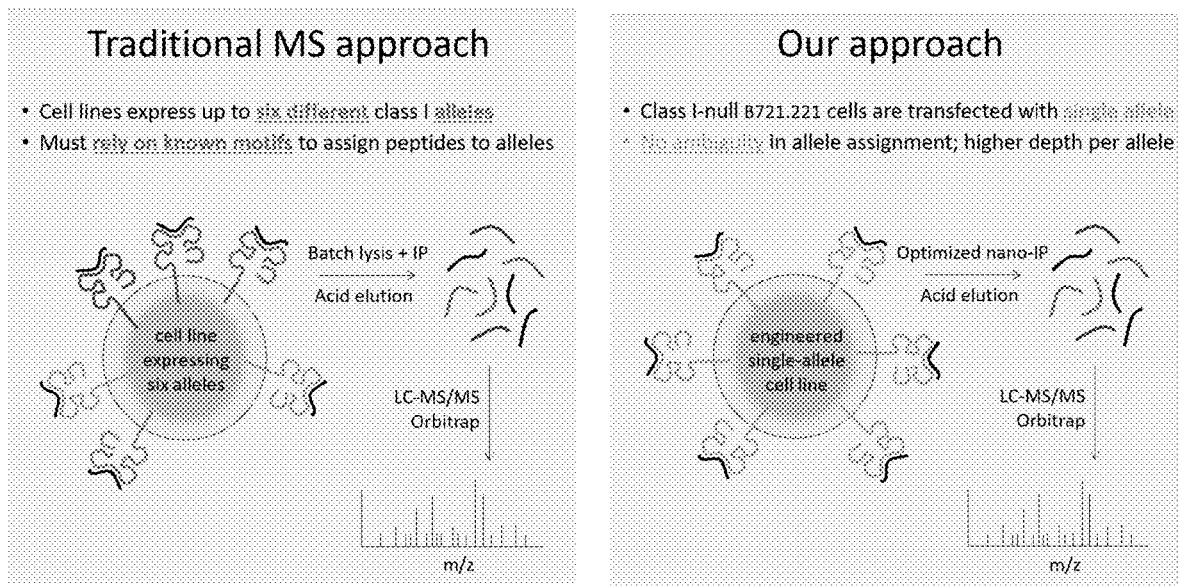
FIG. 5—Cell lines engineered to express a single HLA allele of interest enable high throughput peptide identification via MS and unambiguous assignment of peptides to alleles. Cell lines engineered to express a single HLA allele allow for high-throughput and unambiguous identification of bound peptides.
Figure 6A:
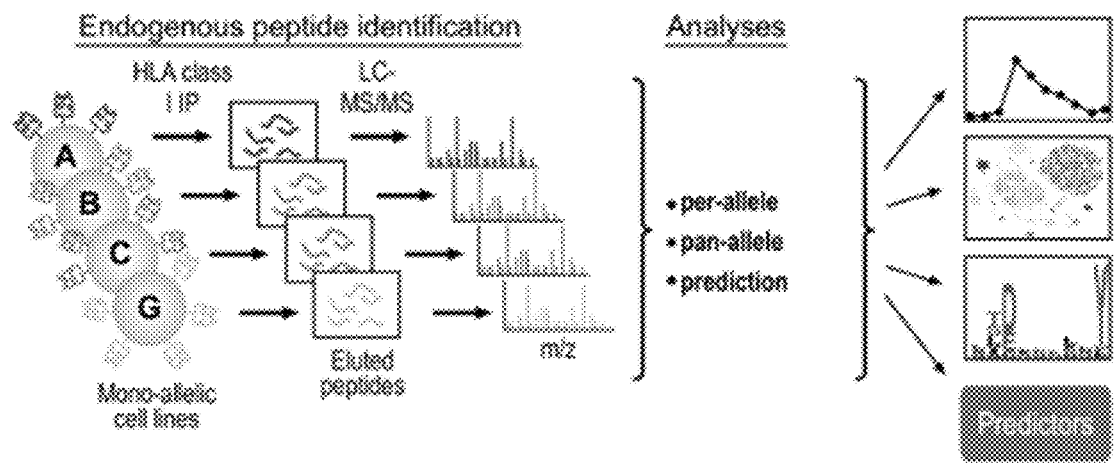
FIGS. 6A-6B—Single-allele approach to improve prediction algorithms.
Figure 6B:
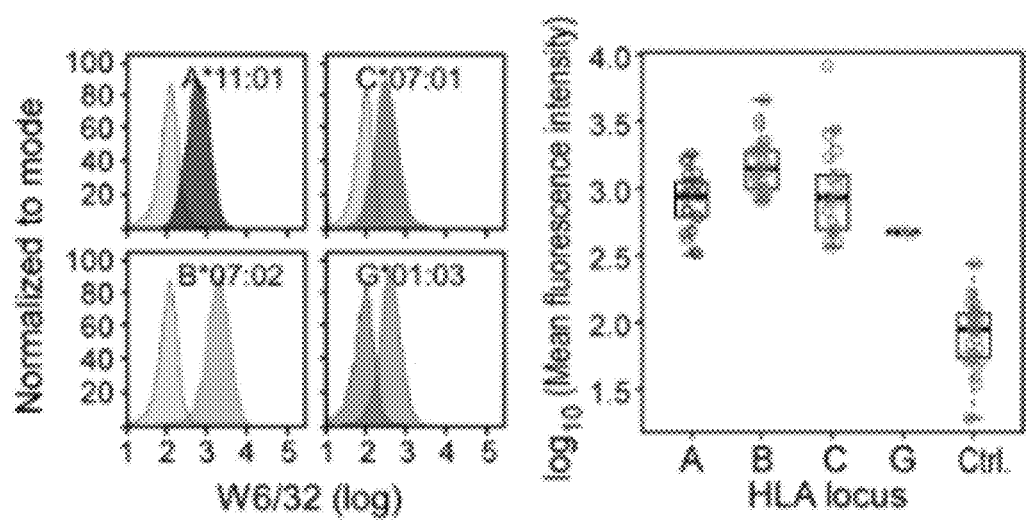
Figure 7:
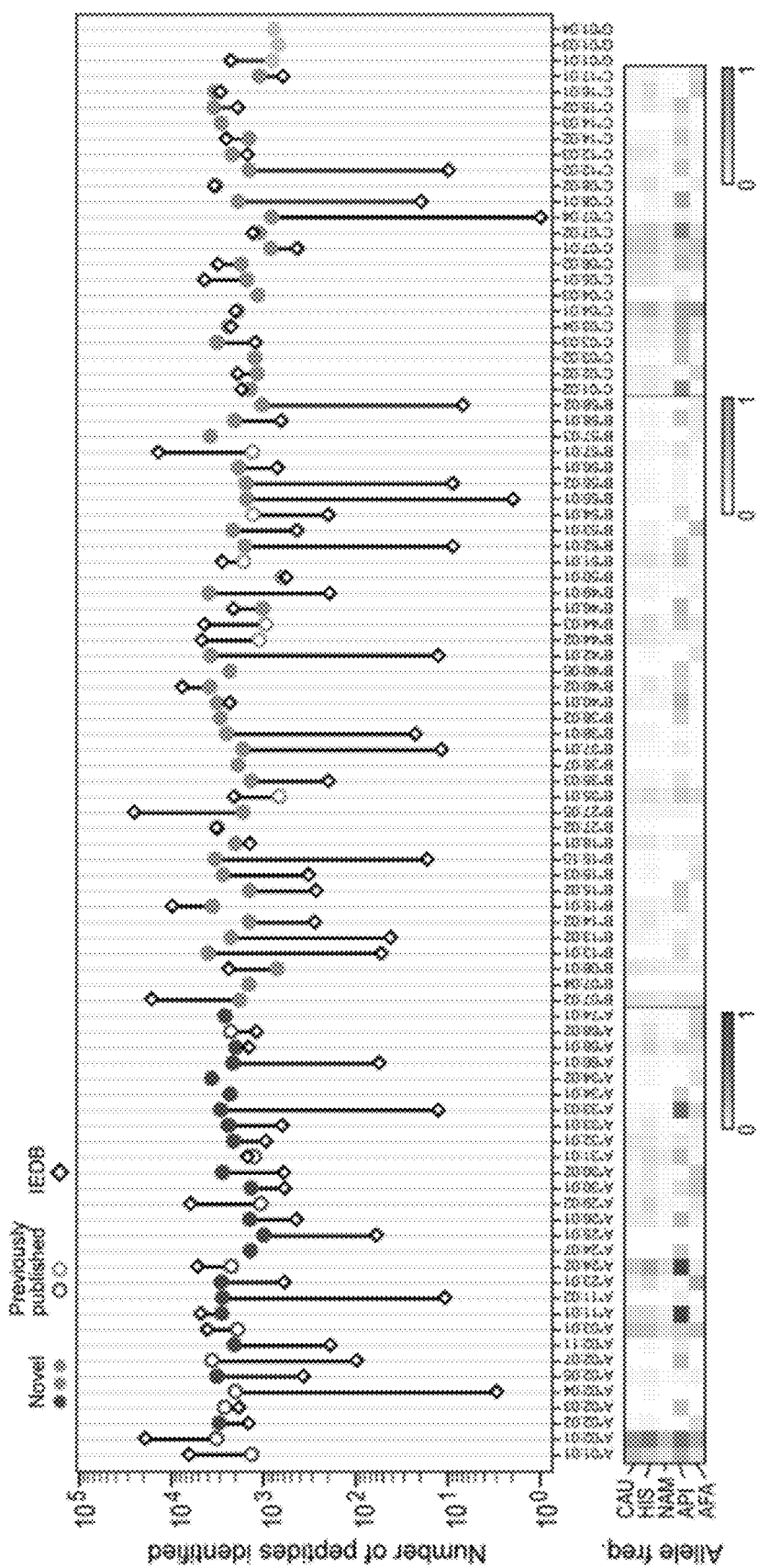
FIG. 7—Over 185,000 peptides were identified across 95 alleles that cover the most frequent alleles in the population. Numbers of HLA-bound peptides identified per allele by MS-based profiling (circles; filled-newly generated data; open-previously reported (Abelin J G, Keskin D B, Sarkizova S, Hartigan C R, Zhang W, Sidney J, Stevens J, Lane W, Zhang G L, Eisenhaure™, Clauser K R, Hacohen N, Rooney M S, Carr S A, Wu C J., 2017. Mass spectrometry profiling of HLA-associated peptidomes in mono-allelic cells enables more accurate epitope prediction. Immunity 46:315-26); or within IEDB (diamonds) (top). Relative population frequency across racial groups per allele (bottom). Massive mono-allelic peptide dataset enables in-depth integrative analysis and improved understanding of epitope presentation rules.
Figure 9:
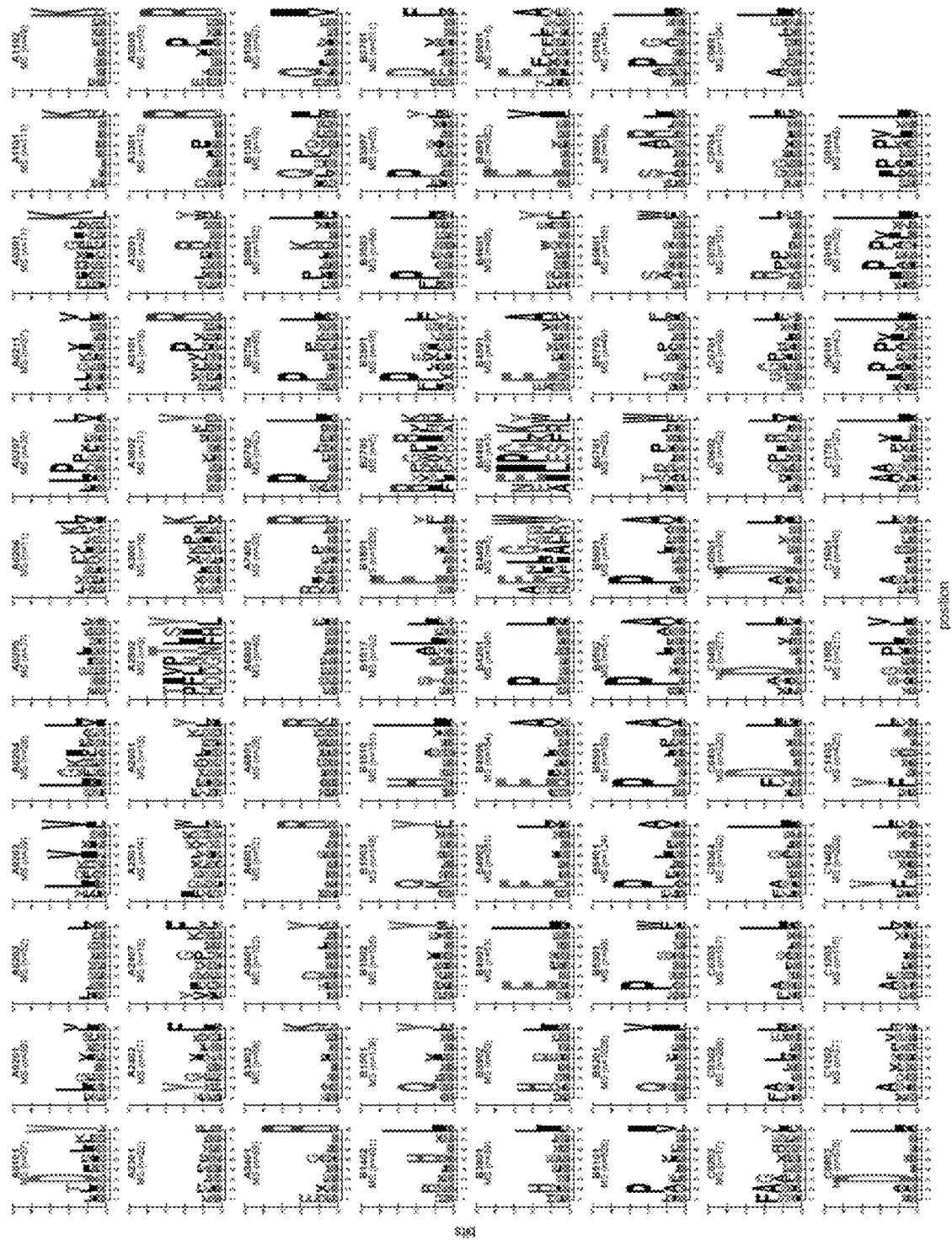
FIG. 9—Profiled 8 mer alleles and motifs.
Figure 10:
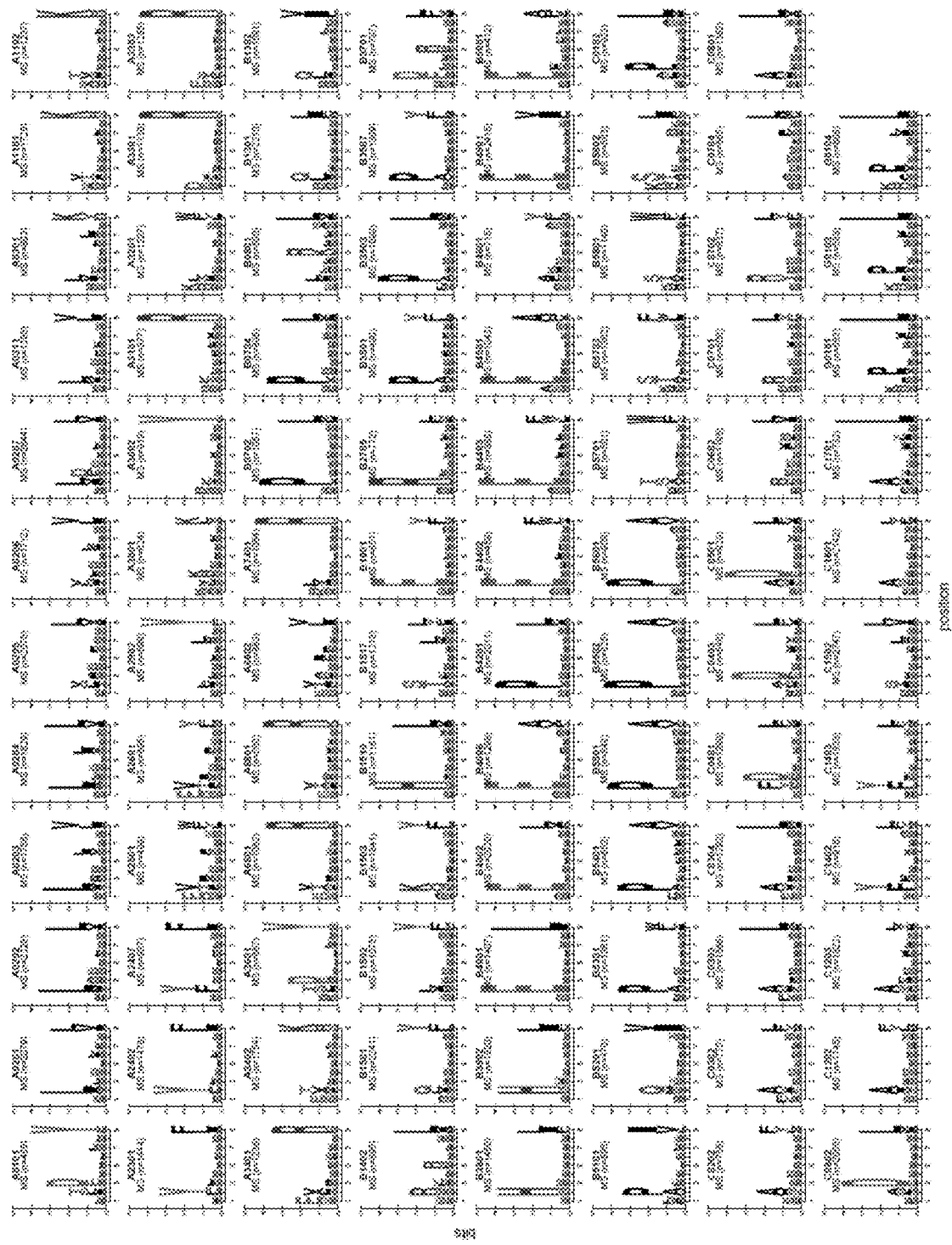
FIG. 10—Profiled 9 mer alleles and motifs.
Figure 11:
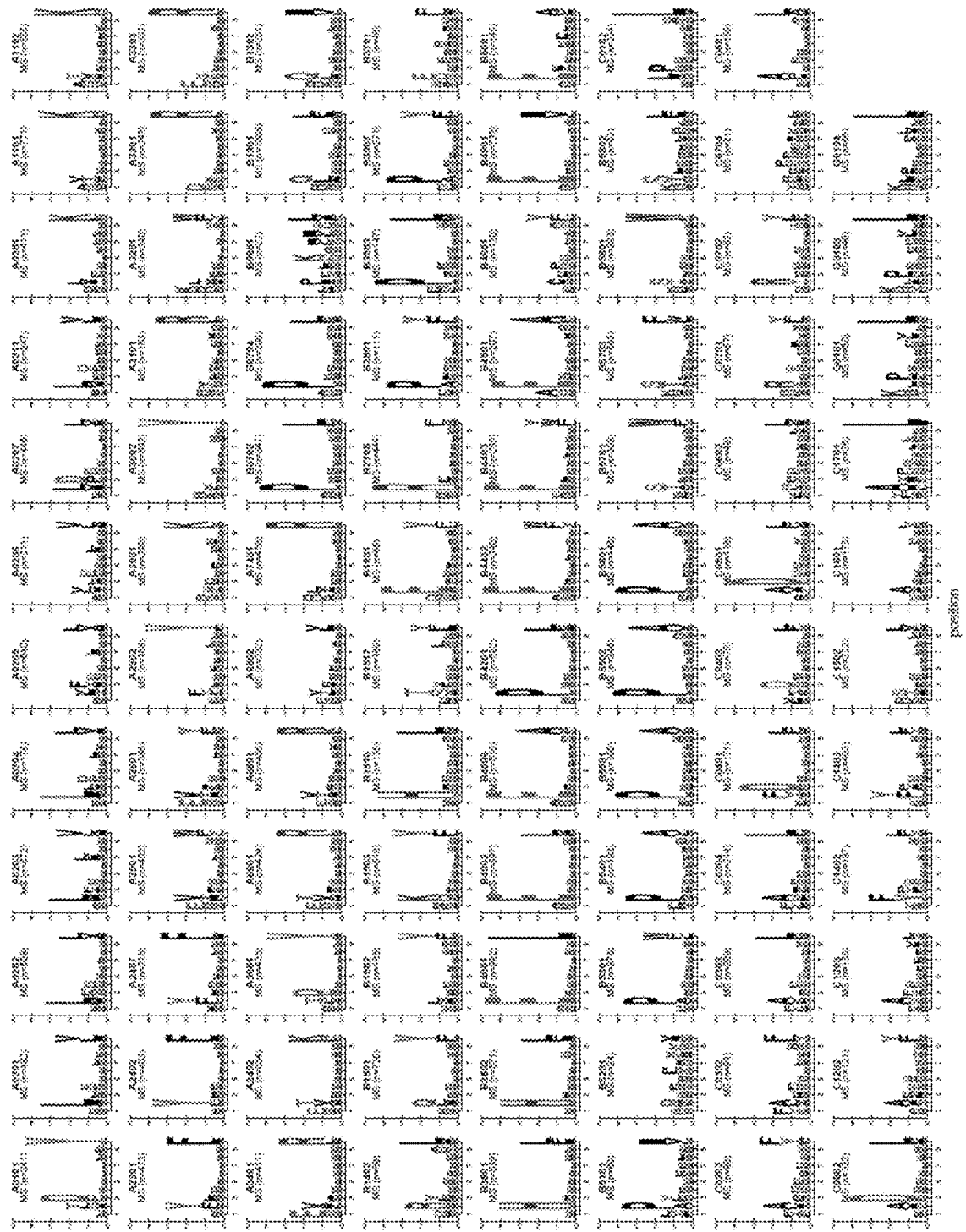
FIG. 11—Profiled 10 mer alleles and motifs.
Figure 12:
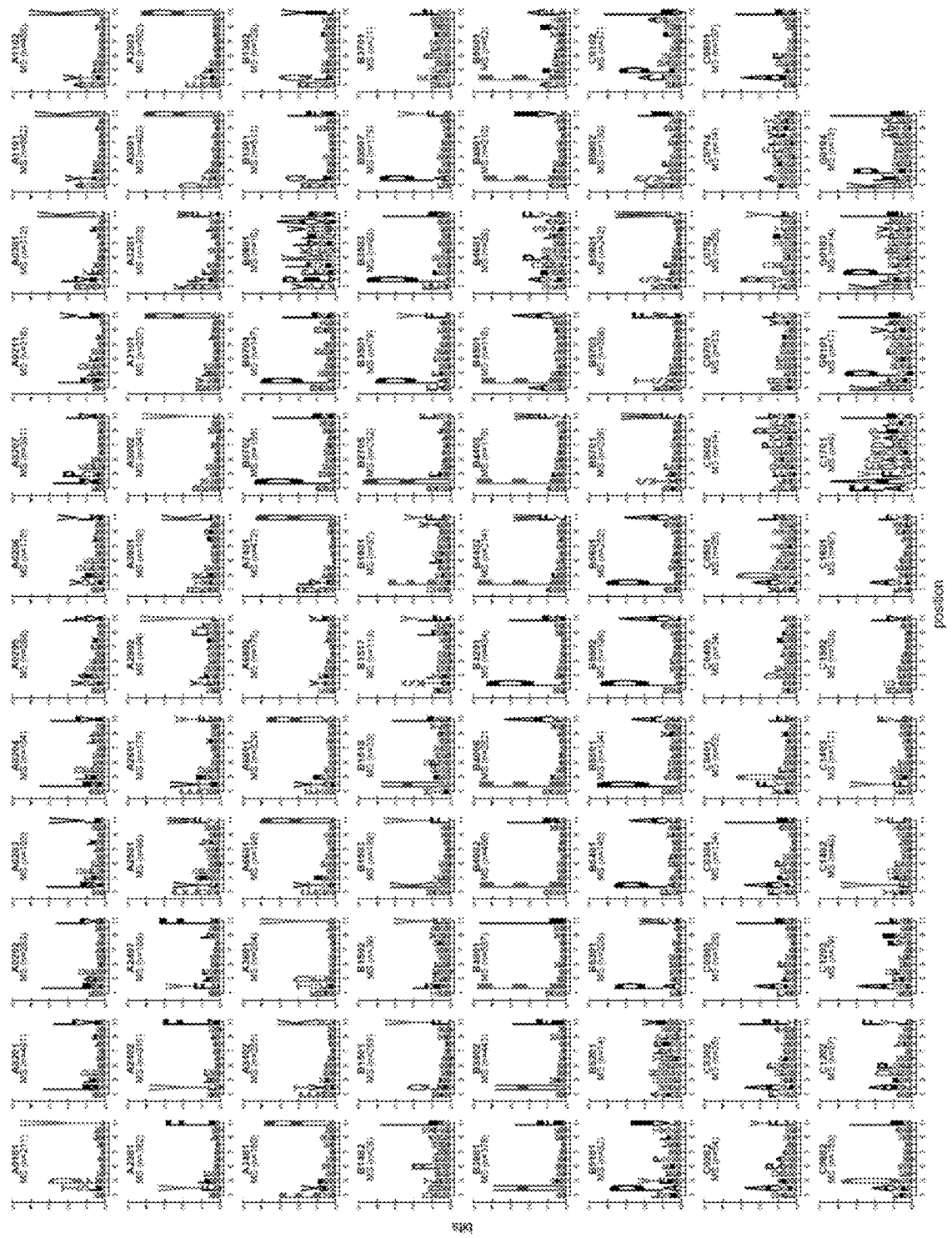
FIG. 12—Profiled 11 mer alleles and motifs.
Figure 13:
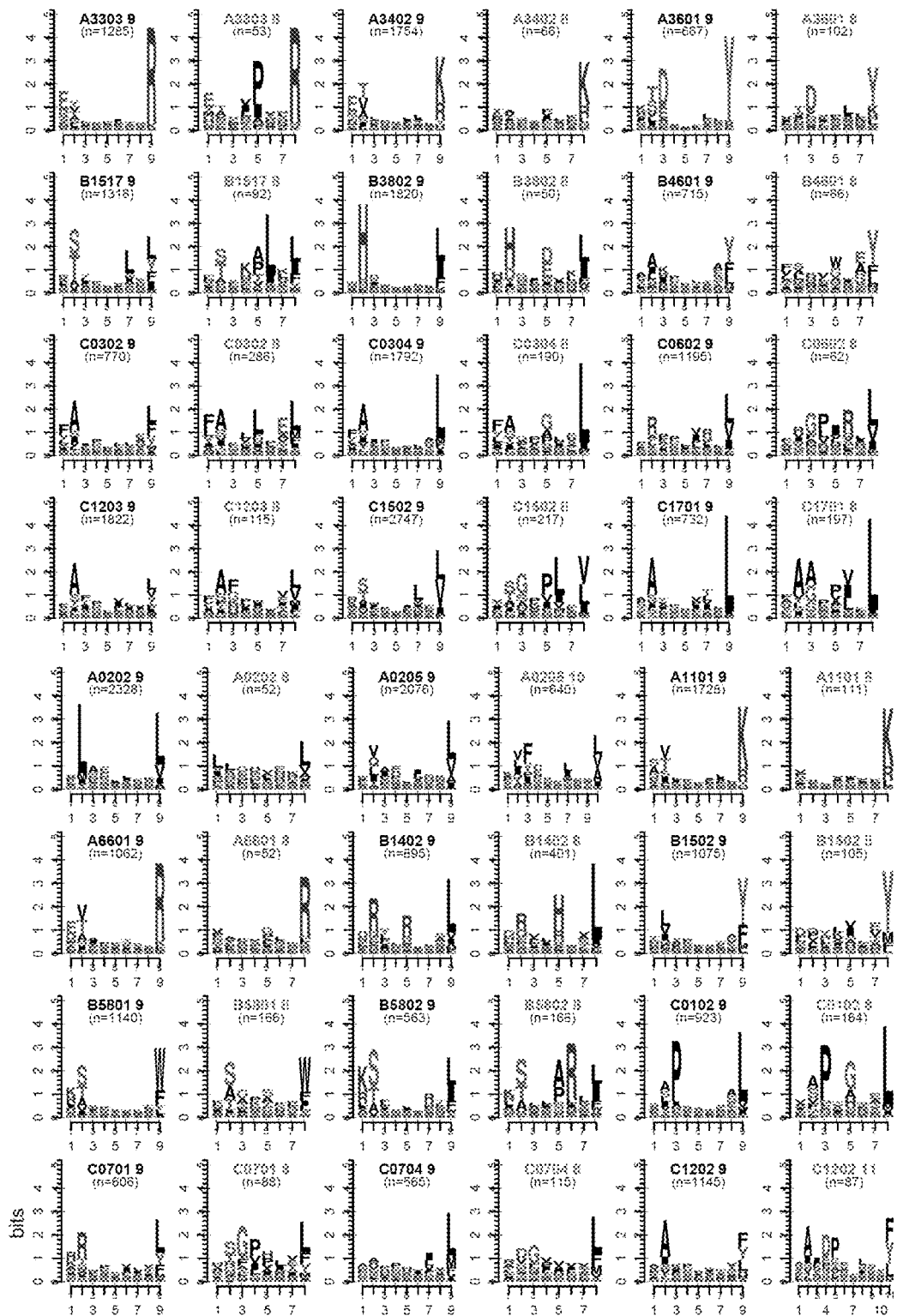
FIG. 13—Alleles with length-specific motifs identified amongst the profiled alleles and motifs. Sequence logos show pairwise comparisons of the 9-mer peptide motif and the non-9-mer motif detected to be different. A alleles tend to have peptides of length 9, 10, and 11. B alleles bind lengths 8 to 12. C alleles present mainly length 8, and 9.
Figure 14:
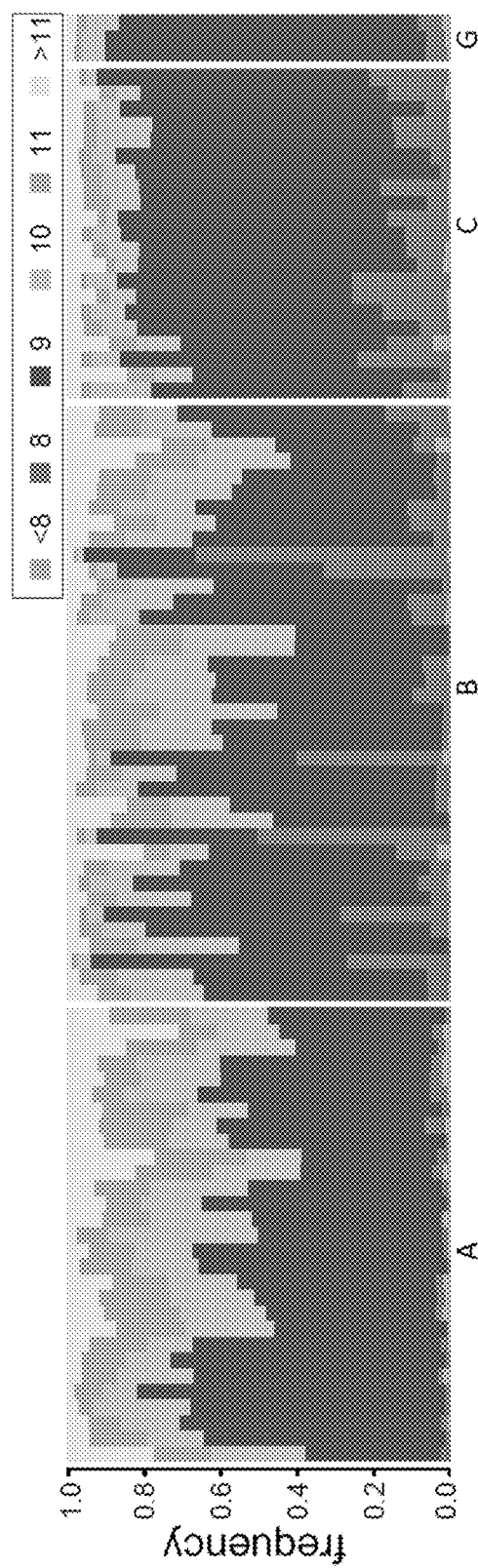
FIG. 14—Peptide length distribution per allele. The frequency of MS-identified peptides of each of the most common binding lengths for HLA class I (8-11) per HLA allele are grouped per HLA gene. Some alleles have the strongest preference for peptides of lengths other than 9. HLA-A alleles present more peptides of length 10 and 11 than B and C alleles. HLA-B and C alleles accommodate shorter peptides better than HLA-A alleles. Differences in the ability to accommodate ligands of various lengths detected amongst HLA-A, B, and C genes.
Figure 15:
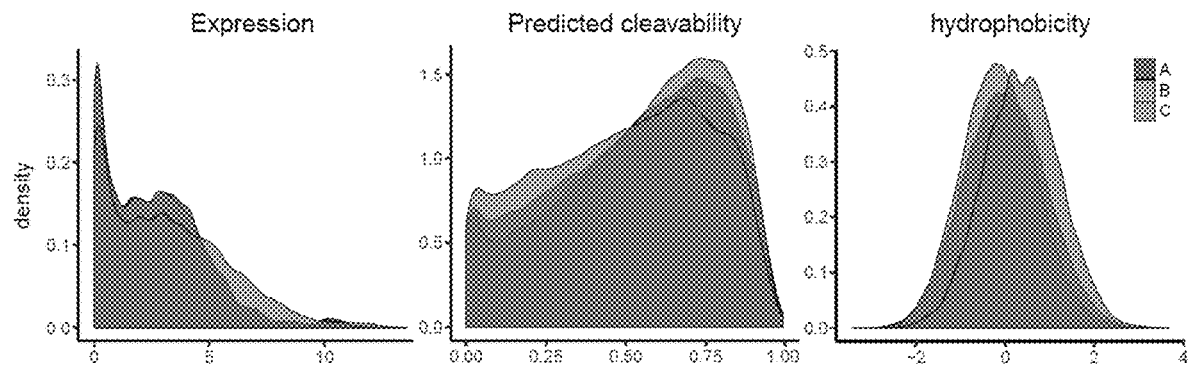
FIG. 15—The distribution of expression (based on RNA-seq), predicted cleavability and hydrophobicity for identified across all alleles. HLA-C alleles bind peptides from proteins with higher expression levels than A, B or G alleles and tend to be more hydrophobic. Intracellular signals, such as expression and proteasomal cleavage, significantly increase the power for predicting endogenously presented epitopes.
Figure 16:
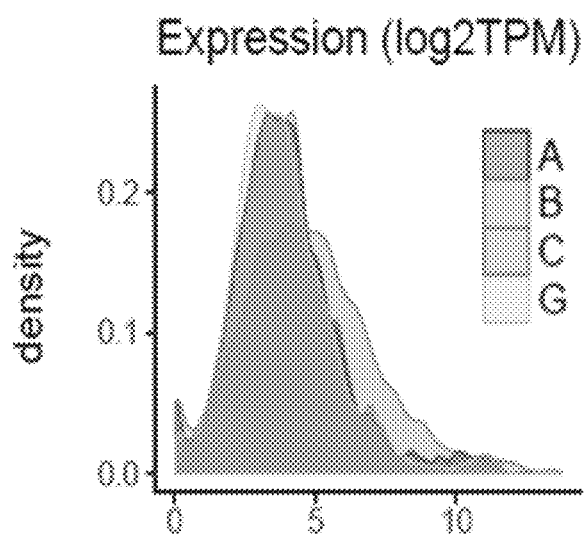
FIG. 16—RNA-Seq. HLA-C alleles favor peptides derived from proteins with higher RNA expression. C alleles have a more shallow binding cleft.
Figure 17:
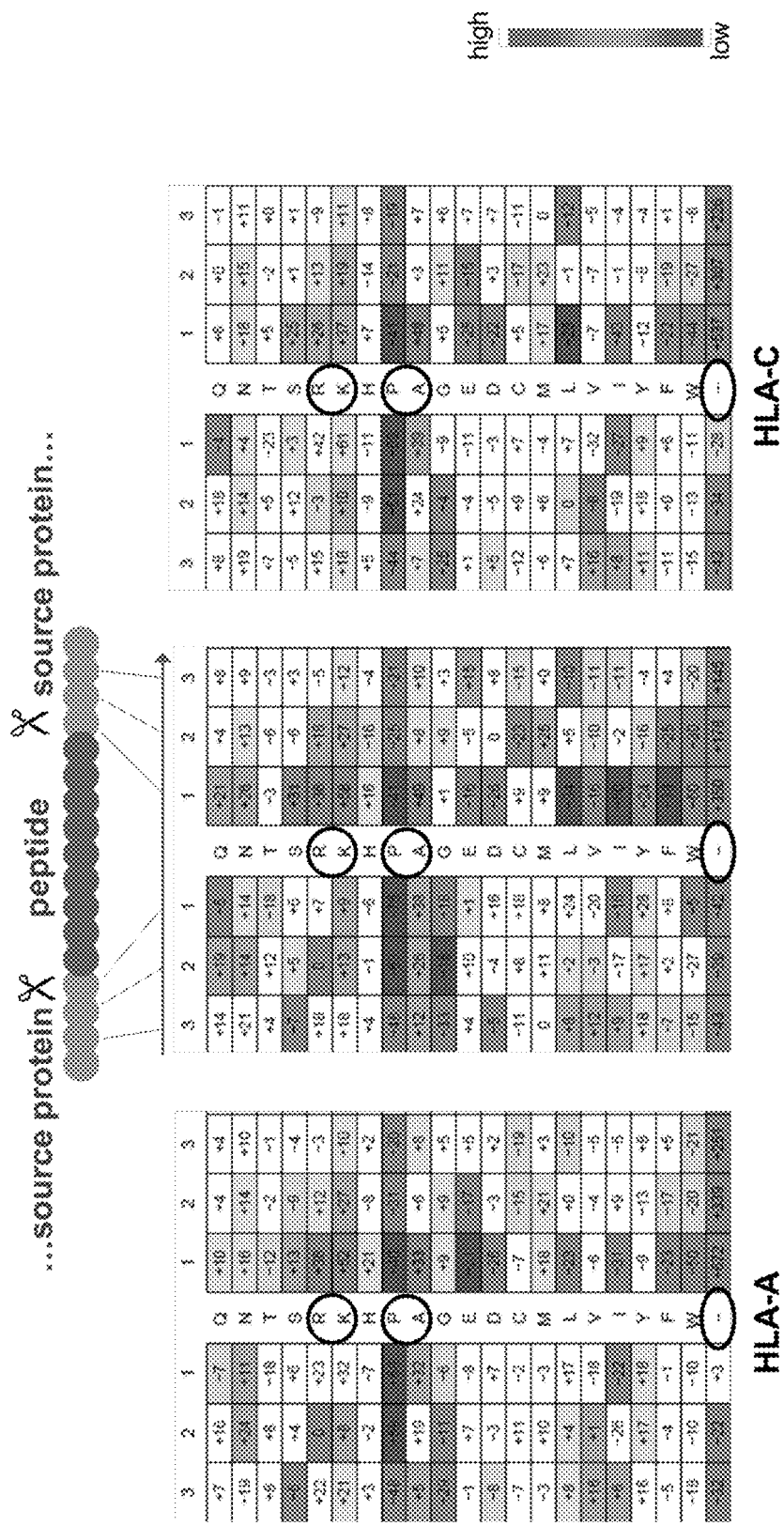
FIG. 17—Cleavage profiles are very similar across HLA-A,B,C alleles. No difference between HLA alleles. Proteasome cleavage happens before peptide loading in the ER. Amino acid distribution up and downstream of HLA-presented peptide. R/K/A are preferred cleavage sites.
Figure 18:
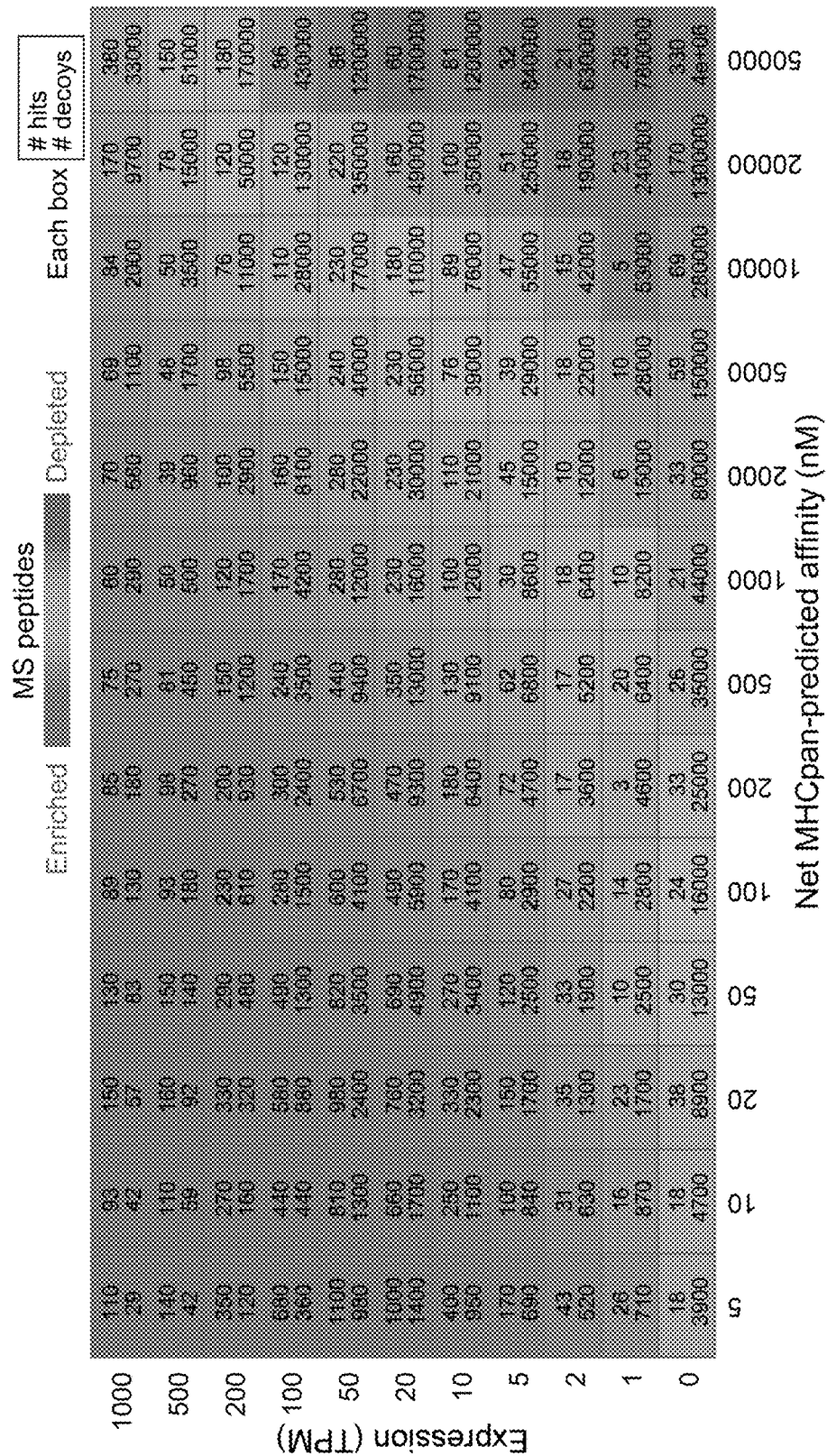
FIG. 18—Hits and decoys are binned according to source transcript expression (based on RNA-seq) and predicted affinity for each allele. Per bin, hit (top) and decoy (bottom) counts are reported. Color is according to the hit:decoy ratio (red: enriched for hits; blue: depleted of hits). High expression compensates for low affinity and vice versa.
Figure 19:
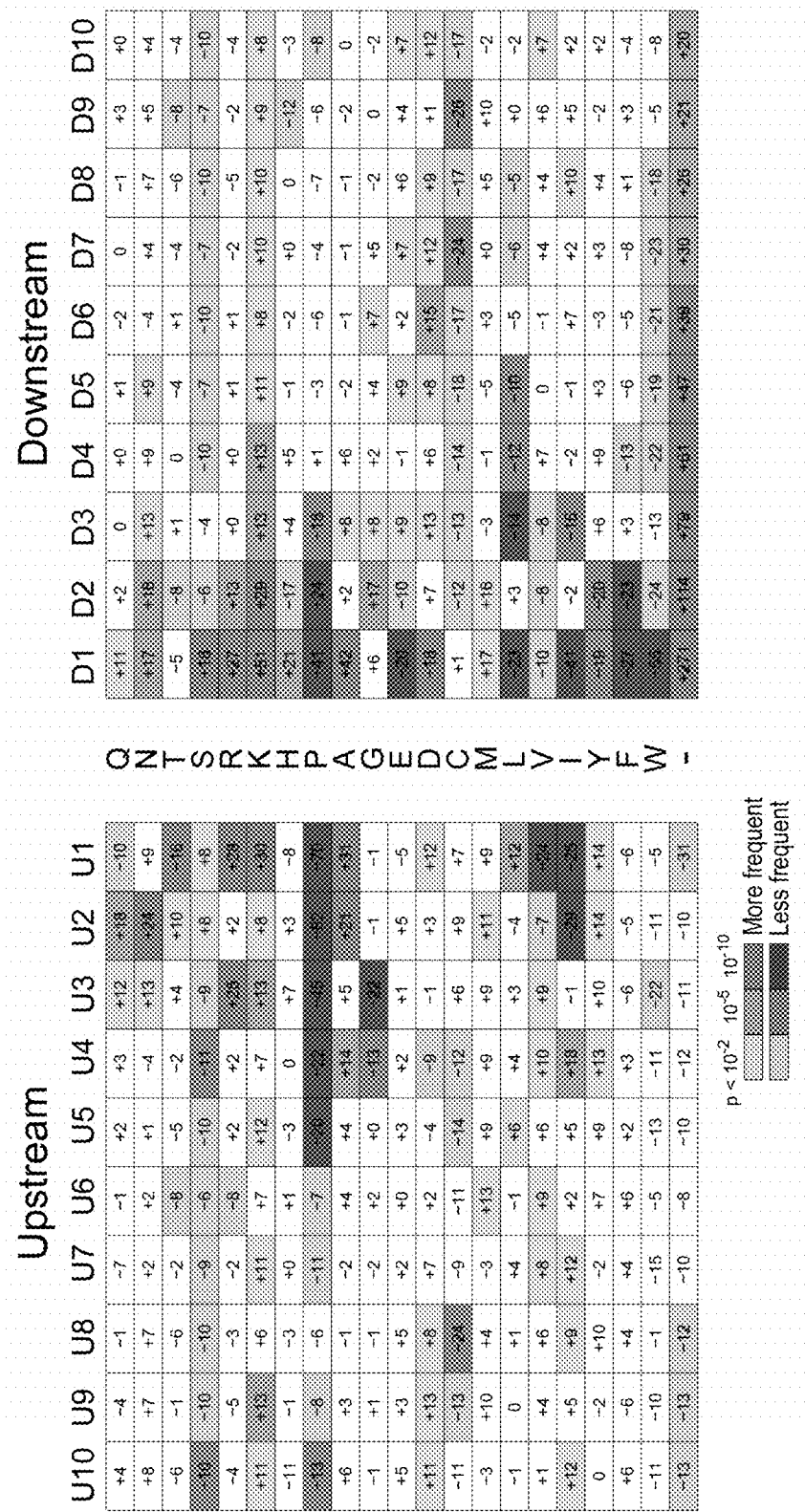
FIG. 19—Heatmap of amino acids frequencies (percent change relative to background) in the protein sequence context (upstream: U10-U1; downstream D1-D10) of HLA peptides identified from mono-allelic cell lines. Colors of heatmap cells indicate directionality (red: enriched; blue: depleted) and p value (see key).
Figure 20:
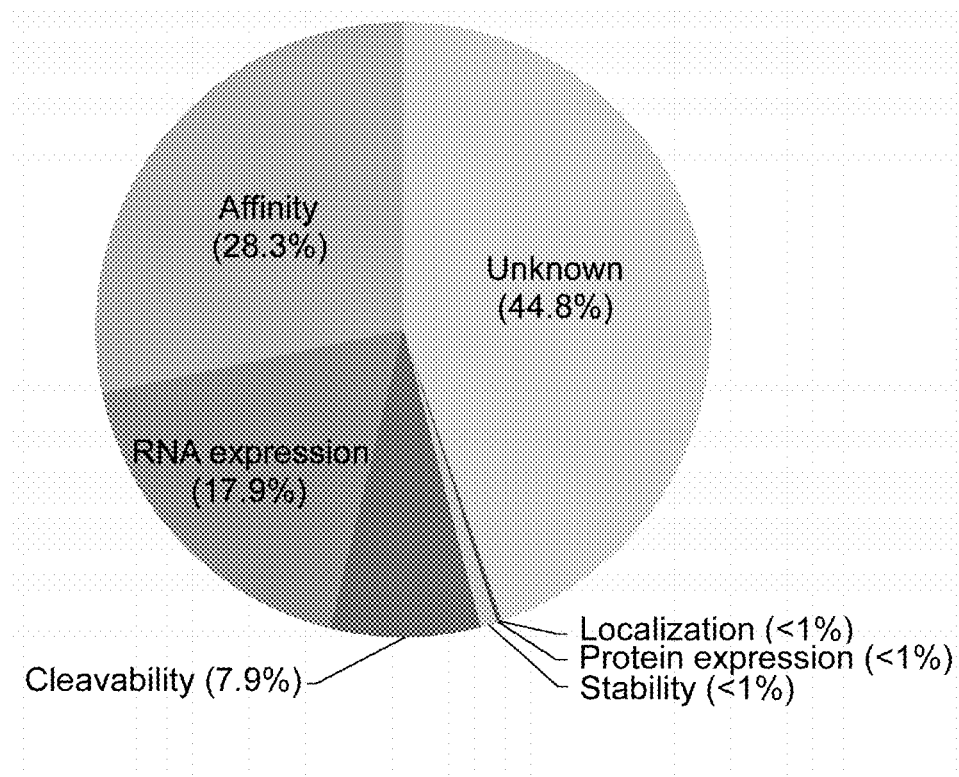
FIG. 20—Contribution of endogenous signals to positive predictive value determined by training linear models, adding the most important feature at a time.
Figure 21:
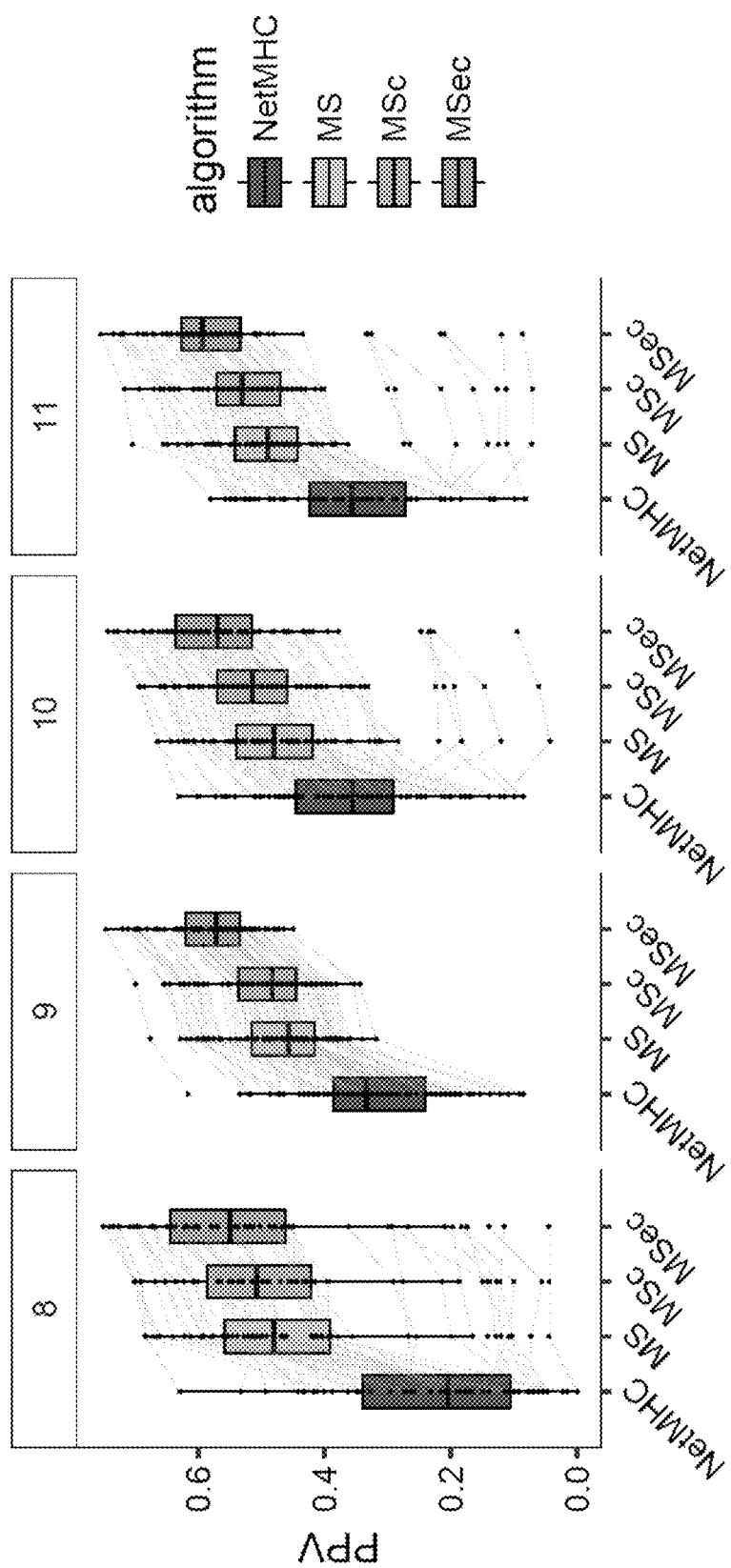
FIG. 21—Neural network models trained on the mono-allelic data outperform state of the art NetMHCpan4-0 algorithm. Gains increase when the likelihood of proteasomal cleavability (C) and expression (E, RNA-seq) are integrated into the model.
Figure 22:
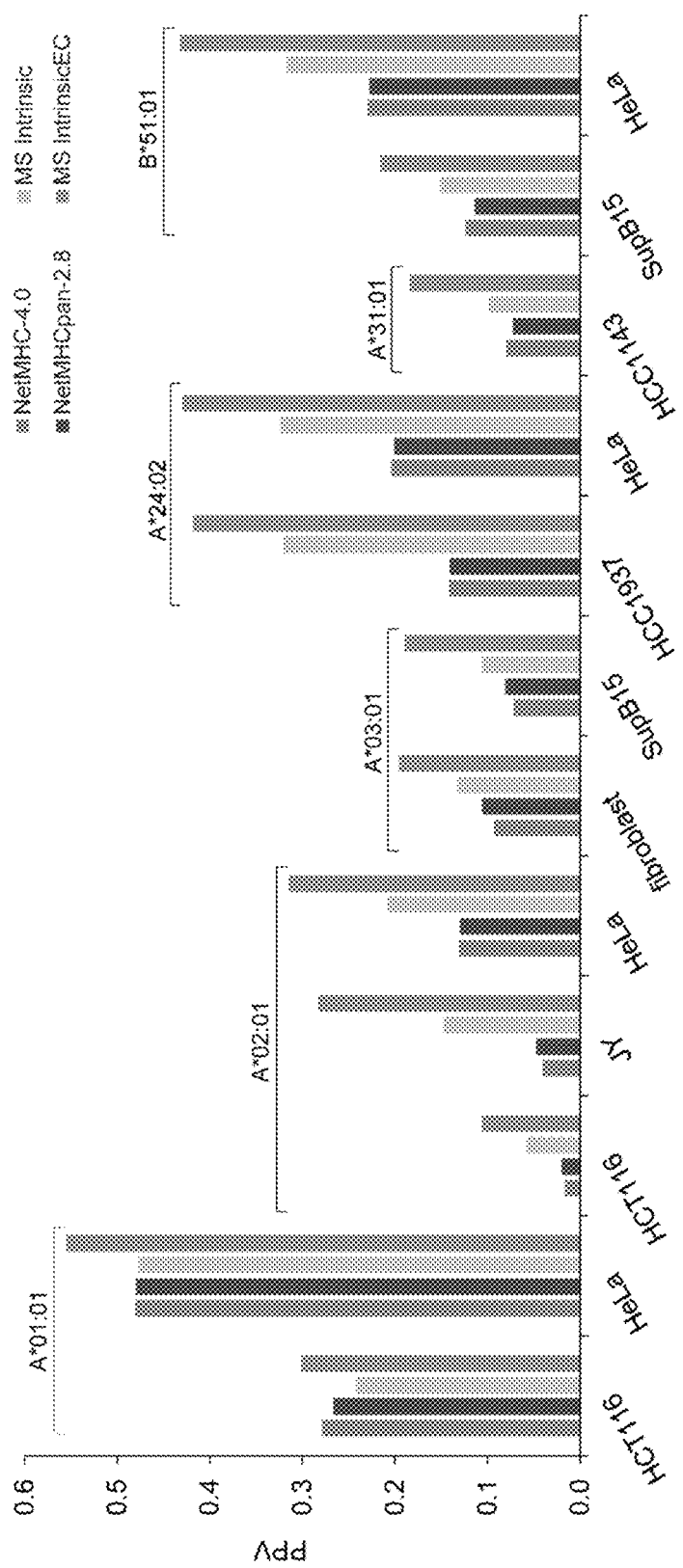
FIG. 22—The ability of Applicants' models to correctly identify peptides presented on HLA were evaluated on external MS datasets spanning multiple cell lines and alleles with a 2× gain in PPV on average.
Figure 23:
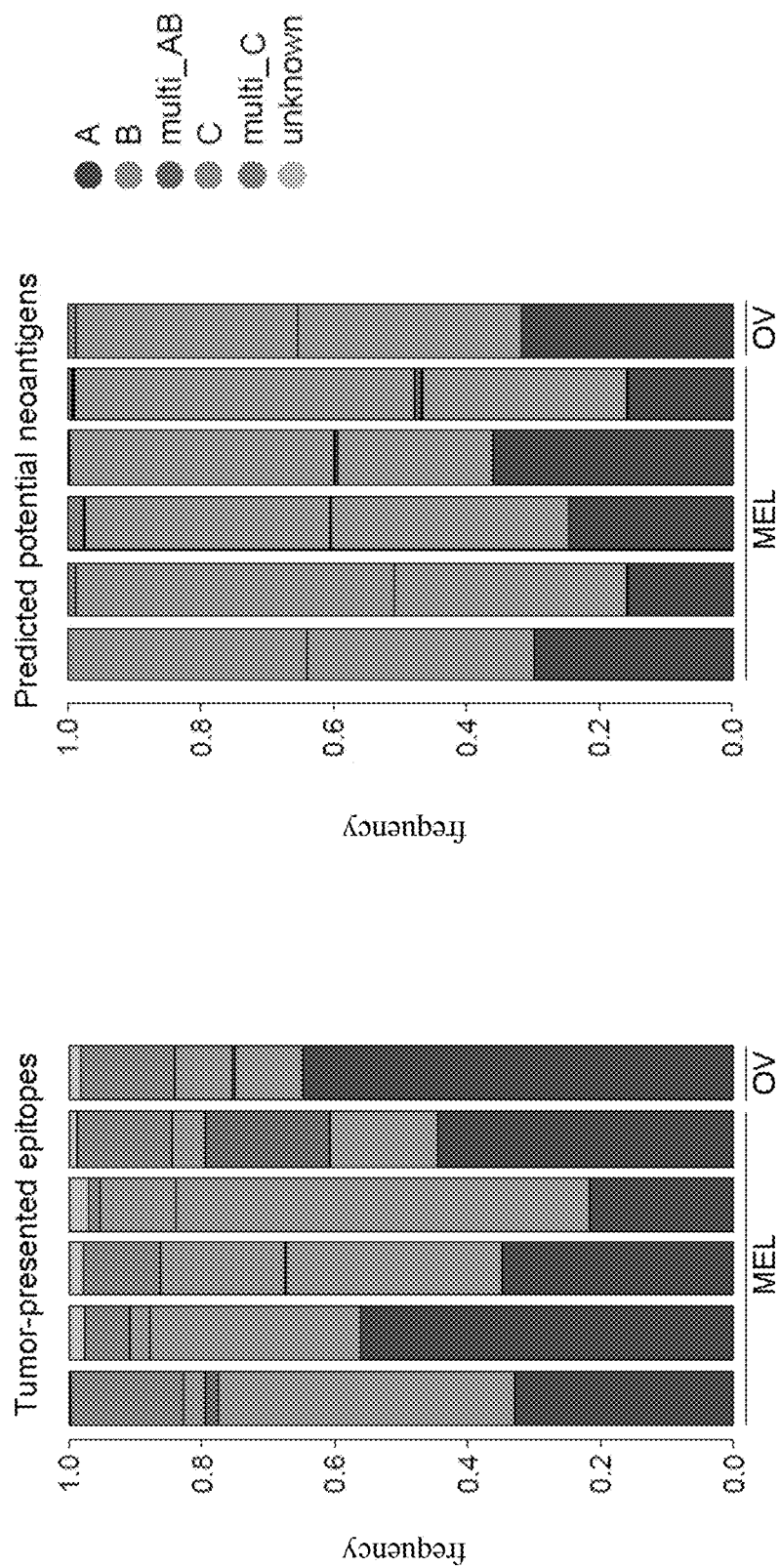
FIG. 23—Applicants evaluated the propensity of HLA-A, B, and C allele to present peptides on the cell surface of fives melanoma and one ovarian patient-derived tumor cell lines. HLA-C peptide amount to 8% of presented peptides while A and B alleles present more than 45% and 33% respectively (left). This is not driven by the identity of tumor specific peptides since peptides derived from tumor-specific mutations distribute evenly across HLA genes (right). Patient-derived tumor cell lines present epitopes on HLA-C alleles.
Figure 24:
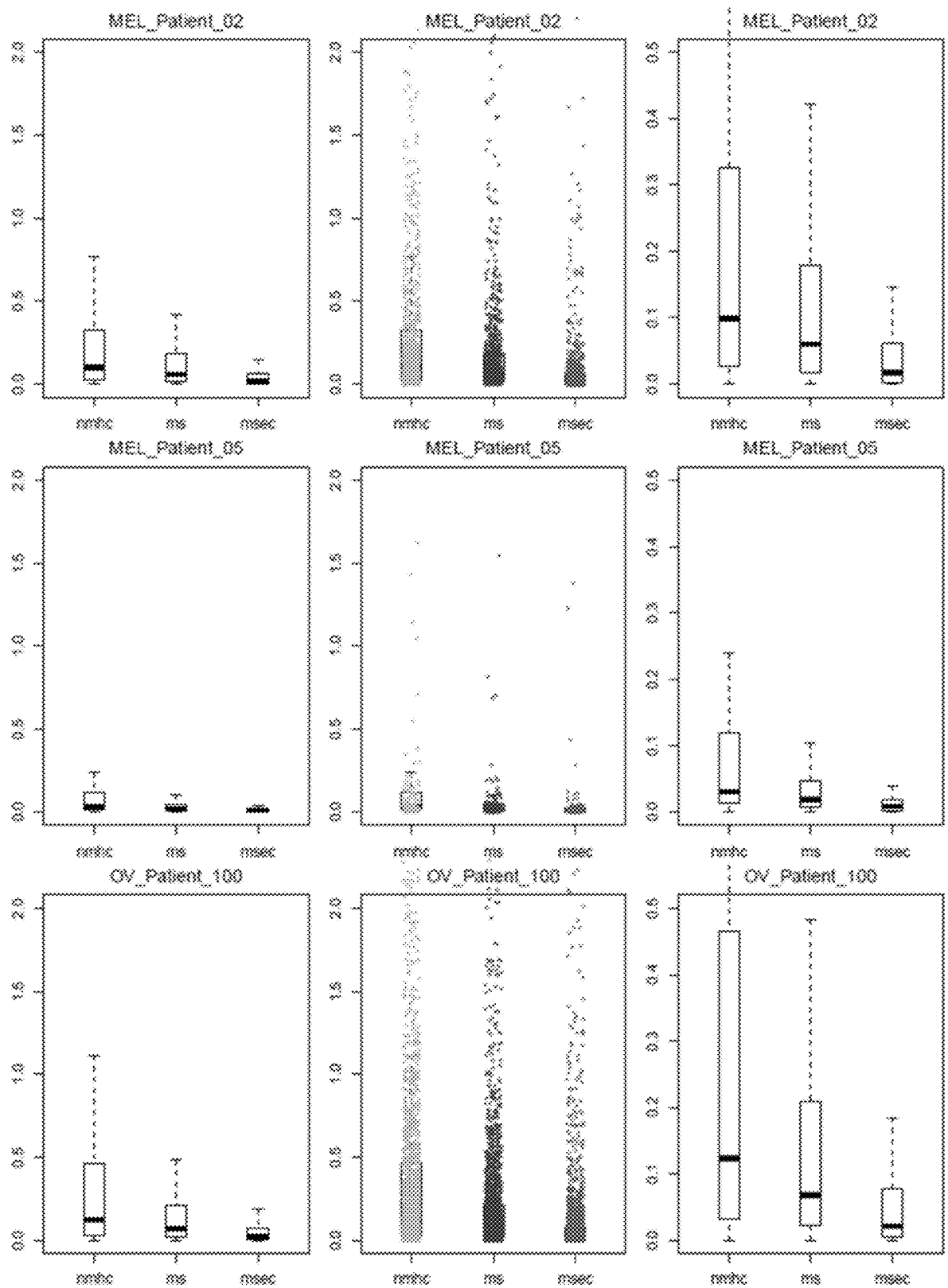
FIG. 24—Model performance on patient discovery data.
Figure 25:
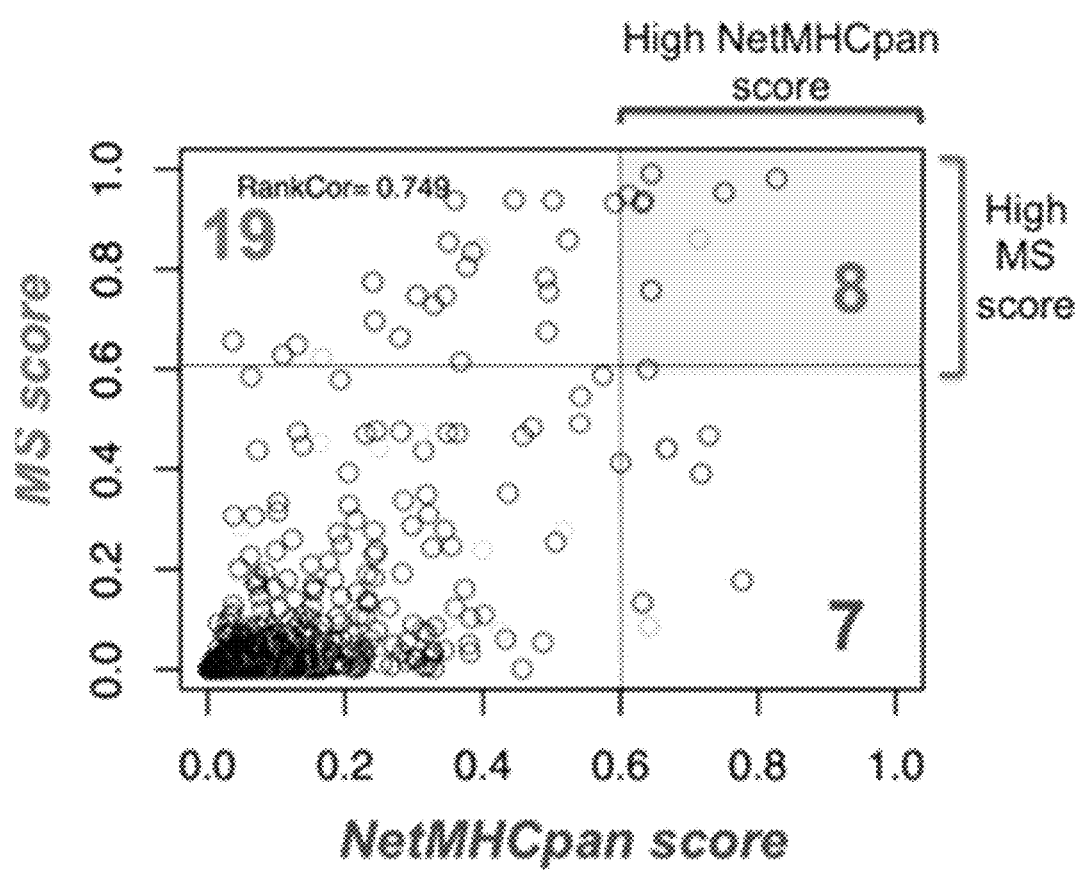
FIG. 25—Comprehensive peptide binding data to single alleles improves antigen prediction. Improvements due in part to inclusion of expression and proteasome cleavability.
Figures 26A, 26B, 26C, 26D:
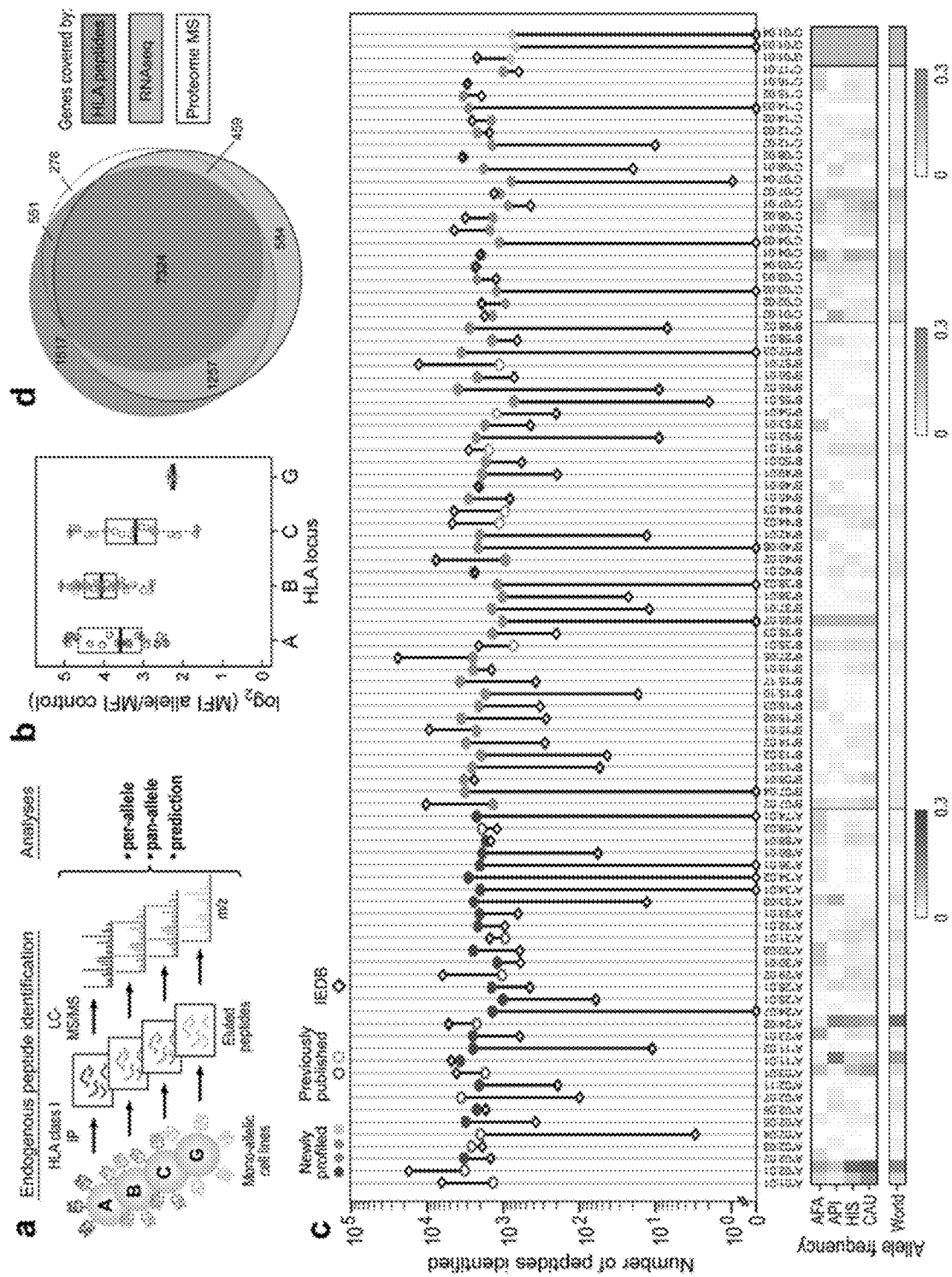
FIGS. 26A-26D—Mass spectrometric characterization of peptides eluted from HLA proteins in mono-allelic cell lines.

The newly generated data nearly doubles the HLA ligands recorded in the Immune Epitope Database (IEDB) which holds 208,885 ligands from 157 human class I alleles, with a mean of 200 peptides per allele (range 1-24,594). Peptides for 80 of 95 alleles were available in IEDB; however, 33 of 95 alleles had fewer than 100 known binders, which hindered reliable motif deduction and accurate de novo prediction (FIG. 26D). For the 15 previously uncharacterized alleles, Applicant identified 1,845 peptides per allele on average (range 693-4,022). From the compiled dataset, Applicant systematically assessed the length distribution, positional entropy, residue frequencies, binding motif, and sub-motif clusters of HLA-bound peptides per allele (FIG. 32I-32L) and created an interactive website for data exploration (mhc.tools). Altogether, these data and tools greatly expand the current knowledge of HLA class I-bound peptides and are publicly available. These tools provide further information on the identified peptides as discussed herein and in sequence listing.

Figures 27A, 27B, 27C, 27D:
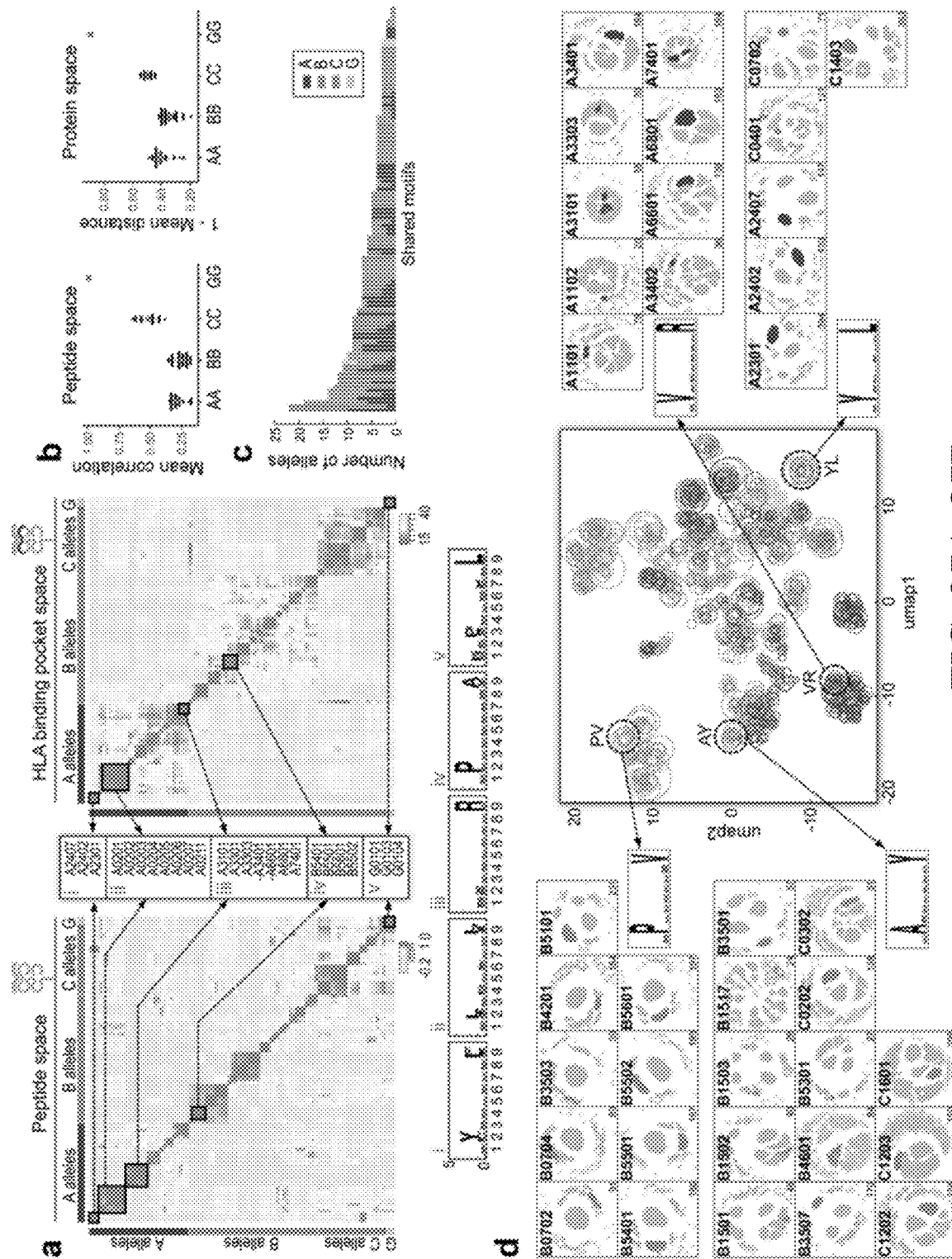
FIGS. 27A-27D—Identification of shared motifs and submotifs amongst HLA-A, B, C and G alleles.
Figure 33A:
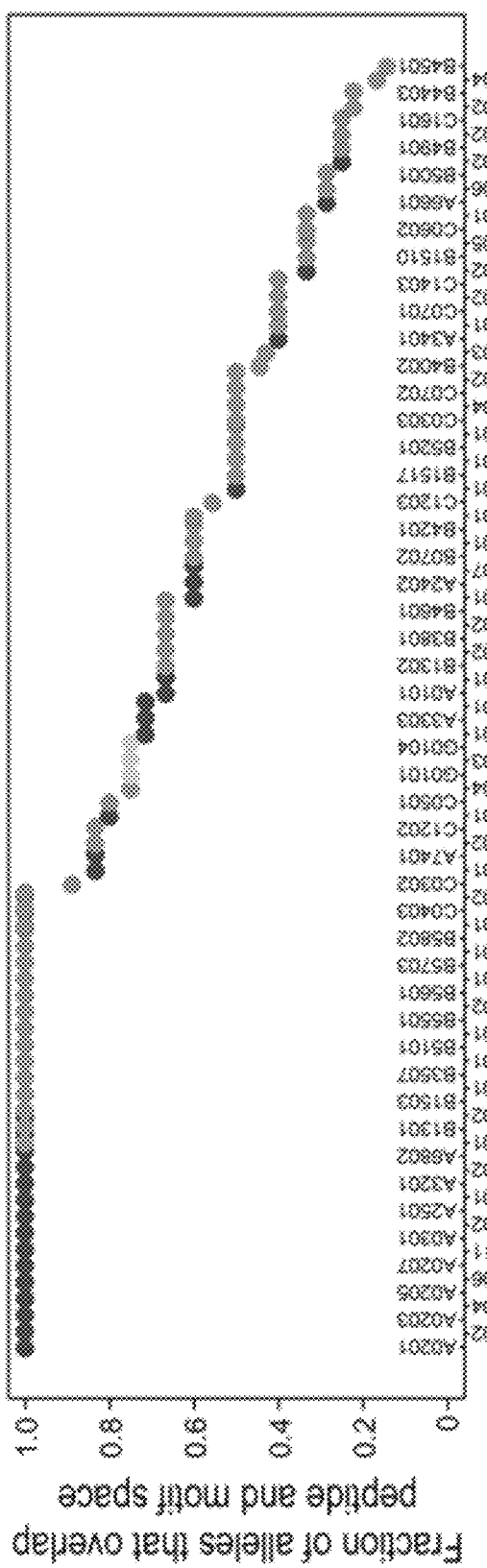
FIGS. 33A-33C—FIG. 33A) Fraction of neighbor alleles in motif space that are also neighbors in HLA-binding pocket space.

Identification of HLA Binding Motifs and Sub-Motifs that were Shared Across Alleles Since the numbers of peptide identifications per allele were only weakly correlated with surface HLA levels (Spearman's ρ=0.44, p<0.001, n=79 newly generated cell lines), differential binding potential likely contributes to the variation in peptide numbers (FIG. 32M-32N). To better understand the basis for differential binding, Applicant compared HLA alleles based on the motifs of their observed ligands and the physicochemical properties of binding pocket residues in the HLA protein. By computing pairwise correlations between the peptide binding motif of each allele (represented as a vector of frequencies of the 20 amino acids at every position), Applicant found groups of alleles sharing unique HLA-A and -B motifs (FIG. 27A—left). HLA alleles belonging to supertypes such as HLA-A*02 clustered together (FIG. 27A—inset ii) as did split antigen serotypes such as HLA-B*54,55,56 and HLA-A*23,24 (FIG. 27A—inset i, iv) (Sette and Sidney 1998; Robinson et al. 2015; Robinson et al. 2000). The pairwise correlations showed minimal motif sharing outside of the dominant groups (mean motif correlation of each HLA-A allele to all other -A alleles; and each HLA-B allele to all other -B alleles was 0.28 and 0.25, respectively, FIG. 27B-left). HLA-C motifs were more similar to each other (mean correlation 0.51), thus sharing more overlapping motifs, consistent with previous studies indicating that HLA-C (and HLA-G) alleles were more evolutionarily recent, with less divergence amongst alleles (Parham, P. & Moffett, A. Variable NK cell receptors and their MHC class I ligands in immunity, reproduction and human evolution. Nat. Rev. Immunol. 13, 133-144 (2013)). The patterns of similarity revealed by binding motifs were mirrored by similarities in the HLA binding clefts, quantified by physicochemical properties of HLA residues in contact with the ligand (FIG. 27A—right;

FIG. 27B—right). To assess the agreement of the two approaches, for each allele, Applicant counted the number of neighboring alleles in motif space analysis that were also proximal in pocket space (FIG. 33A). This correspondence maps the rules of ligand preference onto HLA protein sequence and serves as the basis for creating pan-allele predictors that rely on transfer learning from characterized to uncharacterized alleles (Nielsen et al. 2007).

Figure 33B:
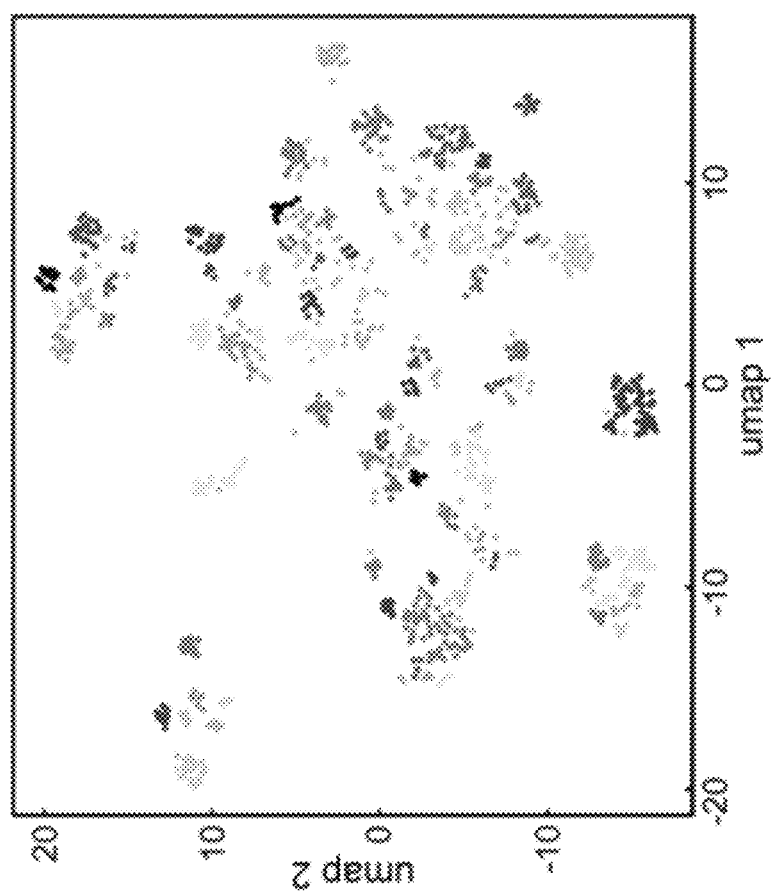
Figure 33B:
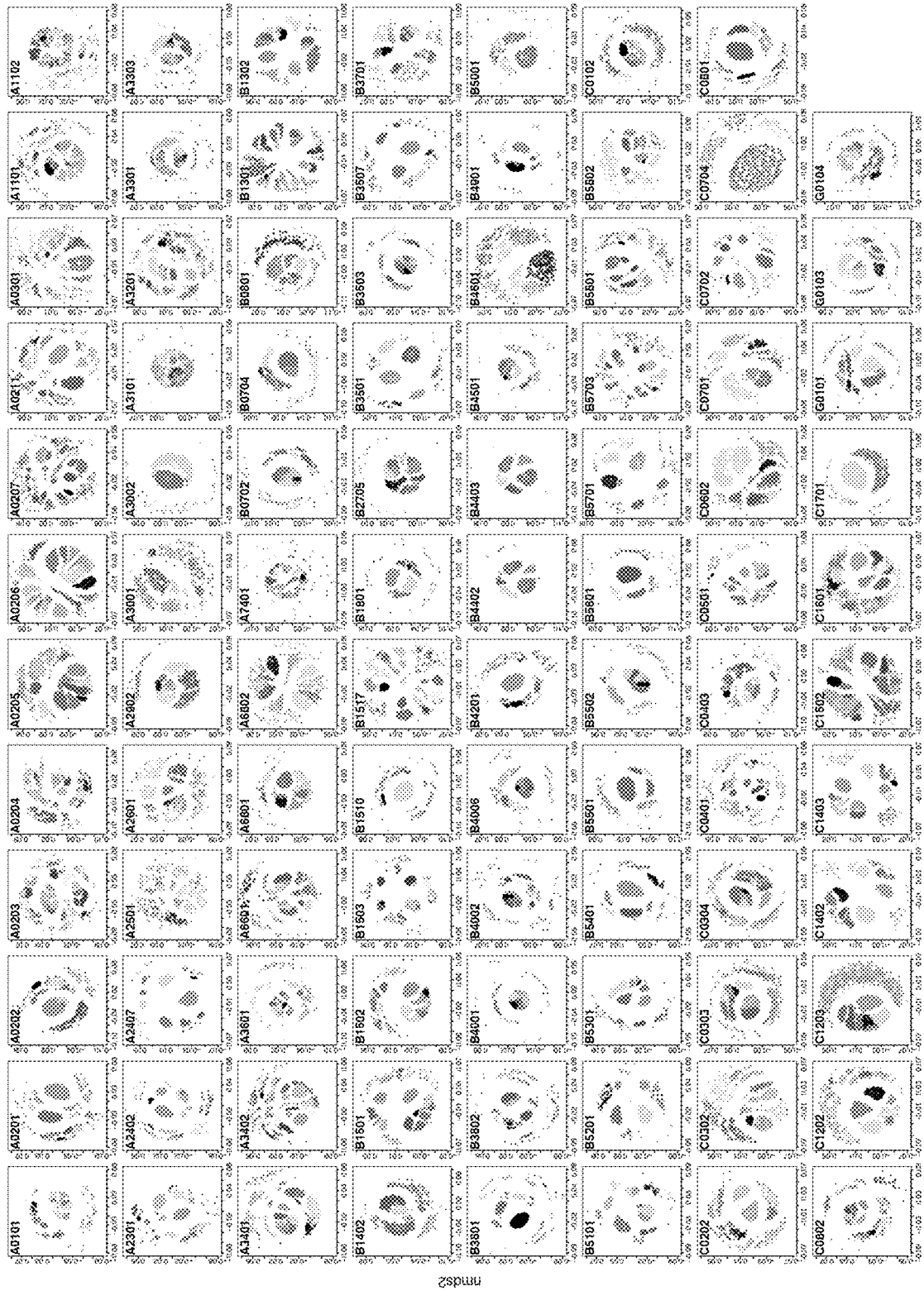

To delineate allele similarity at finer granularity, Applicant decomposed each aggregate motif per allele into sub-motifs by computing inter-peptide distances, projecting them onto 2-dimensional space of peptide coordinates and clustering the peptides, obtaining 1,133 submotifs (>20 peptides per cluster) across the 95 alleles (FIG. 33B). More than half of the clusters containing motifs originating from HLA-A or -B alleles were contributed solely by either HLA-A alleles or HLA-B alleles (FIG. 27C). For example, the motif xVxxxxxxR was found to be shared across subclusters amongst the -11:01, -11:02, -31:01, -33:03, -34:01, -34:02, -66:01, -68:01, and -74:01 alleles of HLA-A; likewise, the motif xPxxxxxxV was shared by subclusters amongst the -07:02, -07:04, -35:03, 42:01, 51:01, -54:01, -55:01, -55:02 and -56:01 alleles of HLA-B. The majority of submotifs that included HLA-C alleles overlapped with subclusters from HLA-A and/or -B alleles (e.g. xYxxxxxxL is shared amongst A*23:01, A*24:02, A*24:07, C*04:01, C*07:02, C*14:03; xAxxxxxxY was shared amongst B*15:01, B*15:02, B*15:03, B*15:17, B*35:03, B*35:07, B*46:01, B*53:01, C*02:02, C*03:02, C*12:01, C*12:03, C*16:01) (FIG. 27D, FIG. 33C), further reinforcing the notion that HLA-A and -B alleles had more divergent structure than the evolutionarily 'younger' HLA-C alleles. The overlaps in submotifs across alleles lended itself as the basis for optimizing epitope selection such that a minimal set of epitopes covers an optimal set of multiple alleles and thus individuals.

Figures 28A, 28B, 28C:
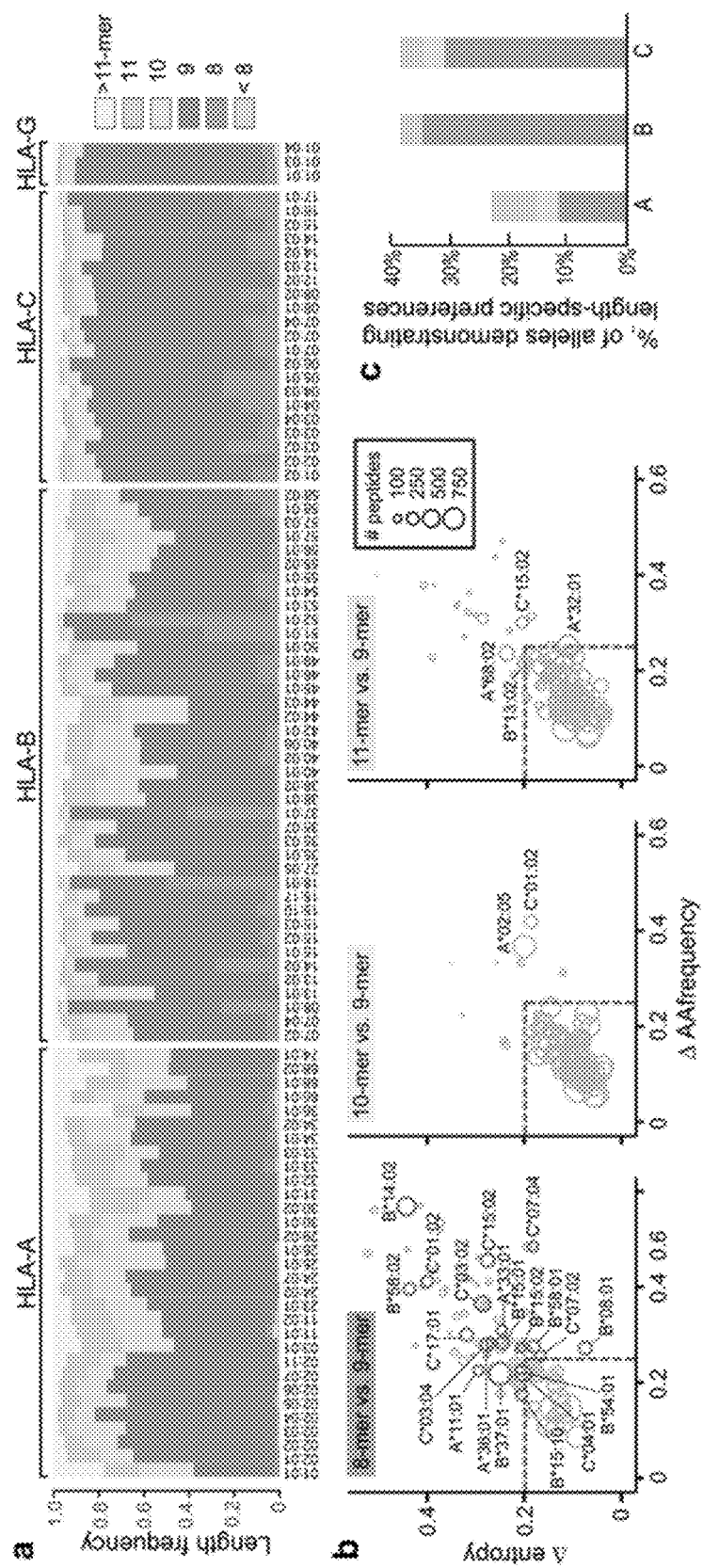

Length-Specific Differences in Ligand Preferences were Detectable Among HLA Alleles and Loci Preferences for varying peptide lengths were observed for specific alleles, with 9-mer peptides as the prevailing HLA ligand length. Unbiased evaluation of length distributions per allele in the dataset of 12,970 8-mers, 111,898 9-mers, 29,956 10-mers, and 18,202 11-mers (FIG. 28A), revealed that 9-mers were consistently the predominant length across alleles, except for a small number of HLA-B alleles that preferred 8-mers. After 9-mers, 10- and 11-mers were frequently found for HLA-A and -B alleles with B alleles having greater variation in length preferences, while 8-mers predominated for HLA-C alleles (p<0.001 all comparisons, Welch's two sample t-test). Applicant also found length-specific variations in motifs. To systematically identify potential length-specific binding motifs, Applicant generated pseudo motifs by dropping middle residues from 10- and 11-mers to compare to 9-mers or from 9-mers to compare to 8-mers, and evaluated the changes in frequency and entropy at every peptide position (FIG. 28B). This analysis yielded 26 differences across HLA-A, -B, and C alleles (20 8-mer, 2 10-mer, and 4 11-mer motifs) out of 178 motifs with at least 100 identified 8-, 10-, or 11-mer peptides, that had an absolute difference in residue frequency with the true 9-mer motif of >0.25 or an absolute difference in entropy of >0.2 at any position (FIGS. 28B-28C). The most notable changes in entropy were at position 5 for 8-mers compared to 9-mers (p<10-8, FIG. 34A). This residue position was implicated in structural changes of certain HLA-alleles upon binding as it allowed embedding of these short peptides in the cleft (Rist et al. 2013; Maenaka et al.

2000). For example, Applicant found the A*33:01 8-mer motif (n=112) to had a strong preference for proline and isoleucine at position 5 which is absent in the 9-, 10-, or 11-mer motifs. B*14:02 8-mers (n=401) were enriched in histidine at position 5 and lacked tyrosine enrichment at position 2 compared to the 9-mer motif (n=913). C*01:02 gained proline as an additional anchor residue in position 3 for all lengths, 8-mers (n=164) had glycine or alanine preference at position 5 whereas most 10-mers (n=224) contained leucine (11-mers alanine and leucine) instead of alanine or serine in position 2. Selected peptides were confirmed as strong binders in in vitro binding assays, despite poor predicted affinity by NetMHC (FIGS. 28D-28E; FIG. 34B). Collectively, these observations motivated a more explicit approach of modeling HLA peptide binding characteristics of different lengths.

Peptide-Extrinsic Properties Varied Per HLA and Length

Since HLA-bound peptides captured from the cell surface were reflective of the cell-endogenous processes that shape the ligandome, Applicant assessed whether HLA-A, -B, —C, and -G ligands of different peptide lengths were preferentially derived from peptides with variable extrinsic properties. Applicant found that HLA-C bound peptides were biased towards higher expression and hydrophobicity ($p<1\times10^{-10}$, Welch's two sample t-test; FIG. 28F). HLA-C also showed a preference toward peptides with poorer proteasome cleavability scores ($p=1\times10^{-10}$; Welch's two sample t-test), although an examination of peptide properties stratified by length revealed that this is likely driven by the higher frequency of 8-mer peptides bound by HLA-C alleles as they were observed to have lower cleavage scores (FIGS. 28f-28G; FIG. 34A). These observations agreed with prior structural analyses that have reported more shallow HLA-C binding clefts (Kaur et al. 2017), as higher abundance and elevated hydrophobicity of cognate peptides could compensate for decreased binding stability. Applicant noted that HLA-G peptides had an even stronger bias towards lower cleavability scores ($p<1\times10^{-10}$; Welch's two sample t-test), possibly due to the lack of HLA-G training data for the cleavability predictor and may suggest differential protease activity in shaping the HLA-G ligandome (Celik et al. 2018). Other differences with smaller effect sizes were also observed which altogether prompted Applicants to model extrinsic properties per HLA loci in pan-allele predictors.

Interferon Stimulation had Minimal Impact on Peptide Trimming Signatures

Figures 29A, 29B, 29C:
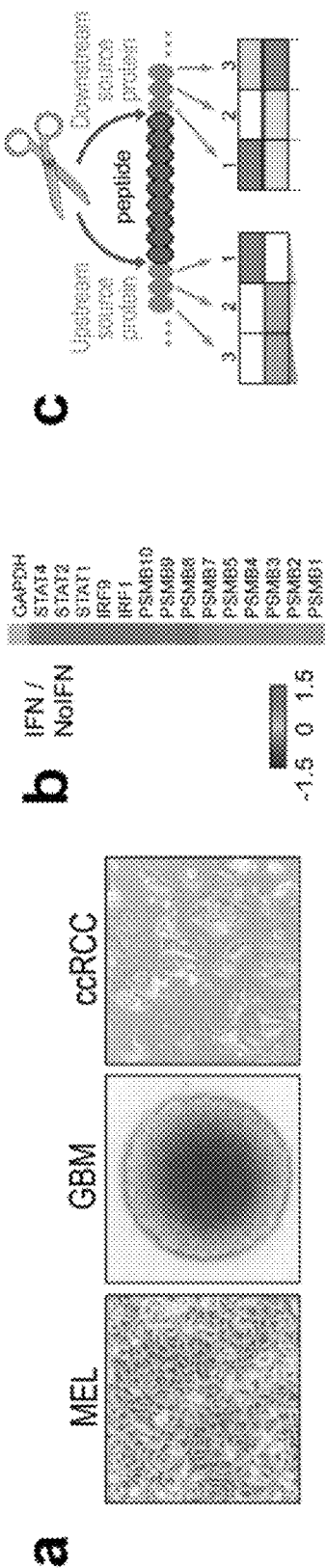
FIGS. 29A-29F—Proteasomal shaping of the HLA-associated peptidome.

Exposure to inflammation can impact proteasomal processing preferences, but the extent to which it alters the HLA-associated peptidome in normal and cancerous human tissues has not been completely elucidated. Therefore, Applicant generated a series of patient tumor cell lines, derived from melanoma (MEL; n=4), glioblastoma (GBM; n=3) and clear cell renal cell carcinoma (ccRCC; n=1) specimens (FIG. 29A), and assessed the effect of IFNγ stimulation on the processing of HLA-bound ligands. As expected, full proteome analysis of one of the GBM samples revealed IFNγ treatment to result in elevated expression of immunoproteasome-specific subunits (PSMB8, PSMB9, PSMB10) and genes involved in interferon regulating pathways (e.g., STAT1, STAT2, STAT4, IRF1, IRF9), along with reduced expression of constitutive proteasome subunits (e.g. PSMB5, PSMB7) (FIG. 29B). Likewise, for all 7 IFNγ-matched samples, Applicant observed an increase of 2.4-5.6% in peptides derived from IFNγ-response genes post stimulation. Applicant also analyzed external datasets from lung epithelial cell lines exposed to IFNγ and TNFα (Javitt et al. 2019) and primary skin fibroblast tissues (Bassani-Sternberg et al. 2015). Finally, Applicant sequenced and examined eluted ligands from a normal primary skin sample.

Figure 29D:
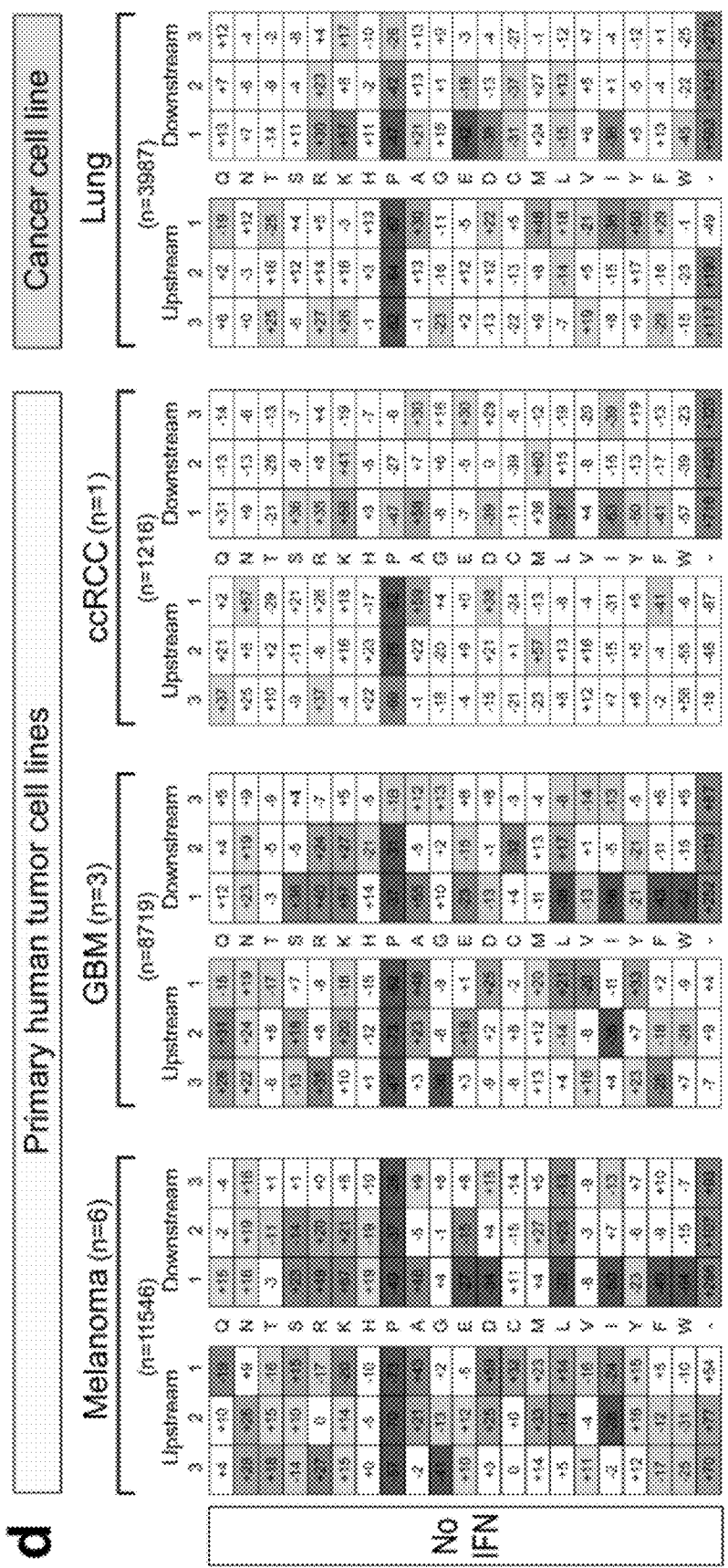
Figure 29D:
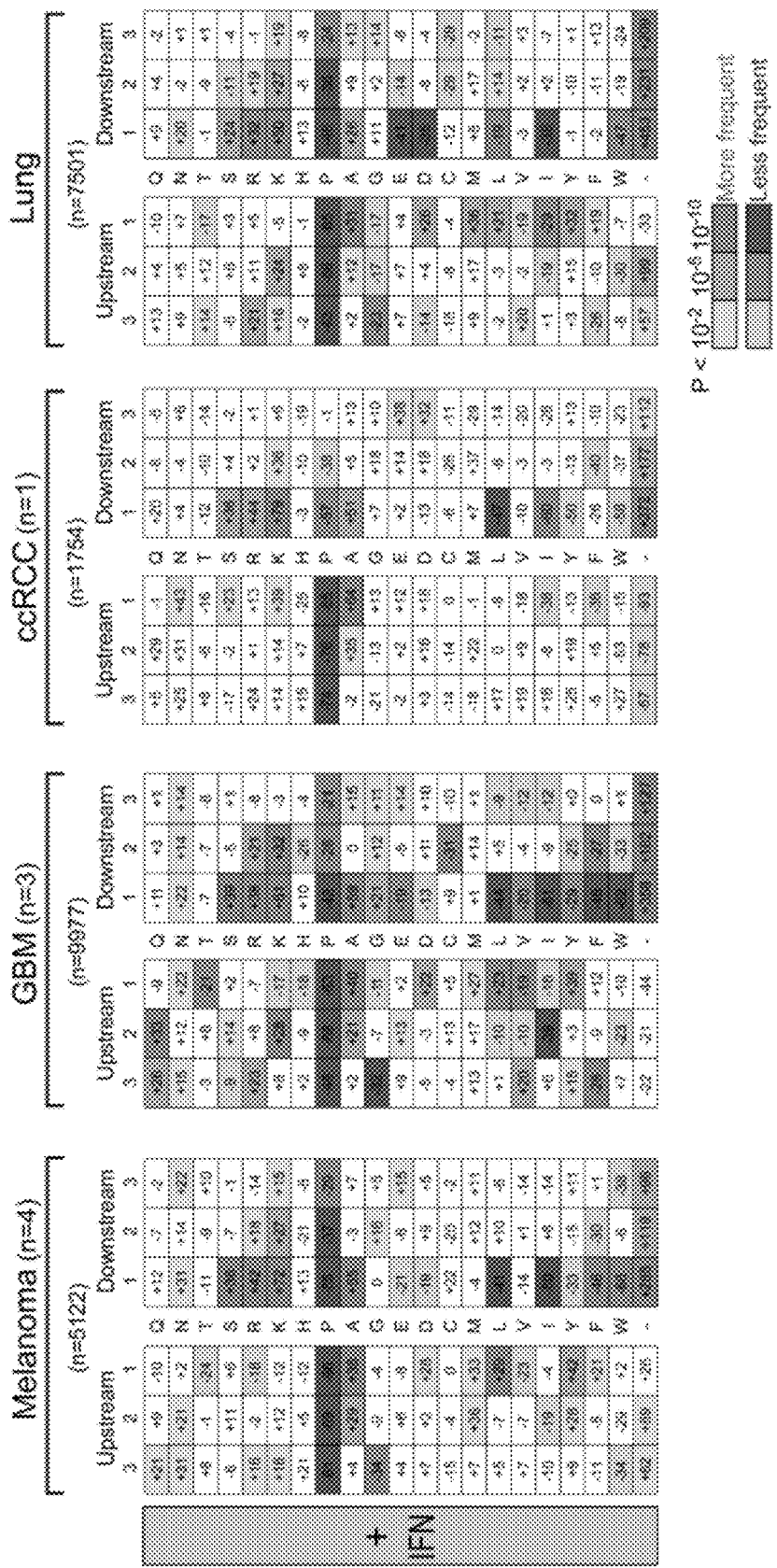
Figures 29E, 29F:
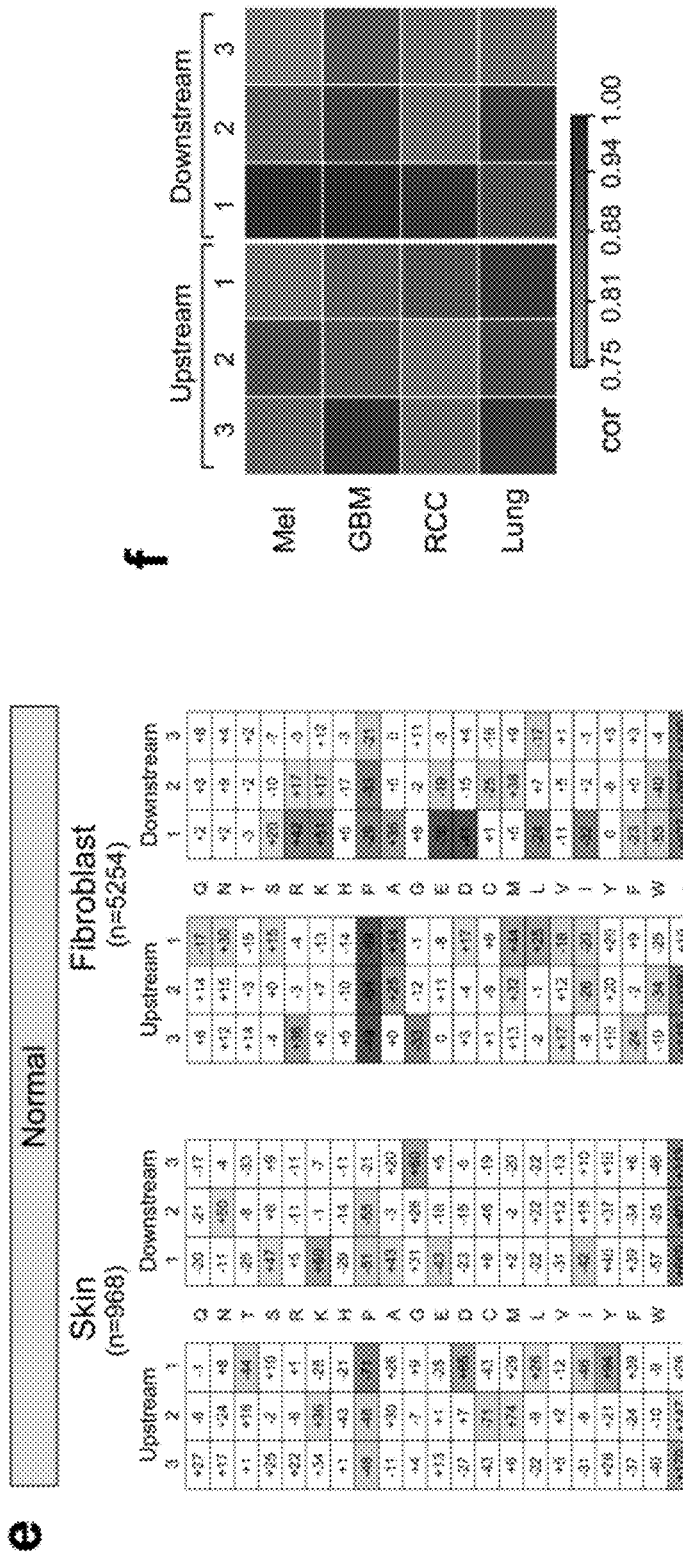

To assess proteolytic cleavage preferences in the untreated and treated dataset, Applicant calculated the enrichment of residues upstream and downstream of observed peptides in the protein sequence versus a set of decoys drawn from the proteome, controlling for HLA motif biases by matching the first two and last two decoy positions to observed peptides (FIG. 29F). As before, in the untreated dataset (FIG. 29D-top), Applicant observed an enrichment for A, K, S and R as downstream residues as well as in peptides derived from protein C-terminus (indicated by '-') (Abelin et al. 2017). Upstream residues R and K were not enriched after Applicant removed potential tryptic peptide contaminants from the datasets. Proline on the other hand was depleted at both termini in all samples, likely due to steric hindrance. Acidic residues (E, D), as well as certain hydrophobic residues (I, L, F, W) were underrepresented downstream of HLA-associated peptides.

Applicant observed strong correlations between proteasomal signatures of untreated and IFNγ-treated samples suggesting that immunoproteasome activation has minimal impact on the processing of HLA-presented ligands in malignant cells (FIG. 29D-29E; Spearman's $\rho>0.76$). Consistently, cleavage preferences in IFNγ-treated and untreated tumor samples had similar differences when compared to non-cancerous primary skin and fibroblast tissues (FIG. 29E; FIG. 35A). Applicant also considered whether IFNγ alters the proportions of allele utilization, especially with regard to C-terminal anchors (see FIG. 31A-31D).

Figures 30A, 30B:
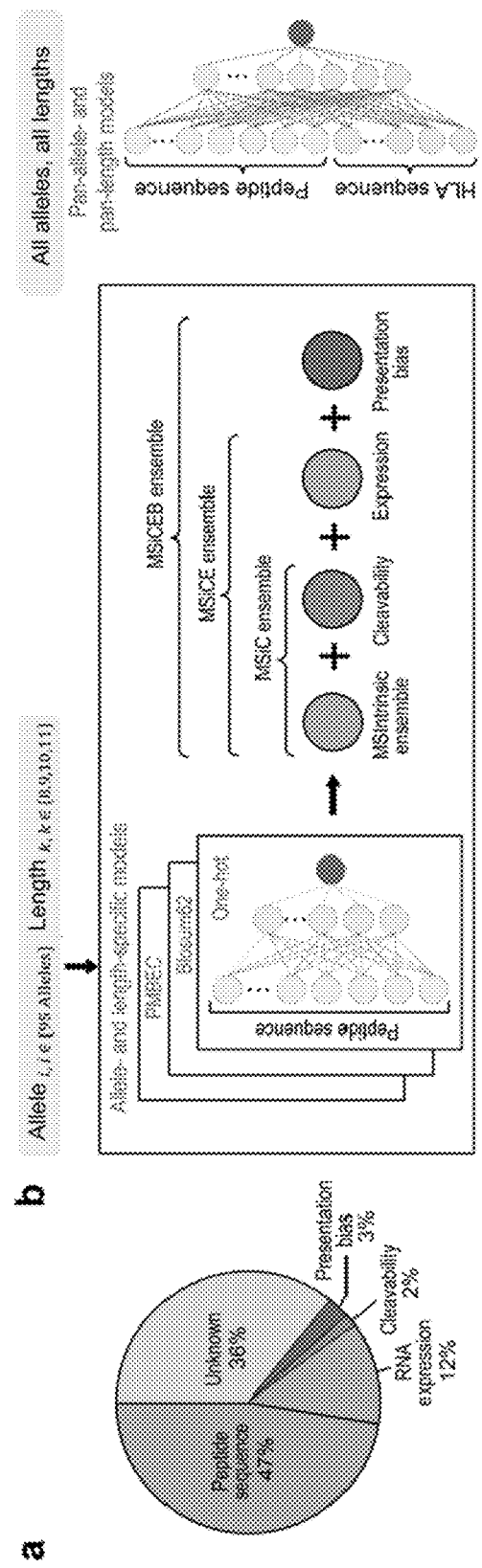
FIGS. 30A-30G—Length-specific and pan-allele MS-based models outperform state of the art predictors.

Generation and Performance of Allele-and-Length-Specific and Pan-Allele-Pan-Length Predictive Models of Antigen Presentation Multivariate models incorporating endogenous HLA-presentation descriptors, such as peptide source abundance and likelihood of proteasomal cleavage, outperform affinity-trained predictors (Abelin et al. 2017; and Bassani-Sternberg, et al. 2015). With the extended dataset of 95 alleles, Applicant re-evaluated the predictive contribution of these variables (FIG. 36A-36B) and also assessed two other features: 1) gene presentation bias; and 2) translation quantification via ribosome profiling. Presentation bias quantified the discrepancy between expected and observed number of MS-identified peptides per gene in a given set of samples and can boost recall of lowly expressed peptides (Bulik-Sullivan et al. 2018), while ribosomal profiling captures actively translated mRNA molecules and could provide a more accurate proxy for peptide precursor abundance (Methods). Additionally, Applicant utilized the MS-trained predictors as the first variable, instead of NetMHC affinity, in order to account for any MS data properties which might have overestimated the contribution of cleavability which was the first MS data-based feature in the previous analysis. To evaluate predictive power, Applicant constructed evaluation datasets consisting of the observed allele- and length-specific binders in the MS data (n) along with 999*n random decoys from the human proteome and considered the fraction of true binders in the top 0.1% peptides in the evaluation dataset ranked by prediction scores (i.e., positive predictive value (PPV)). The MS models trained on peptide sequence features alone (described herein) achieved an average PPV across the 95 alleles of 47% (FIG. 30A). Integrating RNA-seq as a proxy for peptide abundance boosted PPV to 60%, while protein abundance (iBAQ) achieved 54% PPV, respectively. Combining RNA-seq with Ribo-seq reached a PPV of 61% (Ribo-seq data not shown). Protein presentation bias and cleavability were the next most predictive variables adding 2.9% and 1.5% to PPV. Based on these results, Applicant trained prediction models that integrate intrinsic peptide features (MSintrinsic, or MSi) with extrinsic properties: cleavability (C), expression (E) and gene presentation bias (B).

Figures 30C, 30D, 30E, 30F, 30G:
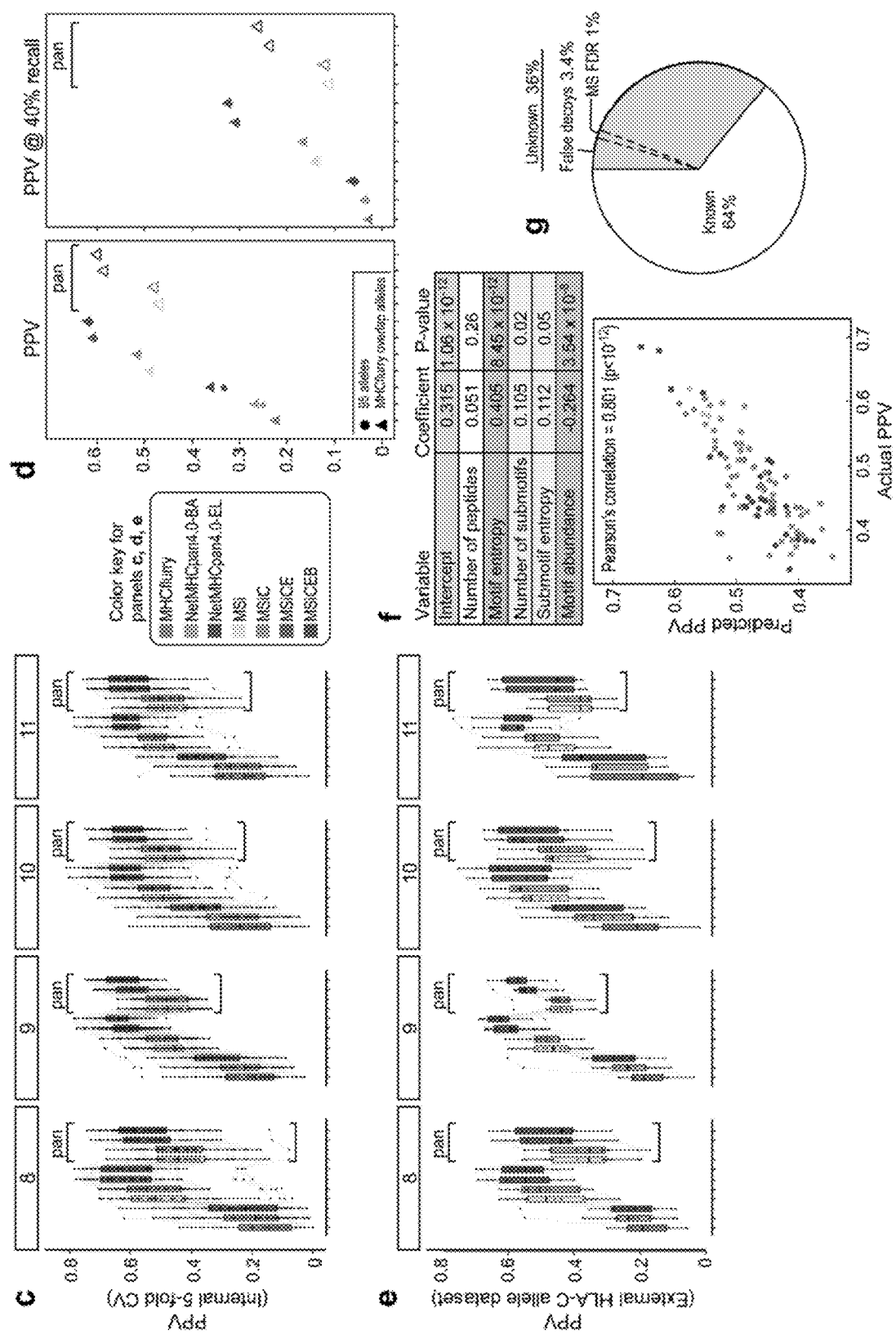

The observed length-specific binding motifs (FIG. 28A-28G) in conjunction with the high frequency of non-9-mer presentation for some alleles motivated the generation of length-specific binding predictors, trained exclusively on ligands of specific lengths (8-, 9-, 10-, or 11-mers), without 'borrowing' information from 9-mer peptides for other lengths (FIG. 30B—left). Additionally, to enable prediction for any HLA allele (beyond the MS dataset), Applicant built a pan-allele-pan-length model (panMSintrinsic or panMSi, FIG. 30B—right). Model performance was compared against the most recent version of NetMHCpan, 4.0 (Jurtz et al. 2017), as it incorporated training data derived from binding affinity (BA) or MS-sequenced eluted peptide (EL) datasets (including previously published 16 alleles), as well as against MHCflurry, reported to outperform NetMHC, especially for non-9-mers (O'Donnell et al. 2018). In a standard 5-fold cross validation (CV) of the length-specific models, Applicant found an average improvement in the MS-based peptide sequence-only models (MSi) across lengths of 2.2-, 1.9- and 1.5-fold compared to MHCflurry (for overlapping alleles), NetMHCpan4.0-BA and NetMHCpan4.0-EL (95 alleles), respectively (FIG. 30C). Models which additionally integrated cleavability (MSiC) added +2.6% to PPV, cleavability and expression (MSiCE) an additional +9.3%, or cleavability expression and gene presentation bias (MSiCEB) a further +1.1% PPV, ultimately achieving 2.7-, 2.4-, and 1.8-fold improvements compared to the benchmark algorithms, and with MSiCEB contributing an additional 1.1% to PPV. Length-specific models for 8-, 10- and 11-mers outperformed the corresponding non-length-specific models currently used (FIG. 30C) with average increases of +15, +18, +26, and +27% PPV for MSi, MSiC, MSiCE and MSiCEB over NetMHCpan4.0-EL, respectively. The largest benefits were observed for 8-mer models, which was not unexpected since 8-mer motifs were most different from 9-mer motifs (FIG. 28B—left). Ultimately, MSiCEB achieved 2.7-, 2.4- and 1.8-fold improvements compared to the three benchmark algorithms.

Although the performance of the pan-allele pan-length models was on average highly comparable to non-pan models (mean and median differences –2% PPV) and improvements over the non-pan models were observed for over 35% of allele-length combinations, Applicant also noted several cases with considerable decrease in predictive power (FIG. 30C). As anticipated, the subpar performance of pan models in these cases largely coincided with alleles for which non-9-mer motifs were different from the 9-mer motif (FIG. 28B). Compared to prior algorithms, the largest gains in PPV were observed for poorly characterized alleles (+20% PPV for HLA-C and +38% for HLA-G for MSi against NetMHCpan4.0-EL as the best scoring amongst the benchmark algorithms), but gains were also observed for all other alleles (+12% for HLA-A and +14% for HLA-B), even when only the 16 previously profiled alleles were considered (+9% for HLA-A and +5% for HLA-B). Length-specific models for 8-, 10-, and 11-mers outperformed the corresponding non-length-specific models currently used (FIG. 30C) with average increases of +15, +18, +26, and +27% PPV for MSi, MSiC, MSiCE, respectively. The largest benefits were observed for 8-mer models, which was not unexpected since 8-mer motifs were most different from 9-mer motifs (FIG. 28B—left).

Applicant proposed PPV at 0.1% of the top hits as a more suitable metric to evaluate HLA presentation predictors[4] because of the importance of assessing true positive rates at the realistic 0.1% prevalence of binders (the approximate rate of true binders among random 9-mers; Methods). A recent study quantified model performance using a different version of PPV, where the fraction of true positive calls out of all predictions necessary to retrieve 40% of the true binders is calculated, and the hits:decoys ratio in the evaluation set was modified from 1:999 to a 1:100007 (i.e. 'PPV at 40% recall'). Due to these differences, the two metrics are not directly comparable. Using a PPV at 40% recall, Applicant found that MSi outperforms MHCflurry, NetMHCpan-BA and NetMHCpan-EL by 5-, 4-, and 2-fold, while MSiCEB achieved 12-, 10-, and 6-fold improvements (FIG. 30D). Finally, Applicant observed similar gains in PPV compared to MHCflurry and NetMHCpan when evaluating an external dataset of HLA-C and -G binders (Di Marco et al. 2017) (FIG. 30E). In summary, Applicant observed a 2× improvement in PPV (using the top 0.1% of the dataset) compared to existing predictors, which corresponds to a 6-12× gain at 40% recall.

Motif Complexity and Motif Abundance Largely Explained PPV Variability

Applicant observed that some allele models were harder to learn than others, with 9-mer-specific models (MSi) PPV values ranging from 37% to 68%. This variation was not readily explained by the amount of training data available as model performance plateaus at several hundred peptides (Abelin et al. 2017) and more than 375 9-mer peptides were identified for all alleles. Since PPVs after the addition of endogenous features (MSiCEB) were strongly correlated with PPVs achieved with the simple model (Pearson's correlation=0.92, p-value<$2.2\times10^{-16}$), and since Applicant observed differences in the allele-specific motifs and sub-motifs (FIG. 32D; FIG. 33B), Applicant posited that PPV variability was driven by differential complexity in the peptide repertoire of each allele. To account for the information content of the main binding motif, Applicant summed the entropy along each peptide position, expecting that higher information content implies more easily-learned motifs. Similarly, Applicant considered all sub-motifs identified per allele by summing positional entropies over the sub-motifs, each weighted by the number of supporting peptides, and the number of submotifs normalized by the total number of peptides. Finally, Applicant utilized the natural frequency of amino acids to model the abundance of each binding motif since motifs that are more likely to occur are also more likely to contribute potential binders to the random decoy set and thereby decrease PPV. To assess if these variables were predictive of PPV, Applicant used a multivariate linear model fit, controlling for the size of the training data (Methods). PPVs predicted by the multivariate linear model strongly correlated to actual PPV values (Pearson's $\rho$=0.8, p-value<2e-16; FIG. 30F). The number of peptides identified per allele was not predictive, while the entropy of the main motif, and the number and entropy of submotifs were positively associated with PPV, and motif abundance strongly negatively contributed to PPV. Based on the model coefficients Applicant estimated that motif abundance could be responsible for ~3.4% of the unexplained PPV. An additional 1% could be due to false positive MS identification at 1% FDR (FIG. 30G). Overall, these findings suggested that limitations in prediction accuracy can be in large part attributed to motif complexity and abundance.

Peptides Proposed to be Derived from Proteasomal Splicing had Poor Predicted Binding Scores Peptides derived from proteasomally-ligated fragments ('spliced peptides') have been recently proposed as a major component of the HLA ligandome (Liepe et al. 2016; Faridi et al. 2018). Since the collection of mono-allelic data covered the HLA alleles evaluated in those studies, Applicant compared the binding potential of reported linear and splice-proposed peptide sets using the de novo predictors. Consistent with previous analyses (Mylonas et al. 2018; Rolfs et al. 2018), Applicant found that the majority of splice-proposed peptides had poor predicted binding. For example, 81% of canonical linear peptides described in Liepe et al. had an HLA-binding likelihood score >0.75 but only 28% of the splice-proposed peptides reported were recovered at the same threshold (FIG. 35B—left; Methods). Similarly, 84% of the linear peptides described in Faridi et al. had an HLA-binding likelihood score >0.75, while only 36% cis- and 37% trans-splice-proposed peptides reported satisfied the same cutoff (FIG. 35B—right). While spliced peptides have been reported to make up 30% of the HLA class I peptidome (Liepe et al. 2016), Applicants computational results suggest that no more than 11% (37% of 30%) of presented HLA ligands could be derived from spliced peptides, a number previously shown likely to be further diminished by factors such as ambiguity in peptide spectral matches and variability in sequence database search strategies (Mylonas et al. 2018).

Figure 31A:
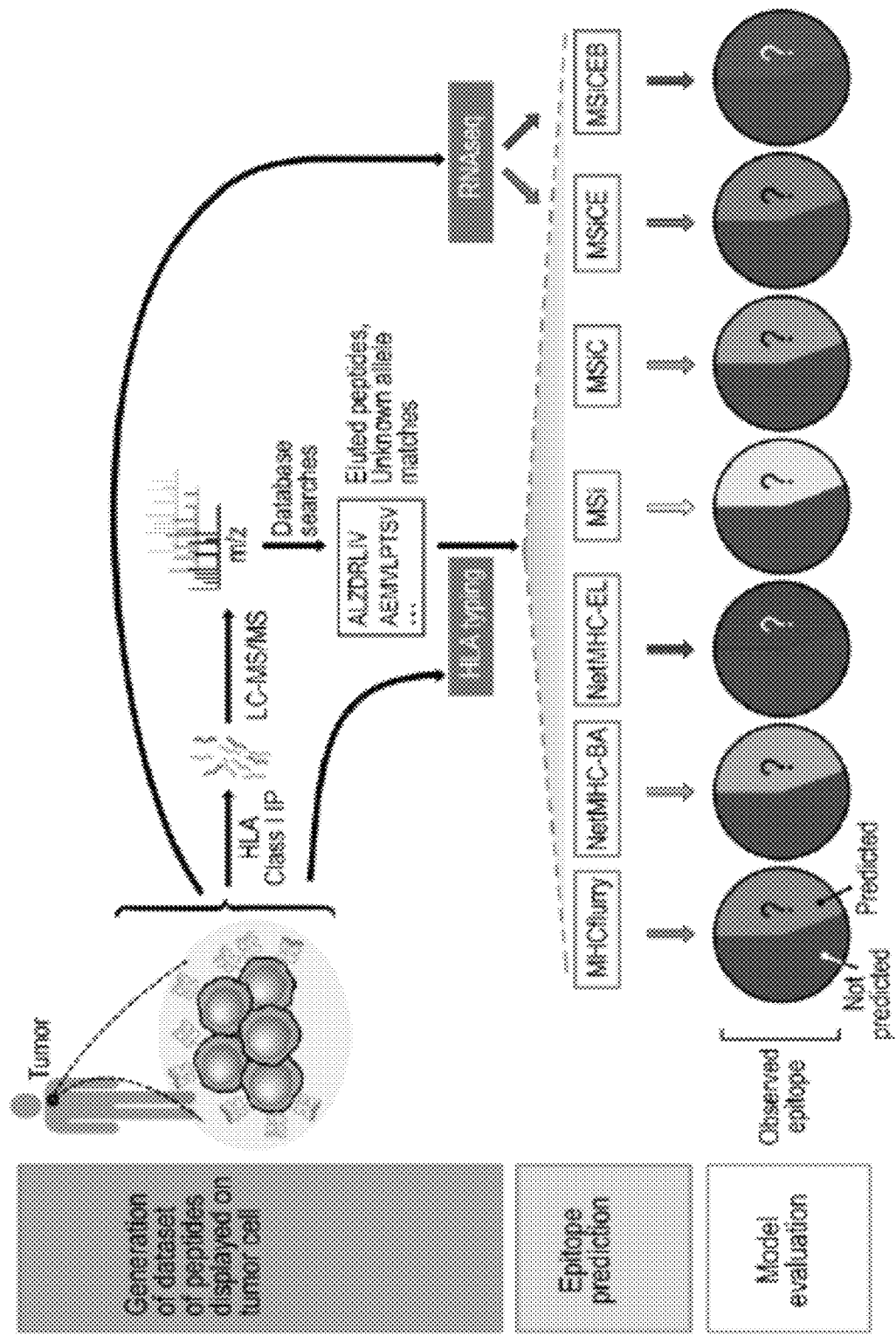
FIGS. 31A-31D—Evaluation of novel MS-based predictors against directly observed peptides displayed on primary tumor cells.
Figure 31B:
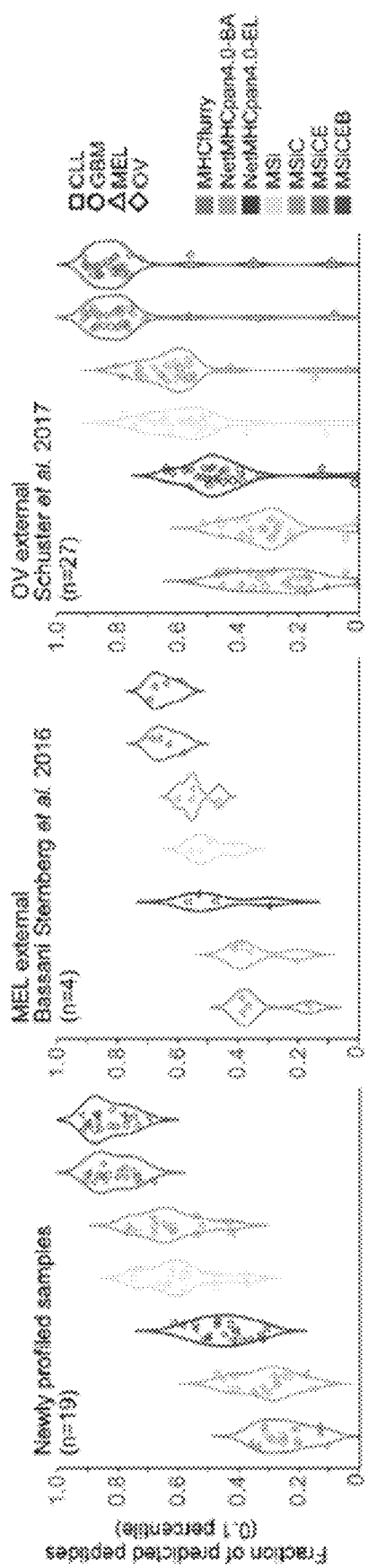

Leading Sensitivity Performance of MS-Trained Integrative Algorithms Validates in HLA-Associated Peptidomes from Patient-Derived Tumors To evaluate the utility of the predictive models for clinical samples, Applicant assessed their sensitivity to retrieve HLA-bound peptides observed on patient-derived tumor cell lines. To this end Applicant (i) used MS to identify 51,531 HLA-associated peptides from 11 tumor samples (3 chronic lymphocytic leukemia, 1 ovarian, 3 glioblastoma, 4 melanoma) and utilized external peptide datasets from 4 melanoma (Bassani-Sternberg et al. 2016) and 27 ovarian (Schuster et al. 2017) tumors; (ii) predicted the likelihood that each observed peptide is presented per HLA allele per sample; (iii) compared the proportions of correctly predicted peptides amongst a large set of random genomic peptides relative to 3 established tools (FIG. 31A). The mono-allelic dataset covered 50 of 57 unique HLA alleles found amongst the 42 patient samples used in the evaluation. For covered alleles, predictions were made with the allele-and-length-specific models, while missing alleles were scored by the pan-allele-pan-length predictors. Observed ligands which scored better than 99.9% of random peptides for at least one allele (top 0.1 percentile) were considered as correct identifications. Across malignancies, Applicant consistently observed a higher proportion of observed peptides predicted by the MS-based models compared to existing algorithms (FIG. 31B, FIG. 37). At the 0.1 percentile threshold, 26% of observed peptides were called by MHCflurry, followed by 31% and 46% predicted by NetMHCpan4.0-BA and -EL, respectively, compared to 56%, 60%, 77%, and 78% predicted by MSi, MSiC, MSiCE, and MSiCEB, on average across all samples.

Figures 31C, 31D:
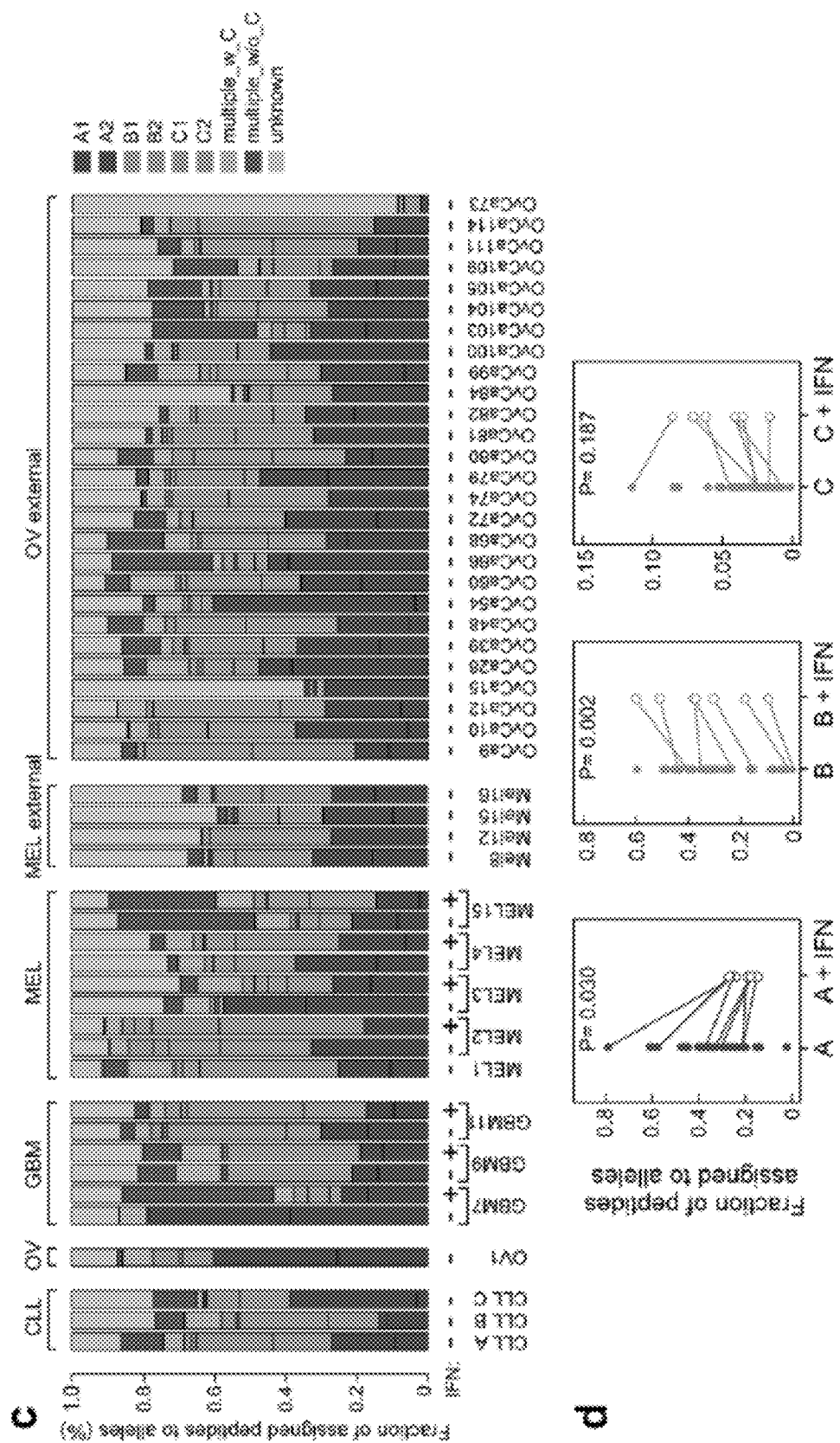

Allele Contribution to Peptide Presentation Varied by Individual and Changed with IFNγ Stimulation Since MS-detected epitopes were assigned to the best-scoring HLA-allele(s), this allowed calculation of allele frequency among the presented peptides (FIG. 31C). Notably, 3% of peptides on average were uniquely assigned to C alleles and an additional 6% of peptides were compatible with a C allele jointly with other alleles, thus suggesting that HLA-C has the potential to harbor neoantigens. In all 6 samples for which Applicant profiled HLA-associated peptidomes +/−IFNγ treatment, Applicant observed a shift towards HLA-B presentation (p=0.007, Wilcoxon signed-rank test), consistent with HLA-B having two IFNγ-inducible promoter elements (Javitt et al. 2019; Girdlestone 1995). An IFNγ-induced shift in peptide presentation from tryptic-like to chymotryptic-like peptides was demonstrated using the UWB.1 289 cell line which expresses HLA class I alleles of C-terminal tryptic motifs (A*03:01, A*68:01) and C-terminal chymotryptic-like motifs (B*07:02) (Chong et al. 2018). Although the proposed cause was different, their result is consistent with the demonstration of a more general HLA-A to HLA-B presentation shift. Consequently, Applicant further examined the +/−IFNγ patient-derived tumor cell line data and the HLA-B allele combinations of each and found elevated presentation for alleles with both tryptic and chymotryptic C-terminal preferences, suggesting that HLA-B upregulation could be at least in part responsible for a shift in presentation from tryptic-like to chymotryptic-like peptides which was observed in a cell line with a C-terminal chymotryptic-like HLA-B motif (Chong, C. et al. 2018). Finally, the contribution of each allele to the antigen repertoire varied by patient suggesting that profiling of endogenous tumor epitopes can inform allele specific contribution to an individual's HLA ligandome and further guide peptide vaccine selection.

DISCUSSION

The current study demonstrated the superior performance of HLA class I predictors trained on large-scale data of peptides eluted from cellular HLA proteins, consistent with growing appreciation of the value of MS derived datasets for the development of epitope prediction algorithms (Gfeller et al. 2018; Bulik-Sullivan et al. 2018; O'Donnell et al. 2018; Jurtz et al. 2017). For example, while earlier versions of NetMHCpan relied on binding affinity data from curated datasets, more recent versions incorporated eluted peptides from MS data to train predictors and demonstrated improved performance (Jurtz et al. 2017). Using an optimized, high-throughput experimental workflow, Applicant eluted peptides from immunoprecipitated HLA proteins and used high performance mass spectrometry followed by a refined database searching approach to build the largest dataset to date of HLA ligands eluted from single HLA-expressing cell lines. The resulting dataset of >185,000 peptides from 95 alleles greatly expands available knowledge of the human HLA-associated peptidome (Vita et al. 2015), such that at least 95% of individuals worldwide have at least one of their A, B, and C alleles within the dataset. All data are publicly available, thus providing a valuable resource for the scientific community including mass spectrometrists, immunologists as well as basic biologists. To facilitate access to the data, Applicant generated a first-in-class web-based tool for data visualization and interactive exploration and have made the predictors publicly available.

The large dataset afforded an unprecedented opportunity to gain more comprehensive insights into the basis of peptide presentation by HLA-A, -B, —C and -G alleles, each of which impacted how Applicant designed and trained the models. First, Applicant ascertained that peptide presentation does access the entire proteome for potential sources of antigen, in contrast to previous reports (Pearson et al. 2016), which relied on a small number of peptides. Second, the analysis revealed 101 peptide submotifs detected within and amongst alleles, many of which were shared across the 95 HLA alleles. Applicant observed strong similarity in physicochemical features of the HLA-C alleles along with their greater promiscuity in binding peptides, compared to the more divergent HLA-A and -B alleles. Moreover, HLA-C alleles only rarely had unique submotif clusters that were not also shared with HLA-A and B alleles, consistent with their recent evolutionary history (Parham and Moffett, 2013). This may increase competition with HLA-A and B alleles for peptides and may explain the observation that HLA-C epitopes originate from more highly expressed genes. Indeed, the degree of complexity and entropy of each allele was a strong determining feature for accuracy in prediction. Third, Applicant detected not only differences in length preference of the HLA bound peptides based on allele, but that ~10% of alleles displayed changes in epitope based on length. Altogether, the detailed knowledge that Applicant gained from the extensive dataset enabled Applicant to generate allele-and-length-specific and pan-allele-pan-length prediction models. Applicant demonstrated that the models outperformed state of the art algorithms, most prominently for understudied alleles or those with length-specific preferences. Fourth, Applicant found no major impact on proteasomal cleavage preferences across primary tumor cells of different lineages when exposed to IFNγ. While IFNγ signaling broadly modulated gene expression thereby altering the genes that HLA ligands derive from and increases presentation on HLA-B owing to its upregulation (Javitt et al. 2019), Applicant did not observe prominent differences in favored protease cleavage sites in malignant cells. This is consistent with the expression of both constitutive and immunoproteasome subunits in cancers and supports the application of a unified cleavability predictor.

Although other investigators have begun to incorporate MS data into their predictors (Jurtz et al. 2017; O'Donnell et al. 2018; Bulik-Sullivan et al. 2018; Gfeller et al. 2018), the validations on internal and external mono-allelic data as well as primary tumor ligandomes reveal that Applicant's models perform better at predicting HLA-presented epitopes compared to current tools. This can be attributed to several factors: (i) Applicant's models are the only ones trained exclusively on MS data of eluted peptides from mono-allelic cell lines; (ii) Applicant integrated several critical endogenous features, such as peptide cleavage and gene expression and make this integrated tool freely available; (iii) Applicant rich dataset reliably captured not only allele-but also length-specific motifs, widely covering the space of HLA binding preferences, and when available, Applicant preferentially predicted with allele-and-length-specific models for their demonstrated accuracy over pan-allele-pan-length predictors which were employed for uncharacterized alleles.

Despite improvements in epitope prediction, Applicant recognizes that further innovations are required if Applicants are to achieve near perfect accuracy. Applicant offers evidence that allele complexity and motif abundance may partially drive the observed variability in prediction power across alleles. The former implies a benefit in obtaining even larger training datasets, while the latter necessitates techniques to determine non-binders at large scale to collect reliable true negative datasets against which to evaluate model performance. Other innovations that could further boost prediction accuracy include increased LC-MS/MS instrument sensitivity and the development of reliable methods for de novo HLA peptide identification. Pertinent to peptide presentation prediction in tumor cells, better accuracy can be achieved by taking into account the uneven allele utilization and weighting predictions accordingly. While Applicant includes expression as a variable in the predictions, it is important to note that RNA-seq of tumors may not be representative of all clones and usually includes non-malignant cells, making it necessary to purify malignant cells for expression measurements. Finally, Applicant emphasizes that the models do not predict whether the HLA-presented peptides can interact with the T cell receptors in an individual, a problem that remains unsolved.

Data Availability

The original mass spectra, the protein sequence database, and tables of peptide spectrum matches for each allele have been deposited in the public proteomics repository MassIVE and are accessible at ftp://MSV?@massive.ucsd.edu when providing the dataset password: immunopeptidome. If requested, also provide the username: MSV?. Data for 16 initial alleles can be downloaded from MassIVE under the identifier MassIVE: MSV000080527.

B721.221 RNA Seq Data is Deposited GSE131267.

Melanoma RNA-seq data are deposited in dbGaP (www.ncbi.nlm.nih.gov/projects/gap/cgi-bin/study.cgi?study_id=phs001451.v1.p1, (Ott et al. 2017)). Glioblastoma bulk RNA-seq data are available through dbGaP (www.ncbi.nlm.nih.gov/gap) with accession number phs001519.v1.p1 ref.

Methods

Generation of HLA-A, B and C single allele cell lines. Single HLA allele-expressing cDNA vectors in a pcDNA-3 backbone were ordered from GenScript@. The HLA class I deficient B721.221 cell line was transfected with the HLA allele expression vectors using lipofectamine, as described previously (Ott, P. A. et al. 2017; and Pearson, H. et al. 2016). Cell lines with stable surface HLA expression were generated first through selection using 800 μg/ml G418 (Thermo Scientific), followed by enrichment of HLA positive cells through up to 2 serial rounds of fluorescence-activated cell sorting (FACS) and isolation using a pan-HLA antibody (W6/32; Santa Cruz) on a FACSAria II instrument (BD Biosciences). Priority was given to HLA alleles with lack of binding data in public databases or over 1% frequency in the US organ donor registry populations13.

Generation of primary human samples. All human tissues were obtained through DFCI or Partners Healthcare approved IRB protocols. Conditions for growth and in vitro propagation of melanoma and GBM tumor cell lines and of monocyte-derived dendritic cells were described previously15,37. PBMC from patients with chronic lymphocytic leukemia (CLL) were enriched for CD19 positive CLL tumor cells and were used in IP/MS analysis. Tumor specimens from patients with clear cell renal cell carcinoma (ccRCC) were collected following informed consent for enrollment on a tissue collection research protocol approved by the Dana-Farber/Harvard Cancer Center Institutional Review Board (IRB). Surgically resected ccRCC tumor tissue was mechanically dissociated with scalpels, and then enzymatically dissociated using a mixture of collagenase D (Roche), Dispase (STEMCELL Technologies), and DNase I (New England BioLabs) at room temperature, and filtered through a 100 micron cell strainer using the sterile plunger of a syringe. Red blood cells were lysed using ammonium-chloride-potassium buffer (Gibco). The cell suspension was stained for viability (Zombie Aqua; BioLegend), anti-CD45 (BV605; BD Biosciences), and anti-carbonic anhydrase IX (PE; R&D Systems). Viable, CD45-negative, CAIX-positive tumor cells were isolated by FACS (BD FACSAria II cell sorter; BD Biosciences). Cells were cultured in a specialized growth medium consisting of OptiMEM GlutaMax media (Gibco), 5% fetal bovine serum, 1 mM sodium pyruvate (Gibco), 100 units/mL penicillin and streptomycin, 50 micrograms/mL gentamicin, 5 micrograms/mL insulin (Sigma), and 5 ng/mL epidermal growth factor (Sigma). Following successive passages, CAIX expression was confirmed by flow cytometry (anti-CAIX, PE-conjugated; R&D Systems) and by immunohistochemical analysis of a cell pellet. Ovarian cancer patient-derived cells were propagated within a xenograft model, which was generated by serial passaging of tumor cells from a patient with advanced ovarian cancer. These cells originated from solid tumor or pleural effusion (3 million cells/mouse) that were injected orthotopically in the abdominal cavity in NOD-SCID mice (8-week old, Jackson labs). Tumor growth was monitored weekly by observing mice for signs of abdominal distension. Cells were harvested 4 months after initial injection and banked for future experiments. For interferon stimulation, cultured cells were stimulated with 2000 Unit/ml of IFNg (Peprotech) for 3 days and were used in IP/MS analysis.

For primary tumors and patient cell lines, HLA-peptide complexes were immunoprecipitated from 0.1 to 0.2 g tissue or up to 50 million cells. Solid tumor samples were dissociated using tissue homogenizer (Fisher Scientific 150) and HLA complexes were enriched as described above. 10 mm skin punch biopsies were obtained from healthy human skin discarded during skin surgeries. Subcutaneous fat was removed and remaining skin was snap frozen prior to processing. For skin HLA immunoprecipitations, frozen samples were dissociated in lysis buffer using TissueRuptor™ before immunoprecipitation (Qiagen).

HLA peptide enrichment and LC-MS/MS analysis. Soluble lysates from up to 50 million single HLA expressing B721-221 cells were immunoprecipitated with W6/32 antibody (sc-32235, Santa Cruz) as described previously (Abelin, J. G. et al. 2017). 10 mM iodoacetamide was added to the lysis buffer to alkylate cysteines for 71 alleles. Peptides of up to three IPs were combined, acid eluted either on StageTips or SepPak cartridges32, and analyzed in technical duplicates using LC-MS/MS. Peptides were resuspended in 3% ACN, 5% FA and loaded onto an analytical column (20-30 cm, 1.9 m C18 Reprosil beads (Dr. Maisch HPLC GmbH), packed in-house PicoFrit 75 M inner diameter, 10 µM emitter (New Objective)). Peptides were eluted with a linear gradient (EasyNanoLC 1000 or 1200, Thermo Scientific) ranging from 6-30% Buffer B (either 0.1% FA or 0.5% AcOH and 80% or 90% ACN) over 84 min, 30-90% B over 9 min and held at 90% Buffer B for 5 min at 200 nl/min. During data dependent acquisition, peptides were analyzed on a QExactive Plus (QE+), QExactive HF (QE-HF) or Fusion Lumos (Thermo Scientific). Full scan MS was acquired at a resolution of 70,000 (QE+) or 60,000 (QE-HF and Lumos) from 300-1,800 m/z or 300-1,700 m/z (Lumos). AGC target was set to 1e6 and 5 msec max injection time for QE type instruments and 4e5 and 50 ms for Lumos. The top 10 (Lumos, QE+), 12 (QE+), 15 (QE-HF) precursors per cycle were subjected to HCD fragmentation at resolution 17,500 (QE+) or 15,000 (QE-HF, Lumos). The isolation width was set to 1.7 m/z with a 0.3 m/z offset for QE and 1.0 m.z and no offset for Lumos, the collision energy was set to optimal for the instrument used ranging from 25 to 30 NCE, AGC target was 5E4 and max fill time 120 ms (QE+ and Lumos) or 100 ms (QE-HF). For Lumos measurements, precursors of 800-1700 m/z were also subjected to fragmentation if they were singly charged. Dynamic exclusion was enabled with a duration of 15 sec (QE+), 10 secs (QE-HF) or 5 sec (Lumos). Up to four IPs were combined, acid eluted and analyzed in inject replicates.

HLA peptide identification using Spectrum Mill. Mass spectra were interpreted using the Spectrum Mill software package v6.1 pre-Release (Agilent Technologies, Santa Clara, CA). MS/MS spectra were excluded from searching if they did not have a precursor MH+ in the range of 600-4000, had a precursor charge >5, or had a minimum of <5 detected peaks. Merging of similar spectra with the same precursor m/z acquired in the same chromatographic peak was disabled. Prior to searches, all MS/MS spectra had to pass the spectral quality filter with a sequence tag length >2 (i.e. minimum of 4 masses separated by the in-chain masses of 3 amino acids). MS/MS spectra were searched against a protein sequence database that contained 98,298 entries, including all UCSC Genome Browser genes with hg19 annotation of the genome and its protein coding transcripts (63,691 entries), common human virus sequences (30,181 entries), recurrently mutated proteins observed in tumors from 26 tissues (4,167 entries), as well as 259 common laboratory contaminants including proteins present in cell culture media and immunoprecipitation reagents. Mutation files for 26 tumor tissue types were obtained from the Broad GDAC portal (gdac.broadinstitute.org). Recurrent mutations in the coding region within each of the 26 tumor types (frequency=3 for stomach adenocarcinoma, uterine corpus endometrial carcinoma; frequency=5 for adrenocortical carcinoma, pancreatic adenocarcinoma, melanoma; frequency=2 for rest) were included. MS/MS search parameters included: no-enzyme specificity; fixed modification: cysteinylation of cysteine; variable modifications: carbamidomethylation of cysteine, oxidation of methionine, and pyroglutamic acid at peptide N-terminal glutamine; precursor mass tolerance of ±10 ppm; product mass tolerance of +10 ppm, and a minimum matched peak intensity of 30%. Variable modification of carbamidomethylation of cysteine was only used for HLA alleles that included an alkylation step (performed in 2017 or later). Peptide spectrum matches (PSMs) for individual spectra were automatically designated as confidently assigned using the Spectrum Mill autovalidation module to apply target-decoy based FDR estimation at the PSM level of <1% FDR. Peptide auto-validation was done separately for each HLA allele with an auto thresholds strategy to optimize score and delta Rank1-Rank2 score thresholds separately for each precursor charge state (1 thru 4) across all LC-MS/MS runs for an HLA allele. Score threshold determination also required that peptides had a minimum sequence length of 7, and PSMs had a minimum backbone cleavage score (BCS) of 5. BCS is a peptide sequence coverage metric and the BCS threshold enforces a uniformly higher minimum sequence coverage for each PSM, at least 4 or 5 residues of unambiguous sequence. The BCS score is a sum after assigning a 1 or 0 between each pair of adjacent AA's in the sequence (max score is peptide length-1). To receive a score, cleavage of the peptide backbone must be supported by the presence of a primary ion type for HCD: b, y, or internal ion C-terminus (i.e. if the internal ion is for PWN then BCS is credited only for the backbone bond after the N). The BCS metric serves to decrease false-positives associated with spectra having fragmentation in a limited portion of the peptide that yields multiple ion types. PSMs were consolidated to the peptide level to generate lists of confidently observed peptides for each allele using the Spectrum Mill Protein/Peptide summary module's Peptide-Distinct mode with filtering distinct peptides set to case sensitive. A distinct peptide was the single highest scoring PSM of a peptide detected for each allele. MS/MS spectra for a particular peptide may have been recorded multiple times (e.g. as different precursor charge states, from replicate IPs, from replicate LC-MS/MS injections). Different modification states observed for a peptide were each reported when containing amino acids configured to allow variable modification; a lowercase letter indicates the variable modification (C-cysteinylated, c-carbamidomethylated).

MS/MS data from patient derived cell lines was handled as described above except that they were searched against the database mentioned above with further inclusion of patient specific neoantigen sequences (Ott, P. A. et al. 2017; and Keskin, D. B. et al. 2019).

Filtering of MS-identified peptides. The list of LC-MS/MS identified peptides was filtered to remove potential contaminants in the following ways: (1) peptides observed in negative controls runs (blank beads and blank IPs); (2) peptides originating from the following species: 'STRSG', 'HEVBR', 'ANGI0432', 'ANGI0394', 'ANGI0785', 'ANGI0530', 'ACHLY', 'PIG', 'ANGI0523', 'RABIT', 'STAAU', 'CHICK', 'Pierce-iRT', 'SOYBN', 'ARMRU', 'SHEEP' as common laboratory contaminants including proteins present immunoprecipitation reagents. Note that BOVINE peptides derived from cell culture media were not excluded as they appear to have undergone processing and presentation and exhibit anchor residue motifs consistent with the human peptides observed for each allele; (3) peptides which were also identified in a tryptically-digested full proteome Jurkat sample; (4) peptides for which both the preceding and C-term amino acids were tryptic residues (R or K); (5) all possible leader peptides of lengths 8-11 from HLA-A, -B, -C, and -G (first exon, n=410) as they are likely to be presented by HLA-E; (6) peptides with negative deltaFwRevScore as likely falling in the 1% false positive MS identifications; (7) peptides identified for 20 or more of the 95 alleles (n=168); (8) peptides identified as potential C*01:02 contaminants in other alleles due to residual C*01:02 expression in B721.221 (n=383). These peptides were identified by scoring all peptides with the allele-specific C*01:02 model and selecting those with predicted likelihood binding score >0.95 that were also outlier for the allele (mean distance to the nearest 10 peptides >90 percentile).

RNA sequencing and quantification of B721.221 mono allelic cell lines and patient cell lines. RNA from 721.221 cells expressing HLA-C*04:01 and C*07:01 was isolated using RNeasy mini kit (QIAGEN). The Nextera XT kit from Illumina and the Smart-seq2 protocol were employed to generate full length cDNA and sequencing libraries that were sequenced with (38 bp paired-end) on a Nextseq 550 (Ilumina). The data were deposited in the NCBI Gene Expression Omnibus (GEO accession number GSE131267). This new data was used in conjunction with RNA-seq data from four previously sequenced alleles: HLA-A*29:02, B*51:01, B*54:01, and B*57:01 (GSE93315)4.

RNA-Seq data were aligned to the UCSC transcriptome annotation (hg19, downloaded June 2015) using Bowtie2 (bowtie2-2.2.1, default parameters38) and gene expression was quantified using to RSEM (rsem-1.2.19, default parameters39). Transcripts per million (TPM) values were averaged across alleles and the expression of each peptide was determined as the sum of the expression of the transcripts containing that peptide.

RNA-seq data from melanoma and glioblastoma patient cell lines were available in dbGaP (www.ncbi.nlm.nih.gov/projects/gap/cgi-bin/study.cgi?study_id=phs001451.v1.p1) 15 and (www.ncbi.nlm.nih.gov/projects/gap/cgi-bin/study.cgi?study_id=phs001519.v1.p1)37.

Deep proteome profiling of the B721.221 cell line and GBM H4512-BT145. Protein expression of B721.221 and GBM H4152-BT145 cell line was assessed as described previously40. Briefly, cell pellets of B721 expressing A*03:01, B*55:01 and C*07:01 as well as pellets of H4512-BT145 with and without IFNγ treatment were lysed in 8M Urea and digested to peptides using LysC and Trypsin (Promega). For GBM, peptides were labeled with TMT before pooling (Thermo Fisher), B721 analysis was performed labelfree with a 1:1:1 mix using the three monoallelic cell lines. 100 µg peptides were pooled and separated into 24 fractions using offline high pH reversed phase fractionation. One g per fraction was loaded onto an analytical column (20-30 cm, 1.9 um C18 Reprosil beads (Dr. Maisch), packed in-house PicoFrit 75 uM inner diameter, 10 uM emitter (New Objective)). Peptides were eluted with a linear gradient (EasyNanoLC 1000 or 1200, Thermo Scientific) ranging from 6-30% Buffer B (either 0.1% FA or 0.5% AcOH and 80% or 90% ACN) over 84 min, 30-90% B over 9 min and held at 90% Buffer B for 5 min at 200 nl/min. During data dependent acquisition, peptides were analyzed on a Fusion Lumos (Thermo Scientific). Full scan MS was acquired at a 60,000 from 300-1,800 m/z. AGC target was set to 4e5 and 50 ms. The top 20 precursors per cycle were subjected to HCD fragmentation at 15,000 resolution with an isolation width of 0.7 m/z, 30 NCE, 3e4 AGC target and 50 ms max injection time. For TMT experiments, resolution was set to 60,000 and 34NCE. Dynamic exclusion was enabled with a duration of 45 sec.

Spectra were searched using Spectrum Mill against the above database, specifying Trypsin/P as digestion enzyme, allowing 4 missed cleavages. Carbamidomethylation was set to fixed, acetylation at the protein N-terminus, oxidized methionine, pyroglutamic acid, deamidated asparagine and pyrocarbamidomethyl cysteine were set as variable modifications. Match tolerances were set to 20 ppm on MS1 and MS2 level. Peptides were filtered to 1% FDR and rolled up into protein groups. For comparison to RNAseq and HLA peptide data, proteins were collapsed to gene level using human identifiers only and filtered for two unique peptides per gene. For label free quantitation, the summed intensities of observed peptides for a given protein was divided by the theoretical count of tryptic peptides in that protein (iBAQ)[41]. For the GBM experiment in FIG. 29B, the ratio of protein level TMT intensity of the 127 channel over the 126 channel was used to evaluate relative protein changes in protein expression upon IFNγ treatment in the GBM sample.

Calculation of HLA Allele population frequencies, related to FIGS. 26A-26D. The HLA-A, -B, and -C allele frequencies are based on a meta-analysis of high-resolution HLA allele frequency data describing 497 population samples representing approximately 66,800 individuals from throughout the world[14]. The cumulative phenotypic frequency (CPF) of the alleles was calculated using $CPF = 1 - (1 - \Sigma_{i \in C} p_i)^2$, assuming Hardy-Weinberg proportions for the genotypes[12], where $p_i$ is the population frequency of the $i^{th}$ alleles within a subset of HLA-A, -B, or C alleles, denoted C.

The top 13 alleles (from A*24:02 to A*34:01) cover more than 95% and the top 29 alleles cover almost 100% of the population, the 39 B-alleles cover more than 95% of the population, the top 13 alleles (from C*07:02 to C*14:02) cover more than 95% of the population and the top 22 alleles cover almost 100% of the population. Frequencies were taken from pypop.org/popdata/2008/byfreq-A.php.html, pypop.org/popdata/2008/byfreq-B.php.html, www.pypop.org/popdata/2008/byfreq-C.php.

Immune Epitope Database (IEDB) data access and preparation, related to FIGS. 26A-26D. A curated set of previously identified HLA class I ligand was downloaded from the Immune Epitope Database (IEDB) at www.iedb.org/ downloader.php?file_name=doc/mhc_ligand_full.zip (accessed on Jun. 14, 2018)[36]. Records were filtered to MHC allele class=I, Epitope Object Type=Linear peptide, and Allele Name consistent with human HLA class I nomenclature with 4-digit typing (i.e. regex: "^HLA-[ABCG]\\*[0-9]{2}:[0-9]{2}$"). Peptides with quantitative measurements in units other than nM were removed and so were the following three assay types due to detected inconsistency between predicted (NetMHC 3.0) and actual affinity: "purified MHC/direct/radioactivity/dissociation constant KD", "purified MHC/direct/fluorescence/half maximal effective concentration (EC50)" and "cellular MHC/direct/fluorescence/half maximal effective concentration (EC50)". A peptide was considered a binder if it had a quantitative affinity of <500 nM or qualitative label of "Positive", "Positive-High", "Positive-Intermediate", or "Positive-Low". In cases where multiple records are available for the same {peptide, allele}pair, Applicant either took the mean affinity or removed the peptide when the difference between the maximum and minimum log-transformed affinities (1−log(nM)/log(50000)) was >0.2. Similarly, peptides with multiple qualitative records were removed if the same number of positive and negative labels were found or kept otherwise. Previously published data for 16 HLA-A and B alleles was removed from the analysis of IEDB counts (PubMedID=28228285).

Computational Analyses of MS-Identified and IEDB Peptides, Related to FIGS. 26A-26d.

Sequence Logo Plots

To capture and compare binding motifs between groups of peptides, sequence logo plots were generated using the motifStack R package for MS-identified peptides (FIG. 32I) and IEDB peptides (FIG. 32J) of length 8, 9, 10, and 11. Sequence logos are a standard way of representing the frequency of each of the 20 amino acids at each peptide position together with the information content (entropy) at each peptide position: the overall height of each position is determined by the entropy at that position and the height of each amino acid within is scaled according to its frequency.

Entropy

Figure 32K:
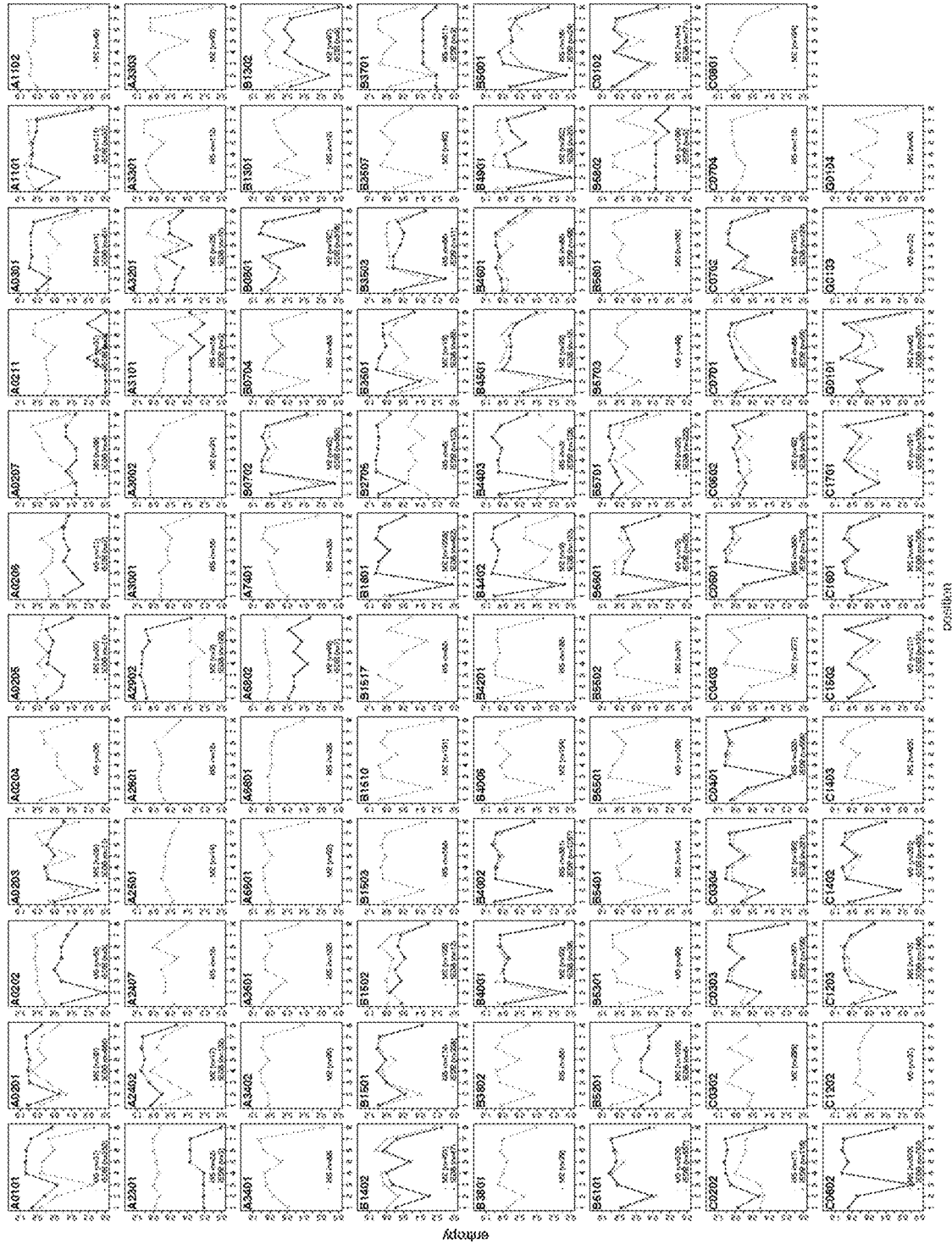
FIG. 32K) Entropy plots per peptide length (8-11 mers) for 95 alleles for MS and IEDB data.
Figure 32K:
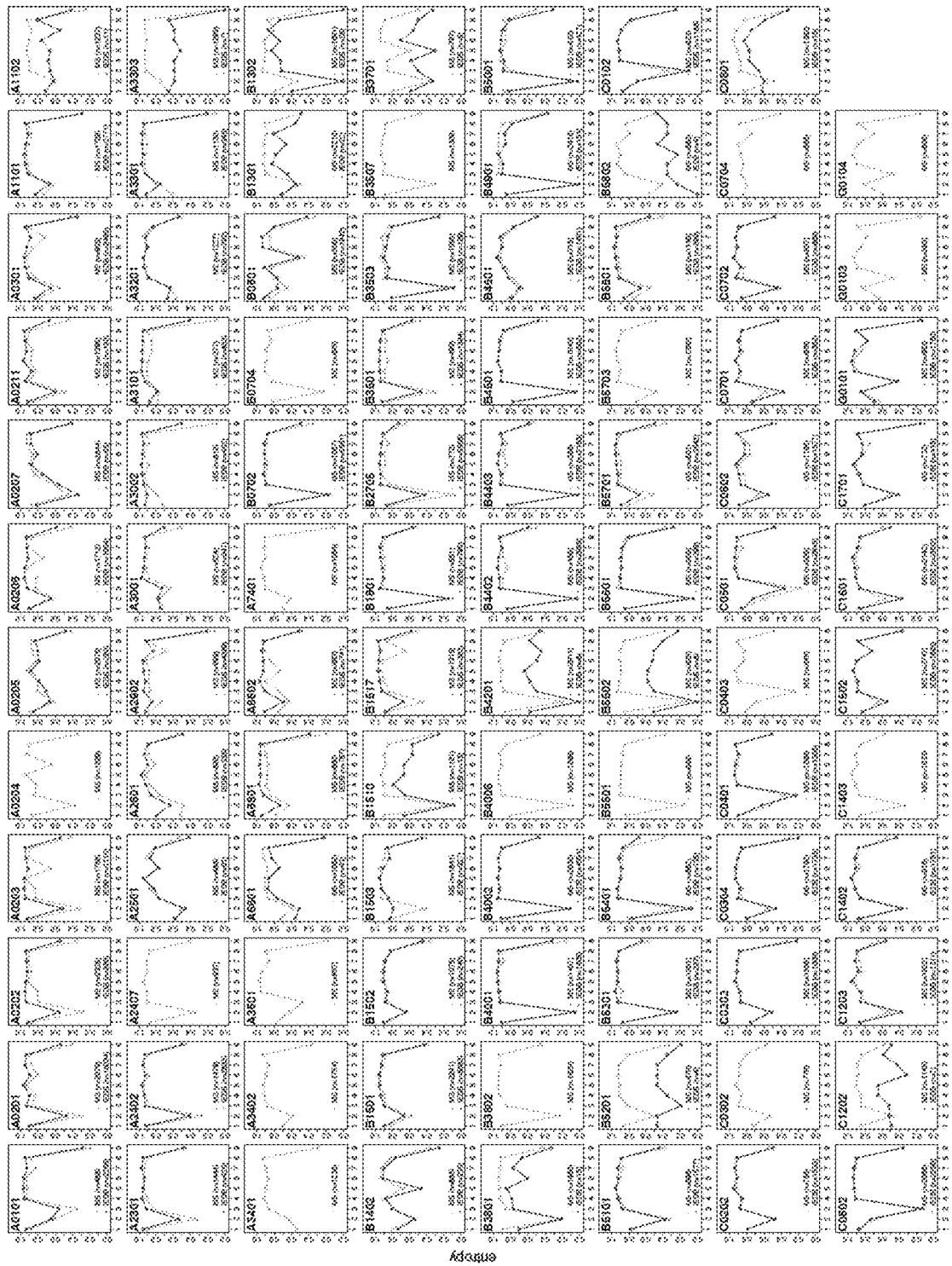
Figure 32K:
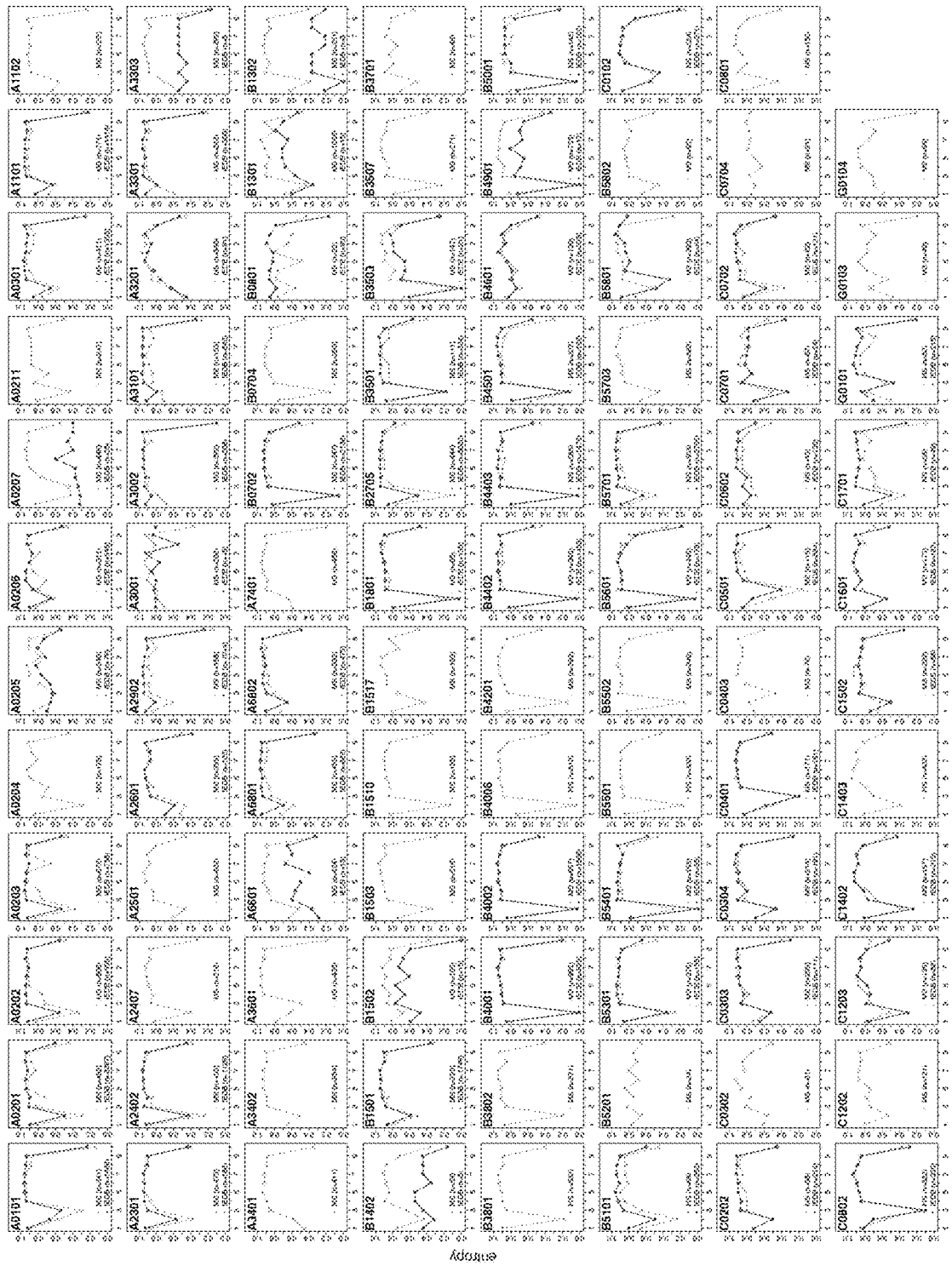
Figure 32K:
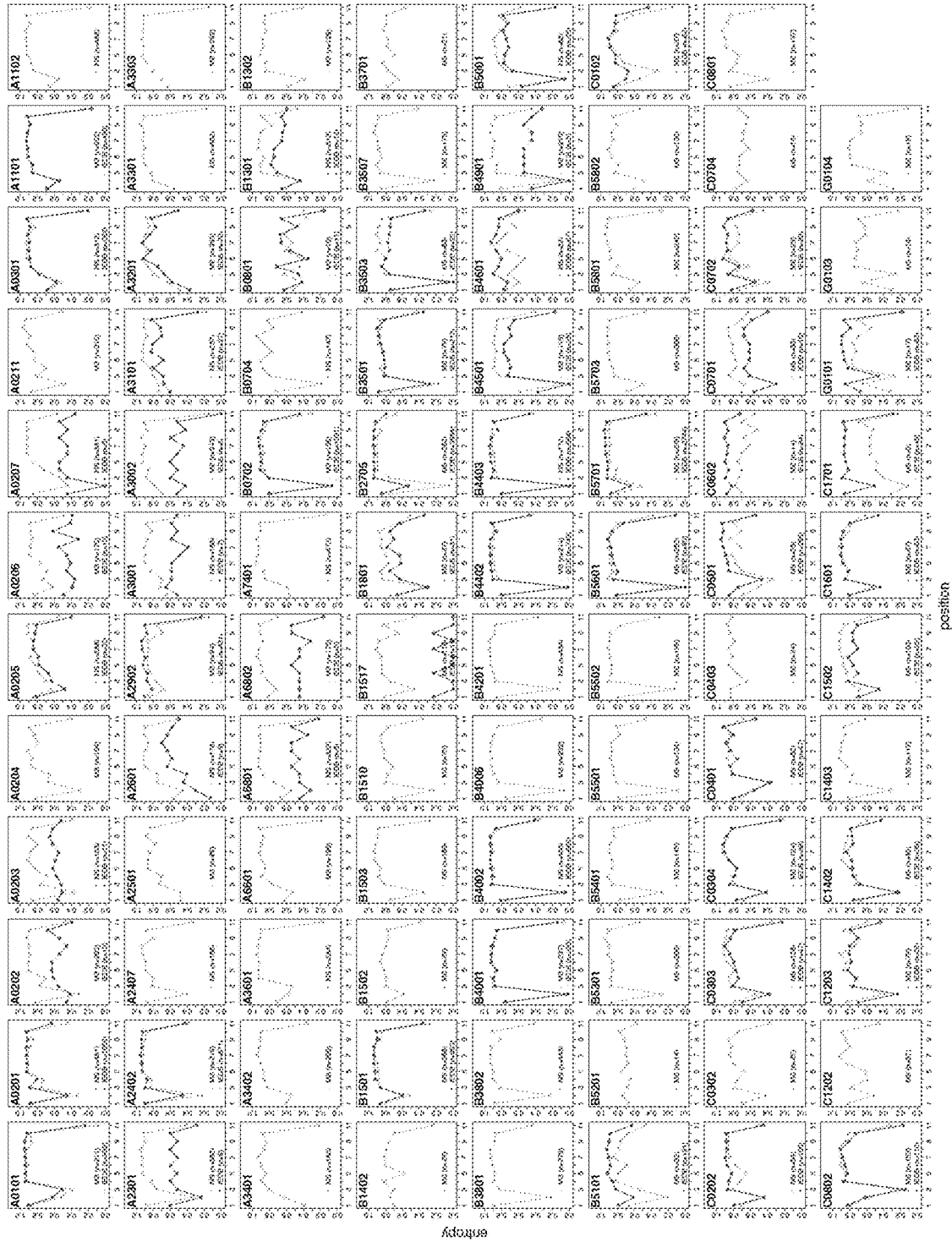
Figure 32L:
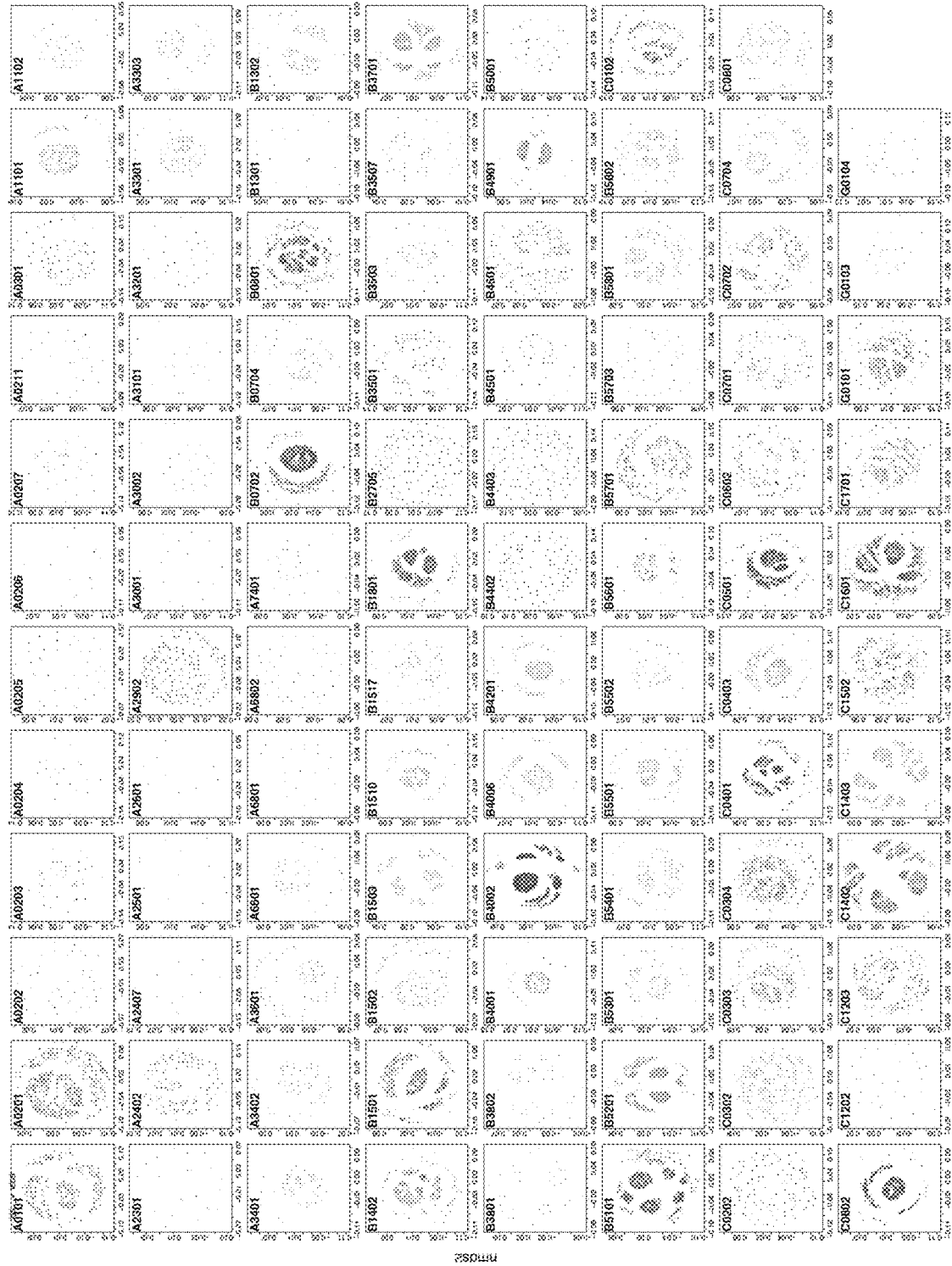
FIG. 32L) NMDS plots per peptide length (8-11 mers) for 95 alleles overlaying MS and IEDB data.
Figure 32L:
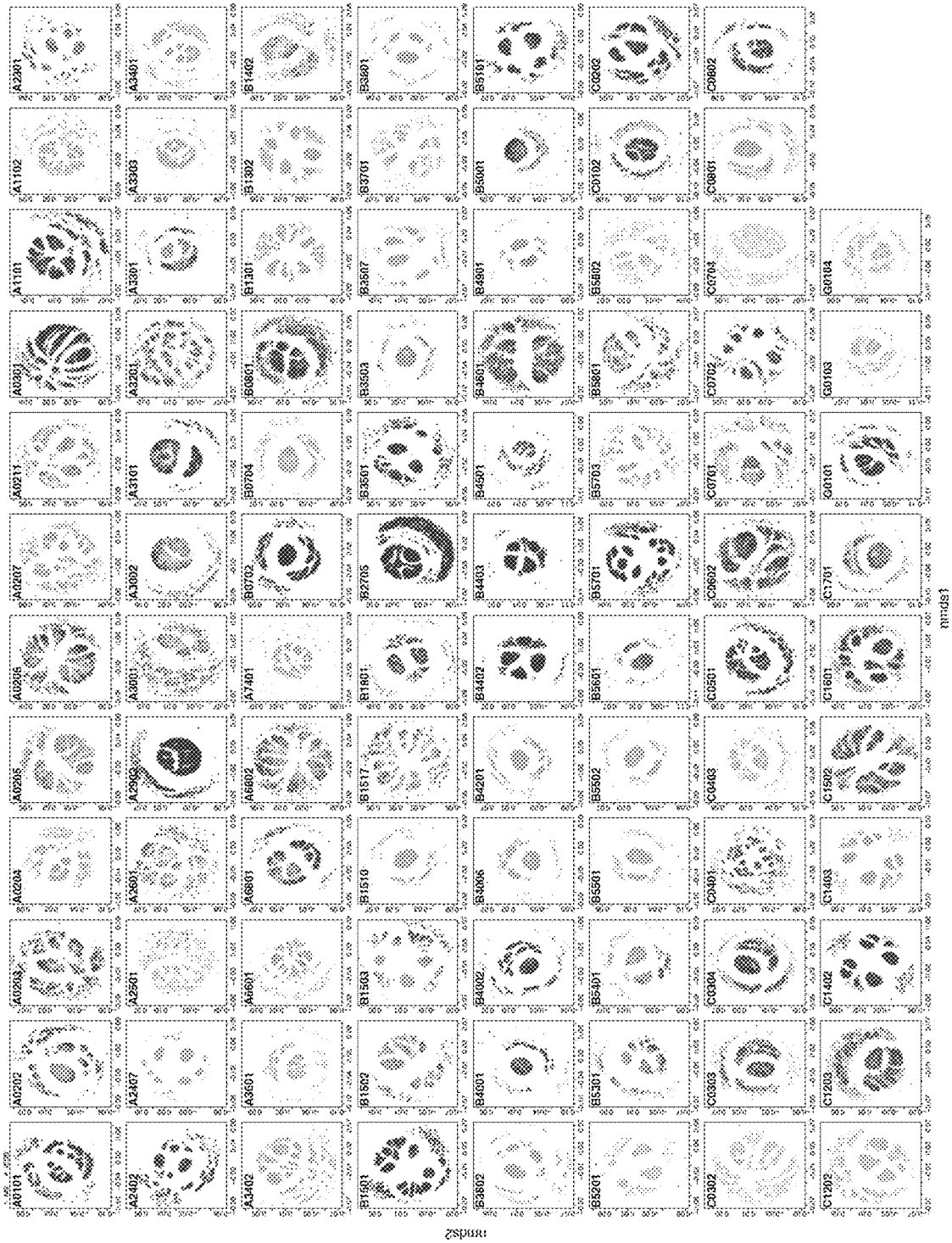
Figure 32L:
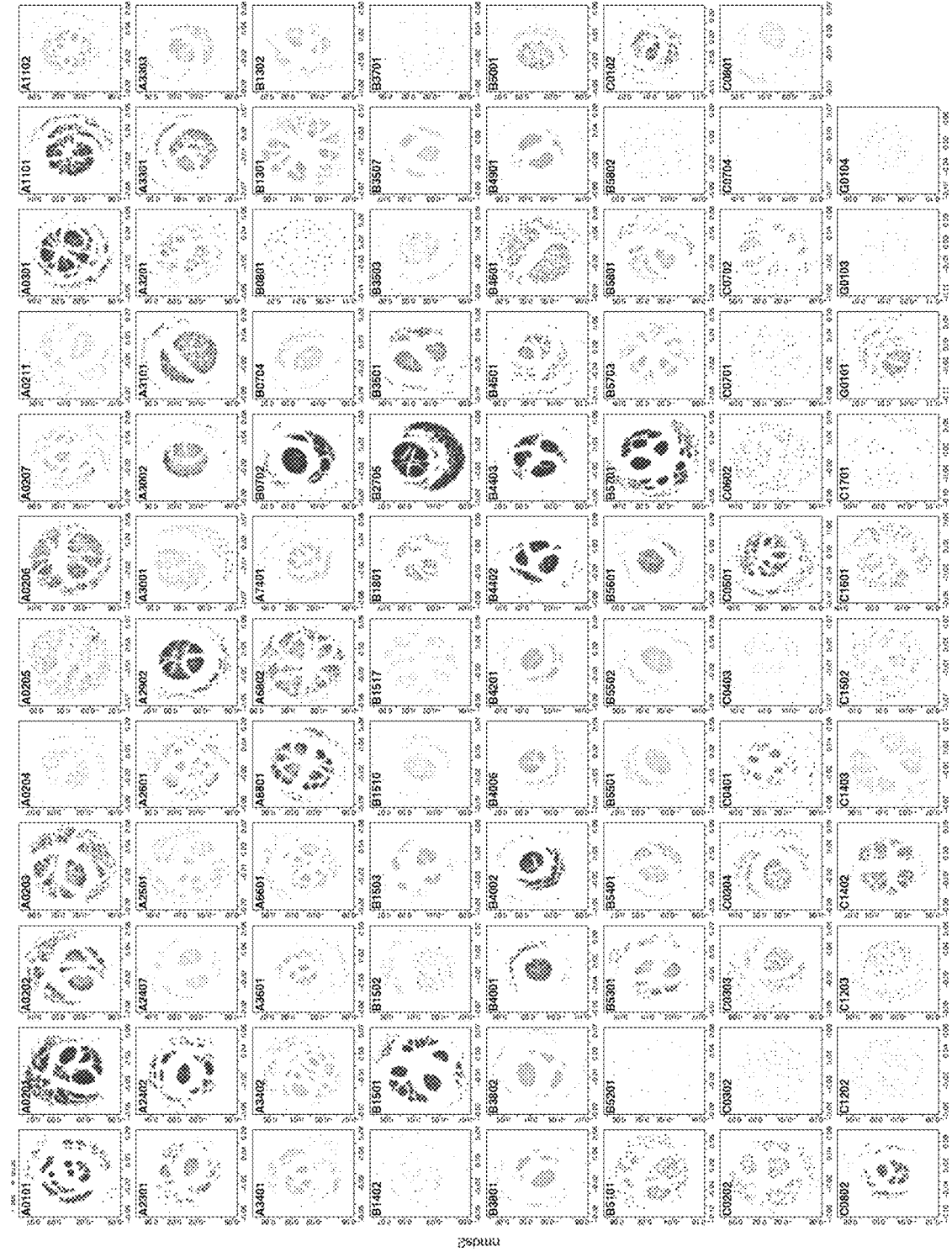
Figure 32L:
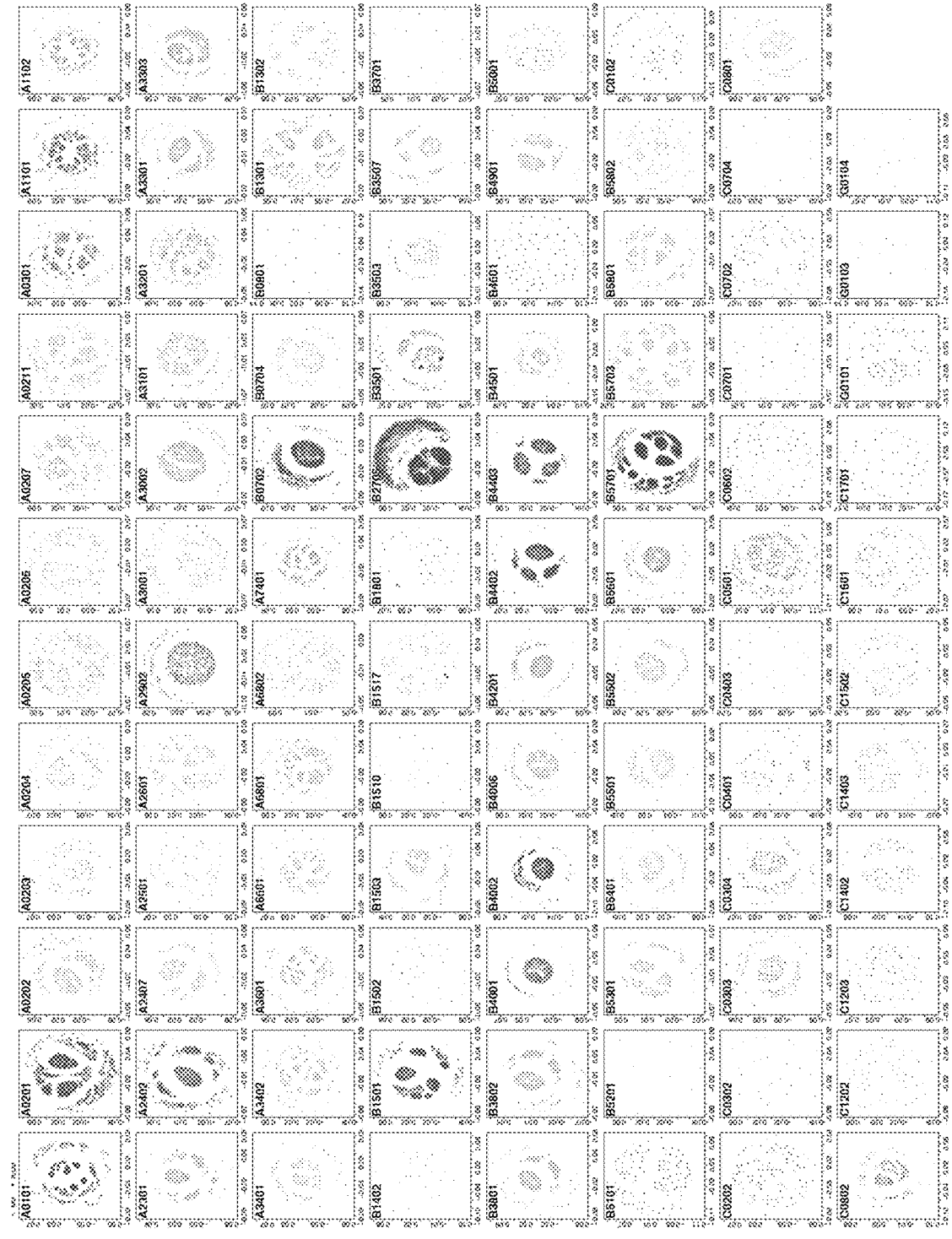

The entropy at each peptide position (i.e. 1 through n for n-mer peptides, n∈{8,9,10,11}) was calculated for each allele based on all MS-identified peptides identified for that allele (MS entropy) and then similarly for all IEDB binders (nM<500) (IEDB entropy). The computation was performed with MolecularEntropy( ) function from HDMD R package, where entropy values are normalized by log(20) such that entropy of 0 indicates a position with no variation while entropy of 1 indicates that all amino acids are equally likely to be observed at that position (FIG. 32K).

Peptide Distance

The following peptide distance metric was defined and computed between every pair of peptides of given length in the MS and IEDB sets:

$$D(A, s_1, s_2) = \frac{1}{L}\sum_{i=1}^{L} distPMBEC(s_{1i}, s_{2i}) * (1 - H_{Ai})$$

where $s_1$ and $s_2$ are peptide sequences; L is the length of the peptide sequences, n∈{8,9,10,11}; distPMBEC=maxPMBEC−PMBEC is a 20×20 matrix of residue dissimilarities derived from a pre-computed matrix of residue similarities biased by their HLA binding properties[42]; $H_{Ai}$ is the [0,1]-scaled entropy at position i for the allele A associated with $s_1$ and $s_2$, computed from the MS data.

Peptide Distance Visualization and Sub-Clustering of Binding Motifs

Pairwise peptide distance matrices per allele and per length (8-11) were computed between every pair of peptides in the MS and IEDB datasets as described above. Since the matrix contains relative peptide distances rather than absolute Cartesian coordinates, Applicant used non-metric multidimensional scaling (NMDS) to visualize the peptides in two demotions, revealing the sub-groups of peptides that make up the main motif (nmds( ) function from ecodist R package) (FIG. 32K). Density based clustering was then performed on the two-dimensional projection to assign peptides to clusters (submotifs) (dbscan( ) function from dbscan R package) (FIG. 32K, FIG. 33B).

Allele similarity analyses, related to FIGS. 27A-27D. To assess which alleles are similar to each other Applicant considered similarity according to the observed binding motifs (peptide space) as well as similarity according to the HLA binding grooves (HLA binding pocket or HLA protein space). Similarity in peptide space was evaluated by tabulating the frequency of each of the 20 amino acids at each position along the peptide sequence (1 through 9) per allele, forming a vector of size 20*9=180. The pairwise correlations of these frequency vectors were used to quantify similarity (FIG. 27A).

To evaluate similarity in HLA binding pocket space, HLA protein sequences were downloaded from IMGT®, the international ImMunoGeneTics information System® www.imgt.org (hla.alleles.org/alleles/text_index.html, accessed May 5, 2018) and aligned. From the full HLA protein sequences Applicants selected positions which are in contact with the peptide (within a distance of 2A) or positions that are most frequently mutated across alleles to represent the binding pocket: {7, 9, 13, 24, 31, 45, 59, 62, 63, 65, 66, 67, 69, 70, 71, 73, 74, 76, 77, 80, 81, 84, 95, 97, 99, 110, 114, 116, 118, 138, 143, 147, 150, 152, 156, 158, 159, 163, 167, 171}(FIG. 27B). The residue at each position of the binding pocket was featurized by its amino acid physical properties encoded as 10 Kidera Factors (available from R package Peptides v2.4, data(AAdata))[43] and 3 principal components derived from a dimensionality reduction of a large set of physicochemical properties[44]. The full binding pocket was represented by the concatenated list of positions and allele similarity was assessed by Euclidean distance.

Given the two approaches to evaluating allele similarity (motif space and pocket space), Applicants assessed how well they agree by identifying the closest neighbors for each allele in motif space and the closest neighbors for each allele in pocket space and counting how many of the former are also found in the latter (FIG. 33A). The closest neighbor in motif space were considered to be alleles with correlation greater than 97.5% of all pairwise correlations. Analogously, closest neighbor alleles in pocket space were considered to be alleles within distance less than 97.5% of all pairwise distances.

Figure 33C:
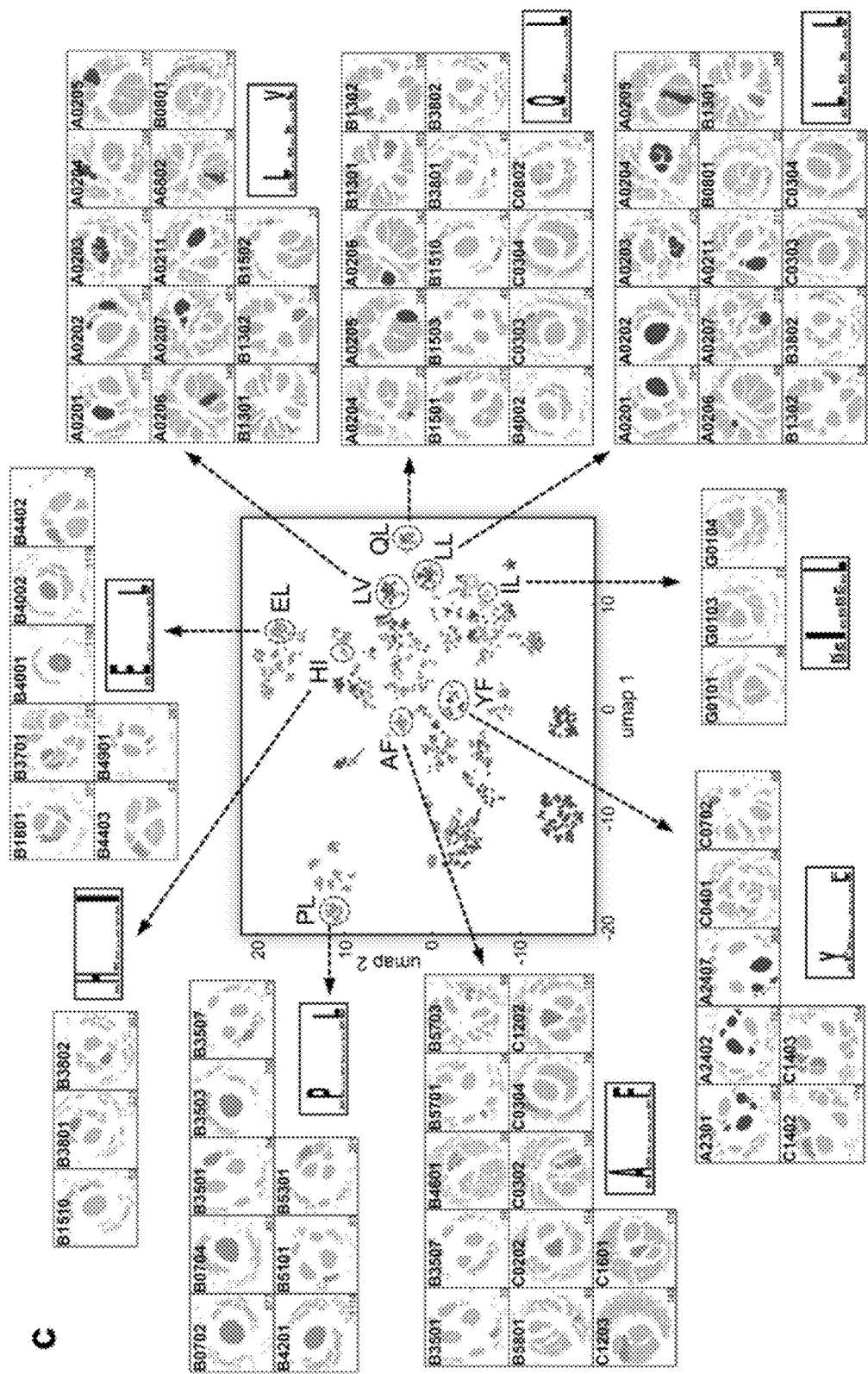

Analysis of submotifs across alleles, related to FIGS. 27A-27D. Grouping the 9-mer peptides identified for each allele into sub-motifs (see Peptide distance visualization and sub-clustering of binding motifs) identified 1133 sub-motifs across the 95 alleles supported by at least 20 peptides (FIG. 27D, FIG. 33C). To determine whether any of those sub-motifs are shared by two or more alleles, each sub-motif was represented as a vector of amino acid frequencies per peptide position (analogously to main motifs representation in allele similarity analysis), projected onto two dimensions (umap( ) function from R package umap v0.2)45, and clustered (dbscan( ) function from dbscan R package). This approach identified 101 distinct clusters of sub-motifs with 1-22 alleles participating in each (FIGS. 27C and 27D, FIGS. 33B, 33C).

Evaluation and validation of length-dependent motif differences, related to FIGS. 28A-28G. To compare 8-mer motifs to 9-mer motifs, Applicant generated pseudo 8-mer motifs from 9-mers by dropping middle residues (positions 4, 5, or 6). To compare 10- and 11-mer motifs to 9-mers Applicant generated pseudo 9-mer motifs by dropping middle residues from 10-mers (positions 5 or 6) and 11-mers (positions 5 and 6, or 6 and 7). The pseudo motif which was most similar to the true motif was used to evaluate the change in frequency and entropy at every peptide position. 8-, 10-, or 11-mer motifs with at least 100 identified peptides, that had an absolute difference in residue frequency with the true motif of >0.25 or an absolute difference in entropy of >0.2 at any position were considered as different. For example, if proline is observed at position 5 in 5% of peptides associated with motif1 but 40% of peptides associated with motif2 the absolute difference in frequency is 10.05-0.40|=0.35>0.25, thus deeming motif1 and motif2 different.

To experimentally validate the observed length-specific motifs Applicant selected 18 peptides from 3 alleles representing 4 length-specific motifs that were predicted to be strong binders by the algorithm (MSi) but weak binders according to NetMHCpan-4.0 and tested them for binding in in vitro binding assays. Peptide affinity measurements were performed at Immunitrack, Copenhagen, Denmark employing their NeoScreen platform as previously described[46].

Computation validation of IFNγ treatment response, related to FIGS. 29A-29F. For each MEL, GBM, and ccRCC sample with and without IFNγ treatment Applicant counted the number of MS-identified HLA-bound peptides that match to IFNγ-induced genes using entries in the HALLMARK_INTERFERON_GAMMA_RESPONSE geneset46 (downloaded from software.broadinstitute.org/gsea/msigdb/download_geneset.jsp?geneSetName=HALLMARK_INTERFERON_GAMMA_RESPONSE&fileType=txt). The fraction of peptides that map to IFNγ genes in untreated vs treated samples was used as a proxy for confirming IFNγ response.

Analysis of Peptide Processing Signatures, Related to FIGS. 29A-29F.

The analysis of preferred cleavage residues upstream and downstream of each MS-identified peptide was performed as in Abelin et al, 2017. Briefly, for each MS-identified peptide (hit), the 3 upstream and 3 downstream amino acids were determined (context), with protein termini denoted as "-". To construct a background set, each hit was matched to 100 random human peptides that have the same first two and last two amino acids as the hit (to control for presentation biases). Peptide processing preferences were identified by calculating the relative enrichment of each amino acid at each context position (percent change in hits over decoys) and significance was assessed by chi-squared test. (FIGS. 29D, 29E).

This approach was applied to all MEL, GBM, and ccRCC+/−IFNγ samples profiled in this study to compare peptide processing signatures with and without IFNγ stimulation. In addition, a published datasets of lung cancer cells, untreated (UT) or treated with TNFα and IFNγ (T+I), was utilized in this analysis25. As the reported peptides were identified using MaxQuant with match between runs enabled, all peptides have an intensity value in both conditions. Thus, to derive the two processing signatures Applicant took peptides with log 10 median intensity >6 from either UT ('-IFNγ' signature) or T+I ('+IFNγ' signature) condition.

PPV vs PPV at 40% Recall, related to FIGS. 30A-30G. To evaluate predictive power, Applicants constructed datasets consisting of the observed allele- and length-specific binders in the MS data (n) along with 999*n random decoys from the human proteome and considered the fraction of correctly predicted binders in the top 0.1% of the dataset (i.e. positive true positive calls true positive calls predictive value, $$\left(\text{i.e. positive predictive value,} \quad PPV = \frac{\text{true positive calls}}{\text{all positive calls}} = \frac{\text{true positive calls}}{n}\right).$$

Applicants advocated for the PPV evaluation metric in Abelin et al.[4], over the commonly used AUC, because it is better suited for the HLA presentation prediction problem space where a relatively small number of true binders need to be identified amongst an excess of non-binders. Each HLA allele is expected to present a repertoire of approximately ~10,000 peptides[36,48-51] among the $1.1 \times 10^7$ 9-mer peptides in the proteome, meaning that approximately only 1 out of a thousand peptides (0.1%) gets presented.

The definition of PPV described above is equivalent to PPV at recall=PPV % since the number of positive calls equals the number of true positives. A different version of this metric used recently to quantify algorithm performance is PPV at recall=40%, that is $$PPV_{40\% \ Recall} = \frac{\text{true positive calls}}{\text{all positive calls}} = \frac{\text{true positive calls}^7}{\text{positive calls when 40\% of the } n \text{ true positives have been called}}.$$

In addition, Bulik-Sullivan et al. used a dataset with a ratio of 1 hit:10,000 decoys for the evaluation of single-allele dataset, rather than a ratio of 1:999 used by Applicants, which reduced PPV. Due to these differences, model performance evaluated with PPV is not comparable to model performance evaluated with $PPV_{40\% \ recall, \ h:d=1:10000}$ (FIG. 30D).

Assessment of Predictive Contribution of Variables, Related to FIGS. 30A-30G.

The potential contribution of intracellular signals to predicting endogenously-presented peptides was assessed by building multivariate logistic regression models with various combinations of the following features4:

RNA-seq expression—the level of expression of each peptide was determined as the sum of the expression of the transcripts containing that peptide, and log-transformed ($\log_2(\text{TPM}+1)$).

Ribo-seq expression—the translation level of each peptide was derived from Ribo-seq data from mono-allelic B721.221 cells analogously to RNA-seq quantification.

Protein expression—iBAQ values, calculated by summing the intensities of observed peptides for a given gene by the theoretical count of tryptic peptides in the gene[41], were log-transformed (with zeros set to one tenth the minimum observed iBAQ value).

Cleavability likelihood: the cleavability score of each peptide was predicted by a de novo cleavability predictor trained on external multi-allelic MS-data[4].

Presentation bias—the HLA-presentation bias of each gene was calculated based on the log ratio of observed to expected MS-identified peptides. The number of observed peptides per gene was the count of unique 9-mers in the collection of B721.221 mono-allelic MS data that map to the gene (protein IDs and GeneSymbol IDs were mapped via tables kgProtAlias, kgXref available from genome.ucsc.edu/cgi-bin/hgTables). The number of expected peptides per gene was defined as all possible unique 9-mers tiled along the length of the protein, multiplied by the expression level of the corresponding gene (to account for the increased likelihood of observing a peptide with higher expression), and scaled to sum to the total number of observed peptides.

Localization—the cellular localization of each peptide was assigned according to the localization(s) of its source protein(s). Protein localization information was obtained from Uniprot (ftp.uniprot.org/pub/databases/uniprot/current_release/knowledgebase/complete/uniprot_sprot.dat.gz) and Uniprot IDs were mapped to UCSC annotations via the following tables ftp.uniprot.org/pub/databases/uniprot/current_release/knowledgebase/idmapping/by_organism/HUMAN_9606_idmapping.dat.gz, genome.ucsc.edu/cgi-bin/hgTables kgProtAlias, kgXref. Protein localization categories were represented by 7 binary variables corresponding to "Cell Membrane" (if the localization field contained the text "cell membrane"), "Mitochondria" ("mitochondr"), "Nucleus" ("nucle"), "Cytoplasm" ("cytoplasm"), "ER" ("Endoplasmic reticulum"), "Secreted" ("secret"), "Late Endosome" ("late endo").

The first feature in each multivariate model was the predicted likelihood of peptide-HLA binding according to the MS-based models (MSi, see next section). The cumulative contribution of each endogenous variable was evaluated by iteratively adding them to the multivariate model one at a time. The most informative feature was retained in the model and the process was repeated with the remaining variables. Multivariate models were built for each allele, utilizing 9-mer peptides only, and performance was evaluated by PPV (see previous section). The incremental gain in average PPV across the 95 alleles was considered as the contribution of each variable.

Prediction of Cleavability, Related to FIG. 30.

A novel cleavability predictor based on MS data was developed as previously described[4]. Briefly, a neural network model was trained on previously published HLA-IP MS identifications[32] where a negative set was generated by selecting 10 length- and termini-matched (first two and last two positions) peptides from the human proteome per positive. To ensure that targets and decoys would be drawn from a similar set of source genes, the 10 were selected at random (with replacement) using a probability weight proportional to the number of positive training examples mapping to the source transcript. Each training example is a sequence that captures 30 upstream residues, the peptide, and 30 downstream residues. Residues were binary encoded (i.e. isA, isC, isD, isE, isF, isG, isH, isI, isK, isL, isM, isN, isP, isQ, isR, isS, isT, isV, isW, isY, and isBlank) where isBlank represents a transcript termini, and also represented by their properties (i.e. pKA, volume, and polarity (www.proteinsandproteomics.org/content/free/tables_1/table08.pdf)). Featurized positions included U3, U2, U1, N1, N2, N3, C3, C2, C1, D1, D2, and D3 as well as a weighted average of positions U30 ... U4 (W=1 ... 27), a weighted average of positions D4 ... D30 (W=27 ... 1), and an unweighted average of positions N3 ... C3. These data were used to train a neural network (2 hidden layers of 50 and 10 nodes; 20% dropout for regularization; keras neural networks library (github.com/fchollet/keras)).

Assessment of predictive contribution of variables, related to FIG. 30. The potential contribution of intracellular signals to predicting endogenously-presented peptides was assessed by building multivariate logistic regression models with various combinations of the following features[4]:

1. RNA-seq expression—the level of expression of each peptide was determined as the sum of the expression of the transcripts containing that peptide, and log-transformed ($\log_2(TPM+1)$).
2. Ribo-seq expression—the translation level of each peptide was derived from Ribo-seq data from monoallelic B721.221 cells analogously to RNA-seq quantification.
3. Protein expression—iBAQ values, calculated by summing the intensities of observed peptides for a given gene by the theoretical count of tryptic peptides in the gene[41], were log-transformed (with zeros set to one tenth the minimum observed iBAQ value).
4. Cleavability likelihood: the cleavability score of each peptide was predicted by a de novo cleavability predictor trained on external multi-allelic MS-data as in Applicants previous work[4] (described in the previous section). When a peptide could be mapped to multiple source proteins the average of the cleavability scores was taken.
5. Presentation bias—the HLA-presentation bias of each gene was calculated based on the log ratio of observed to expected MS-identified peptides. The number of observed peptides per gene was the count of unique 9-mers in the collection of B721.221 mono-allelic MS data that map to the gene (protein IDs and GeneSymbol IDs were mapped via tables kgProtAlias, kgXref available from genome.ucsc.edu/cgi-bin/hgTables). The number of expected peptides per gene was defined as all possible unique 9-mers tiled along the length of the protein, multiplied by the expression level of the corresponding gene (to account for the increased likelihood of observing a peptide with higher expression), and scaled to sum to the total number of observed peptides.
6. Localization—the cellular localization of each peptide was assigned according to the localization(s) of its source protein(s). Protein localization information was obtained from Uniprot (ftp.uniprot.org/pub/databases/uniprot/current_release/knowledgebase/complete/uniprot_sprot.dat.gz) and Uniprot IDs were mapped to UCSC annotations via the following tables ftp.uniprot.org/pub/databases/uniprot/current_release/knowledgebase/idmapping/by_organism/HUMAN_9606_idmapping.dat.gz, genome.ucsc.edu/cgi-bin/hgTables kgProtAlias, kgXref. Protein localization categories were represented by 7 binary variables corresponding to "Cell Membrane" (if the localization field contained the text "cell membrane"), "Mitochondria" ("mitochondr"), "Nucleus" ("nucle"), "Cytoplasm" ("cytoplasm"), "ER" ("Endoplasmic reticulum"), "Secreted" ("secret"), "Late Endosome" ("late endo").

The first feature in each multivariate model was the predicted likelihood of peptide-HLA binding according to the MS-based machine leaning models (MSi, see next section). Applicants utilized the MS-trained predictors as the first variable, instead of NetMHC affinity, in order to account for any MS data properties which might have overestimated the contribution of cleavability which was the first MS data-based feature in the previous analysis. The cumulative contribution of each endogenous variable was evaluated by iteratively adding them to the multivariate model one at a time. The most informative feature was retained in the model and the process was repeated with the remaining variables. Multivariate models were built for each allele, utilizing 9-mer peptides only, and performance was evaluated by PPV (see previous section). The incremental gain in average PPV across the 95 alleles was considered as the contribution of each variable.

Development of Integrative HLA-Binding Prediction Models.

Overview of Model Training Procedure

Machine learning models were created to predict the likelihood that a given peptide will be endogenously presented by a given HLA class I molecule. The positive training set consisted of MS-identified peptides from the set of 95 B721.221 mono-allelic cell lines (hits). The negative set consisted of random peptides drawn from the human proteome which did not overlap with the hits (decoys). Note that one decoys set was used for training and a separate non-overlapping decoy set was used for evaluation. The number of positive and negative training examples were balanced by sampling 10× #hits decoys, and sampling the hits 10 times with replacement (this was done after splitting the data into folds to ensure that each hit is only present in one unique fold). Training was carried out in a standard 5-fold cross validation (CV) procedure: training data was split into 5 equal parts, each part was left out one at a time and a model was trained on the remaining 4 parts, obtaining 5 models each of which is evaluated on its corresponding left out set. The 5-fold CV training was repeated 3 times with different model initialization random seeds. The final predictions score for each peptide was the average of the 3 initializations. Neural network models were trained using the Theano and keras python libraries.

Allele-and-Length-Specific Models

To build models that are both allele- and length-specific only the MS-hits identified for that particular allele and length were used to train the model. This was done for each of the 95 alleles and for lengths 8, 9, 10, and 11 where at least 40 peptides were identified. The MSIntrinsic (or MSi) neural network models were fully-connected with one hidden layer of size 50 and tanh activation. Training was carried out in batches of size 30, for 10 epochs, and early-stopping determined by evaluating on a 20% hold-out partition of the training set to avoid overfitting. Three different models were trained with three different encodings of the peptide sequence: (1) one-hot (a.k.a. Binary or dummy) encoding; (2) similarity encoding using the blosum62 matrix; (3) similarity encoding based on the PMBEC matrix[42]. In addition to the peptide sequence encoding features, the MSi models included the following features:

1. Amino acid properties—each peptide residue was represented by the first three principal components derived from a dimensionality reduction of a large set of physicochemical properties 4.
2. Peptide-level characteristic—8 peptide-level features were computed with the R package peptides: "boman", "hmoment", "hydrophobicity", "helixbend", "sidechain", "xstr", "partspec", "pkc".

The logit-transformed output scores from MSi models were used as input features to train logistic regression models that integrate endogenous signals: MSiC models were trained with two features (MSi scores, and cleavability), MSiCE were trained with three input features (MSi scores, cleavability, and expression), and MSiCEB were trained with four input features (MSi scores, cleavability, expression, and presentation bias). Note that despite expression having a larger predictive contribution over cleavability, the cleavability feature is incorporated first to the integrative models (i.e. MSiC, MSiCE instead of MSiE, MSiEC) to allow for samples which lack expression data to utilize the cleavability since upstream and downstream peptide context sequences are readily available from the source protein.

Pan-Allele-Pan-Length Models

Pan models were trained similarly with some differences. A single panMSi model was trained with all 8-11-mer peptides identified across the 95 alleles. The panMSi neural networks had additional input features to describe the binding pocket of the HLA protein—each binding pocket residue was represented with 10 Kidera factors and 3 PCs (see Allele similarity analyses, related to FIGS. 27A-27D). The size of the hidden layer was 250, batch size was 5000, and the hidden layer activation function was rectified linear unit (ReLU). Training proceeded for 15 epochs with early-stopping determined by lack of improvement in 4 consecutive epochs.

To construct integrative pan models Applicant considered the four HLA genes (HLA-A, HLA-B, HLA-C, and HLA-G) and the four lengths (8, 9, 10, 11) separately: linear panMSiC, panMSiCE, and panMSiCEB models were trained for all HLA-A alleles and peptides of length 8, all HLA-A alleles and peptides of length 9, all HLA-A alleles and peptides of length 10, and all HLA-A alleles and peptides of length 10, and analogously for HLA-B, C, and G.

Modelling PPV Variability, Related to FIGS. 30A-30G

A linear regression model was trained to predict the achieved PPV (MSi, 9-mer models) given the following variables:

1. The total number of 9-mer hits observed for the allele
2. The sum of entropies at positions 1 through 9 (main motif entropy)
3. The number of identified submotifs for the allele
4. The sum of submotif entropies
5. Estimated abundance of the binding motif calculated by weighting the frequency of each residue at each peptide position by the natural abundance frequency of each of the 20 amino acids.

Evaluation of model performance in multi-allelic samples, related to FIGS. 31A-31D. To evaluate model performance in multi-allelic patient samples, each tumor-presented peptide was scored for binding to each of the sample-specific HLA alleles. To compare scores for different alleles, each score was converted to percentile rank. To this end, empirical cumulative distribution functions (R package stats, function ecdf( )) were computed for each model (including benchmark algorithms) from the scores of a background set of 1e6 random decoys. Each decoy set was constructed such that it contains proportions of 8, 9, 10, and 11-mers that are equal to the observed length distribution for the allele (or the HLA gene in the case of pan models). A peptide was considered to be correctly identified as a binder if the predicted binding score for at least one of the alleles in the sample was better than 99.9% of the scores in the corresponding decoy set (0.1 percentile rank; evolution was also performed at different rank thresholds, FIGS. 36). This approach is very similar to the % Ranks introduced by NetMHC8. A peptide was assigned to the allele(s) for which it had % rank score <0.1, where assignment to more than one allele was allowed.

Data availability. The original mass spectra for 79 newly described mono-allelic datasets, the protein sequence database, and tables of peptide spectrum matches for all 95 alleles have been deposited in the public proteomics repository MassIVE (massive.ucsd.edu) and are accessible at ftp://MSV000084172@massive.ucsd.edu when providing the dataset password: monoallelic. If requested, also provide the username: MSV000084172. Mass spectrometry data for the 16 previously published mono-allelic datasets in MassIVE can be downloaded at ftp://massive.ucsd.edu/MSV000080527. Datasets for the patient samples are accessible at ftp://MSV000084198@massive.ucsd.edu when providing the dataset username: MSV000084198 and password: patients.

B721.221 RNA seq data for HLA-C(C*04:01, C*07:01) is deposited under GEO: GSE131267. Melanoma RNA-seq data are deposited in dbGaP (www.ncbi.nlm.nih.gov/projects/gap/cgi-bin/study.cgi?study_id=phs001451.v1.p1[15]). Glioblastoma bulk RNA-seq data are available through dbGaP (www.ncbi.nlm.nih.gov/gap) with accession number phs001519.v1.p1[37].

Example 3—Prediction of Peptide Binding Based on Crystal Structure of HLA Molecules This example describes the method for predicting peptides that are capable of binding to a given HLA molecule based on its crystal structure. HLA protein structure information is used to improve binding prediction. A key step to developing a model is validation of the model using peptides that bind to the HLA allele as described herein (i.e., >185,000 peptides eluted from 95 HLA-A, B, C and G mono-allelic cell lines). In certain embodiments, structural features are combined with the prediction methods based on one or more variables selected from the group consisting of peptide sequence, amino acid physical properties, peptide physical properties, expression level of the source protein of a peptide within a cell, protein stability, protein translation rate, protein degradation rate, translational efficiencies from ribosomal profiling, protein cleavability, protein localization, motifs of host proteins that facilitate TAP transport, whether host protein is subject to autophagy, motifs that favor ribosomal stalling, protein features that favor nonsense-mediated mRNA decay (NMD) and peptide cleavability.

The crystal structures for HLA molecules are obtained from the Protein Data Bank (PDB, www.rcsb.org). The structure of binding pocket for each HLA molecule is provided. Applicants developed a protein-peptide docking tool by modifying FlexPepDock and coarse-grained Monte Carlo protein-peptide docking procedures. The simulation process is initiated by inputting a starting structure (i.e. side-chain prepacked to avoid interference) and a set of peptides (Raveh et al., Rosetta FlexPepDock ab-initio: simultaneous folding, docking and refinement of peptides onto their receptors. PLoS One. 2011; 6:e18934.). For each starting structure, 200 output models are generated. For each peptide, approximately 30 million docking modeling are tested. Feature maps for each peptide are generated, and the total energy, interface energy, peptide energy, and a weighted sum of all energies are assessed (FIG. 38). Based on these simulations, Applicants extract features that are used to train the prediction model. These features are used for training a variety models for predicting the binding of peptides to a given HLA allele molecule.

As a proof of concept, the applicants used three different models for training that use the identical input data sets. These models include DUMMY model, 1D model, and CNN model. The DUMMY model is characterized by using single hidden layer neural network and peptide sequence information only. The features of DUMMY model include dummy peptide encoding, PCA peptide encoding, and Kidera peptide-level features. The 1D model is characterized by single hidden layer neural network and uses of structural feature with 19 channels of 9(peptide)*100 (HLA) positions. The CNN model is characterized by convolutional neural network that convolves along the peptide in windows of 3 residues, using structure feature with 19 channels of 9(peptide)*100 (HLA) positions, and slower to train. The models can be evaluated by using any of the peptides bound to alleles as described herein. The models can be further trained using the features that most closely predict actual peptides identified as binding to an HLA allele as described herein. Three HLA alleles (A02:01, A11:01, and B14:02) were used to evaluate the models. The numbers of positive for the allele (npos) and negative for the allele (nneg) of peptides along with the unique number of decoys (ndec) used in training and evaluation are shown in FIG. 39. The residues with bit score are also shown in FIG. 39. The results show that generally the CNN model has the best performance when evaluated in both metrics of area under the curve for the ROC curve (AUC, FIG. 40A) and positive predictive value (PPV, FIG. 40B). For alleles A02:01 and A11:01, the CNN model and the 1D model achieved high scores for both AUC and PPV, while the DUMMY model yields much lower values in AUC and PPV. For allele B14:02, the three models yield similar values in AUC and PPV (FIG. 40A-40B).

REFERENCES

1. Lefranc, M.-P. et al. IMGT®, the international ImMunoGeneTics information System® 25 years on. *Nucleic Acids Res.* 43, D413-22 (2015).
2. Robinson, J. et al. The IPD and IMGT/HLA database: allele variant databases. *Nucleic Acids Res.* 43, D423-31 (2015).
3. Jurtz, V. et al. NetMHCpan-4.0: Improved Peptide-MHC Class I Interaction Predictions Integrating Eluted Ligand and Peptide Binding Affinity Data. *The Journal of Immunology* 199, 3360-3368 (2017).
4. Abelin, J. G. et al. Mass Spectrometry Profiling of HLA-Associated Peptidomes in Mono-allelic Cells Enables More Accurate Epitope Prediction. *Immunity* 46, 315-326 (2017).
5. O'Donnell, T. J. et al. MHCflurry: Open-Source Class I MHC Binding Affinity Prediction. *Cell Syst* 7, 129-132.e4 (2018).
6. Gfeller, D. et al. The Length Distribution and Multiple Specificity of Naturally Presented HLA-I Ligands. *J. Immunol.* 201, 3705-3716 (2018).
7. Bulik-Sullivan, B. et al. Deep learning using tumor HLA peptide mass spectrometry datasets improves neoantigen identification. *Nat. Biotechnol.* (2018). doi:10.1038/nbt.4313.
8. Nielsen, M. & Andreatta, M. NetMHCpan-3.0; improved prediction of binding to MHC class I molecules integrating information from multiple receptor and peptide length datasets. *Genome Med.* 8, 33 (2016).
9. Rajasagi, M. et al. Systematic identification of personal tumor-specific neoantigens in chronic lymphocytic leukemia. *Blood* 124, 453-462 (2014).
10. de Kruijf, E. M. et al. HLA-E and HLA-G expression in classical HLA class I-negative tumors is of prognostic value for clinical outcome of early breast cancer patients. *J. Immunol.* 185, 7452-7459 (2010).
11. Zhang, R.-L. et al. Predictive value of different proportion of lesion HLA-G expression in colorectal cancer. *Oncotarget* 8, 107441-107451 (2017).
12. Dawson, D. V., Ozgur, M., Sari, K., Ghanayem, M. & Kostyu, D. D. Ramifications of HLA class I polymorphism and population genetics for vaccine development. *Genet. Epidemiol.* 20, 87-106 (2001).
13. Gragert, L., Madbouly, A., Freeman, J. & Maiers, M. Six-locus high resolution HLA haplotype frequencies derived from mixed-resolution DNA typing for the entire US donor registry. *Hum. Immunol.* 74, 1313-1320 (2013).
14. Solberg, O. D. et al. Balancing selection and heterogeneity across the classical human leukocyte antigen loci: a meta-analytic review of 497 population studies. *Hum. Immunol.* 69, 443-464 (2008).
15. Ott, P. A. et al. An immunogenic personal neoantigen vaccine for patients with melanoma. *Nature* 547, 217-221 (2017).
16. Pearson, H. et al. MHC class I-associated peptides derive from selective regions of the human genome. *J. Clin. Invest.* 126, 4690-4701 (2016).
17. Sette, A. & Sidney, J. HLA supertypes and supermotifs: a functional perspective on HLA polymorphism. *Curr. Opin. Immunol.* 10, 478-482 (1998).
18. Robinson, J., Malik, A., Parham, P., Bodmer, J. G. & Marsh, S. G. E. IMGT/HLA Database—a sequence database for the human major histocompatibility complex. *Tissue Antigens* 55, 280-287 (2000).
19. Parham, P. & Moffett, A. Variable NK cell receptors and their MHC class I ligands in immunity, reproduction and human evolution. *Nat. Rev. Immunol.* 13, 133-144 (2013).
20. Nielsen, M. et al. NetMHCpan, a method for quantitative predictions of peptide binding to any HLA-A and -B locus protein of known sequence. *PLoS One* 2, e796 (2007).
21. Rist, M. J. et al. HLA peptide length preferences control CD8+ T cell responses. *J. Immunol.* 191, 561-571 (2013).
22. Maenaka, K. et al. Nonstandard Peptide Binding Revealed by Crystal Structures of HLA-B*5101 Complexed with HIV Immunodominant Epitopes. *The Journal of Immunology* 165, 3260-3267 (2000).
23. Kaur, G. et al. Structural and regulatory diversity shape HLA-C protein expression levels. *Nat. Commun.* 8, 15924 (2017).
24. Celik, A. A., Simper, G. S., Hiemisch, W., Blasczyk, R. & Bade-Döding, C. HLA-G peptide preferences change in transformed cells: impact on the binding motif *Immunogenetics* 70, 485-494 (2018).
25. Javitt, A. et al. Pro-inflammatory Cytokines Alter the Immunopeptidome Landscape by Modulation of HLA-B Expression. *Front. Immunol.* 10, 141 (2019).
26. Bassani-Sternberg, M., Pletscher-Frankild, S., Jensen, L. J. & Mann, M. Mass spectrometry of human leukocyte antigen class I peptidomes reveals strong effects of protein abundance and turnover on antigen presentation. *Mol. Cell. Proteomics* 14, 658-673 (2015).
27. Liepe, J. et al. A large fraction of HLA class I ligands are proteasome-generated spliced peptides. *Science* 354, 354-358 (2016).
28. Faridi, P. et al. A subset of HLA-I peptides are not genomically templated: Evidence for cis- and trans-spliced peptide ligands. *Sci Immunol* 3, (2018).
29. Mylonas, R. et al. Estimating the contribution of proteasomal spliced peptides to the HLA-I ligandome. *Mol. Cell. Proteomics* 17, 2347-2357 (2018).
30. Rolfs, Z., Solntsev, S. K., Shortreed, M. R., Frey, B. L. & Smith, L. M. Global Identification of Post-Translationally Spliced Peptides with Neo-Fusion. *J Proteome Res.* (2018). doi:10.1021/acs.jproteome.8b00651.
31. Di Marco, M. et al. Unveiling the Peptide Motifs of HLA-C and HLA-G from Naturally Presented Peptides and Generation of Binding Prediction Matrices. *J. Immunol.* 199, 2639-2651 (2017).
32. Bassani-Sternberg, M. et al. Direct identification of clinically relevant neoepitopes presented on native human melanoma tissue by mass spectrometry. *Nat. Commun.* 7, 13404 (2016).
33. Schuster, H. et al. The immunopeptidomic landscape of ovarian carcinomas. *Proc. Natl. Acad. Sci. U.S.A.* 114, E9942-E9951 (2017).
34. Girdlestone, J. Regulation of HLA Class I Loci by Interferons. *Immunobiology* 193, 229-237 (1995).
35. Chong, C. et al. High-throughput and Sensitive Immunopeptidomics Platform Reveals Profound Interferonγ-Mediated Remodeling of the Human Leukocyte Antigen (HLA) Ligandome. *Mol. Cell. Proteomics* 17, 533-548 (2018).
36. Vita, R. et al. The immune epitope database (IEDB) 3.0. *Nucleic Acids Res.* 43, D405-12 (2015).
37. Keskin, D. B. et al. Neoantigen vaccine generates intratumoral T cell responses in phase Ib glioblastoma trial. *Nature* 565, 234-239 (2019).
38. Langmead, B. & Salzberg, S. L. Fast gapped-read alignment with Bowtie 2. *Nat. Methods* 9, 357-359 (2012).
39. Li, B. & Dewey, C. N. RSEM: accurate transcript quantification from RNA-Seq data with or without a reference genome. *BMC Bioinformatics* 12, 323 (2011).
40. Mertins, P. et al. Reproducible workflow for multiplexed deep-scale proteome and phosphoproteome analysis of tumor tissues by liquid chromatography-mass spectrometry. *Nat. Protoc.* 13, 1632-1661 (2018).
41. Ishihama, Y. et al. Exponentially modified protein abundance index (emPAI) for estimation of absolute protein amount in proteomics by the number of sequenced peptides per protein. *Mol. Cell. Proteomics* 4, 1265-1272 (2005).
42. Kim, Y., Sidney, J., Pinilla, C., Sette, A. & Peters, B. Derivation of an amino acid similarity matrix for peptide: MHC binding and its application as a Bayesian prior. *BMC Bioinformatics* 10, 394 (2009).
43. Kidera, A., Konishi, Y., Oka, M., Ooi, T. & Scheraga, H. A. Statistical analysis of the physical properties of the 20 naturally occurring amino acids. *J. Protein Chem.* 4, 23-55 (1985).
44. Bremel, R. D. & Homan, E. J. An integrated approach to epitope analysis I: Dimensional reduction, visualization and prediction of MHC binding using amino acid principal components and regression approaches. *Immunome Res.* 6, 7 (2010).
45. McInnes, L., Healy, J. & Melville, J. UMAP: Uniform Manifold Approximation and Projection for Dimension Reduction. arXiv [stat.ML] (2018).
46. Harndahl, M. et al. Peptide binding to HLA class I molecules: homogenous, high-throughput screening, and affinity assays. *J. Biomol. Screen.* 14, 173-180 (2009).
47. Liberzon, A. et al. The Molecular Signatures Database (MSigDB) hallmark gene set collection. *Cell Syst* 1, 417-425 (2015).
48. Bassani-Sternberg, M., Pletscher-Frankild, S., Jensen, L. J. & Mann, M. Mass Spectrometry of Human Leukocyte Antigen Class I Peptidomes Reveals Strong Effects of Protein Abundance and Turnover on Antigen Presentation. *Molecular & Cellular Proteomics* 14, 658-673 (2015).
49. Hunt, D. F. et al. Characterization of peptides bound to the class I MHC molecule HLA-A2.1 by mass spectrometry. *Science* 255, 1261-1263 (1992).
50. Rammensee, H. G., Friede, T. & Stevanoviic, S. MHC ligands and peptide motifs: first listing. *Immunogenetics* 41, 178-228 (1995).
51. Rammensee, H., Bachmann, J., Emmerich, N. P., Bachor, O. A. & Stevanović, S. SYFPEITHI: database for MHC ligands and peptide motifs. *Immunogenetics* 50, 213-219 (1999).
52. Raveh B1, London N, Zimmerman L, & Schueler-Furman O. Rosetta FlexPepDock ab-initio: simultaneous folding, docking and refinement of peptides onto their receptors. *PLoS One.* 6:e18934 (2011).

Various modifications and variations of the described methods, pharmaceutical compositions, and kits of the invention will be apparent to those skilled in the art without departing from the scope and spirit of the invention. Although the invention has been described in connection with specific embodiments, it will be understood that it is capable of further modifications and that the invention as claimed should not be unduly limited to such specific embodiments. Indeed, various modifications of the described modes for carrying out the invention that are obvious to those skilled in the art are intended to be within the scope of the invention. This application is intended to cover any variations, uses, or adaptations of the invention following, in general, the principles of the invention and including such departures from the present disclosure come within known customary practice within the art to which the invention pertains and may be applied to the essential features herein before set forth.

SEQUENCE LISTING

The patent contains a lengthy sequence listing. A copy of the sequence listing is available in electronic form from the USPTO web site (https://seqdata.uspto.gov/?pageRequest=docDetail&DocID=US12394502B2). An electronic copy of the sequence listing will also be available from the USPTO upon request and payment of the fee set forth in 37 CFR 1.19(b)(3).

What is claimed is:

1. A method of identifying one or more selected candidate peptides capable of binding a class I major histocompatibility complex (MHC) molecule of a single human leukocyte antigen (HLA) allele, the method comprising:
   a. generating at least 100 models simulating occupancy for each of one or more candidate peptides on an HLA binding pocket, wherein the HLA binding pocket is in (i) a crystal structure of the MHC molecule of the single HLA allele or (ii) a crystal structure of a similar MHC molecule;
   b. extracting structural features indicative of occupancy from the at least 100 models of step (a); and
   c. providing the structural features extracted in step (b) to a machine learning algorithm, wherein the machine learning algorithm has been trained using a prior dataset comprising:
      peptide sequence features of one or more binding peptides on the HLA binding pocket,
      peptide sequence features of one or more non-binding peptides on the HLA binding pocket,
      structural features of one or more binding peptides on the HLA binding pocket, and
      structural features of one or more non-binding peptides on the HLA binding pocket,
   whereby the machine learning algorithm outputs selected candidate peptides for binding the MHC molecule of the single HLA allele
   thereby identifying one or more selected candidate peptides capable of binding the MHC molecule of the single HLA allele.

2. The method of claim 1,
   wherein the machine learning algorithm is trained with one or more peptides bound to MHC molecules in cell lines mono-allelic for the HLA allele; and/or
   wherein simulating occupancy is performed using one or more protein-peptide docking models and/or molecular dynamics simulation; and/or
   wherein the machine learning algorithm comprises one or more peptide encoding schemes.

3. The method of claim 2, wherein the one or more peptide encoding schemes comprise one-hot/dummy encoding, blosum62 encoding, or peptide: MHC binding energy covariance (PMBEC) encoding.

4. The method of claim 1, wherein each selected candidate peptide is predicted to bind one or more MHC molecules of one or more HLA alleles; and/or
   wherein the selected candidate peptides capable of binding the MHC molecule of the single HLA allele are 8, 9, 10, or 11 amino acids in length; and/or
   wherein the selected candidate peptides capable of binding the MHC molecule of the single HLA allele are any combination of peptides selected from the group consisting of 8, 9, 10, and 11 amino acids in length.

5. The method of claim 1, wherein each selected candidate peptide is predicted to bind one or more MHC molecules of one or more HLA alleles, and wherein the prediction is evaluated using metrics comprising area under a curve for a receiver operating characteristic curve and positive predictive value.

6. The method of claim 1, wherein the candidate peptides are selected from a subject and the MHC molecule of the single HLA allele is expressed in the subject.

7. The method of claim 6, wherein the subject is suffering from a disease or condition.

8. The method of claim 7, wherein the disease or condition is selected from the group consisting of cancer, an infection, an autoimmune disease, and a transplant.

9. The method of claim 8, wherein the peptides are identified by nucleic acid sequencing of a sample obtained from the subject, wherein the sample comprises tumor cells, infected cells, cells targeted by an autoimmune response, or cells to be transplanted.

10. The method of claim 8, wherein the disease is cancer and the peptides are neoantigens and/or novel unannotated open reading frames (nuORFs).

11. The method of claim 1, wherein the one or more binding peptides are selected from the group consisting of: A*01:01 (SEQ ID Nos: 44-1120); A*02:01 (SEQ ID Nos: 1121-4202); A*02:02 (SEQ ID Nos: 4203-7373); A*02:03 (SEQ ID Nos: 7374-9953); A*02:04 (SEQ ID Nos: 9954-11940); A*02:05 (SEQ ID Nos: 11941-14981); A*02:06 (SEQ ID Nos: 14982-17191); A*02:07 (SEQ ID Nos: 117192-20710); A*02:11 (SEQ ID Nos: 20711-22696); A*03:01 (SEQ ID Nos: 22697-24233); A*11:01 (SEQ ID Nos: 24234-27505); A*11:02 (SEQ ID Nos: 27506-29812); A*23:01 (SEQ ID Nos: 29813-32133); A*24:02 (SEQ ID Nos: 32134-34347); A*24:07 (SEQ ID Nos: 34348-35681); A*25:01 (SEQ ID Nos: 35682-36682); A*26:01 (SEQ ID Nos: 36683-37957); A*29:02 (SEQ ID Nos: 37958-38921); A*30:01 (SEQ ID Nos: 38922-40029); A*30:02 (SEQ ID Nos: 40030-42114); A*31:01 (SEQ ID Nos: 42115-42919); A*32:01 (SEQ ID Nos: 42920-44874); A*33:01 (SEQ ID Nos: 44875-46761); A*33:03 (SEQ ID Nos: 46762-49053); A*34:01 (SEQ ID Nos: 49054-50948); A*34:02 (SEQ ID Nos: 50949-53677); A*36:01 (SEQ ID Nos: 53678-55165); A*66:01 (SEQ ID Nos: 55166-56901); A*68:01 (SEQ ID Nos: 56902-58374); A*68:02 (SEQ ID Nos: 58375-59804); A*74:01 (SEQ ID Nos: 59805-61821); B*07:02 (SEQ ID Nos: 61822-63473); B*07:04 (SEQ ID Nos: 63474-64885); B*08:01 (SEQ ID Nos: 64886-65609); B*13:01 (SEQ ID Nos: 65610-69419); B*13:02 (SEQ ID Nos: 69420-71587); B*14:02 (SEQ ID Nos: 71588-72970); B*15:01 (SEQ ID Nos: 72971-76378); B*15:02 (SEQ ID Nos: 76379-77762); B*15:03 (SEQ ID Nos: 77763-80458); B*15:10 (SEQ ID Nos: 80459-81940); B*15:17 (SEQ ID Nos: 81941-83632); B*18:01 (SEQ ID Nos: 83633-85593); B*27.05 (SEQ ID Nos: 85594-87076); B*35:01 (SEQ ID Nos: 87077-87772); B*35:03 (SEQ ID Nos: 87773-89157); B*35:07 (SEQ ID Nos: 89158-90977); B*37:01 (SEQ ID Nos: 90978-92452); B*38:01 (SEQ ID Nos: 92453-94858); B*38:02 (SEQ ID Nos: 94859-97742); B*40:01 (SEQ ID Nos: 97743-100731); B*40:02 (SEQ ID Nos: 100732-104409); B*40:06 (SEQ ID Nos: 104410-106653); B*42:01 (SEQ ID Nos: 106612-019885); B*44:02 (SEQ ID Nos: 109886-110903); B*44:03 (SEQ ID Nos: 110904-111749); B*45:01 (SEQ ID Nos: 111750-113153); B*46:01 (SEQ ID Nos: 113154-114113); B*49:01 (SEQ ID Nos: 114114-117833); B*50:01 (SEQ ID Nos: 117834-118468); B*51:01 (SEQ ID Nos: 118469-119991); B*52:01 (SEQ ID Nos: 119992-121525); B*53:01 (SEQ ID Nos: 121526-123560); 54:01 (SEQ ID Nos: 123561-124684); B*55:01 (SEQ ID Nos: 124685-126136); B*55:02 (SEQ ID Nos: 126137-127557); B*56:01 (SEQ ID Nos: 127558-129239); B*57:01 (SEQ ID Nos: 129240-130274); B*57:03 (SEQ ID Nos: 130275-132636); B*58:01 (SEQ ID Nos: 132637-134577); B*58:02 (SEQ ID Nos: 134578-135530); C*01:02 (SEQ ID Nos: 135531-136878); C*02:02 (SEQ ID Nos: 136879-137802); C*03:02 (SEQ ID Nos: 137803-138984); C*03:03 (SEQ ID Nos: 138985-141074); C*03:04 (SEQ ID Nos: 141075-143394); C*04:01 (SEQ ID Nos: 143395-145236); C*04:03 (SEQ ID Nos: 145237-146269); C*05:01 (SEQ ID Nos: 146270-147708); C*06:02 (SEQ ID Nos: 147709-149028); C*07:01 (SEQ ID Nos: 149029-149822); C*07:02 (SEQ ID Nos: 149823-150900); C*07:04 (SEQ ID Nos: 150901-151615); C*08:01 (SEQ ID Nos: 151616-153388); C*08:02 (SEQ ID Nos: 153389-156499); C*12:02 (SEQ ID Nos: 156500-157889); C*12:03 (SEQ ID Nos: 157890-160043); C*14:02 (SEQ ID Nos: 160044-161408); C*14:03 (SEQ ID Nos: 161409-164186); C*15:02 (SEQ ID Nos: 164187-167475); C*16:01 (SEQ ID Nos: 167476-170317); C*17:01 (SEQ ID Nos: 170318-171281); G*01:01 (SEQ ID Nos: 171282-172073); G*01:03 (SEQ ID Nos: 172074-172742) and G*01:04 (SEQ ID Nos: 172743-173477).

12. The method of claim 1, wherein the structural features are selected from the group consisting of energies of attraction, energies of repulsion, energies of solvation, energies of side chain and backbone hydrogen bonds, energies of side chain and backbone conformations, Lennard-Jones attractive potential between atoms in different residue, Lennard-Jones repulsive potential between atoms in different residues, Lazaridis-Karplus solvation energy, Lennard-Jones repulsive potential between atoms in the same residue, coulombic electrostatic potential with a distance-dependent dielectric, proline ring closure energy and energy of psi angle of preceding residue, backbone-backbone hbonds close in primary sequence, backbone-backbone hbonds distant in primary sequences, sidechain-backbone hydrogen bond energy, sidechain-sidechain hydrogen bond energy, disulfide geometry potential, Ramachandran preferences, omega dihedral in the backbone, internal energy of sidechain rotamers as derived from Dunbrack's statistics, probability of amino acid at phi/psi, and reference energy for each amino acid.

13. The method of claim 1, wherein the prior dataset used to train the machine learning algorithm further comprises data selected from the group consisting of:
 amino acid physical properties, peptide physical properties, expression level of a source protein of each peptide, protein stability, protein translation rate, protein degradation rate, translational efficiencies from ribosomal profiling, protein cleavability, protein localization, motifs of host proteins that facilitate TAP transport, whether host protein is subject to autophagy, motifs that favor ribosomal stalling, protein features that favor nonsense-mediated mRNA decay (NMD), peptide cleavability, dummy peptide encoding, PCA peptide encoding, and Kidera peptide-level features.

14. The method of claim 1, wherein the machine learning algorithm comprises a neural network model.

15. The method of claim 14, wherein the neural network model comprises a single hidden layer neural network model and/or a convolutional neural network model.

16. A method of identifying one or more selected candidate peptides capable of binding a class I major histocompatibility complex (MHC) molecule of a single human leukocyte antigen (HLA) allele, the method comprising:
 a. generating at least 100 models simulating occupancy for each of one or more candidate peptides on an HLA binding pocket, wherein the HLA binding pocket is in (i) a crystal structure of the MHC molecule of the single HLA allele or (ii) a crystal structure of a similar MHC molecule;
 b. extracting structural features indicative of occupancy from the at least 100 models of step (a); and
 c. providing the structural features extracted in step (b) to a machine learning algorithm, wherein the machine learning algorithm has been trained using a prior dataset comprising (i) peptide sequence features of one or more binding peptides on the HLA binding pocket, peptide sequence features of one or more non-binding peptides on the HLA binding pocket, structural features of one or more binding peptides on the HLA binding pocket, and structural features of one or more non-binding peptides on the HLA binding pocket and (ii) non-structural features of the one or more binding peptides and non-structural features of the one or more non-binding peptides, whereby the machine learning algorithm outputs selected candidate peptides for binding the MHC molecule of the single HLA allele, thereby identifying one or more selected candidate peptides capable of binding the MHC molecule of the single HLA allele.

17. The method of claim 16, wherein the prior dataset used to train the machine learning algorithm further comprises data selected from the group consisting of: amino acid physical properties, peptide physical properties, expression level of the source protein of a peptide, protein stability, protein translation rate, protein degradation rate, translational efficiencies from ribosomal profiling, protein cleavability, protein localization, motifs of host proteins that facilitate TAP transport, whether host protein is subject to autophagy, motifs that favor ribosomal stalling, protein features that favor nonsense-mediated mRNA decay (NMD), peptide cleavability, dummy peptide encoding, PCA peptide encoding, and Kidera peptide-level features.

18. A method of identifying one or more selected candidate peptides capable of binding a class I major histocompatibility complex (MHC) molecule of a single human leukocyte antigen (HLA) allele, the method comprising:

a. generating at least 100 models simulating occupancy for each of one or more candidate peptides on an HLA binding pocket, wherein the HLA binding pocket is in (i) a crystal structure of the MHC molecule of the single HLA allele or (ii) a crystal structure of a similar MHC molecule, wherein the output models are generated by a peptide docking tool and comprise one or more protein-peptide docking models;

b. extracting structural features indicative of occupancy from the at least 100 models of step (a); and c. providing the structural features extracted in step (b) to a machine learning algorithm, wherein the machine learning algorithm has been trained using a prior dataset comprising (i) peptide sequence features of one or more binding peptides on the HLA binding pocket, peptide sequence features of one or more non-binding peptides on the HLA binding pocket, structural features of one or more binding peptides on the HLA binding pocket, and structural features of one or more non-binding peptides on the HLA binding pocket and (ii) non-structural features of the one or more binding peptides and non-structural features of the one or more non-binding peptides, whereby the machine learning algorithm outputs selected candidate peptides for binding the MHC molecule of the single HLA allele, thereby identifying one or more selected candidate peptides capable of binding the MHC molecule of the single HLA allele.

19. The method of claim 18, herein the peptide docking tool is selected from the group consisting of FlexPepDock, DockTope, pDOCK and HADDOCK.

* * * * *